US012435043B2

(12) United States Patent
Hartman et al.

(10) Patent No.: US 12,435,043 B2
(45) Date of Patent: Oct. 7, 2025

(54) INHIBITORS OF NLRP3 INFLAMMASOME

(71) Applicants: George Hartman, Lansdale, PA (US); Paul Humphries, Menlo Park, CA (US); Kevin Edward Leif Wilhelmsen, Albany, CA (US)

(72) Inventors: George Hartman, Lansdale, PA (US); Paul Humphries, Menlo Park, CA (US); Kevin Edward Leif Wilhelmsen, Albany, CA (US)

(73) Assignee: BioAge Labs, Inc., Richmond, CA (US)

( * ) Notice: Subject to any disclaimer, the term of this patent is extended or adjusted under 35 U.S.C. 154(b) by 0 days.

(21) Appl. No.: 18/353,370

(22) Filed: Jul. 17, 2023

(65) Prior Publication Data

US 2024/0051923 A1 Feb. 15, 2024

Related U.S. Application Data

(62) Division of application No. 17/701,856, filed on Mar. 23, 2022, now Pat. No. 11,702,391.

(60) Provisional application No. 63/219,538, filed on Jul. 8, 2021, provisional application No. 63/164,780, filed on Mar. 23, 2021.

(51) Int. Cl.

| | |
|---|---|
| ***A61K 31/4353*** | (2006.01) |
| ***C07D 231/56*** | (2006.01) |
| ***C07D 235/06*** | (2006.01) |
| ***C07D 401/12*** | (2006.01) |
| ***C07D 403/12*** | (2006.01) |
| ***C07D 405/12*** | (2006.01) |
| ***C07D 413/12*** | (2006.01) |
| ***C07D 417/12*** | (2006.01) |
| ***C07D 471/04*** | (2006.01) |

(52) U.S. Cl.

CPC ........ *C07D 231/56* (2013.01); *A61K 31/4353* (2013.01); *C07D 235/06* (2013.01); *C07D 401/12* (2013.01); *C07D 403/12* (2013.01); *C07D 405/12* (2013.01); *C07D 413/12* (2013.01); *C07D 417/12* (2013.01); *C07D 471/04* (2013.01)

(58) Field of Classification Search

CPC .................................................. A61K 31/4353

See application file for complete search history.

(56) References Cited

U.S. PATENT DOCUMENTS

2022/0324812 A1 10/2022 Hartman et al.

FOREIGN PATENT DOCUMENTS

| | | | |
|---|---|---|---|
| CN | 111 329 993 | A | 6/2020 |
| EP | 2 269 990 | A1 | 1/2011 |
| EP | 3 660 003 | A1 | 6/2020 |
| WO | WO 2004/099143 | A1 | 11/2004 |
| WO | WO 2008/006561 | A1 | 1/2008 |
| WO | WO 2012/101453 | A1 | 8/2012 |
| WO | WO 2013/126856 | A1 | 8/2013 |
| WO | WO 2016/081290 | A1 | 5/2016 |
| WO | WO 2019/001416 | A1 | 1/2019 |
| WO | WO 2019/193342 | A1 | 10/2019 |
| WO | WO 2020/097389 | A1 | 5/2020 |

OTHER PUBLICATIONS

Fischer et al., "Age-Dependent Changes in the Cochlea", *Gerontology* 1-7 (2019).

Franceshi et al., "Inflamm-aging: An Evolutionary Perspective on Immunosenescence", *Annals of the New York Academy of Sciences* 908(1):244-254 (2000).

Hubbard et al., "Frailty, inflammation and the elderly" *Biogerontology* 11(5):635-641 (2010).

International Search Report and Written Opinion for International Application No. PCT/US2022/021461, mailed Jun. 14, 2022, 15 pages.

Kang et al., "Synthesis and structure-activity relationships of novel fused ring analogues of Q203 as antitubercular agents", *European Journal of Medicinal Chemistry* 136(1):420-427 (2017), doi:10.1016/j.ejmech.2017.05.021.

Le Prell et al., "Noise-induced hearing loss and its prevention: current issues in mammalian hearing" *Current Opinion in Physiology* 18:32-36 (2020).

(Continued)

*Primary Examiner* — Brian E McDowell

(74) *Attorney, Agent, or Firm* — Lathrop GPM LLP; Brian C. Trinque; Nicole Sassu

(57) ABSTRACT

The present disclosure relates to compounds that act as inhibitors of NLRP3 inflammasomes; pharmaceutical compositions comprising the compounds; and methods of treating disorders associated with inflammation and inflammaging, including hearing loss and other diseases associated with aging; wherein the inhibitors of NLRP3 inflammasomes are compounds of Formula VII:

(VII)

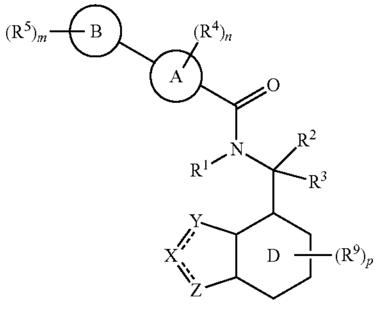

or a pharmaceutically acceptable salt thereof.

15 Claims, No Drawings

(56) References Cited

OTHER PUBLICATIONS

Montalvao et al., "Synthesis and Biological Evaluation of 2-Aminobenzothiazole and Benzimidazole Analogs Based on the Clathrodin Structure", *Archiv der Pharmzie—Chemistry in Life Sciences* 349(2):137-149 (2016); doi:10.1002/ardp.201500365.
Nakanishi et al., "NLRP3 mutation and cochlear autoinflammation cause syndromic and nonsyndromic hearing loss DFNA34 responsive to anakinra therapy", *PNAS* 114(37):E7766-E7775 (2017).
Nakanishi et al., "Genetic Hearing Loss Associated With Autoinflammation", *Frontiers in Neurology* 11(Art. 141):1-7 (2020).
Schwaid et al., "Strategies for Targeting the NLRP3 Inflammasome in the Clinical and Preclinical Space", *Journal of Medicinal Chemistry* 64(1):101-122 (2021).
Yao et al., "Inflammation and Immune Systems Alterations in Frailty", *Clinics in Geriatric Medicine* 27(1):79-87 (2011).
Yee et al., "Zika virus infection causes widespread damage to the inner ear", *Hearing Research* 395:1-15 (2020).
Zahid et al., "Pharmacological Inhibitors of the MLRP3 Inflammasome", *Frontiers in Immunology* vol. 10, Article 2538 (2019); doi:10.3389/fimmu.2019.02538.
U.S. Appl. No. 17/701,856 / 2022-0324812 A1 / U.S. Pat. No. 11,702,391, filed Mar. 23, 2022 / Oct. 13, 2022/ Jul. 18, 2023, George Hartman.
U.S. Appl. No. 17/930,895 / 2023-0051130 A1 / U.S. Pat. No. 11,708,334, filed Sep. 9, 2022 / Feb. 16, 2023 / Jul. 25, 2023, George Hartman.
U.S. Appl. No. 18/323,939, filed May 24, 2023, George Hartman.
U.S. Appl. No. 18/353,410, filed Jul. 17, 2023, George Hartman.
U.S. Appl. No. 18/353,422, filed Jul. 17, 2023, George Hartman.

INHIBITORS OF NLRP3 INFLAMMASOME

RELATED APPLICATIONS

This application claims priority to U.S. Provisional Application No. 63/164,780, filed on Mar. 23, 2021, and U.S. Provisional Application No. 63/219,538, filed on Jul. 8, 2021, the entire contents of which are hereby incorporated in its entirety.

BACKGROUND

Aging frailty poses a very concerning problem for the overall health and well-being of individuals and is characterized as a syndrome of multisystem physiological dysregulation.

Aging frailty is a geriatric syndrome characterized by weakness, low physical activity, slowed motor performance, exhaustion, and unintentional weight loss (Yao, X. et al., Clinics in Geriatric Medicine 27(1): 79-87 (2011)). Furthermore, there are many studies showing a direct correlation between aging frailty and inflammation (Hubbard, R. E., et al., Biogerontology 11(5):635-641 (2010)). Immunosenescence is characterized by a low grade, chronic systemic inflammatory state known as inflammaging (Franceshi, C. et al., Annals of the New York Academy of Sciences 908:244-254 (2000)). This heightened inflammatory state or chronic inflammation found in aging and aging frailty leads to immune dysregulation and a complex remodeling of both innate and adaptive immunity.

Inhibiting the NLRP3 inflammasome, an oligomeric protein complex that includes ASC and caspase-1, mediates inflammation in an extensive number of preclinical models (Schwaid, A. G., *J. Med. Chem.* 2021, 64(1), 101-122). At the same time, the NLRP3 inflammasome is part of a larger pro-inflammatory pathway, whose modulation is also being explored. NLRP3 is an inflammasome sensor protein that has been well studied in a number of disease contexts. Many different indications are associated with the NLRP3 inflammasome including diseases related to aging, cryopyrin-associated periodic syndrome (CAPS), nonalcoholic steatohepatitis (NASH), gout, coronary artery disease, Crohn's disease, osteoarthritis, rheumatoid arthritis, Alzheimer's disease, Parkinson's disease, intestinal disorders, acute respiratory distress syndrome (ARDS), amyotrophic lateral sclerosis (ALS), cancer, and dermatological diseases.

Inflammation, as well as activation of the NLRP3 inflammasome, have also been shown to result in hearing loss (Nakanishi, H., et al., *Frontiers in Neurology,* 2020, 11, 1-7; Nakanishi, H., et al., *PNAS,* 2017, E7766-E7775). The inflammation-related hearing loss can be age-dependent (Fischer, N., et al., *Gerontology,* 2019, 1-7), noise-induced (Le Prell, C. G., et al. *Current Opinion in Physiology,* 2020, 18, 32-36), and the result of a viral infection such as Zika virus and coronavirus (Yee, K. T., et al., *Hearing Research,* 2020, 395, 1-15).

The NLRP3 inflammasome is therefore a promising drug target. The breadth of the indications it is implicated in speak to the need for therapeutics that target the NLRP3 inflammasome.

SUMMARY

Provided here are compounds that inhibit the NLRP3 inflammasome. As such, these compounds are useful in the treatment of a variety of indications, including inflammaging and inflammation.

In an aspect, provided herein is a compound of Formula I:

(I)

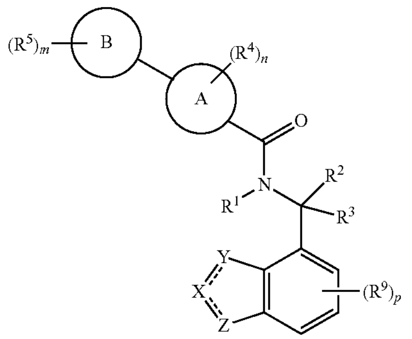

or a pharmaceutically acceptable salt thereof.

In an embodiment, the compound of Formula I is a compound of Formula II:

(II)

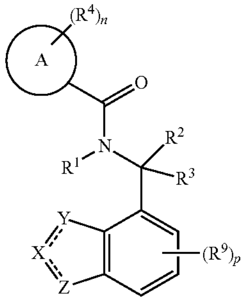

or a pharmaceutically acceptable salt thereof.

In another aspect, provided herein is a compound of Formula III:

(III)

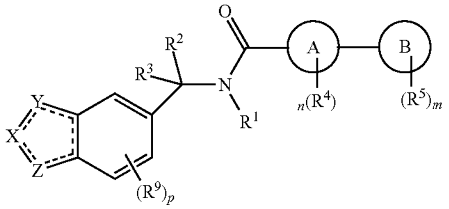

or a pharmaceutically acceptable salt thereof.

In yet another aspect, provided herein is a compound of Formula IV:

(IV)

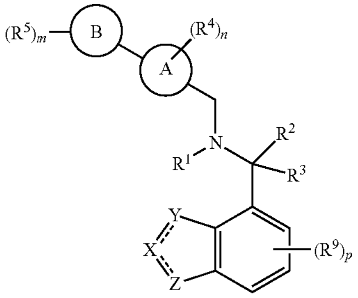

or a pharmaceutically acceptable salt thereof.

In still another aspect, provided herein is a compound of Formula V:

(V)

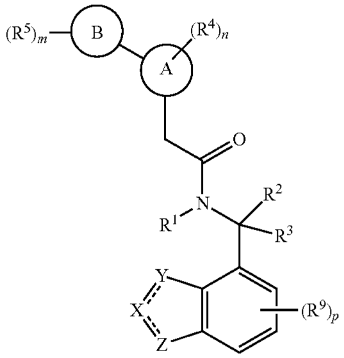

or a pharmaceutically acceptable salt thereof.

In an aspect, provided herein is a compound of Formula VI:

(VI)

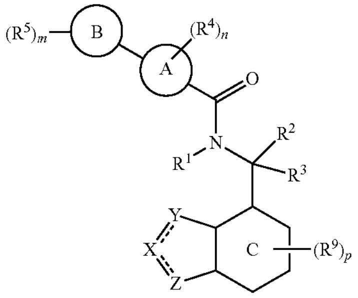

or a pharmaceutically acceptable salt thereof.

In an aspect, provided herein is a compound of Formula VI:

(VII)

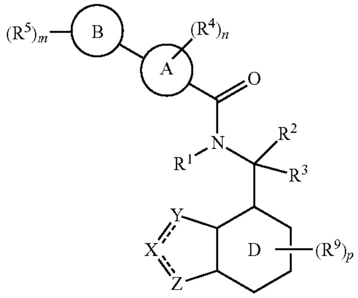

or a pharmaceutically acceptable salt thereof.

In another aspect, provided herein is a compound of Formula X:

(X)

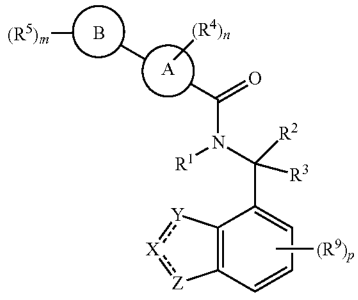

or a pharmaceutically acceptable salt thereof.

In yet another aspect, provided herein is a pharmaceutical composition comprising a compound described herein, or a pharmaceutically acceptable salt thereof, and a pharmaceutically acceptable carrier.

In yet another aspect, provided herein is a method of inhibiting NLRP3 inflammasome in a subject in need thereof comprising administering to the subject a therapeutically effective amount of a compound described herein.

DETAILED DESCRIPTION

Provided here are compounds that inhibit the NLRP3 inflammasome. As such, these compounds, as well as pharmaceutical compositions that comprise these compounds, are useful in the treatment of a variety of indications, including inflammaging. Inflammation, and other age-related diseases.

Definitions

Listed below are definitions of various terms used to describe the compounds and compositions disclosed herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art.

Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, 1%, and ±0.1% from the specified value, as such variations are appropriate to perform the disclosed methods.

The term "administration" or the like as used herein refers to the providing a therapeutic agent to a subject. Multiple techniques of administering a therapeutic agent exist in the art including, but not limited to, intravenous, oral, aerosol, parenteral, ophthalmic, pulmonary, and topical administration.

The term "treat," "treated," "treating," or "treatment" includes the diminishment or alleviation of at least one symptom associated or caused by the state, disorder or disease being treated. In certain embodiments, the treatment comprises alleviating or preventing the symptoms of inflammaging and age-related disorders.

As used herein, the term "contacting" refers to the bringing together of indicated moieties in an in vitro system or an in vivo system. For example, "contacting" a cell with a compound includes the administration of a compound of the present invention to an individual, subject, or patient, such as a human, as well as, for example, introducing a compound into a sample containing a purified preparation containing the cell.

As used herein, the term "cell" is meant to refer to a cell that is in vitro, ex vivo, or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the disclosure with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol;

phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the present disclosure, and are physiologically acceptable to the patient. Supplementary active compounds may also be incorporated into the compositions. The "pharmaceutically acceptable carrier" may further include a pharmaceutically acceptable salt of the compound disclosed herein. Other additional ingredients that may be included in the pharmaceutical compositions are known in the art and described, for example, in Remington's Pharmaceutical Sciences (Genaro, Ed., Mack Publishing Co., 1985, Easton, PA), which is incorporated herein by reference.

As used herein, "inflammaging" is defined as chronic sterile inflammation that is associated with numerous age-related diseases.

As used herein, "age-related disorder" refers to disorders that are associated with the aging process. Stated alternatively, age-related disorders are diseases associated with the elderly. Non-limiting examples of age-related diseases include atherosclerosis and cardiovascular disease, cancer, arthritis, cataracts, osteoporosis, type 2 diabetes, hypertension, and Alzheimer's disease. The incidence of all of these diseases increases exponentially with age.

As used herein, the term "alkyl," by itself or as part of another substituent means, unless otherwise stated, a straight or branched chain hydrocarbon having the number of carbon atoms designated (i.e., $C_1$-$C_6$ alkyl means an alkyl having one to six carbon atoms) and includes straight and branched chains. Examples include methyl, ethyl, propyl, isopropyl, butyl, isobutyl, tert butyl, pentyl, neopentyl, and hexyl. Other examples of $C_1$-$C_6$ alkyl include ethyl, methyl, isopropyl, isobutyl, n-pentyl, and n-hexyl.

As used herein, the term "haloalkyl" refers to an alkyl group, as defined above, substituted with one or more halo substituents, wherein alkyl and halo are as defined herein. Haloalkyl includes, by way of example, chloromethyl, trifluoromethyl, bromoethyl, chlorofluoroethyl, and the like.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" means a non-aromatic carbocyclic system that is fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl. In an embodiment, cycloalkyl refers to $C_{3-10}$ cycloalkyl. In another embodiment, cycloalkyl refers to $C_{3-6}$ cycloalkyl.

As used herein, the term "heterocyclyl" or "heterocycloalkyl" means a non-aromatic carbocyclic system containing 1, 2, 3 or 4 heteroatoms selected independently from N, O, and S and having 1, 2 or 3 rings wherein such rings may be fused, wherein fused is defined above. Heterocyclyl also includes bicyclic structures that may be bridged or spirocyclic in nature with each individual ring within the bicycle varying from 3-8 atoms, and containing 0, 1, or 2 N, O, or S atoms. The term "heterocyclyl" includes cyclic esters (i.e., lactones) and cyclic amides (i.e., lactams) and also specifically includes, but is not limited to, epoxidyl, oxetanyl, tetrahydro-furanyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]-hexanyl, 6-azabicyclo[3.1.1]heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]nonanyl, and 8-oxabicyclo[3.2.1]octanyl. In an embodiment, heterocycloalkyl refers to 3-10 membered heterocycloalkyl. In another embodiment, heterocycloalkyl refers to 4-10 membered heterocycloalkyl. In another embodiment, heterocycloalkyl refers to 3-6 membered heterocycloalkyl.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl. In some embodiments, aryl groups have 6 carbon atoms. In some embodiments, aryl groups have from six to ten carbon atoms. In some embodiments, aryl groups have from six to sixteen carbon atoms. In an embodiment, the aryl group has six to ten carbon atoms.

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. The term "heteroaryl" includes, but is not limited to, furanyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta-[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. In embodiment, heteroaryl is 5-10 membered heteroaryl. In another embodiment, heteroaryl is 5-6 membered heteroaryl.

It is to be understood that if an aryl, heteroaryl, cycloalkyl, or heterocyclyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thienyl" means 2- or 3-thienyl, and so forth.

Compounds

Provided herein are compounds that are inhibitors of the NLRP3 inflammasome and are thus useful in the treatment of inflammatory disorders, including cancer and other proliferation diseases.

In an aspect, provided herein is a compound of Formula I:

(I)

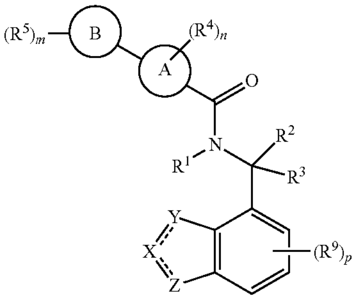

or a pharmaceutically acceptable salt thereof;

wherein

⎓ is an optional double bond;

X is CH or N;

Y and Z are each independently selected from the group consisting of NH, $NR^9$, O, S, N, CH, and $CR^9$;

Ring A is selected from the group consisting of $C_{5-10}$ aryl, 5-6 membered heteroaryl, $C_{4-10}$ cycloalkyl, and 4-10 membered heterocycloalkyl;

Ring B is selected from the group consisting of phenyl, 5-6 membered heteroaryl, $C_{3-6}$ cycloalkyl, and 3-6 membered heterocycloalkyl;

alternatively, Ring B is absent and m is 0;

$R^1$ is selected from the group consisting of H, $C_{1-6}$ alkyl, and $C_{3-6}$ cycloalkyl, wherein alkyl and cycloalkyl are each optionally substituted with $R^6$;

$R^2$ and $R^3$ are each independently selected from the group consisting of H, $C_{1-6}$ alkyl, $C_{3-6}$ cycloalkyl, and 3-6 membered heterocycloalkyl;

alternatively, $R^2$ and $R^3$, together with the atom to which they are attached, form a ring selected from the group consisting of $C_{3-7}$ cycloalkyl and 3-7 membered heterocycloalkyl;

each $R^4$ is independently selected from the group consisting of $C_{1-6}$ alkyl, halo, OH, $OR^6$, $NH_2$, $NH(C_{1-6}alkyl)$, $N(C_{1-6}\ alkyl)_2$, $NHCOR^6$, CN, $C_{1-6}$ haloalkyl, $C_{3-7}$ cycloalkyl, 3-7 membered heterocycloalkyl, and $COR^6$;

alternatively, two $R^4$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^5$ is independently selected from the group consisting of H, $C_{1-6}$ alkyl, $C_{1-6}$ haloalkyl, halo, OH, $OR^6$, $NH_2$, $NH(C_{1-6}\ alkyl)$, $N(C_{1-6}\ alkyl)_2$, $NHCOR^6$, CN, $C_{3-7}$ cycloalkyl, 3-7 membered heterocycloalkyl, $COR^6$, and $SO_2R^6$;

alternatively, two $R^5$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^6$ is independently selected from the group consisting of $C_{1-6}$ alkyl, $C_{0-6}$ alkyl-$C_{6-10}$ aryl, $C_{0-6}$ alkyl-5-10 membered heteroaryl, $OC_{1-6}$ alkyl, $C_{3-6}$ cycloalkyl, halo, $NH_2$, $NH(C_{1-6}\ alkyl)$, and $N(C_{1-6}\ alkyl)_2$;

each $R^7$ is independently selected from the group consisting of $C_{1-6}$ alkyl, $C_{1-6}$ haloalkyl, halo, OH, $OC_{1-6}$ alkyl, $NH_2$, $NH(C_{1-6}\ alkyl)$, $N(C_{1-6}\ alkyl)_2$, CN, $COR^8$, and $SO_2R^8$;

each $R^8$ is independently selected from the group consisting of $C_{1-6}$ alkyl, $OC_{1-6}$ alkyl, halo, $NH_2$, $NH(C_{1-6}\ alkyl)$, and $N(C_{1-6}\ alkyl)_2$;

each $R^9$ is independently selected from the group consisting of $C_{1-6}$ alkyl, $OC_{1-6}$ alkyl, halo, CN, OH, $NH_2$, $NH(C_{1-6}\ alkyl)$, and $N(C_{1-6}\ alkyl)_2$;

m is 0, 1, 2, or 3;

n is 1, 2, or 3; and p is 0, 1, 2, or 3.

In an embodiment of Formula I, Ring A is selected from the group consisting of $C_{6-10}$ aryl, 5-6 membered heteroaryl, and $C_{4-10}$ cycloalkyl.

In an embodiment, the compound of Formula I is a compound of Formula Ia:

(Ia)

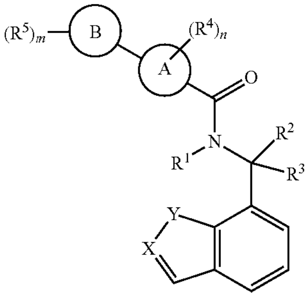

or a pharmaceutically acceptable salt thereof;

wherein

X is CH or N;

Y is NH, O, or S;

Ring A is phenyl or 5-6 membered heteroaryl;

Ring B is selected from the group consisting of phenyl, 5-6 membered heteroaryl, $C_{3-6}$ cycloalkyl, and 3-6 membered heterocycloalkyl;

$R^1$ is H or $C_{1-6}$ alkyl;

$R^2$ and $R^3$ are each independently H or $C_{1-6}$ alkyl;

each $R^4$ is independently selected from the group consisting of $C_{1-6}$ alkyl, halo, OH, $OR^6$, $NH_2$, $NH(C_{1-6}\ alkyl)$, $N(C_{1-6}\ alkyl)_2$, $NHCOR^6$, CN, $C_{1-6}$ haloalkyl, $C_{3-7}$ cycloalkyl, 3-7 membered heterocycloalkyl, and $COR^6$;

each $R^5$ is independently selected from the group consisting of H, $C_{1-6}$ alkyl, $C_{1-6}$ haloalkyl, halo, OH, $OR^6$, $NH_2$, $NH(C_{1-6}\ alkyl)$, $N(C_{1-6}\ alkyl)_2$, $NHCOR^6$, CN, $C_{3-7}$ cycloalkyl, 3-7 membered heterocycloalkyl, $COR^6$, and $SO_2R^6$;

each $R^6$ is independently selected from the group consisting of $C_{1-6}$ alkyl, $C_{6-10}$ aryl, $C_{5-10}$ heteroaryl, $OC_{1-6}$ alkyl, $C_{3-6}$ cycloalkyl, halo, $NH_2$, $NH(C_{1-6}\ alkyl)$, and $N(C_{1-6}\ alkyl)_2$;

m is 1, 2, or 3; and n is 0, 1, 2, or 3.

In another embodiment, Ring A is selected from the group consisting of phenyl, pyridine, pyrimidine, and pyrazine. In yet another embodiment, Ring A is selected from the group consisting of phenyl, pyridine, pyridazine, pyrimidine, imidazole, pyrazole, and $C_{3-6}$ cycloalkyl.

In an embodiment, two $R^4$, together with the atoms to which they are attached, together with Ring A, form a ring selected from the group consisting of dihydrobenzofuran, benzofuran, dihydrobenzooxazine, dihydrobenzodioxine, indazole, and indole, all of which are optionally substituted with one, two, or three $R^7$.

In still another embodiment, $R^1$ is $C_{1-6}$ alkyl or $C_{3-6}$ cycloalkyl, optionally substituted with $C_{1-6}$ alkyl.

In an embodiment, Y is NH, X is N, and Z is CH. In another embodiment, Y is NH, X is CH, and Z is CH. In yet another embodiment, Y is CH, X is N, and Z is NH. In still another embodiment, Y is CH, X is CH, and Z is N.

In an embodiment, the compound of Formula I is a compound of Formula Ib:

(Ib)

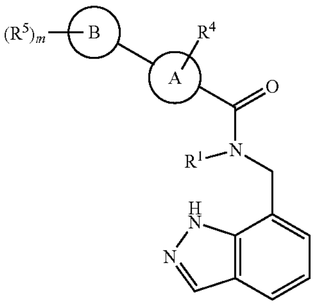

or a pharmaceutically acceptable salt thereof.

In another embodiment, the compound of Formula I is a compound of Formula Ic:

(Ic)

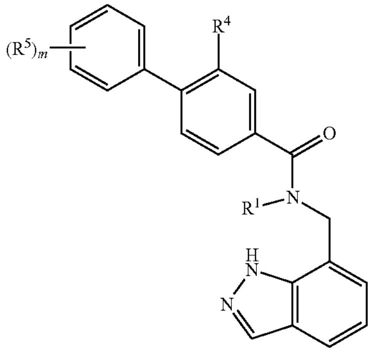

or a pharmaceutically acceptable salt thereof.

In yet another embodiment, the compound of Formula I is a compound of Formula Id:

(Id)

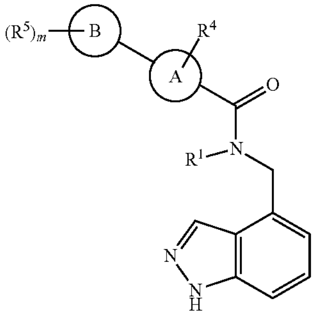

or a pharmaceutically acceptable salt thereof.

In still another embodiment, $R^4$ is $OC_{1-6}$ alkyl.

In an embodiment, $R^5$ is selected from the group consisting of $C_{1-6}$ alkyl, $C_{1-6}$ haloalkyl, halo, $NH_2$, CN, $CONH_2$, $CONH(C_{1-6}$ alkyl), and $SO_2NH_2$.

In another embodiment, Ring B is not absent.

In an embodiment, m is 1 and n is 1. In another embodiment, m is 0 and n is 0. In another embodiment, m is 1 and n is 0. In another embodiment, m is 0 and n is 1.

In another embodiment, the compound of Formula I is selected from the group consisting of a compound from Table 1.

TABLE 1

| Structure | No. |
| --- | --- |
| 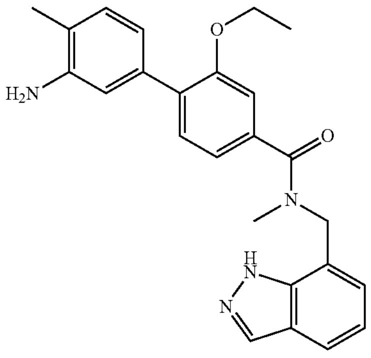 [SMILES: CCOc1cc(C(=O)N(C)Cc2cccc3cn[nH]c23)ccc1-c1ccc(C)c(N)c1] | 001 |
| 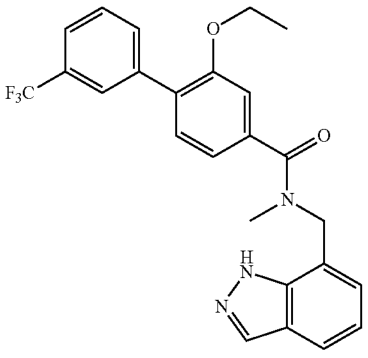 [SMILES: CCOc1cc(C(=O)N(C)Cc2cccc3cn[nH]c23)ccc1-c1cccc(C(F)(F)F)c1] | 002 |

TABLE 1-continued
| Structure | No. |
|---|---|
| 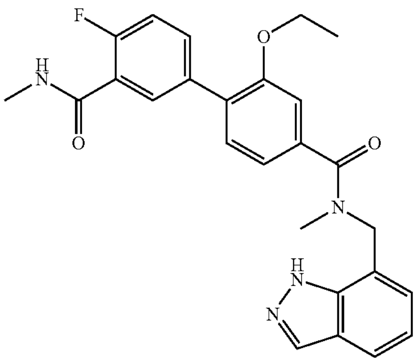 [SMILES: CCOc1cc(C(=O)N(C)Cc2cccc3cn[nH]c23)ccc1-c1ccc(F)c(C(=O)NC)c1] | 003 |
| 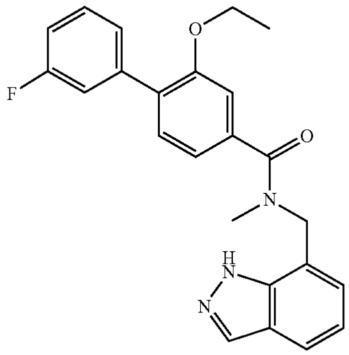 [SMILES: CCOc1cc(C(=O)N(C)Cc2cccc3cn[nH]c23)ccc1-c1cccc(F)c1] | 004 |
| 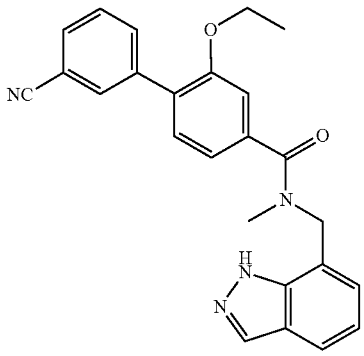 [SMILES: CCOc1cc(C(=O)N(C)Cc2cccc3cn[nH]c23)ccc1-c1cccc(C#N)c1] | 005 |
| 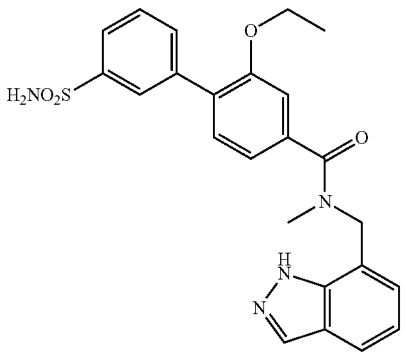 [SMILES: CCOc1cc(C(=O)N(C)Cc2cccc3cn[nH]c23)ccc1-c1cccc(S(N)(=O)=O)c1] | 006 |
TABLE 1-continued
| Structure | No. |
|---|---|
| 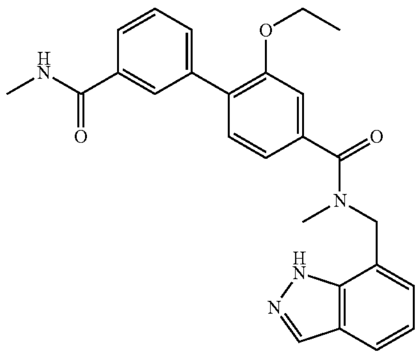 [SMILES: CCOc1cc(C(=O)N(C)Cc2cccc3cn[nH]c23)ccc1-c1cccc(C(=O)NC)c1] | 007 |
| 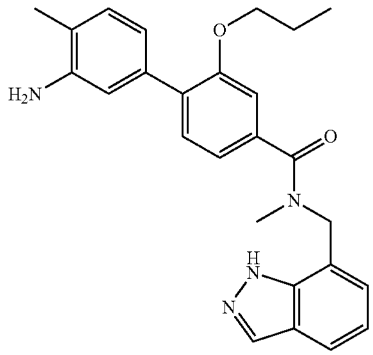 [SMILES: CCCOc1cc(C(=O)N(C)Cc2cccc3cn[nH]c23)ccc1-c1ccc(C)c(N)c1] | 008 |
| 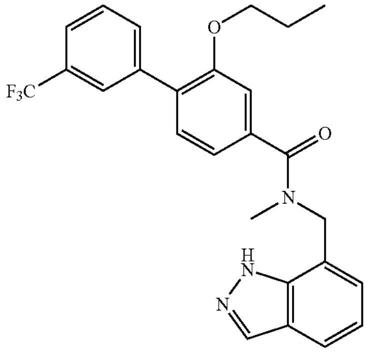 [SMILES: CCCOc1cc(C(=O)N(C)Cc2cccc3cn[nH]c23)ccc1-c1cccc(C(F)(F)F)c1] | 009 |
| 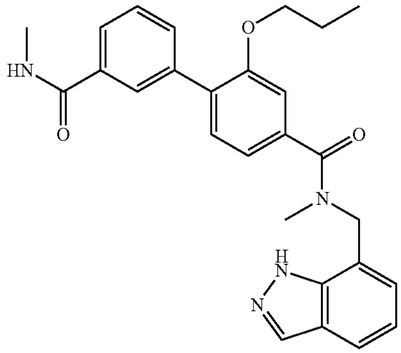 [SMILES: CCCOc1cc(C(=O)N(C)Cc2cccc3cn[nH]c23)ccc1-c1cccc(C(=O)NC)c1] | 010 |

TABLE 1-continued
| Structure | No. |
|---|---|
| 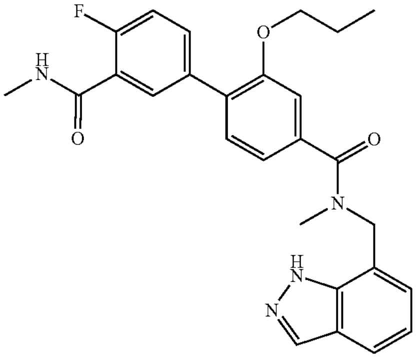 [SMILES: CCCOc1cc(C(=O)N(C)Cc2cccc3cn[nH]c23)ccc1-c1ccc(F)c(C(=O)NC)c1] | 011 |
| 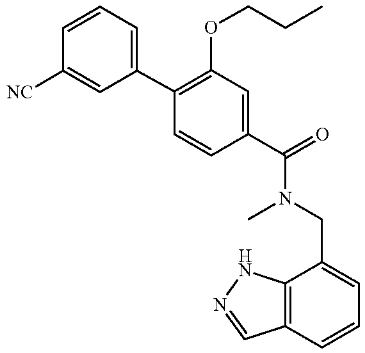 [SMILES: CCCOc1cc(C(=O)N(C)Cc2cccc3cn[nH]c23)ccc1-c1cccc(C#N)c1] | 012 |
| 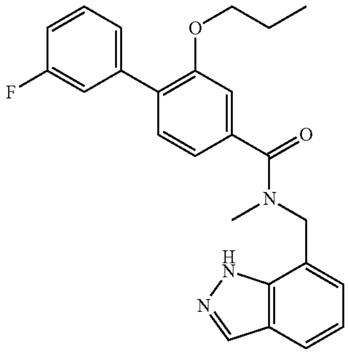 [SMILES: CCCOc1cc(C(=O)N(C)Cc2cccc3cn[nH]c23)ccc1-c1cccc(F)c1] | 013 |
| 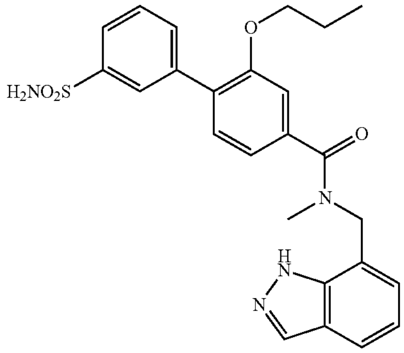 [SMILES: CCCOc1cc(C(=O)N(C)Cc2cccc3cn[nH]c23)ccc1-c1cccc(S(N)(=O)=O)c1] | 014 |
TABLE 1-continued
| Structure | No. |
|---|---|
| 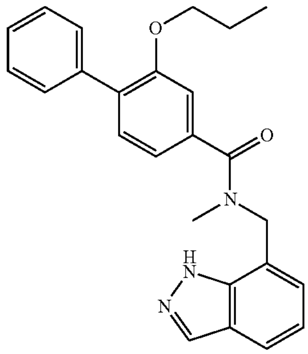 [SMILES: CCCOc1cc(C(=O)N(C)Cc2cccc3cn[nH]c23)ccc1-c1ccccc1] | 017 |
| 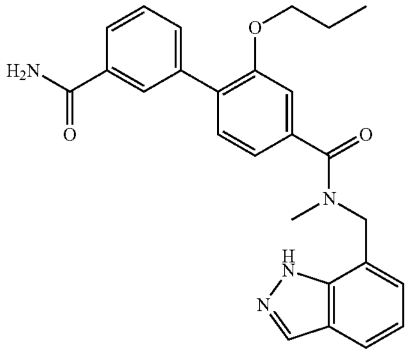 [SMILES: CCCOc1cc(C(=O)N(C)Cc2cccc3cn[nH]c23)ccc1-c1cccc(C(N)=O)c1] | 018 |
| 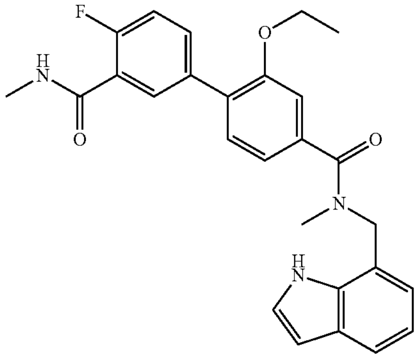 [SMILES: CCOc1cc(C(=O)N(C)Cc2cccc3cc[nH]c23)ccc1-c1ccc(F)c(C(=O)NC)c1] | 019 |
| 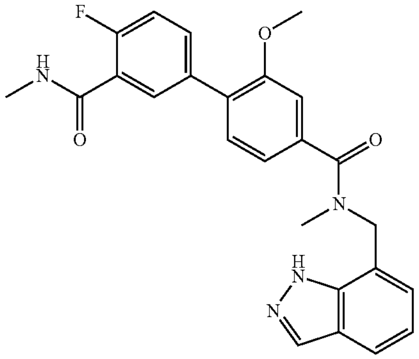 [SMILES: CNC(=O)c1cc(-c2ccc(C(=O)N(C)Cc3cccc4cn[nH]c34)cc2OC)ccc1F] | 020 |

TABLE 1-continued
| Structure | No. |
|---|---|
| 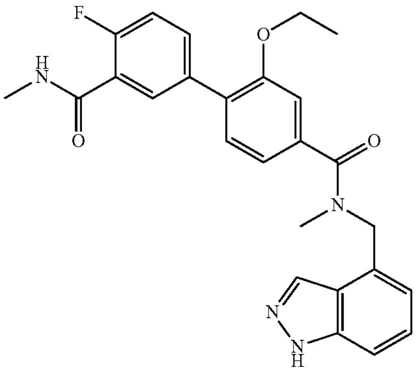 [SMILES: CCOc1cc(C(=O)N(C)Cc2cccc3[nH]ncc23)ccc1-c1ccc(F)c(C(=O)NC)c1] | 021 |
| 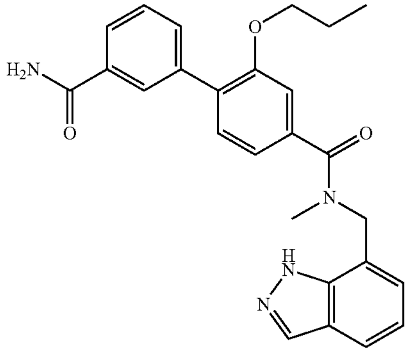 [SMILES: CCCOc1cc(C(=O)N(C)Cc2cccc3cn[nH]c23)ccc1-c1cccc(C(N)=O)c1] | 022 |
| 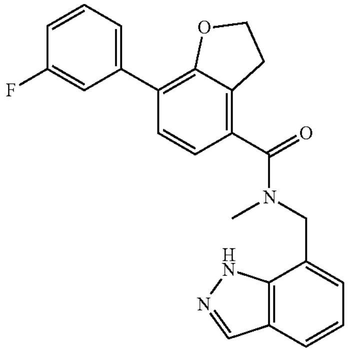 [SMILES: CN(Cc1cccc2cn[nH]c12)C(=O)c1ccc(-c2cccc(F)c2)c2c1CCO2] | 023 |
or a pharmaceutically acceptable salt thereof.
In another embodiment, the compound of Formula I is selected from the group consisting of a compound in Table 2.
TABLE 2
| Structure | No. |
|---|---|
| 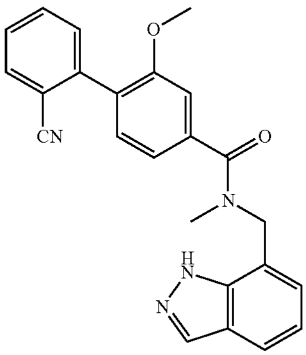 [SMILES: COc1cc(C(=O)N(C)Cc2cccc3cn[nH]c23)ccc1-c1ccccc1C#N] | 028 |
| 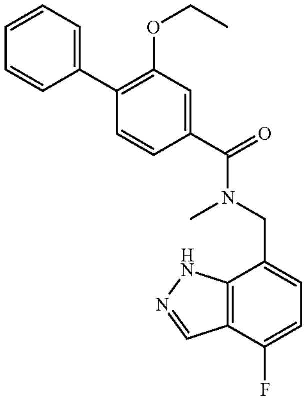 [SMILES: CCOc1cc(C(=O)N(C)Cc2ccc(F)c3cn[nH]c23)ccc1-c1ccccc1] | 029 |
| 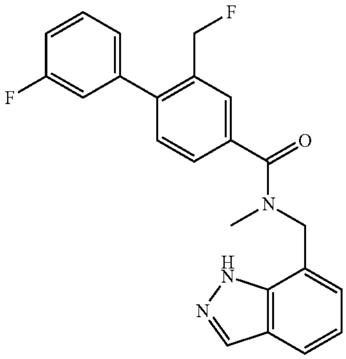 [SMILES: CN(Cc1cccc2cn[nH]c12)C(=O)c1ccc(-c2cccc(F)c2)c(CF)c1] | 030 |
| 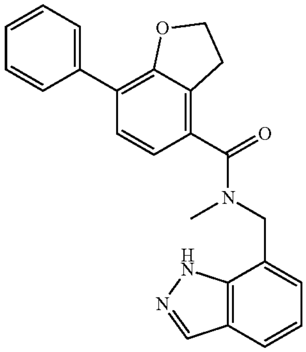 [SMILES: CN(Cc1cccc2cn[nH]c12)C(=O)c1ccc(-c2ccccc2)c2c1CCO2] | 031 |

TABLE 2-continued
| Structure | No. |
|---|---|
| 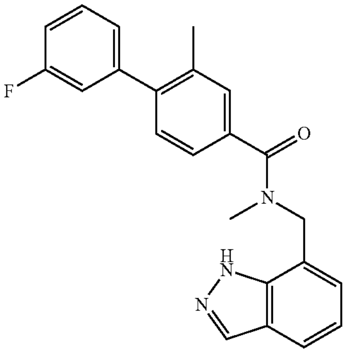 [SMILES: Cc1cc(C(=O)N(C)Cc2cccc3cn[nH]c23)ccc1-c1cccc(F)c1] | 032 |
| 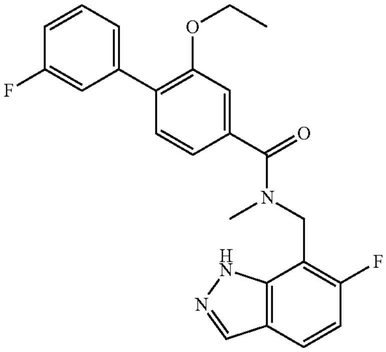 [SMILES: CCOc1cc(C(=O)N(C)Cc2c(F)ccc3cn[nH]c23)ccc1-c1cccc(F)c1] | 033 |
| 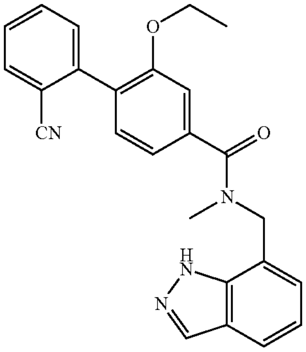 [SMILES: CCOc1cc(C(=O)N(C)Cc2cccc3cn[nH]c23)ccc1-c1ccccc1C#N] | 034 |
| 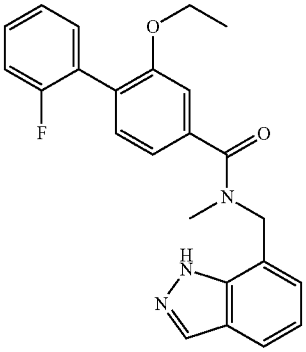 [SMILES: CCOc1cc(C(=O)N(C)Cc2cccc3cn[nH]c23)ccc1-c1ccccc1F] | 035 |
TABLE 2-continued
| Structure | No. |
|---|---|
| 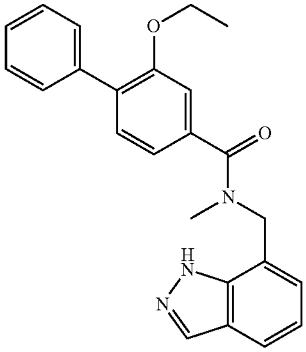 [SMILES: CCOc1cc(C(=O)N(C)Cc2cccc3cn[nH]c23)ccc1-c1ccccc1] | 036 |
| 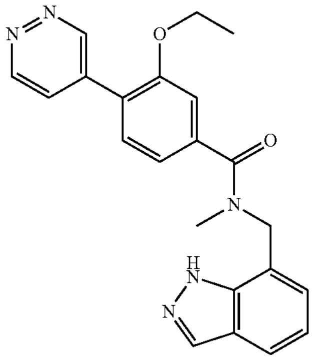 [SMILES: CCOc1cc(C(=O)N(C)Cc2cccc3cn[nH]c23)ccc1-c1ccnnc1] | 037 |
| 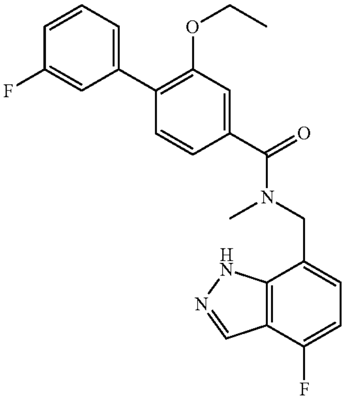 [SMILES: CCOc1cc(C(=O)N(C)Cc2ccc(F)c3cn[nH]c23)ccc1-c1cccc(F)c1] | 038 |
| 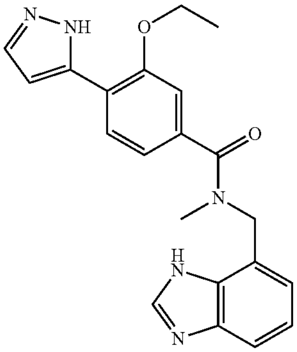 [SMILES: CCOc1cc(C(=O)N(C)Cc2cccc3nc[nH]c23)ccc1-c1ccn[nH]1] | 039 |

TABLE 2-continued
| Structure | No. |
|---|---|
| 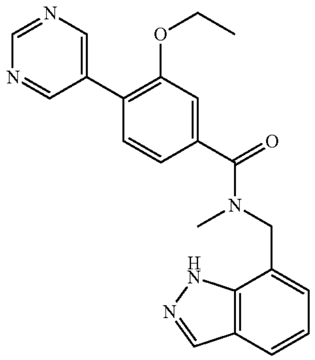 [SMILES: CCOc1cc(C(=O)N(C)Cc2cccc3cn[nH]c23)ccc1-c1cncnc1] | 040 |
| 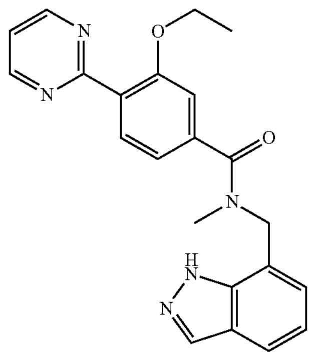 [SMILES: CCOc1cc(C(=O)N(C)Cc2cccc3cn[nH]c23)ccc1-c1ncccn1] | 041 |
| 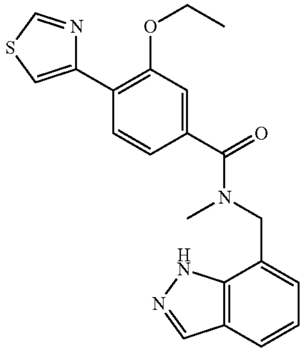 [SMILES: CCOc1cc(C(=O)N(C)Cc2cccc3cn[nH]c23)ccc1-c1cscn1] | 042 |
| 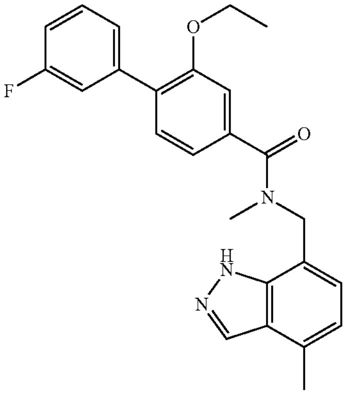 [SMILES: CCOc1cc(C(=O)N(C)Cc2ccc(C)c3cn[nH]c23)ccc1-c1cccc(F)c1] | 043 |
TABLE 2-continued
| Structure | No. |
|---|---|
| 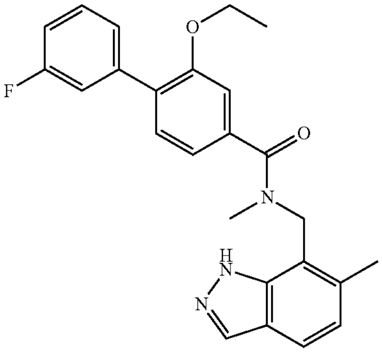 [SMILES: CCOc1cc(C(=O)N(C)Cc2c(C)ccc3cn[nH]c23)ccc1-c1cccc(F)c1] | 044 |
| 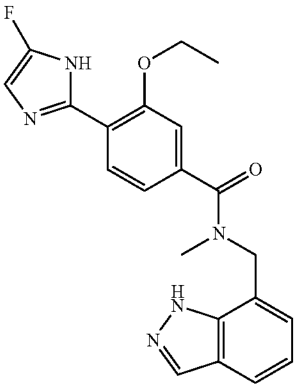 [SMILES: CCOc1cc(C(=O)N(C)Cc2cccc3cn[nH]c23)ccc1-c1ncc(F)[nH]1] | 045 |
| 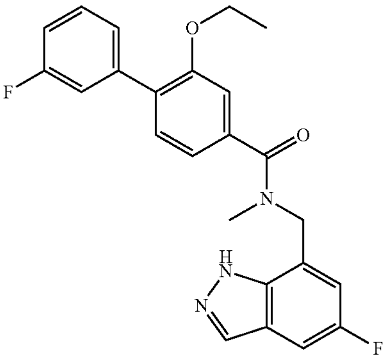 [SMILES: CCOc1cc(C(=O)N(C)Cc2cc(F)cc3cn[nH]c23)ccc1-c1cccc(F)c1] | 046 |
| 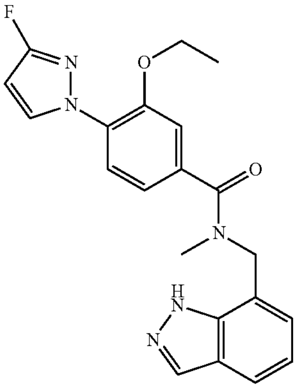 [SMILES: CCOc1cc(C(=O)N(C)Cc2cccc3cn[nH]c23)ccc1-n1ccc(F)n1] | 047 |

TABLE 2-continued
| Structure | No. |
| --- | --- |
| 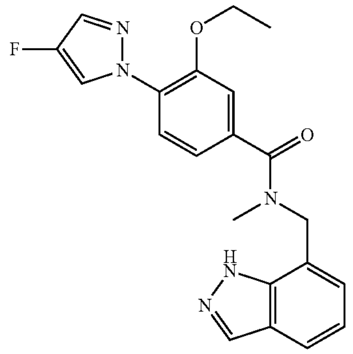 [SMILES: CCOc1cc(C(=O)N(C)Cc2cccc3cn[nH]c23)ccc1-n1cc(F)cn1] | 048 |
| 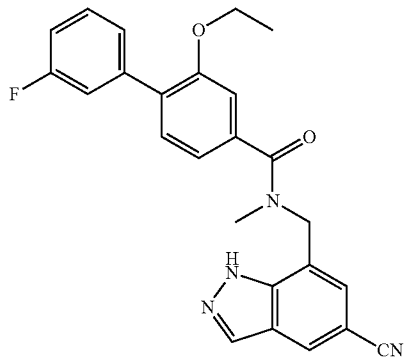 [SMILES: CCOc1cc(C(=O)N(C)Cc2cc(C#N)cc3cn[nH]c23)ccc1-c1cccc(F)c1] | 049 |
| 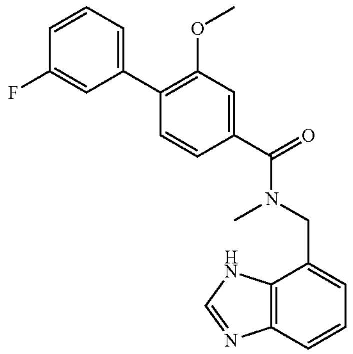 [SMILES: COc1cc(C(=O)N(C)Cc2cccc3nc[nH]c23)ccc1-c1cccc(F)c1] | 050 |
| 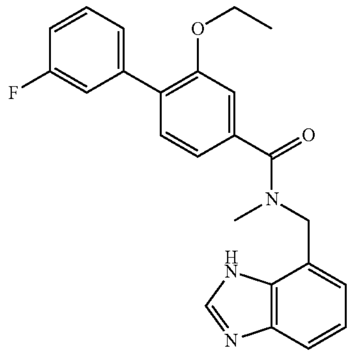 [SMILES: CCOc1cc(C(=O)N(C)Cc2cccc3nc[nH]c23)ccc1-c1cccc(F)c1] | 051 |
TABLE 2-continued
| Structure | No. |
| --- | --- |
| 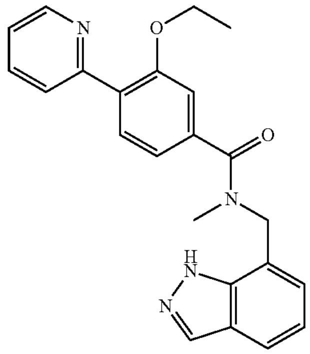 [SMILES: CCOc1cc(C(=O)N(C)Cc2cccc3cn[nH]c23)ccc1-c1ccccn1] | 052 |
| 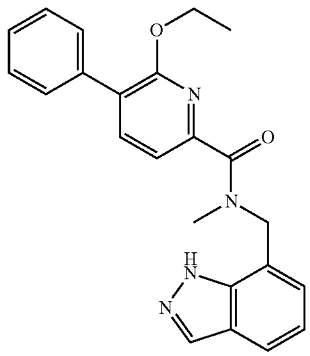 [SMILES: CCOc1nc(C(=O)N(C)Cc2cccc3cn[nH]c23)ccc1-c1ccccc1] | 053 |
| 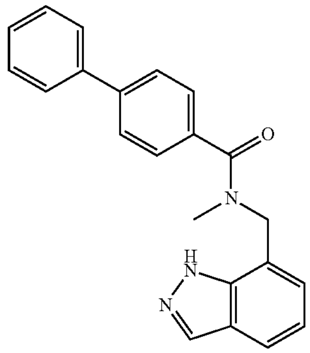 [SMILES: CN(Cc1cccc2cn[nH]c12)C(=O)c1ccc(-c2ccccc2)cc1] | 054 |
| 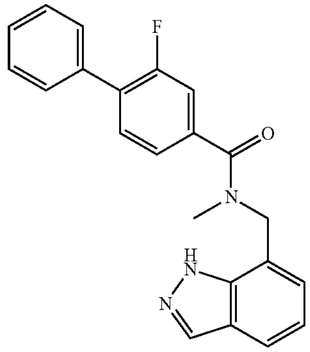 [SMILES: CN(Cc1cccc2cn[nH]c12)C(=O)c1ccc(-c2ccccc2)c(F)c1] | 055 |

TABLE 2-continued
| Structure | No. |
|---|---|
| 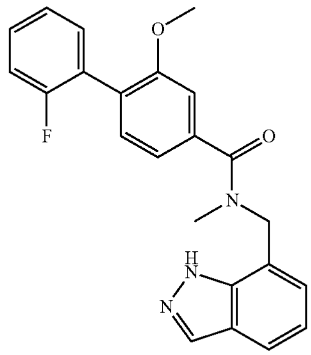 [SMILES: COc1cc(C(=O)N(C)Cc2cccc3cn[nH]c23)ccc1-c1ccccc1F] | 056 |
| 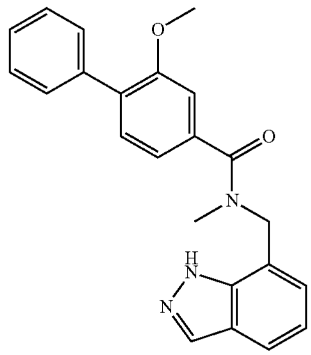 [SMILES: COc1cc(C(=O)N(C)Cc2cccc3cn[nH]c23)ccc1-c1ccccc1] | 057 |
| 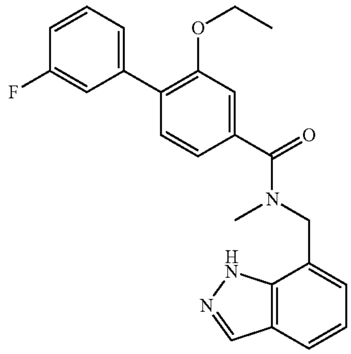 [SMILES: CCOc1cc(C(=O)N(C)Cc2cccc3cn[nH]c23)ccc1-c1cccc(F)c1] | 058 |
| 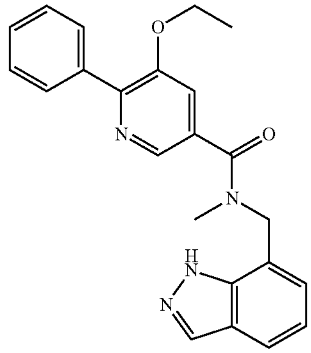 [SMILES: CCOc1cc(C(=O)N(C)Cc2cccc3cn[nH]c23)cnc1-c1ccccc1] | 059 |
TABLE 2-continued
| Structure | No. |
|---|---|
| 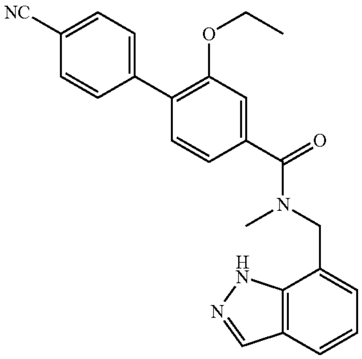 [SMILES: CCOc1cc(C(=O)N(C)Cc2cccc3cn[nH]c23)ccc1-c1ccc(C#N)cc1] | 060 |
| 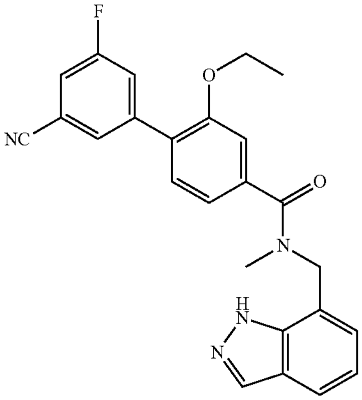 [SMILES: CCOc1cc(C(=O)N(C)Cc2cccc3cn[nH]c23)ccc1-c1cc(F)cc(C#N)c1] | 061 |
| 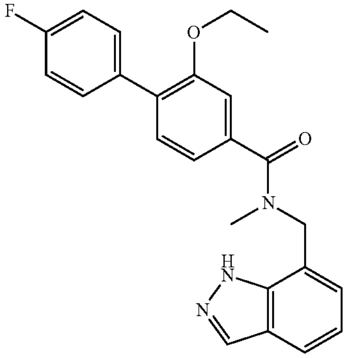 [SMILES: CCOc1cc(C(=O)N(C)Cc2cccc3cn[nH]c23)ccc1-c1ccc(F)cc1] | 062 |
| 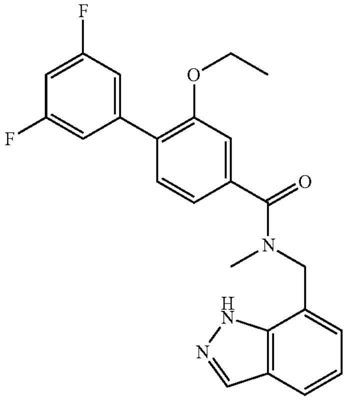 [SMILES: CCOc1cc(C(=O)N(C)Cc2cccc3cn[nH]c23)ccc1-c1cc(F)cc(F)c1] | 063 |

TABLE 2-continued
| Structure | No. |
|---|---|
| 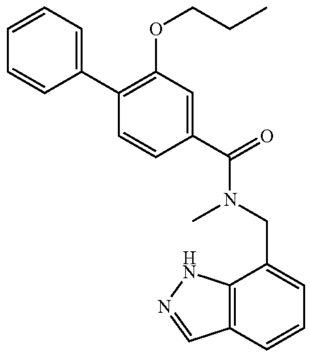 [SMILES: CCCOc1cc(C(=O)N(C)Cc2cccc3cn[nH]c23)ccc1-c1ccccc1] | 064 |
| 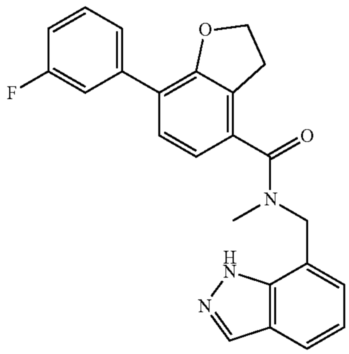 [SMILES: CN(Cc1cccc2cn[nH]c12)C(=O)c1ccc(-c2cccc(F)c2)c2c1CCO2] | 065 |
| 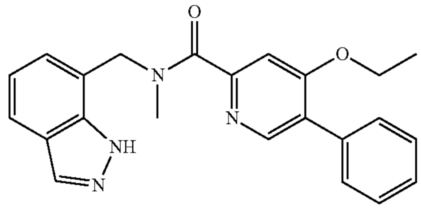 [SMILES: CCOc1cc(C(=O)N(C)Cc2cccc3cn[nH]c23)ncc1-c1ccccc1] | 066 |
| 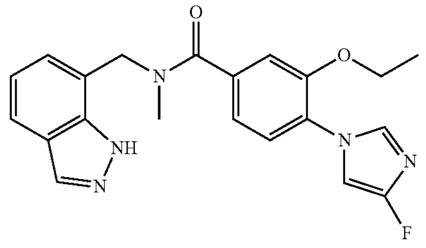 [SMILES: CCOc1cc(C(=O)N(C)Cc2cccc3cn[nH]c23)ccc1-n1cnc(F)c1] | 067 |
| 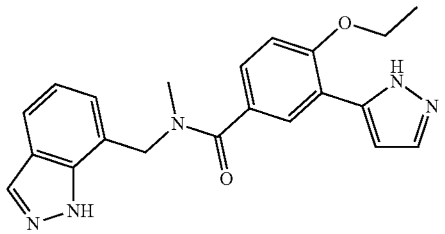 [SMILES: CCOc1ccc(C(=O)N(C)Cc2cccc3cn[nH]c23)cc1-c1ccn[nH]1] | 068 |
TABLE 2-continued
| Structure | No. |
|---|---|
| 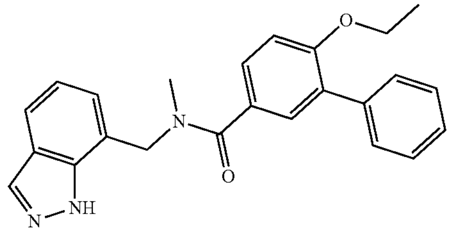 [SMILES: CCOc1ccc(C(=O)N(C)Cc2cccc3cn[nH]c23)cc1-c1ccccc1] | 069 |
| 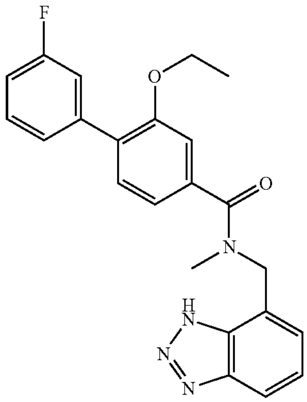 [SMILES: CCOc1cc(C(=O)N(C)Cc2cccc3nn[nH]c23)ccc1-c1cccc(F)c1] | 070 |
| 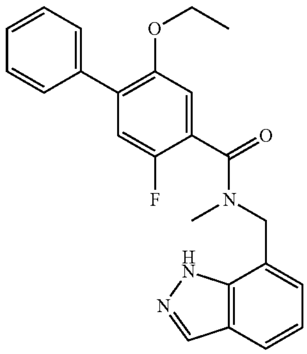 [SMILES: CCOc1cc(C(=O)N(C)Cc2cccc3cn[nH]c23)c(F)cc1-c1ccccc1] | 071 |
| 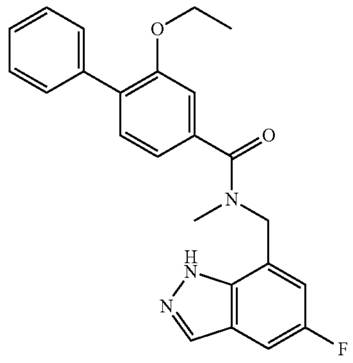 [SMILES: CCOc1cc(C(=O)N(C)Cc2cc(F)cc3cn[nH]c23)ccc1-c1ccccc1] | 072 |

TABLE 2-continued
| Structure | No. |
|---|---|
| 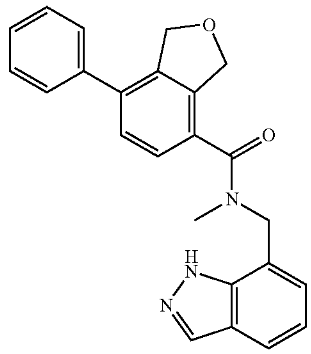 [SMILES: CN(Cc1cccc2cn[nH]c12)C(=O)c1ccc(-c2ccccc2)c2c1COC2] | 073 |
| 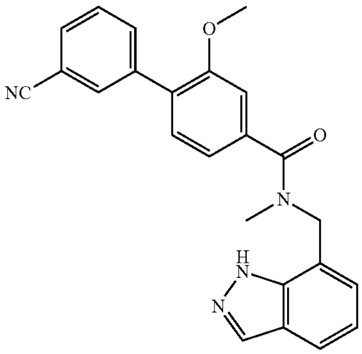 [SMILES: COc1cc(C(=O)N(C)Cc2cccc3cn[nH]c23)ccc1-c1cccc(C#N)c1] | 074 |
| 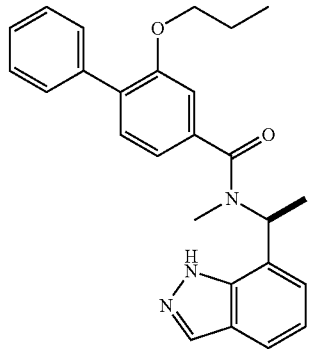 [SMILES: CCCOc1cc(C(=O)N(C)[C@@H](C)c2cccc3cn[nH]c23)ccc1-c1ccccc1] | 075 |
| 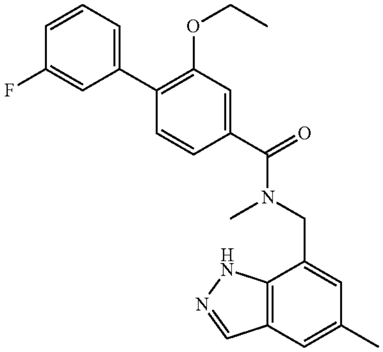 [SMILES: CCOc1cc(C(=O)N(C)Cc2cc(C)cc3cn[nH]c23)ccc1-c1cccc(F)c1] | 076 |
TABLE 2-continued
| Structure | No. |
|---|---|
| 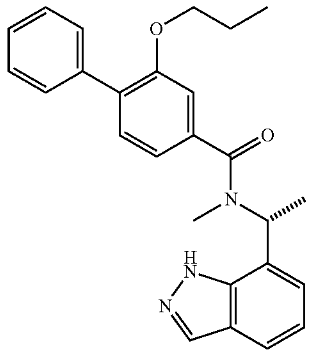 [SMILES: CCCOc1cc(C(=O)N(C)[C@H](C)c2cccc3cn[nH]c23)ccc1-c1ccccc1] | 077 |
| 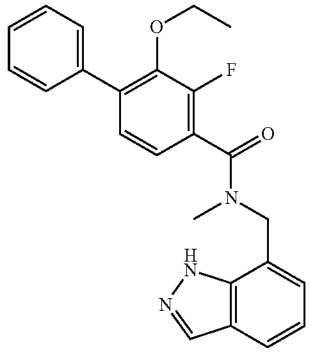 [SMILES: CCOc1c(-c2ccccc2)ccc(C(=O)N(C)Cc2cccc3cn[nH]c23)c1F] | 078 |
| 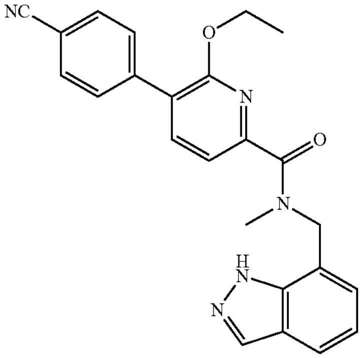 [SMILES: CCOc1nc(C(=O)N(C)Cc2cccc3cn[nH]c23)ccc1-c1ccc(C#N)cc1] | 079 |
| 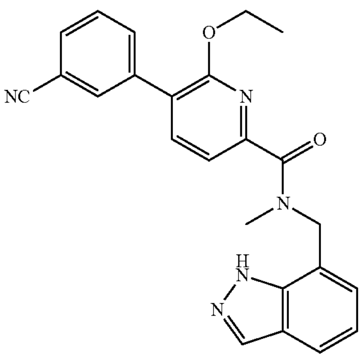 [SMILES: CCOc1nc(C(=O)N(C)Cc2cccc3cn[nH]c23)ccc1-c1cccc(C#N)c1] | 080 |

TABLE 2-continued
| Structure | No. |
|---|---|
| 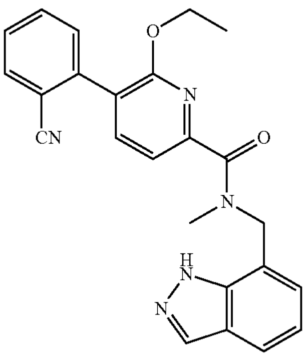 [SMILES: CCOc1nc(C(=O)N(C)Cc2cccc3cn[nH]c23)ccc1-c1ccccc1C#N] | 081 |
| 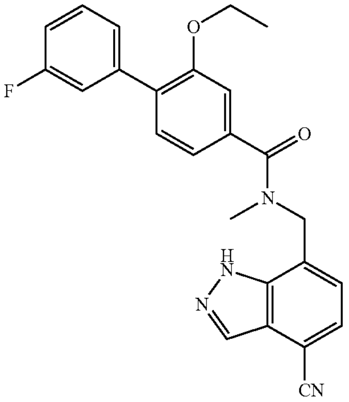 [SMILES: CCOc1cc(C(=O)N(C)Cc2ccc(C#N)c3cn[nH]c23)ccc1-c1cccc(F)c1] | 082 |
| 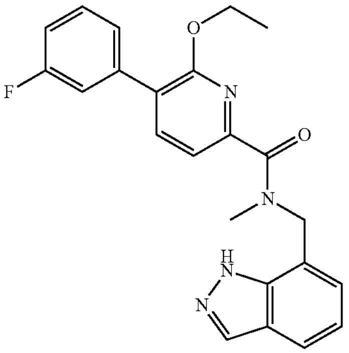 [SMILES: CCOc1nc(C(=O)N(C)Cc2cccc3cn[nH]c23)ccc1-c1cccc(F)c1] | 083 |
| 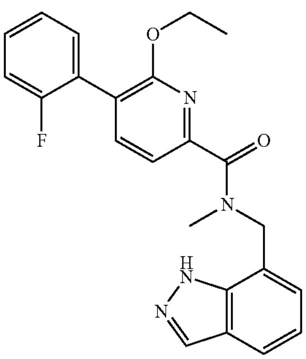 [SMILES: CCOc1nc(C(=O)N(C)Cc2cccc3cn[nH]c23)ccc1-c1ccccc1F] | 084 |
| 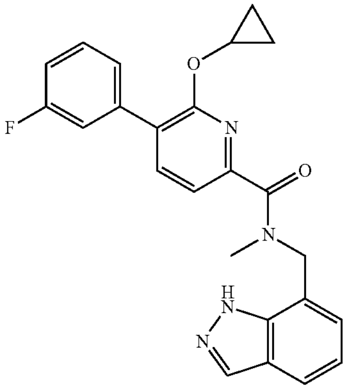 [SMILES: CN(Cc1cccc2cn[nH]c12)C(=O)c1ccc(-c2cccc(F)c2)c(OC2CC2)n1] | 085 |
| 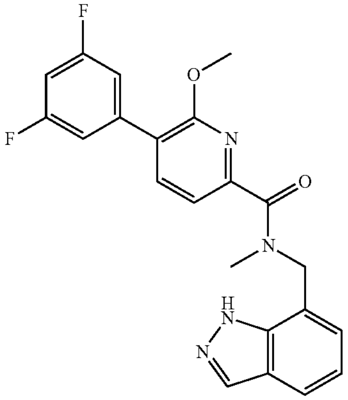 [SMILES: COc1nc(C(=O)N(C)Cc2cccc3cn[nH]c23)ccc1-c1cc(F)cc(F)c1] | 086 |
or a pharmaceutically acceptable salt thereof.
In still another embodiment, the compound of Formula I is a compound of Formula II:
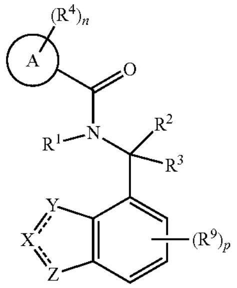
(II)
or a pharmaceutically acceptable salt thereof.
In an embodiment, the compound of Formula II is a compound of Formula IIa:

(IIa)

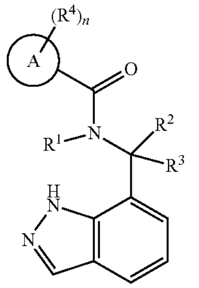

or a pharmaceutically acceptable salt thereof.

In an embodiment, the compound of Formula II is a compound of Formula IIb:

(IIb)

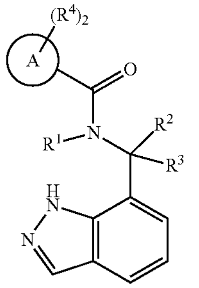

or a pharmaceutically acceptable salt thereof;

wherein two $R^4$, together with Ring A, form a ring selected from the group consisting of dihydrobenzooxazine, dihydrobenzodioxine, indazole, and indole, all of which are optionally substituted with one, two, or three $R^7$.

In another embodiment, the compound of Formula II is selected from the group consisting of a compound in Table 3.

TABLE 3

| Structure | Compound No |
|---|---|
| 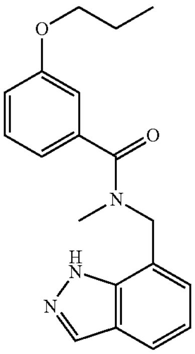 [SMILES: CCCOc1cccc(C(=O)N(C)Cc2cccc3cn[nH]c23)c1] | 015 |

TABLE 3-continued

| Structure | Compound No |
|---|---|
| 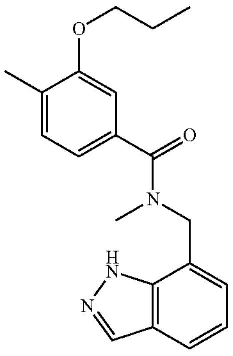 [SMILES: CCCOc1cc(C(=O)N(C)Cc2cccc3cn[nH]c23)ccc1C] | 016 |
| 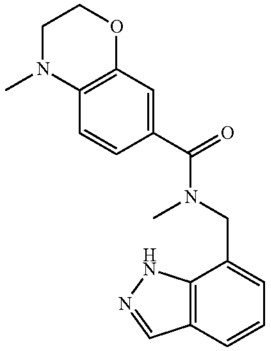 [SMILES: CN(Cc1cccc2cn[nH]c12)C(=O)c1ccc2c(c1)OCCN2C] | 024 |
| 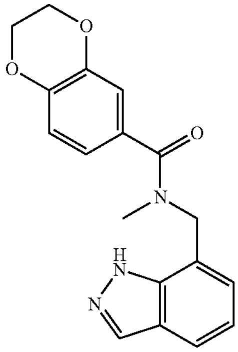 [SMILES: CN(Cc1cccc2cn[nH]c12)C(=O)c1ccc2c(c1)OCCO2] | 025 |
| 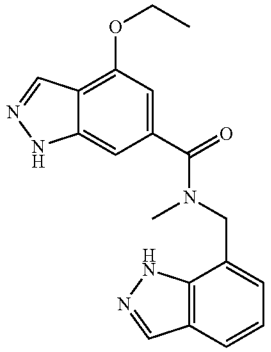 [SMILES: CCOc1cc(C(=O)N(C)Cc2cccc3cn[nH]c23)cc2[nH]ncc12] | 026 |

TABLE 3-continued
| Structure | Compound No |
|---|---|
| 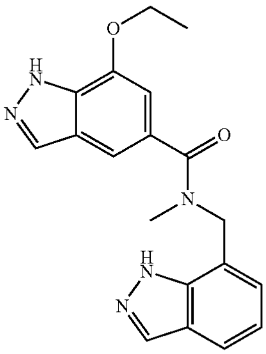 [SMILES: CCOc1cc(C(=O)N(C)Cc2cccc3cn[nH]c23)cc2cn[nH]c12] | 027 |
or a pharmaceutically acceptable salt thereof.
In another embodiment, the compound of Formula II is selected from the group consisting of a compound from Table 4.
TABLE 4
| Structure | No. |
|---|---|
| 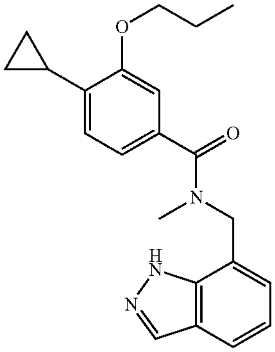 [SMILES: CCCOc1cc(C(=O)N(C)Cc2cccc3cn[nH]c23)ccc1C1CC1] | 087 |
| 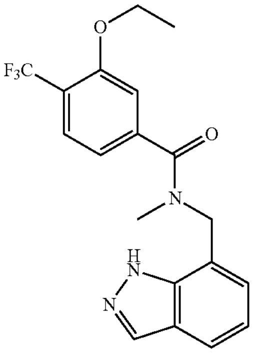 [SMILES: CCOc1cc(C(=O)N(C)Cc2cccc3cn[nH]c23)ccc1C(F)(F)F] | 088 |
TABLE 4-continued
| Structure | No. |
|---|---|
| 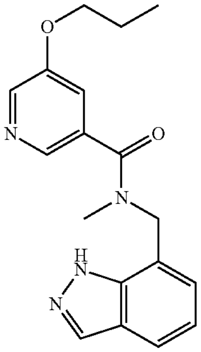 [SMILES: CCCOc1cncc(C(=O)N(C)Cc2cccc3cn[nH]c23)c1] | 089 |
| 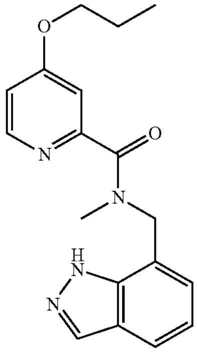 [SMILES: CCCOc1ccnc(C(=O)N(C)Cc2cccc3cn[nH]c23)c1] | 090 |
| 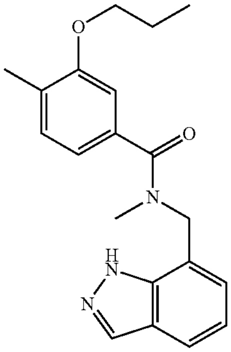 [SMILES: CCCOc1cc(C(=O)N(C)Cc2cccc3cn[nH]c23)ccc1C] | 091 |
| 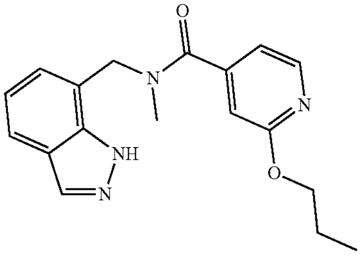 [SMILES: CCCOc1cc(C(=O)N(C)Cc2cccc3cn[nH]c23)ccn1] | 092 |
| 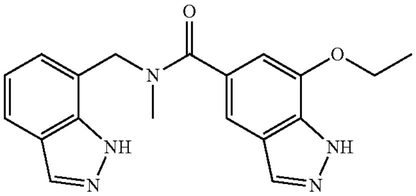 [SMILES: CCOc1cc(C(=O)N(C)Cc2cccc3cn[nH]c23)cc2cn[nH]c12] | 093 |

TABLE 4-continued

| Structure | No. |
|---|---|
| 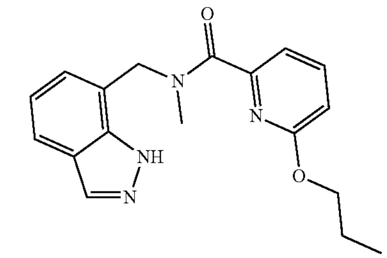 [SMILES: CCCOc1cccc(C(=O)N(C)Cc2cccc3cn[nH]c23)n1] | 094 |
| 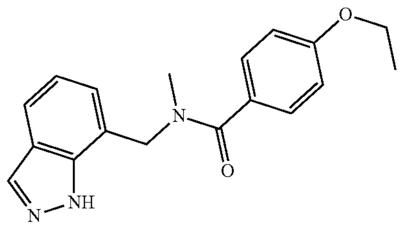 [SMILES: CCOc1ccc(C(=O)N(C)Cc2cccc3cn[nH]c23)cc1] | 095 |
| 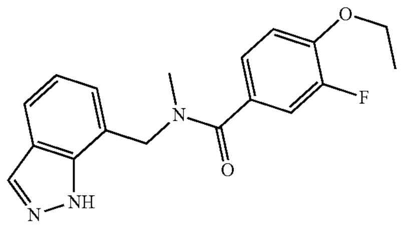 [SMILES: CCOc1ccc(C(=O)N(C)Cc2cccc3cn[nH]c23)cc1F] | 096 |
| 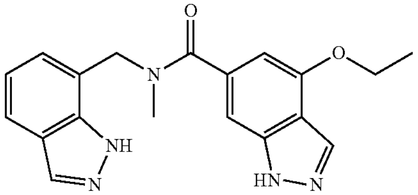 [SMILES: CCOc1cc(C(=O)N(C)Cc2cccc3cn[nH]c23)cc2[nH]ncc12] | 097 |

or a pharmaceutically acceptable salt thereof.

In another aspect, provided herein is a compound of Formula III:

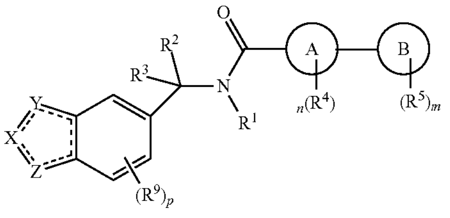

(III)

or a pharmaceutically acceptable salt thereof;

wherein

⎓ is an optional double bond;

X is CH, N, NH, or N($C_{1-6}$ alkyl);

Y and Z are each independently selected from the group consisting of NH, $NR^9$, O, S, N, CH, and $CR^9$;

Ring A is selected from the group consisting of $C_{5-10}$ aryl, 5-6 membered heteroaryl, $C_{3-10}$ cycloalkyl, and 4-10 membered heterocycloalkyl;

Ring B is selected from the group consisting of phenyl, 5-6 membered heteroaryl, $C_{3-6}$ cycloalkyl, and 3-6 membered heterocycloalkyl;

alternatively, Ring B is absent and m is 0;

$R^1$ is selected from the group consisting of H, $C_{1-6}$ alkyl, and $C_{3-6}$ cycloalkyl, wherein alkyl and cycloalkyl are each optionally substituted with $R^6$;

$R^2$ and $R^3$ are each independently selected from the group consisting of H, $C_{1-6}$ alkyl, $C_{3-6}$ cycloalkyl, and 3-6 membered heterocycloalkyl;

alternatively, $R^2$ and $R^3$, together with the atom to which they are attached, form a ring selected from the group consisting of $C_{3-7}$ cycloalkyl and 3-7 membered heterocycloalkyl;

each $R^4$ is independently selected from the group consisting of $C_{1-6}$ alkyl, halo, OH, $OR^6$, $NH_2$, NH($C_{1-6}$ alkyl), N($C_{1-6}$ alkyl)$_2$, $NHCOR^6$, CN, $C_{1-6}$ haloalkyl, $C_{3-7}$ cycloalkyl, 3-7 membered heterocycloalkyl, and $COR^6$;

alternatively, two $R^4$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^5$ is independently selected from the group consisting of $C_{1-6}$ alkyl, $C_{1-6}$ haloalkyl, halo, OH, $OR^6$, $NH_2$, NH($C_{1-6}$ alkyl), N($C_{1-6}$ alkyl)$_2$, $NHCOR^6$, CN, $C_{3-7}$ cycloalkyl, 3-7 membered heterocycloalkyl, $COR^6$, and $SO_2R^6$;

alternatively, two $R^5$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^6$ is independently selected from the group consisting of $C_{1-6}$ alkyl, $C_{0-6}$ alkyl-$C_{6-10}$ aryl, Coe alkyl-5-10 membered heteroaryl, $OC_{1-6}$ alkyl, $C_{3-6}$ cycloalkyl, halo, $NH_2$, NH($C_{1-6}$ alkyl), and N($C_{1-6}$ alkyl)$_2$;

each $R^7$ is independently selected from the group consisting of $C_{1-6}$ alkyl, $C_{1-6}$ haloalkyl, halo, OH, $OC_{1-6}$ alkyl, $NH_2$, NH($C_{1-6}$ alkyl), N($C_{1-6}$ alkyl)$_2$, CN, $COR^1$, and $SO_2R^8$;

each $R^8$ is independently selected from the group consisting of $C_{1-6}$ alkyl, $OC_{1-6}$ alkyl, halo, $NH_2$, NH($C_{1-6}$ alkyl), and N($C_{1-6}$ alkyl)$_2$;

each $R^9$ is independently selected from the group consisting of $C_{1-6}$ alkyl, $OC_{1-6}$ alkyl, halo, CN, OH, $NH_2$, NH($C_{1-6}$ alkyl), and N($C_{1-6}$ alkyl)$_2$;

m is 0, 1, 2, or 3;

n is 1, 2, or 3; and p is 0, 1, 2, or 3.

In an embodiment of Formula III, Ring A is selected from the group consisting of $C_{6-10}$ aryl, 5-6 membered heteroaryl, and $C_{4-10}$ cycloalkyl. In an embodiment, m is 1 and n is 1. In another embodiment, m is 0 and n is 0. In another embodiment, m is 1 and n is 0. In another embodiment, m is 0 and n is 1.

In an embodiment, the compound of Formula III is a compound of Formula IIIa:

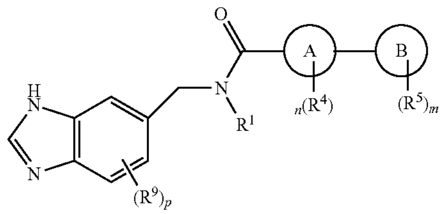
(IIIa)

or a pharmaceutically acceptable salt thereof.

In another embodiment, the compound of Formula III is a compound of Formula IIIb:

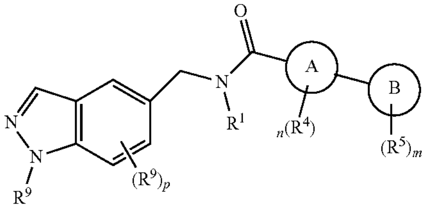
(IIIb)

wherein p is 0, 1, or 2;

or a pharmaceutically acceptable salt thereof.

In yet another embodiment, the compound of Formula III is a compound of Formula IIIc:

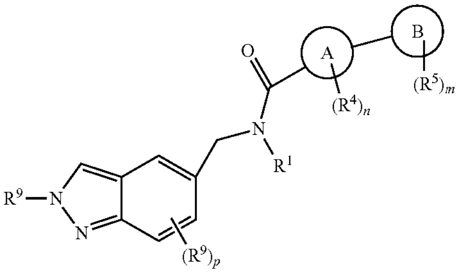
(IIIc)

wherein p is 0, 1, or 2;

or a pharmaceutically acceptable salt thereof.

In still another embodiment, the compound of Formula III is selected from the group consisting of a compound of Table 5.

TABLE 5

| Structure | No. |
|---|---|
| 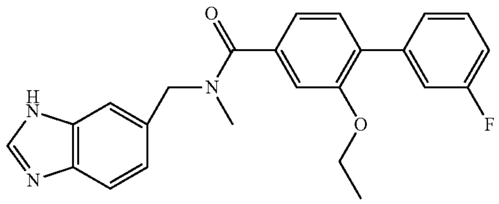 [SMILES: CCOc1cc(C(=O)N(C)Cc2ccc3nc[nH]c3c2)ccc1-c1cccc(F)c1] | 098 |

TABLE 5-continued

| Structure | No. |
|---|---|
| 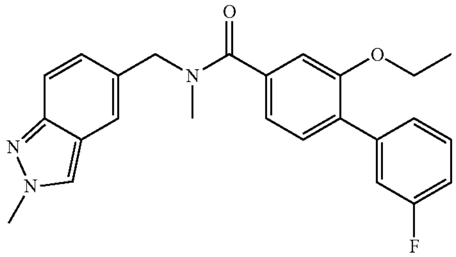 [SMILES: CCOc1cc(C(=O)N(C)Cc2ccc3nn(C)cc3c2)ccc1-c1cccc(F)c1] | 099 |
| 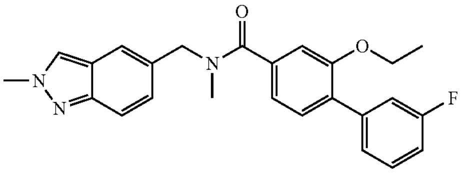 [SMILES: CCOc1cc(C(=O)N(C)Cc2ccc3nn(C)cc3c2)ccc1-c1cccc(F)c1] | 100 |
| 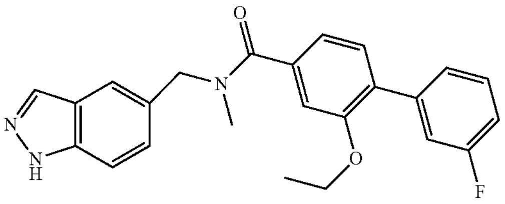 [SMILES: CCOc1cc(C(=O)N(C)Cc2ccc3[nH]ncc3c2)ccc1-c1cccc(F)c1] | 101 |
| 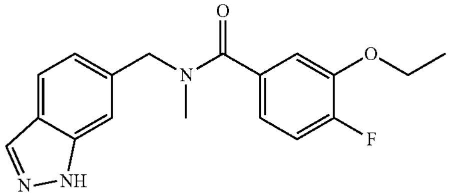 [SMILES: CCOc1cc(C(=O)N(C)Cc2ccc3cn[nH]c3c2)ccc1F] | 102 |
| 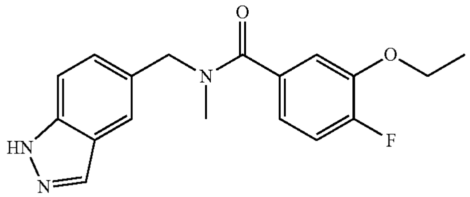 [SMILES: CCOc1cc(C(=O)N(C)Cc2ccc3[nH]ncc3c2)ccc1F] | 103 |
| 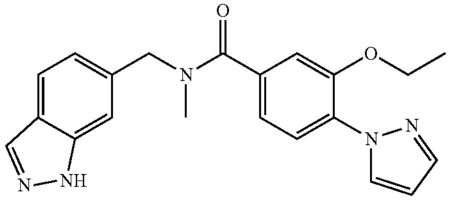 [SMILES: CCOc1cc(C(=O)N(C)Cc2ccc3cn[nH]c3c2)ccc1-n1cccn1] | 104 |
| 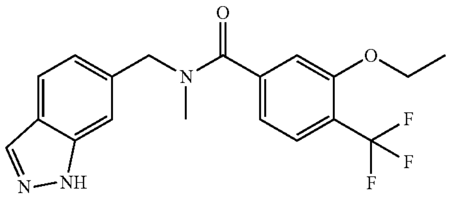 [SMILES: CCOc1cc(C(=O)N(C)Cc2ccc3cn[nH]c3c2)ccc1C(F)(F)F] | 105 |

TABLE 5-continued

| Structure | No. |
|---|---|
| 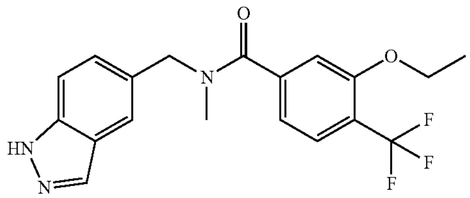 [SMILES: CCOc1cc(C(=O)N(C)Cc2ccc3[nH]ncc3c2)ccc1C(F)(F)F] | 106 |
| 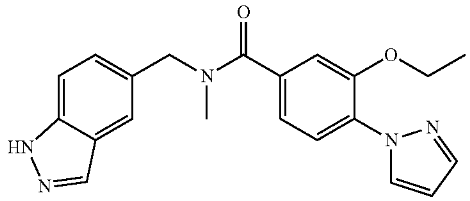 [SMILES: CCOc1cc(C(=O)N(C)Cc2ccc3[nH]ncc3c2)ccc1-n1cccn1] | 107 |
| 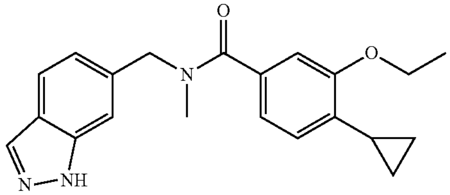 [SMILES: CCOc1cc(C(=O)N(C)Cc2ccc3cn[nH]c3c2)ccc1C1CC1] | 108 |
| 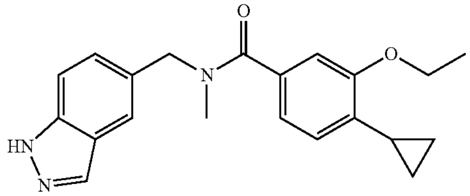 [SMILES: CCOc1cc(C(=O)N(C)Cc2ccc3[nH]ncc3c2)ccc1C1CC1] | 109 |
| 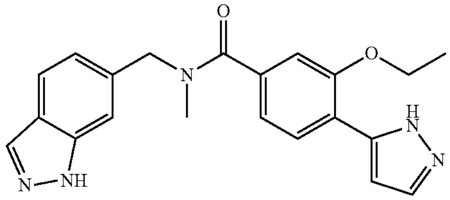 [SMILES: CCOc1cc(C(=O)N(C)Cc2ccc3cn[nH]c3c2)ccc1-c1ccn[nH]1] | 110 |
| 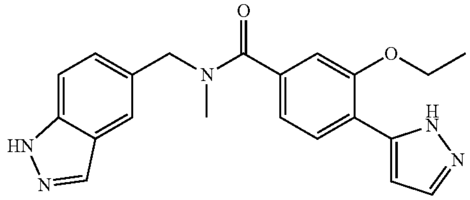 [SMILES: CCOc1cc(C(=O)N(C)Cc2ccc3[nH]ncc3c2)ccc1-c1ccn[nH]1] | 111 |
| 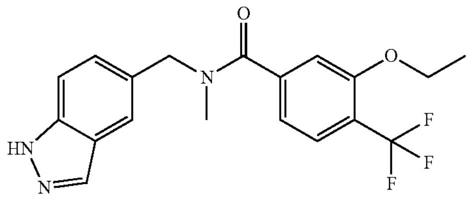 [SMILES: CCOc1cc(C(=O)N(C)Cc2ccc3[nH]ncc3c2)ccc1C(F)(F)F] | 112 |

or a pharmaceutically acceptable salt thereof.

In yet another aspect, provided herein is a compound of Formula IV:

(IV)

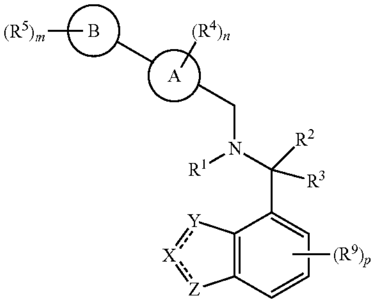

or a pharmaceutically acceptable salt thereof;

wherein $\overline{---}$ is an optional double bond;

X is CH, N, NH, or N($C_{1-6}$ alkyl);

Y and Z are each independently selected from the group consisting of NH, $NR^9$, O, S, N, CH, and $CR^9$;

Ring A is selected from the group consisting of $C_{6-10}$ aryl, 5-6 membered heteroaryl, $C_{3-10}$ cycloalkyl, and 4-10 membered heterocycloalkyl;

Ring B is selected from the group consisting of phenyl, 5-6 membered heteroaryl, $C_{3-6}$ cycloalkyl, and 3-6 membered heterocycloalkyl;

alternatively, Ring B is absent and m is 0;

$R^1$ is selected from the group consisting of H, $C_{1-6}$ alkyl, and $C_{3-6}$ cycloalkyl, wherein alkyl and cycloalkyl are each optionally substituted with $R^6$;

$R^2$ and $R^3$ are each independently selected from the group consisting of H, $C_{1-6}$ alkyl, $C_{3-6}$ cycloalkyl, and 3-6 membered heterocycloalkyl;

alternatively, $R^2$ and $R^3$, together with the atom to which they are attached, form a ring selected from the group consisting of $C_{3-7}$ cycloalkyl and 3-7 membered heterocycloalkyl;

each $R^4$ is independently selected from the group consisting of $C_{1-6}$ alkyl, halo, OH, $OR^6$, $NH_2$, NH($C_{1-6}$ alkyl), N($C_{1-6}$ alkyl)$_2$, $NHCOR^6$, CN, $C_{1-6}$ haloalkyl, $C_{3-7}$ cycloalkyl, 3-7 membered heterocycloalkyl, and $COR^6$;

alternatively, two $R^4$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^5$ is independently selected from the group consisting of $C_{1-6}$ alkyl, $C_{1-6}$ haloalkyl, halo, OH, $OR^6$, $NH_2$, NH($C_{1-6}$ alkyl), N($C_{1-6}$ alkyl)$_2$, $NHCOR^6$, CN, $C_{3-7}$ cycloalkyl, 3-7 membered heterocycloalkyl, $COR^6$, and $SO_2R^6$;

alternatively, two $R^5$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^6$ is independently selected from the group consisting of $C_{1-6}$ alkyl, $C_{0-6}$ alkyl-$C_{6-10}$ aryl, Coe alkyl-5-10 membered heteroaryl, $OC_{1-6}$ alkyl, $C_{3-6}$ cycloalkyl, halo, $NH_2$, NH($C_{1-6}$ alkyl), and N($C_{1-6}$ alkyl)$_2$;

each $R^7$ is independently selected from the group consisting of $C_{1-6}$ alkyl, $C_{1-6}$ haloalkyl, halo, OH, $OC_{1-6}$ alkyl, $NH_2$, NH($C_{1-6}$ alkyl), N($C_{1-6}$ alkyl)$_2$, CN, $COR^8$, and $SO_2R^8$;

each $R^8$ is independently selected from the group consisting of $C_{1-6}$ alkyl, $OC_{1-6}$ alkyl, halo, $NH_2$, $NH(C_{1-6}$ alkyl), and $N(C_{1-6}$ alkyl$)_2$;

each $R^9$ is independently selected from the group consisting of $C_{1-6}$ alkyl, $OC_{1-6}$ alkyl, halo, CN, OH, $NH_2$, $NH(C_{1-6}$ alkyl), and $N(C_{1-6}$ alkyl$)_2$;

m is 0, 1, 2, or 3;

n is 1, 2, or 3; and p is 0, 1, 2, or 3.

In an embodiment of Formula IV, Ring A is selected from the group consisting of $C_{6-10}$ aryl, 5-6 membered heteroaryl, and $C_{4-10}$ cycloalkyl. In an embodiment, m is 1 and n is 1. In another embodiment, m is 0 and n is 0. In another embodiment, m is 1 and n is 0. In another embodiment, m is 0 and n is 1.

In an embodiment, the compound of Formula IV is a compound of Formula IVa:

(IVa)

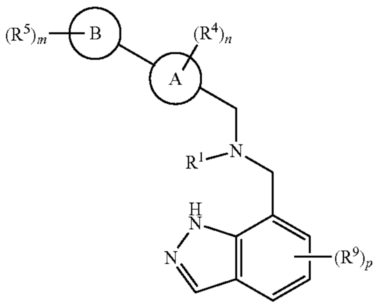

or a pharmaceutically acceptable salt thereof.

In yet another embodiment, the compound of Formula IV is

| Structure | No. |
|---|---|
| 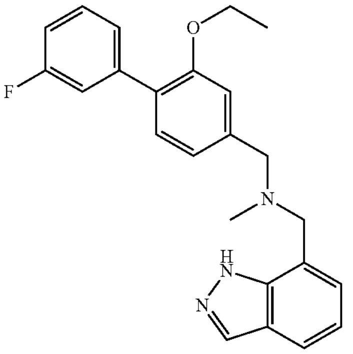 [SMILES: CCOc1cc(CN(C)Cc2cccc3cn[nH]c23)ccc1-c1cccc(F)c1] | 113 |

or a pharmaceutically acceptable salt thereof.

In still another aspect, provided herein is a compound of Formula V:

(V)

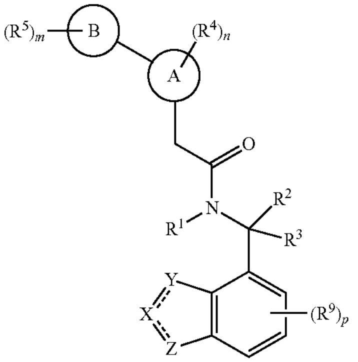

or a pharmaceutically acceptable salt thereof;

wherein

⎓ is an optional double bond;

X is CH, N, NH, or $N(C_{1-6}$ alkyl);

Y and Z are each independently selected from the group consisting of NH, $NR^9$, O, S, N, CH, and $CR^9$;

Ring A is selected from the group consisting of $C_{6-10}$ aryl, 5-6 membered heteroaryl, $C_{3-10}$ cycloalkyl, and 4-10 membered heterocycloalkyl; Ring B is selected from the group consisting of phenyl, 5-6 membered heteroaryl, $C_{3-6}$ cycloalkyl, and 3-6 membered heterocycloalkyl;

alternatively, Ring B is absent and m is 0;

$R^1$ is selected from the group consisting of H, $C_{1-6}$ alkyl, and $C_{3-6}$ cycloalkyl, wherein alkyl and cycloalkyl are each optionally substituted with $R^6$;

$R^2$ and $R^3$ are each independently selected from the group consisting of H, $C_{1-6}$ alkyl, $C_{3-6}$ cycloalkyl, and 3-6 membered heterocycloalkyl;

alternatively, $R^2$ and $R^3$, together with the atom to which they are attached, form a ring selected from the group consisting of $C_{3-7}$ cycloalkyl and 3-7 membered heterocycloalkyl;

each $R^4$ is independently selected from the group consisting of $C_{1-6}$ alkyl, halo, OH, $OR^6$, $NH_2$, $NH(C_{1-6}$ alkyl), $N(C_{1-6}$ alkyl$)_2$, $NHCOR^6$, CN, $C_{1-6}$ haloalkyl, $C_{3-7}$ cycloalkyl, 3-7 membered heterocycloalkyl, and $COR^6$;

alternatively, two $R^4$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^5$ is independently selected from the group consisting of $C_{1-6}$ alkyl, $C_{1-6}$ haloalkyl, halo, OH, $OR^6$, $NH_2$, $NH(C_{1-6}$ alkyl), $N(C_{1-6}$ alkyl$)_2$, $NHCOR^6$, CN, $C_{3-7}$ cycloalkyl, 3-7 membered heterocycloalkyl, $COR^6$, and $SO_2R^6$;

alternatively, two $R^5$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^6$ is independently selected from the group consisting of $C_{1-6}$ alkyl, $C_{0-6}$ alkyl-$C_{6-10}$ aryl, $C_{0-6}$ alkyl-5-10 membered heteroaryl, $OC_{1-6}$ alkyl, $C_{3-6}$ cycloalkyl, halo, $NH_2$, $NH(C_{1-6}$ alkyl), and $N(C_{1-6}$ alkyl$)_2$;

each $R^7$ is independently selected from the group consisting of $C_{1-6}$ alkyl, $C_{1-6}$ haloalkyl, halo, OH, $OC_{1-6}$ alkyl, $NH_2$, $NH(C_{1-6}$ alkyl), $N(C_{1-6}$ alkyl$)_2$, CN, $COR^8$, and $SO_2R^8$;

each $R^8$ is independently selected from the group consisting of $C_{1-6}$ alkyl, $OC_{1-6}$ alkyl, halo, $NH_2$, $NH(C_{1-6}$ alkyl), and $N(C_{1-6}$ alkyl$)_2$;

each $R^9$ is independently selected from the group consisting of $C_{1-6}$ alkyl, $OC_{1-6}$ alkyl, halo, CN, OH, $NH_2$, $NH(C_{1-6}$ alkyl), and $N(C_{1-6}$ alkyl$)_2$;

m is 0, 1, 2, or 3;

n is 1, 2, or 3; and p is 0, 1, 2, or 3.

In an embodiment of Formula V, Ring A is selected from the group consisting of $C_{6-10}$ aryl, 5-6 membered heteroaryl, and $C_{4-10}$ cycloalkyl. In an embodiment, m is 1 and n is 1. In another embodiment, m is 0 and n is 0. In another embodiment, m is 1 and n is 0. In another embodiment, m is 0 and n is 1.

In an embodiment, the compound of Formula V is a compound of Formula Va:

(Va)

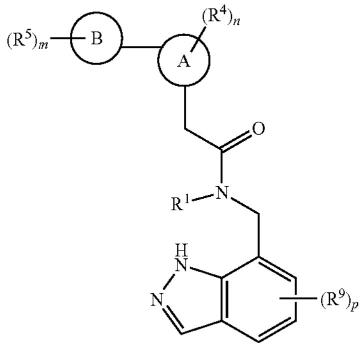

or a pharmaceutically acceptable salt thereof.

In another embodiment, the compound of Formula V is selected from the group consisting of

| Structure | No. |
|---|---|
| 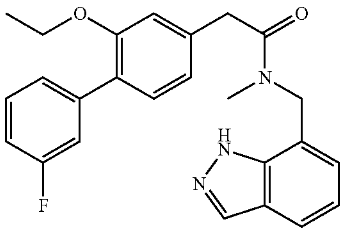 [SMILES: CCOc1cc(CC(=O)N(C)Cc2cccc3cn[nH]c23)ccc1-c1cccc(F)c1] | 114 |
| 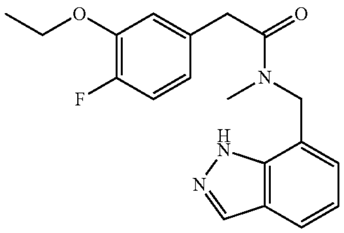 [SMILES: CCOc1cc(CC(=O)N(C)Cc2cccc3cn[nH]c23)ccc1F] | 115 |

or a pharmaceutically acceptable salt thereof.

In another aspect, provided herein is a compound of Formula VI:

(VI)

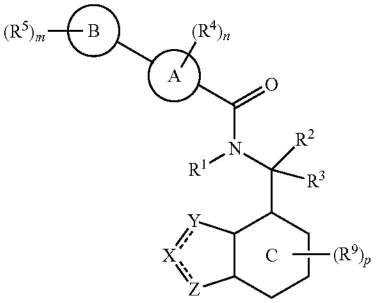

or a pharmaceutically acceptable salt thereof;

wherein

⎓ is an optional double bond;

X is CH, N, NH, or $N(C_{1-6}$ alkyl);

Y and Z are each independently selected from the group consisting of NH, $NR^9$, O, S, N, CH, and $CR^9$;

Ring A is selected from the group consisting of $C_{6-10}$ aryl, 5-6 membered heteroaryl, $C_{3-10}$ cycloalkyl, and 4-10 membered heterocycloalkyl;

Ring B is selected from the group consisting of phenyl, 5-6 membered heteroaryl, $C_{3-6}$ cycloalkyl, and 3-6 membered heterocycloalkyl;

alternatively, Ring B is absent and m is 0;

Ring C is pyridine;

$R^1$ is selected from the group consisting of H, $C_{1-6}$ alkyl, and $C_{3-6}$ cycloalkyl, wherein alkyl and cycloalkyl are each optionally substituted with $R^6$;

$R^2$ and $R^3$ are each independently selected from the group consisting of H, $C_{1-6}$ alkyl, $C_{3-6}$ cycloalkyl, and 3-6 membered heterocycloalkyl;

alternatively, $R^2$ and $R^3$, together with the atom to which they are attached, form a ring selected from the group consisting of $C_{3-7}$ cycloalkyl and 3-7 membered heterocycloalkyl;

each $R^4$ is independently selected from the group consisting of $C_{1-6}$ alkyl, halo, OH, $OR^6$, $NH_2$, $NH(C_{1-6}$ alkyl), $N(C_{1-6}$ alkyl$)_2$, $NHCOR^6$, CN, $C_{1-6}$ haloalkyl, $C_{3-7}$ cycloalkyl, 3-7 membered heterocycloalkyl, and $COR^6$;

alternatively, two $R^4$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^5$ is independently selected from the group consisting of $C_{1-6}$ alkyl, $C_{1-6}$ haloalkyl, halo, OH, $OR^6$, $NH_2$, $NH(C_{1-6}$ alkyl), $N(C_{1-6}$ alkyl$)_2$, $NHCOR^6$, CN, $C_{3-7}$ cycloalkyl, 3-7 membered heterocycloalkyl, $COR^6$, and $SO_2R^6$;

alternatively, two $R^5$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^6$ is independently selected from the group consisting of $C_{1-6}$ alkyl, $C_{0-6}$ alkyl-$C_{6-10}$ aryl, $C_{0-6}$ alkyl-5-10 membered heteroaryl, $OC_{1-6}$ alkyl, $C_{3-6}$ cycloalkyl, halo, $NH_2$, $NH(C_{1-6}$ alkyl), and $N(C_{1-6}$ alkyl$)_2$;

each $R^7$ is independently selected from the group consisting of $C_{1-6}$ alkyl, $C_{1-6}$ haloalkyl, halo, OH, $OC_{1-6}$ alkyl, $NH_2$, $NH(C_{1-6}$ alkyl), $N(C_{1-6}$ alkyl$)_2$, CN, $COR^8$, and $SO_2R^8$;

each $R^8$ is independently selected from the group consisting of $C_{1-6}$ alkyl, $OC_{1-6}$ alkyl, halo, $NH_2$, $NH(C_{1-6}$ alkyl), and $N(C_{1-6}$ alkyl$)_2$;

each $R^9$ is independently selected from the group consisting of $C_{1-6}$ alkyl, $OC_{1-6}$ alkyl, halo, CN, OH, $NH_2$, $NH(C_{1-6}$ alkyl), and $N(C_{1-6}$ alkyl$)_2$;

m is 0, 1, 2, or 3;

n is 1, 2, or 3; and p is 0, 1, 2, or 3.

In an embodiment of Formula VI, Ring A is selected from the group consisting of $C_{6-10}$ aryl, 5-6 membered heteroaryl, and $C_{4-10}$ cycloalkyl. In an embodiment, m is 1 and n is 1. In another embodiment, m is 0 and n is 0. In another embodiment, m is 1 and n is 0. In another embodiment, m is 0 and n is 1.

In another aspect, provided herein is a compound of Formula VII:

(VII)

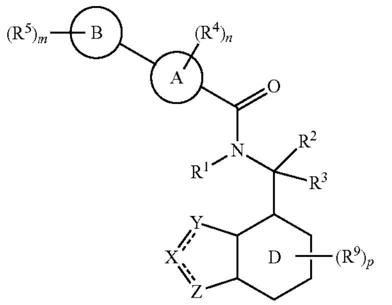

or a pharmaceutically acceptable salt thereof, wherein $\overline{\cdots}$ is an optional double bond;

X is CH, N, NH, or $N(C_{1-6}$ alkyl);

Y and Z are each independently selected from the group consisting of NH, $NR^9$, O, S, N, CH, and $CR^9$;

Ring A is selected from the group consisting of $C_{6-10}$ aryl, 5-10 membered heteroaryl, $C_{3-10}$ cycloalkyl, and 4-10 membered heterocycloalkyl;

Ring B is selected from the group consisting of phenyl, 5-6 membered heteroaryl, $C_{3-6}$ cycloalkyl, and 3-6 membered heterocycloalkyl;

alternatively, Ring B is absent and m is 0;

Ring D is phenyl or pyridine;

$R^1$ is selected from the group consisting of H, $C_{1-6}$ alkyl, $C_{3-6}$ cycloalkyl, $OC_{1-6}$ alkyl, $OC_{3-6}$ cycloalkyl, $O(C_{0-6}$ alkyl-$C_{6-10}$ aryl), $C_{0-6}$ alkyl-$C_{6-10}$ aryl, and OH, wherein alkyl, aryl, and cycloalkyl are each optionally substituted with $R^6$—

$R^2$ and $R^3$ are each independently selected from the group consisting of H, $C_{1-6}$ alkyl, $C_{3-6}$ cycloalkyl, and 3-6 membered heterocycloalkyl;

alternatively, $R^2$ and $R^3$, together with the atom to which they are attached, form a ring selected from the group consisting of $C_{3-7}$ cycloalkyl and 3-7 membered heterocycloalkyl;

each $R^4$ is independently selected from the group consisting of $C_{1-6}$ alkyl, $C_{2-6}$ alkenyl, $C_{2-6}$ alkynyl, halo, OH, $OR^6$, $NH_2$, $NH(C_{1-6}$ alkyl), $N(C_{1-6}$ alkyl$)_2$, $C_{1-6}$ alkyl-$NHCOR^6$, $NHCOR^6$, CN, $C_{1-6}$ haloalkyl, $C_{3-7}$ cycloalkyl, 3-7 membered heterocycloalkyl, and $COR^6$;

alternatively, two $R^4$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^5$ is independently selected from the group consisting of $C_{1-6}$ alkyl, $C_{1-6}$ haloalkyl, halo, OH, $OR^6$, $NH_2$, $NH(C_{1-6}$ alkyl), $N(C_{1-6}$ alkyl$)_2$, $NHCOR^6$, CN, $C_{3-7}$ cycloalkyl, 3-7 membered heterocycloalkyl, $COR^6$, and $SO_2R^6$;

alternatively, two $R^5$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^6$ is independently selected from the group consisting of $C_{1-6}$ alkyl, $C_{2-6}$ alkenyl, $C_{0-6}$ alkyl-$C_{6-10}$ aryl, $C_{0-6}$ alkyl-5-10 membered heteroaryl, $OC_{1-6}$ alkyl, $C_{3-6}$ cycloalkyl, 3-6 membered heterocycloalkyl, halo, $NH_2$, $NH(C_{1-6}$ alkyl), and $N(C_{1-6}$ alkyl$)_2$;

each $R^7$ is independently selected from the group consisting of $C_{1-6}$ alkyl, $C_{1-6}$ haloalkyl, halo, OH, $OC_{1-6}$ alkyl, $NH_2$, $NH(C_{1-6}$ alkyl), $N(C_{1-6}$ alkyl$)_2$, CN, $COR^8$, and $SO_2R^8$;

each $R^8$ is independently selected from the group consisting of $C_{1-6}$ alkyl, $OC_{1-6}$ alkyl, halo, $NH_2$, $NH(C_{1-6}$ alkyl), and $N(C_{1-6}$ alkyl$)_2$;

each $R^9$ is independently selected from the group consisting of $C_{1-6}$ alkyl, $C_{1-6}$ haloalkyl, $C_{1-6}$ alkyl-OH, $OC_{1-6}$ alkyl, $C_{1-6}$ alkyl-O—$C_{1-6}$ alkyl, $O(C_{3-6}$ cycloalkyl), halo, CN, OH, $NH_2$, $NH(C_{1-6}$ alkyl), and $N(C_{1-6}$ alkyl$)_2$;

m is 0, 1, 2, or 3;

n is 0, 1, 2, or 3; and p is 0, 1, 2, or 3.

In an embodiment of Formula VII,

X, Y, and Z are defined as having one of the following core structures:

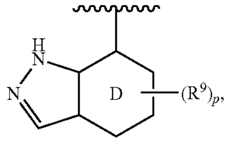
,
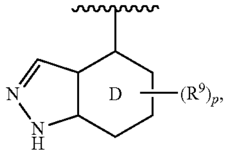
, or
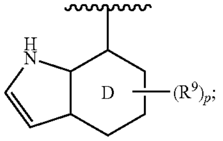
;

Ring A is phenyl or 5-6 membered heteroaryl;

Ring B is phenyl or 5-6 membered heteroaryl;

Ring D is phenyl or pyridine;

$R^1$ is H or $C_{1-3}$ alkyl;

$R^2$ and $R^3$ are each independently selected from the group consisting of H and $C_{1-3}$ alkyl;

each $R^4$ is independently selected from the group consisting of halo, OH, $OR^6$, $NH_2$, $NH(C_{1-3}$ alkyl), $N(C_{1-3}$ alkyl$)_2$, $C_{1-3}$ alkyl-$NHCOR^6$, $NHCOR^6$, CN, $C_{1-3}$ haloalkyl, $C_{3-7}$ cycloalkyl, 3-7 membered heterocycloalkyl, and $COR^6$;

each $R^5$ is independently selected from the group consisting of $C_{1-3}$ alkyl, $C_{1-3}$ haloalkyl, halo, OH, $OR^6$, $NH_2$, $NH(C_{1-3}$ alkyl), $N(C_{1-3}$ alkyl$)_2$, $NHCOR^6$, CN, $C_{3-7}$ cycloalkyl, 3-7 membered heterocycloalkyl, $COR^6$, and $SO_2R^6$;

each $R^6$ is independently selected from the group consisting of $C_{1-6}$ alkyl, $C_{2-6}$ alkenyl, $C_{0-6}$ alkyl-$C_{6-10}$ aryl, $C_{0-6}$ alkyl-5-6 membered heteroaryl, $OC_{1-3}$ alkyl, $C_{3-6}$ cycloalkyl, 3-6 membered heterocycloalkyl, halo, $NH_2$, $NH(C_{1-3}$ alkyl), and $N(C_{1-3}$ alkyl$)_2$;

each $R^9$ is independently selected from the group consisting of $C_{1-3}$ haloalkyl, $C_{1-3}$ alkyl-OH, $OC_{1-3}$ alkyl, halo, and CN;

m is 0, 1, or 2;

n is 0, 1, or 2; and p is 0 or 1.

In another embodiment of Formula VII,

X is N;

Y is NH;

Z is CH;

Ring A is phenyl or 5-6 membered heteroaryl;

Ring B is phenyl or 5-6 membered heteroaryl;

Ring D is phenyl or pyridine;

$R^1$ is H or $C_{1-3}$ alkyl;

$R^2$ and $R^3$ are each independently selected from the group consisting of H and $C_{1-3}$ alkyl;

each $R^4$ is independently selected from the group consisting of halo, OH, $OR^6$, $NH_2$, $NH(C_{1-3}$ alkyl), $N(C_{1-3}$ alkyl$)_2$, $C_{1-3}$ alkyl-$NHCOR^6$, $NHCOR^6$, CN, $C_{1-3}$ haloalkyl, $C_{3-7}$ cycloalkyl, 3-7 membered heterocycloalkyl, and $COR^6$;

each $R^5$ is independently selected from the group consisting of $C_{1-3}$ alkyl, $C_{1-3}$ haloalkyl, halo, OH, $OR^6$, $NH_2$, $NH(C_{1-3}$ alkyl), $N(C_{1-3}$ alkyl$)_2$, $NHCOR^6$, CN, $C_{3-7}$ cycloalkyl, 3-7 membered heterocycloalkyl, $COR^6$, and $SO_2R^6$;

each $R^6$ is independently selected from the group consisting of $C_{1-6}$ alkyl, $C_{2-6}$ alkenyl, $C_{0-6}$ alkyl-$C_{6-10}$ aryl, $C_{0-6}$ alkyl-5-6 membered heteroaryl, $OC_{1-3}$ alkyl, $C_{3-6}$ cycloalkyl, 3-6 membered heterocycloalkyl, halo, $NH_2$, $NH(C_{1-3}$ alkyl), and $N(C_{1-3}$ alkyl$)_2$;

each $R^9$ is independently selected from the group consisting of $C_{1-3}$ haloalkyl, $C_{1-3}$ alkyl-OH, $OC_{1-3}$ alkyl, halo, and CN;

m is 0, 1, or 2;

n is 0, 1, or 2; and p is 0 or 1. In another embodiment, each $R^9$ is independently selected from the group consisting of $C_{1-3}$ alkyl-OH, $C_{1-3}$ haloalkyl, and CN.

In another embodiment, each $R^4$ is independently selected from the group consisting of halo, OH, $OR^6$, $NH_2$, $NH(C_{1-3}$ alkyl), $N(C_{1-3}$ alkyl$)_2$, CN, $C_{1-3}$ haloalkyl, $C_{3-7}$ cycloalkyl, 3-7 membered heterocycloalkyl, and $COR^6$; and each $R^5$ is independently selected from the group consisting of $C_{1-3}$ alkyl, $C_{1-3}$ haloalkyl, halo, OH, $OR^6$, $NH_2$, $NH(C_{1-3}$ alkyl), $N(C_{1-3}$ alkyl$)_2$, CN, $C_{3-7}$ cycloalkyl, 3-7 membered heterocycloalkyl.

In an embodiment, each $R^6$ is independently selected from the group consisting of $C_{1-6}$ alkyl, $C_{2-6}$ alkenyl, $C_{3-6}$ cycloalkyl, halo, $NH_2$, $NH(C_{1-3}$ alkyl), and $N(C_{1-3}$ alkyl$)_2$ In an embodiment, m is 1 and n is 1. In another embodiment, m is 0 and n is 0. In another embodiment, m is 1 and n is 0. In another embodiment, m is 0 and n is 1.

In an embodiment, the compound of Formula VI is a compound of Formula VIa:

(VIa)

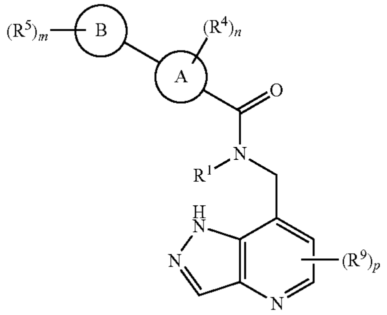

or a pharmaceutically acceptable salt thereof.

In another embodiment, the compound of Formula VI is a compound of Formula VIb:

(VIb)

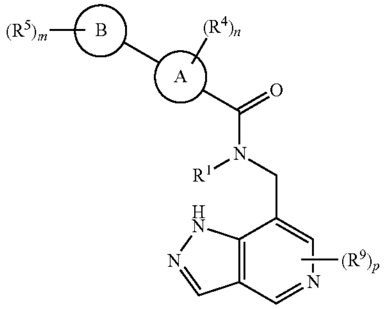

or a pharmaceutically acceptable salt thereof.

In yet another embodiment, the compound of Formula VI is a compound of Formula VIc:

(VIc)

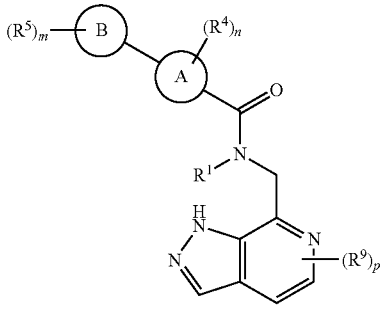

or a pharmaceutically acceptable salt thereof.

In still another embodiment, the compound of Formula VI is selected from the group consisting of a compound in Table 6.

TABLE 6

| Structure | No. |
|---|---|
| 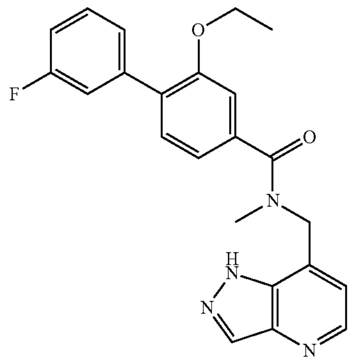 [SMILES: CCOc1cc(C(=O)N(C)Cc2ccnc3cn[nH]c23)ccc1-c1cccc(F)c1] | 116 |
| 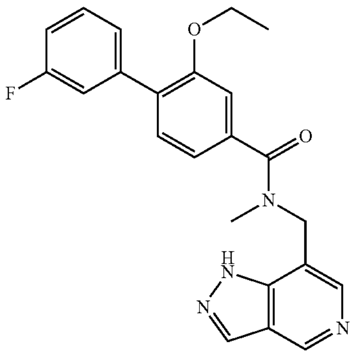 [SMILES: CCOc1cc(C(=O)N(C)Cc2cncc3cn[nH]c23)ccc1-c1cccc(F)c1] | 117 |
| 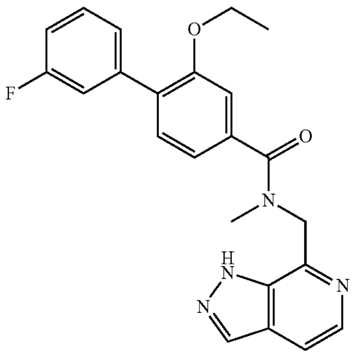 [SMILES: CCOc1cc(C(=O)N(C)Cc2nccc3cn[nH]c23)ccc1-c1cccc(F)c1] | 118 |

or a pharmaceutically acceptable salt thereof.

In an aspect, provided herein is a compound of Formula X:

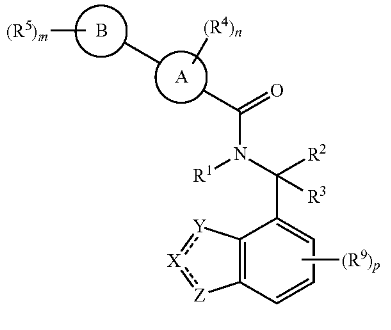

(X)

or a pharmaceutically acceptable salt thereof;

wherein $\overline{---}$ is an optional double bond;

X is CH, N, NH, or N($C_{1-6}$ alkyl);

Y and Z are each independently selected from the group consisting of NH, $NR^9$, O, S, N, CH, and $CR^9$;

Ring A is selected from the group consisting of $C_{6-10}$ aryl, 5-6 membered heteroaryl, $C_{3-10}$ cycloalkyl, and 4-10 membered heterocycloalkyl;

Ring B is selected from the group consisting of phenyl, 5-6 membered heteroaryl, $C_{3-6}$ cycloalkyl, and 3-6 membered heterocycloalkyl;

alternatively, Ring B is absent and m is 0;

$R^1$ is selected from the group consisting of H, $C_{1-6}$ alkyl, and $C_{3-6}$ cycloalkyl, wherein alkyl and cycloalkyl are each optionally substituted with $R^6$;

$R^2$ and $R^3$ are each independently selected from the group consisting of H, $C_{1-6}$ alkyl, $C_{3-6}$ cycloalkyl, and 4-10 membered heterocycloalkyl, wherein alkyl, cycloalkyl, and heterocycloalkyl are each optionally substituted with $R^6$;

alternatively, $R^2$ and $R^3$, together with the atom to which they are attached, form a ring selected from the group consisting of $C_{3-7}$ cycloalkyl and 3-7 membered heterocycloalkyl;

each $R^4$ is independently selected from the group consisting of $C_{1-6}$ alkyl, $C_{1-6}$ alkyl-O—$C_{1-6}$ alkyl, halo, OH, $OR^6$, $NH_2$, NH($C_{1-6}$ alkyl), N($C_{1-6}$ alkyl)$_2$, $NHCOR^6$, CN, $C_{1-6}$ haloalkyl, $C_{3-7}$ cycloalkyl, 3-7 membered heterocycloalkyl, and $COR^6$ wherein alkyl, cycloalkyl, and heterocycloalkyl are each optionally substituted with $R^6$;

alternatively, two $R^4$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^5$ is independently selected from the group consisting of $C_{1-6}$ alkyl, $C_{1-6}$ haloalkyl, halo, OH, $OR^6$, $NH_2$, NH($C_{1-6}$ alkyl), N($C_{1-6}$ alkyl)$_2$, $NHCOR^6$, CN, $C_{3-7}$ cycloalkyl, 3-7 membered heterocycloalkyl, $COR^6$, and $SO_2R^6$;

alternatively, two $R^5$, together with the atoms to which they are attached, form a ring selected from the group consisting of phenyl, 5-6 membered heteroaryl, $C_{4-6}$ cycloalkyl, and 4-6 membered heterocycloalkyl all of which are optionally substituted with one, two, or three $R^7$;

each $R^6$ is independently selected from the group consisting of $C_{1-6}$ alkyl, $C_{1-6}$ haloalkyl, $C_{0-6}$ alkyl-$C_{6-10}$ aryl, $C_{0-6}$ alkyl-5-10 membered heteroaryl, $OC_{1-6}$ alkyl, $C_{3-6}$ cycloalkyl, halo, OH, $NH_2$, NH($C_{1-6}$ alkyl), and N($C_{1-6}$ alkyl)$_2$;

each $R^7$ is independently selected from the group consisting of $C_{1-6}$ alkyl, $C_{1-6}$ haloalkyl, halo, OH, $OC_{1-6}$ alkyl, $NH_2$, NH($C_{1-6}$ alkyl), N($C_{1-6}$ alkyl)$_2$, CN, $COR^8$, and $SO_2R^8$;

each $R^8$ is independently selected from the group consisting of $C_{1-6}$ alkyl, $OC_{1-6}$ alkyl, halo, $NH_2$, NH($C_{1-6}$ alkyl), and N($C_{1-6}$ alkyl)$_2$;

each $R^9$ is independently selected from the group consisting of $C_{1-6}$ alkyl, $OC_{1-6}$ alkyl, halo, CN, OH, $NH_2$, NH($C_{1-6}$ alkyl), N($C_{1-6}$ alkyl)$_2$, C(O)$NHR^8$, C(O)N($R^8$)$_2$, and NHC(O)$R^8$;

m is 0, 1, 2, or 3;

n is 1, 2, or 3; and p is 0, 1, 2, or 3.

In an embodiment of Formula X, Ring A is selected from the group consisting of $C_6$10 aryl, 5-6 membered heteroaryl, and $C_{4-10}$ cycloalkyl. In an embodiment, m is 1 and n is 1. In another embodiment, m is 0 and n is 0. In another embodiment, m is 1 and n is 0. In another embodiment, m is 0 and n is 1.

In an embodiment, the compound of Formula X is selected from the group consisting of a compound in Table 7.

TABLE 7

| Structure | No. |
|---|---|
| 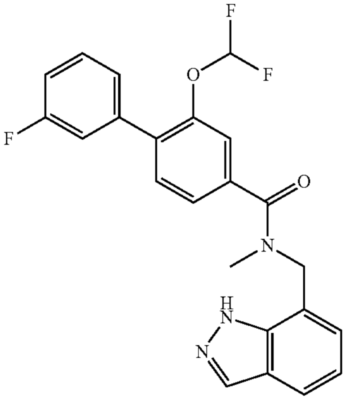 [SMILES: CN(Cc1cccc2cn[nH]c12)C(=O)c1ccc(-c2cccc(F)c2)c(OC(F)F)c1] | 119 |
| 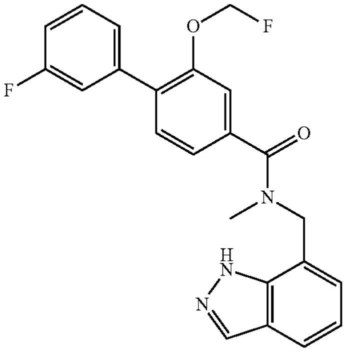 [SMILES: CN(Cc1cccc2cn[nH]c12)C(=O)c1ccc(-c2cccc(F)c2)c(OCF)c1] | 120 |
| 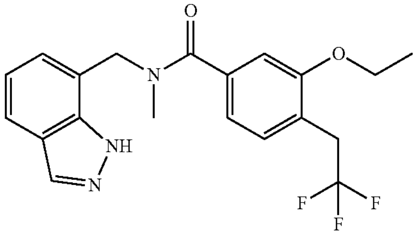 [SMILES: CCOc1cc(C(=O)N(C)Cc2cccc3cn[nH]c23)ccc1CC(F)(F)F] | 121 |
| 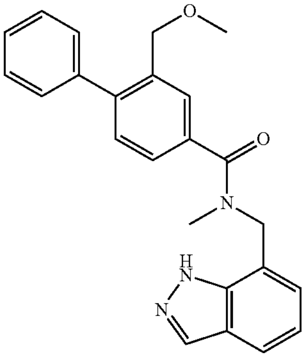 [SMILES: COCc1cc(C(=O)N(C)Cc2cccc3cn[nH]c23)ccc1-c1ccccc1] | 122 |

TABLE 7-continued

| Structure | No. |
|---|---|
| 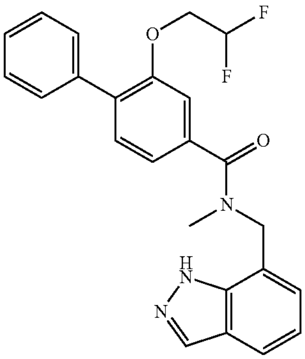 [SMILES: CN(Cc1cccc2cn[nH]c12)C(=O)c1ccc(-c2ccccc2)c(OCC(F)F)c1] | 123 |
| 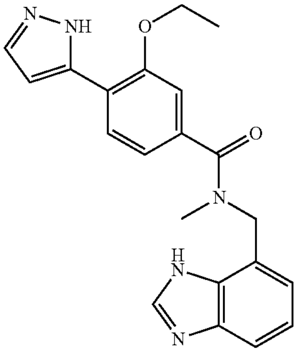 [SMILES: CCOc1cc(C(=O)N(C)Cc2cccc3nc[nH]c23)ccc1-c1ccn[nH]1] | 124 |

or a pharmaceutically acceptable salt hereof.

In another embodiment, the compound of the formulae provided herein is selected from the group consisting of a compound in Table 8.

TABLE 8

| Structure | No. |
|---|---|
| 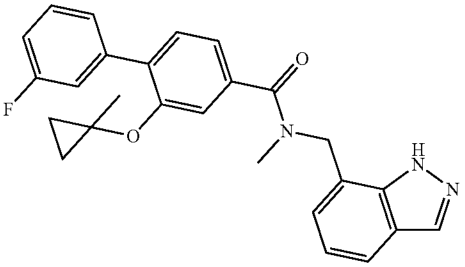 [SMILES: CN(Cc1cccc2cn[nH]c12)C(=O)c1ccc(-c2cccc(F)c2)c(OC2(C)CC2)c1] | 125 |
| 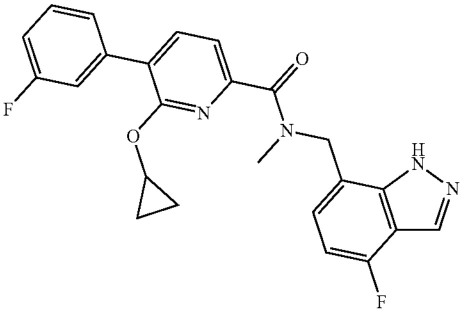 [SMILES: CN(Cc1ccc(F)c2cn[nH]c12)C(=O)c1ccc(-c2cccc(F)c2)c(OC2CC2)n1] | 126 |

TABLE 8-continued
| Structure | No. |
|---|---|
| 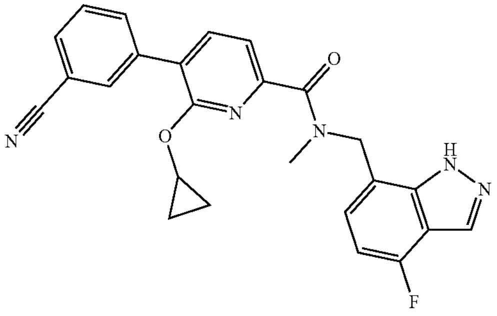 [SMILES: CN(Cc1ccc(F)c2cn[nH]c12)C(=O)c1ccc(-c2cccc(C#N)c2)c(OC2CC2)n1] | 127 |
| 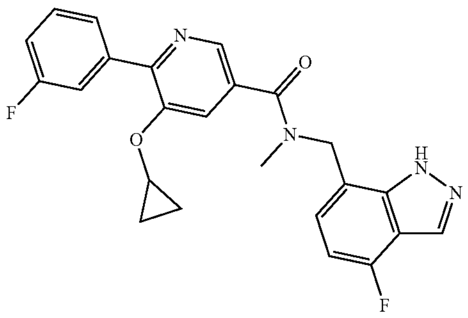 [SMILES: CN(Cc1ccc(F)c2cn[nH]c12)C(=O)c1cnc(-c2cccc(F)c2)c(OC2CC2)c1] | 128 |
| 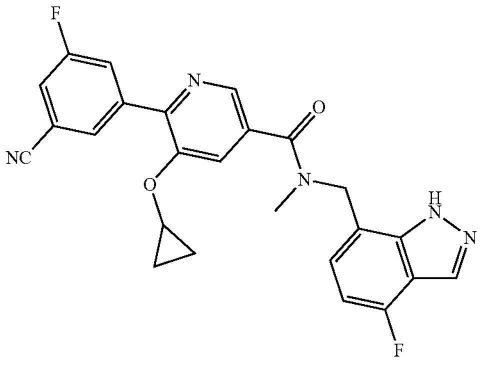 [SMILES: CN(Cc1ccc(F)c2cn[nH]c12)C(=O)c1cnc(-c2cc(F)cc(C#N)c2)c(OC2CC2)c1] | 129 |
| 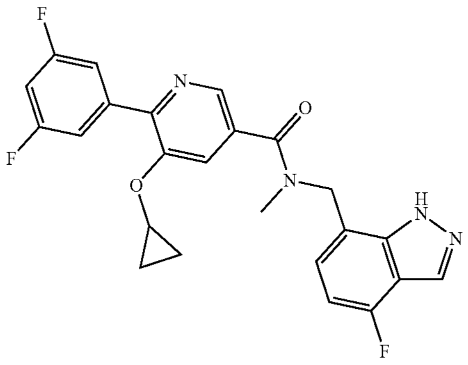 [SMILES: CN(Cc1ccc(F)c2cn[nH]c12)C(=O)c1cnc(-c2cc(F)cc(F)c2)c(OC2CC2)c1] | 130 |
TABLE 8-continued
| Structure | No. |
|---|---|
| 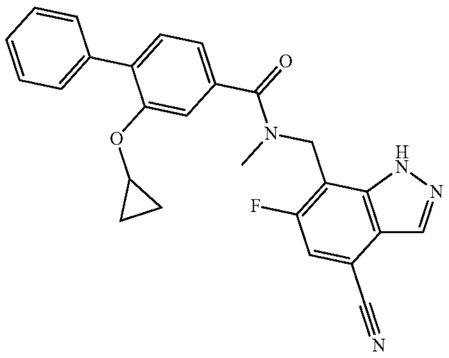 [SMILES: CN(Cc1c(F)cc(C#N)c2cn[nH]c12)C(=O)c1ccc(-c2ccccc2)c(OC2CC2)c1] | 131 |
| 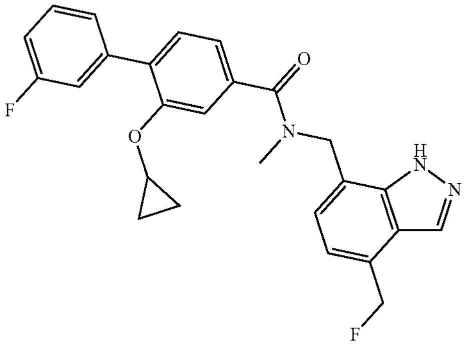 [SMILES: CN(Cc1ccc(CF)c2cn[nH]c12)C(=O)c1ccc(-c2cccc(F)c2)c(OC2CC2)c1] | 132 |
| 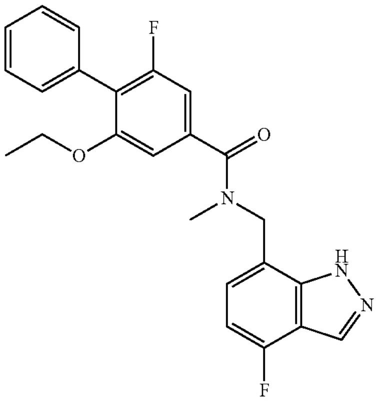 [SMILES: CCOc1cc(C(=O)N(C)Cc2ccc(F)c3cn[nH]c23)cc(F)c1-c1ccccc1] | 133 |
| 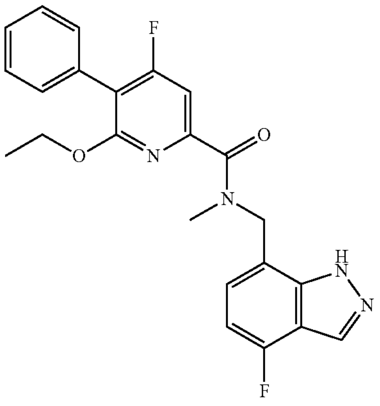 [SMILES: CCOc1nc(C(=O)N(C)Cc2ccc(F)c3cn[nH]c23)cc(F)c1-c1ccccc1] | 134 |

TABLE 8-continued
| Structure | No. |
|---|---|
| 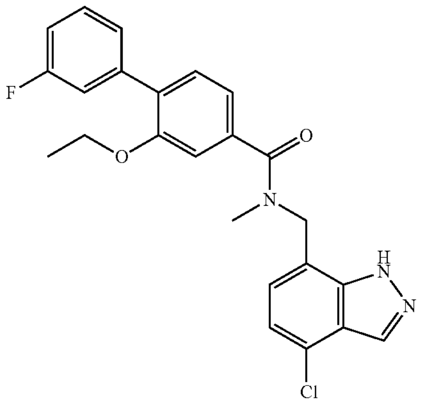 [SMILES: CCOc1cc(C(=O)N(C)Cc2ccc(Cl)c3cn[nH]c23)ccc1-c1cccc(F)c1] | 135 |
| 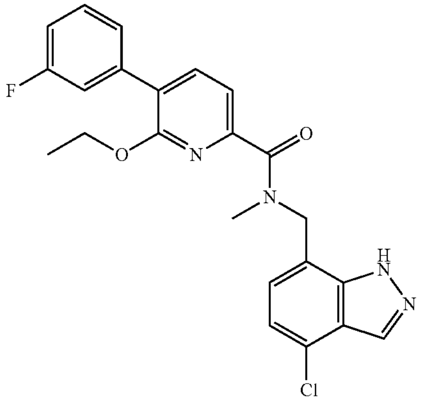 [SMILES: CCOc1nc(C(=O)N(C)Cc2ccc(Cl)c3cn[nH]c23)ccc1-c1cccc(F)c1] | 136 |
| 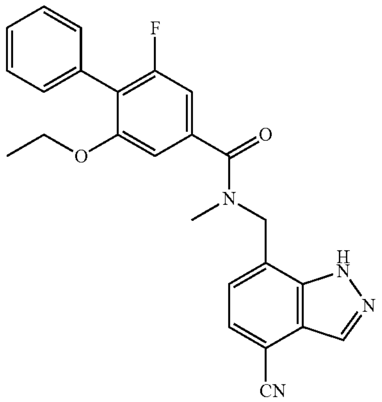 [SMILES: CCOc1cc(C(=O)N(C)Cc2ccc(C#N)c3cn[nH]c23)cc(F)c1-c1ccccc1] | 137 |
TABLE 8-continued
| Structure | No. |
|---|---|
| 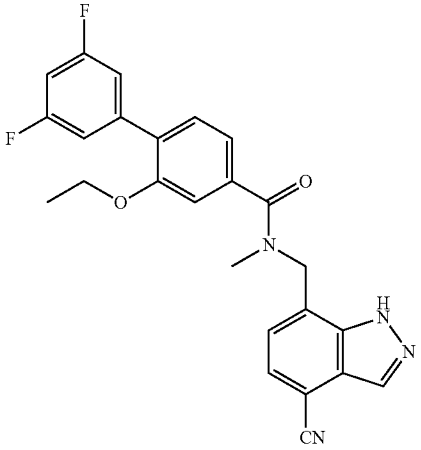 [SMILES: CCOc1cc(C(=O)N(C)Cc2ccc(C#N)c3cn[nH]c23)ccc1-c1cc(F)cc(F)c1] | 138 |
| 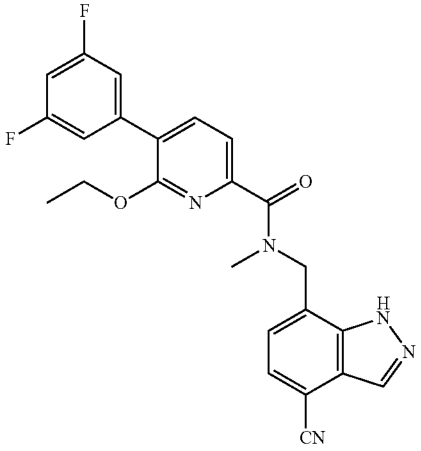 [SMILES: CCOc1nc(C(=O)N(C)Cc2ccc(C#N)c3cn[nH]c23)ccc1-c1cc(F)cc(F)c1] | 139 |
| 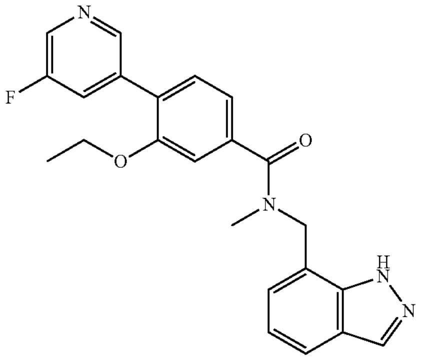 [SMILES: CCOc1cc(C(=O)N(C)Cc2cccc3cn[nH]c23)ccc1-c1cncc(F)c1] | 140 |

TABLE 8-continued
| Structure | No. |
|---|---|
| 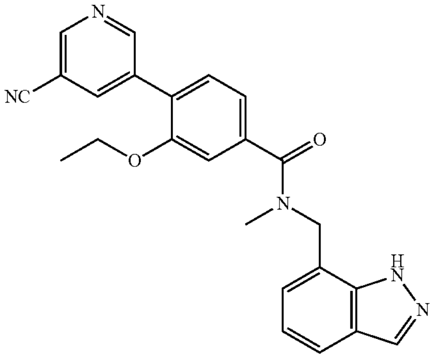 | 141 |
| 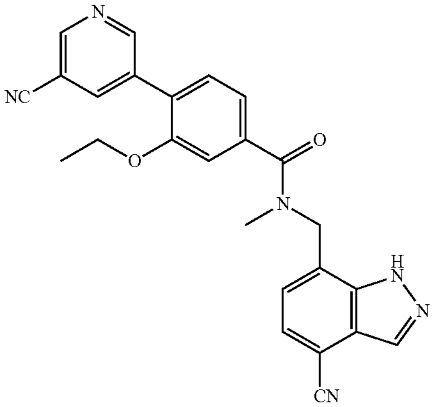 [SMILES: CCOc1cc(C(=O)N(C)Cc2ccc(C#N)c3cn[nH]c23)ccc1-c1cncc(C#N)c1] | 142 |
| 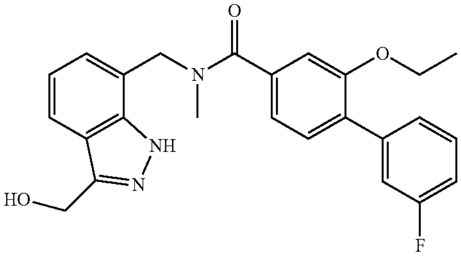 [SMILES: CCOc1cc(C(=O)N(C)Cc2cccc3c(CO)n[nH]c23)ccc1-c1cccc(F)c1] | 143 |
| 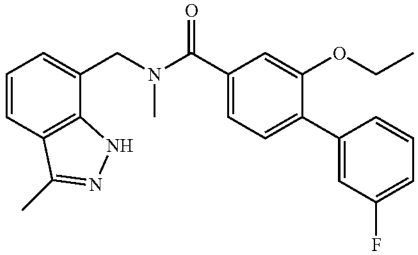 [SMILES: CCOc1cc(C(=O)N(C)Cc2cccc3c(C)n[nH]c23)ccc1-c1cccc(F)c1] | 144 |
| 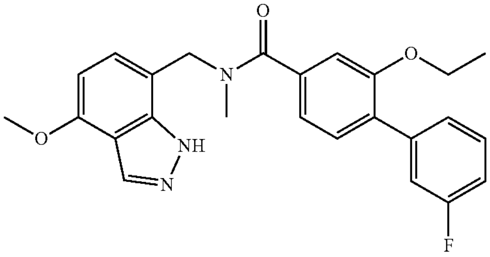 [SMILES: CCOc1cc(C(=O)N(C)Cc2ccc(OC)c3cn[nH]c23)ccc1-c1cccc(F)c1] | 145 |
TABLE 8-continued
| Structure | No. |
|---|---|
| 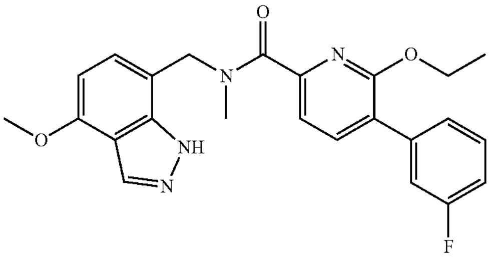 [SMILES: CCOc1nc(C(=O)N(C)Cc2ccc(OC)c3cn[nH]c23)ccc1-c1cccc(F)c1] | 146 |
| 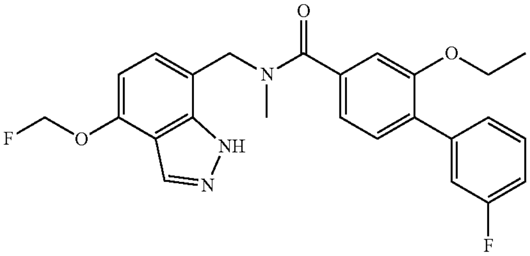 [SMILES: CCOc1cc(C(=O)N(C)Cc2ccc(OCF)c3cn[nH]c23)ccc1-c1cccc(F)c1] | 147 |
| 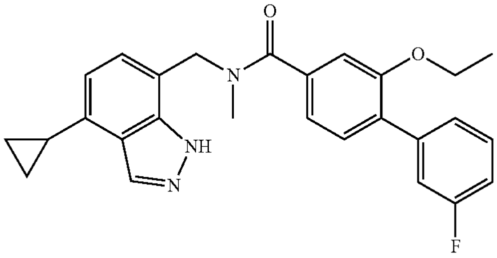 [SMILES: CCOc1cc(C(=O)N(C)Cc2ccc(C3CC3)c3cn[nH]c23)ccc1-c1cccc(F)c1] | 148 |
| 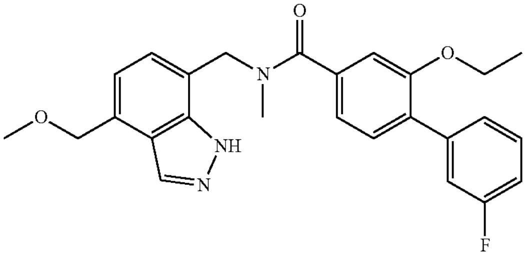 [SMILES: CCOc1cc(C(=O)N(C)Cc2ccc(COC)c3cn[nH]c23)ccc1-c1cccc(F)c1] | 149 |
| 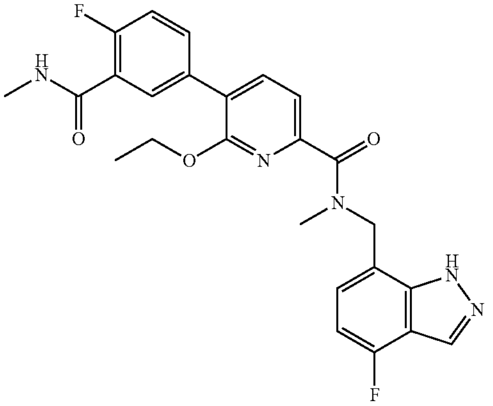 [SMILES: CCOc1nc(C(=O)N(C)Cc2ccc(F)c3cn[nH]c23)ccc1-c1ccc(F)c(C(=O)NC)c1] | 150 |

TABLE 8-continued
| Structure | No. |
|---|---|
| 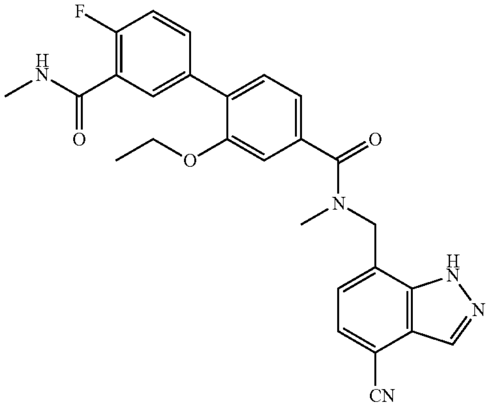 [SMILES: CCOc1cc(C(=O)N(C)Cc2ccc(C#N)c3cn[nH]c23)ccc1-c1ccc(F)c(C(=O)NC)c1] | 151 |
| 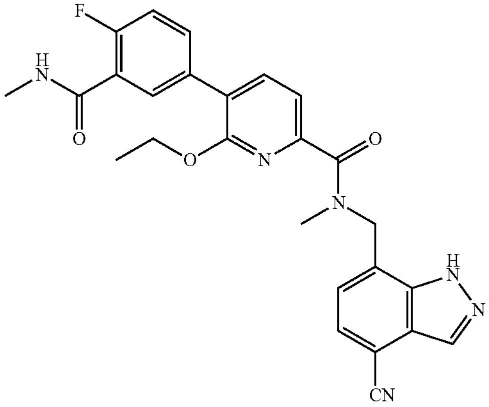 [SMILES: CCOc1nc(C(=O)N(C)Cc2ccc(C#N)c3cn[nH]c23)ccc1-c1ccc(F)c(C(=O)NC)c1] | 152 |
| 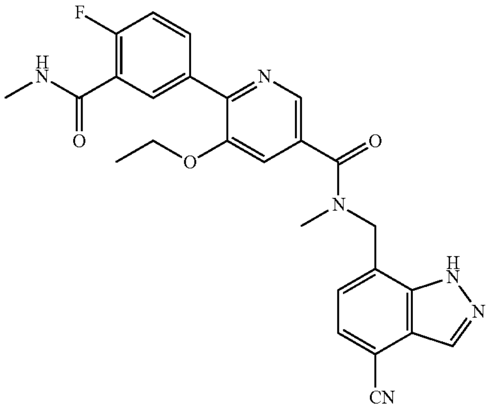 | 153 |
TABLE 8-continued
| Structure | No. |
|---|---|
| 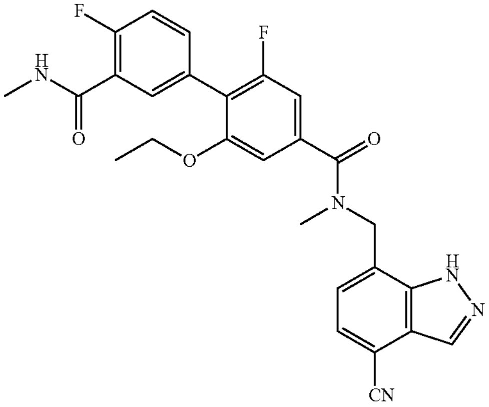 [SMILES: CCOc1cc(C(=O)N(C)Cc2ccc(C#N)c3cn[nH]c23)cc(F)c1-c1ccc(F)c(C(=O)NC)c1] | 154 |
| 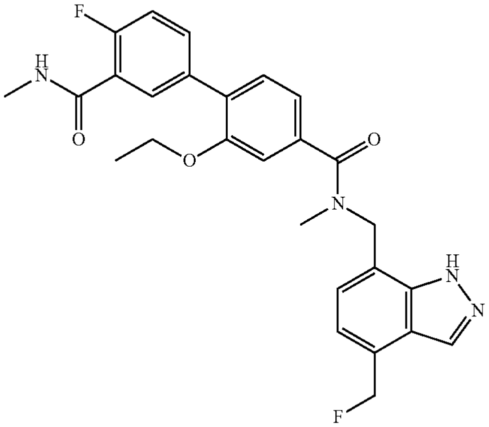 [SMILES: CCOc1cc(C(=O)N(C)Cc2ccc(CF)c3cn[nH]c23)ccc1-c1ccc(F)c(C(=O)NC)c1] | 155 |
| 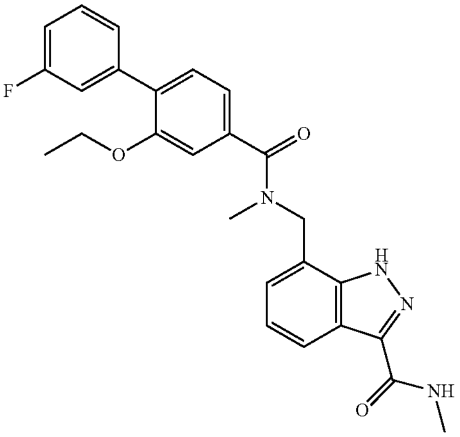 [SMILES: CCOc1cc(C(=O)N(C)Cc2cccc3c(C(=O)NC)n[nH]c23)ccc1-c1cccc(F)c1] | 156 |

TABLE 8-continued
| Structure | No. |
|---|---|
| 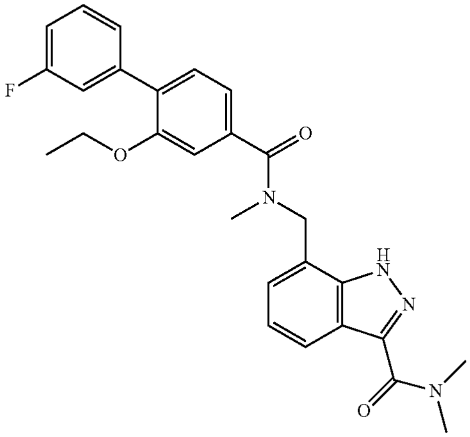 [SMILES: CCOc1cc(C(=O)N(C)Cc2cccc3c(C(=O)N(C)C)n[nH]c23)ccc1-c1cccc(F)c1] | 157 |
| 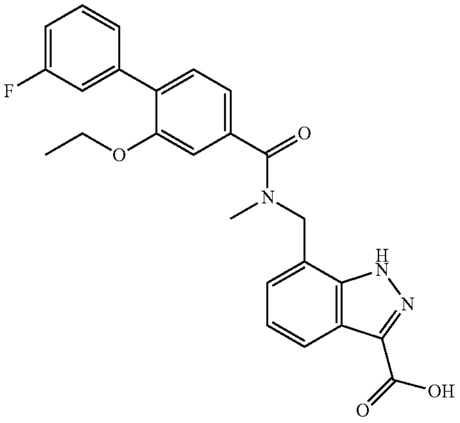 [SMILES: CCOc1cc(C(=O)N(C)Cc2cccc3c(C(=O)O)n[nH]c23)ccc1-c1cccc(F)c1] | 158 |
| 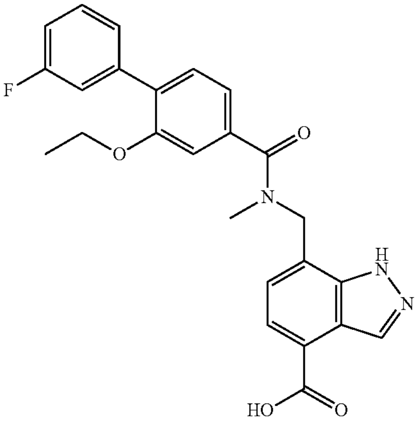 [SMILES: CCOc1cc(C(=O)N(C)Cc2ccc(C(=O)O)c3cn[nH]c23)ccc1-c1cccc(F)c1] | 159 |
TABLE 8-continued
| Structure | No. |
|---|---|
| 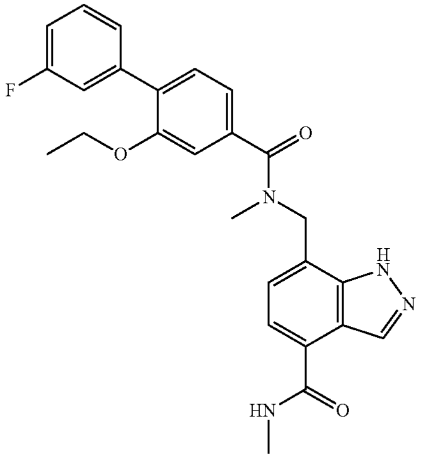 [SMILES: CCOc1cc(C(=O)N(C)Cc2ccc(C(=O)NC)c3cn[nH]c23)ccc1-c1cccc(F)c1] | 160 |
| 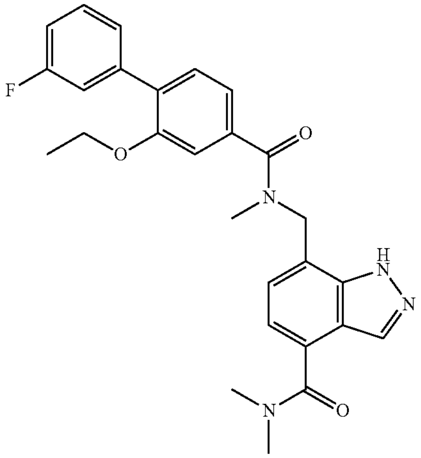 [SMILES: CCOc1cc(C(=O)N(C)Cc2ccc(C(=O)N(C)C)c3cn[nH]c23)ccc1-c1cccc(F)c1] | 161 |
| 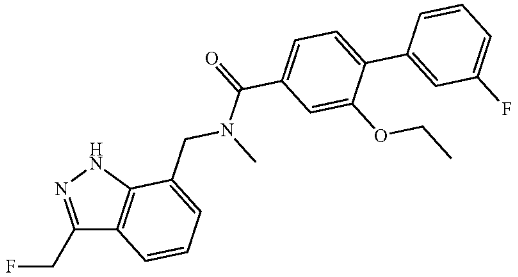 [SMILES: CCOc1cc(C(=O)N(C)Cc2cccc3c(CF)n[nH]c23)ccc1-c1cccc(F)c1] | 162 |
| 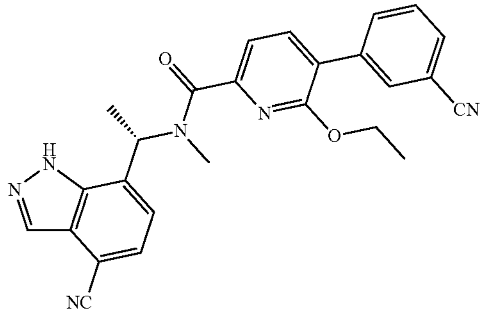 [SMILES: CCOc1nc(C(=O)N(C)[C@@H](C)c2ccc(C#N)c3cn[nH]c23)ccc1-c1cccc(C#N)c1] | 163 |

TABLE 8-continued
| Structure | No. |
|---|---|
| 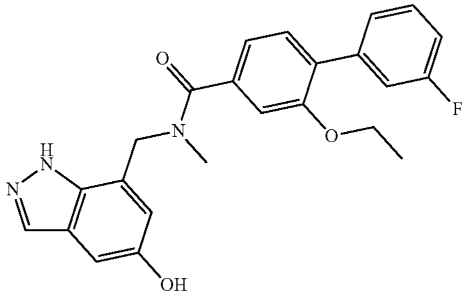 [SMILES: CCOc1cc(C(=O)N(C)Cc2cc(O)cc3cn[nH]c23)ccc1-c1cccc(F)c1] | 164 |
| 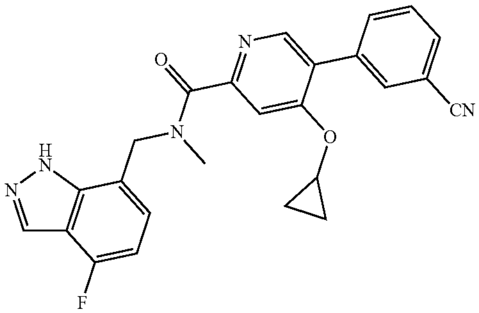 [SMILES: CN(Cc1ccc(F)c2cn[nH]c12)C(=O)c1cc(OC2CC2)c(-c2cccc(C#N)c2)cn1] | 165 |
| 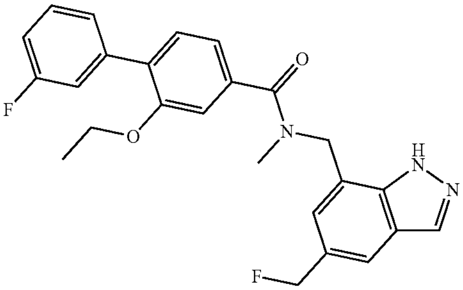 [SMILES: CCOc1cc(C(=O)N(C)Cc2cc(CF)cc3cn[nH]c23)ccc1-c1cccc(F)c1] | 166 |
| 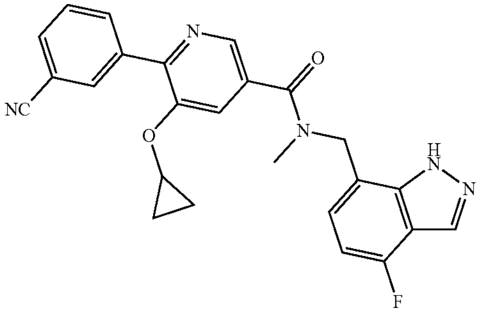 [SMILES: CN(Cc1ccc(F)c2cn[nH]c12)C(=O)c1cnc(-c2cccc(C#N)c2)c(OC2CC2)c1] | 167 |
| 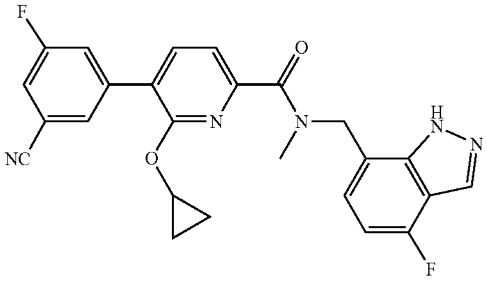 [SMILES: CN(Cc1ccc(F)c2cn[nH]c12)C(=O)c1ccc(-c2cc(F)cc(C#N)c2)c(OC2CC2)n1] | 168 |
TABLE 8-continued
| Structure | No. |
|---|---|
| 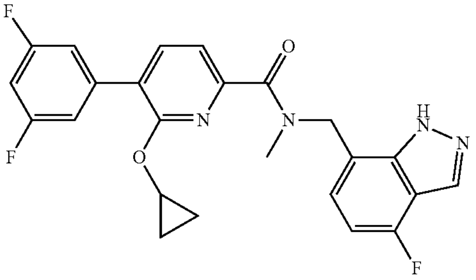 [SMILES: CN(Cc1ccc(F)c2cn[nH]c12)C(=O)c1ccc(-c2cc(F)cc(F)c2)c(OC2CC2)n1] | 169 |
| 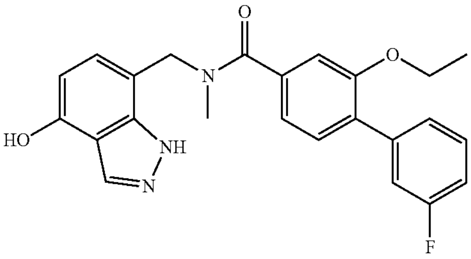 [SMILES: CCOc1cc(C(=O)N(C)Cc2ccc(O)c3cn[nH]c23)ccc1-c1cccc(F)c1] | 170 |
| 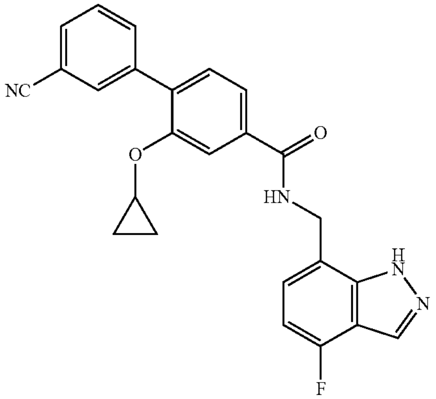 [SMILES: N#Cc1cccc(-c2ccc(C(=O)NCc3ccc(F)c4cn[nH]c34)cc2OC2CC2)c1] | 171 |
| 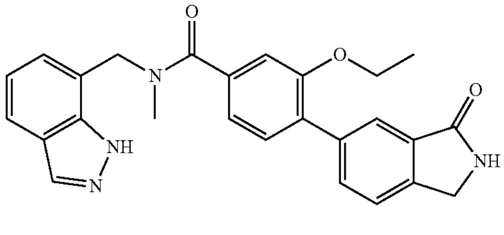 [SMILES: CCOc1cc(C(=O)N(C)Cc2cccc3cn[nH]c23)ccc1-c1ccc2c(c1)C(=O)NC2] | 172 |
| 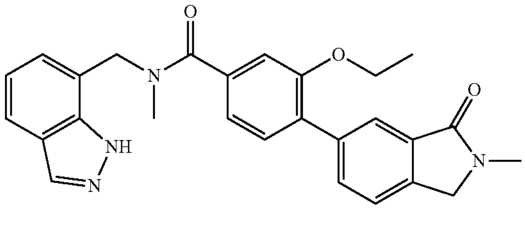 [SMILES: CCOc1cc(C(=O)N(C)Cc2cccc3cn[nH]c23)ccc1-c1ccc2c(c1)C(=O)N(C)C2] | 173 |

TABLE 8-continued
| Structure | No. |
|---|---|
| 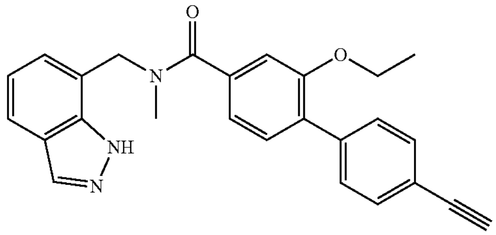 [SMILES: C#Cc1ccc(-c2ccc(C(=O)N(C)Cc3cccc4cn[nH]c34)cc2OCC)cc1] | 174 |
| 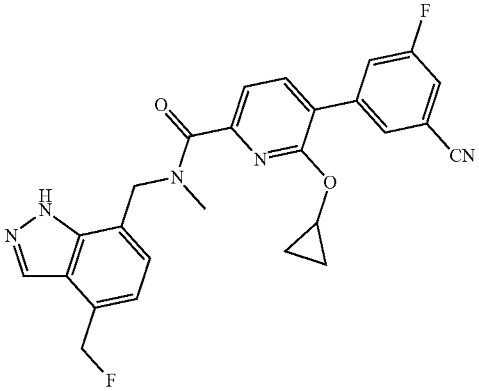 [SMILES: CN(Cc1ccc(CF)c2cn[nH]c12)C(=O)c1ccc(-c2cc(F)cc(C#N)c2)c(OC2CC2)n1] | 175 |
| 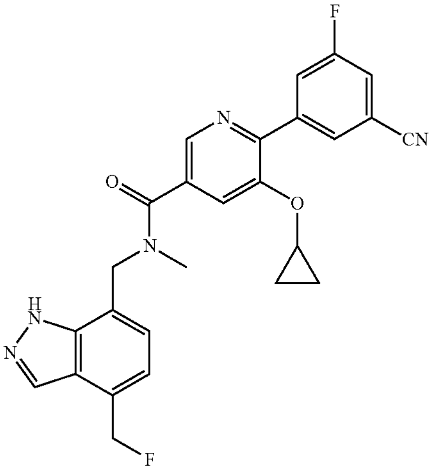 [SMILES: CN(Cc1ccc(CF)c2cn[nH]c12)C(=O)c1cnc(-c2cc(F)cc(C#N)c2)c(OC2CC2)c1] | 176 |
| 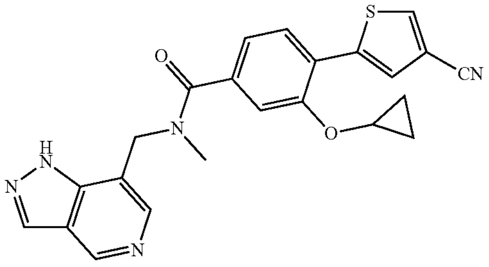 [SMILES: CN(Cc1cncc2cn[nH]c12)C(=O)c1ccc(-c2cc(C#N)cs2)c(OC2CC2)c1] | 177 |
TABLE 8-continued
| Structure | No. |
|---|---|
| 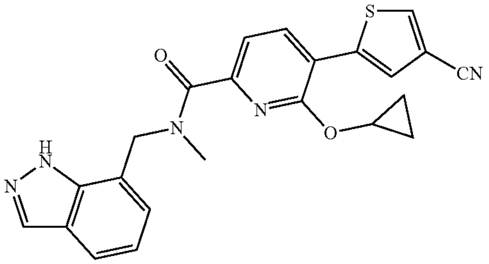 [SMILES: CN(Cc1cccc2cn[nH]c12)C(=O)c1ccc(-c2cc(C#N)cs2)c(OC2CC2)n1] | 178 |
| 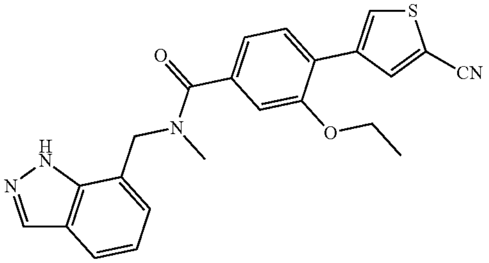 | 179 |
| 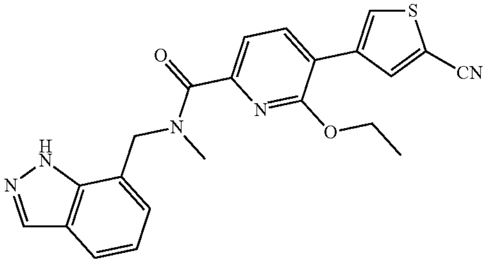 [SMILES: CCOc1nc(C(=O)N(C)Cc2cccc3cn[nH]c23)ccc1-c1csc(C#N)c1] | 180 |
| 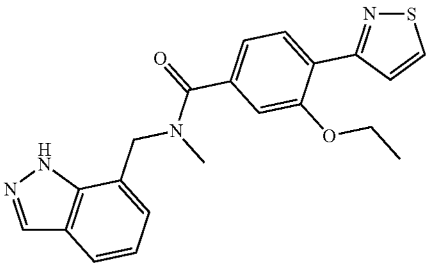 [SMILES: CCOc1cc(C(=O)N(C)Cc2cccc3cn[nH]c23)ccc1-c1ccsn1] | 181 |
| 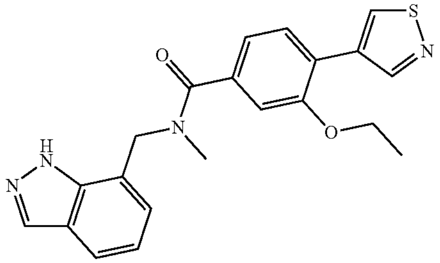 [SMILES: CCOc1cc(C(=O)N(C)Cc2cccc3cn[nH]c23)ccc1-c1cnsc1] | 182 |

TABLE 8-continued
| Structure | No. |
| --- | --- |
| 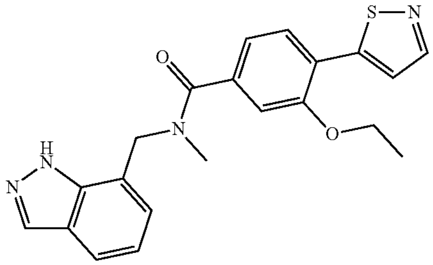 [SMILES: CCOc1cc(C(=O)N(C)Cc2cccc3cn[nH]c23)ccc1-c1ccns1] | 183 |
| 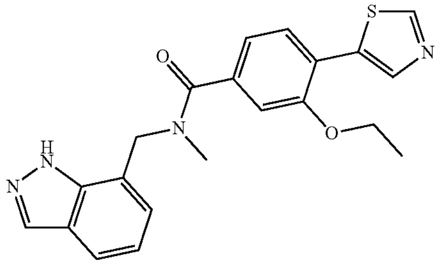 [SMILES: CCOc1cc(C(=O)N(C)Cc2cccc3cn[nH]c23)ccc1-c1cncs1] | 184 |
| 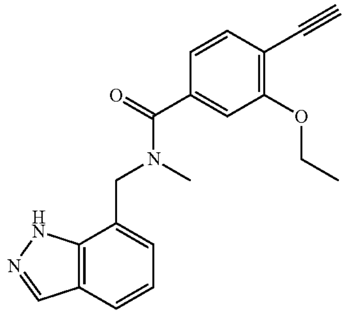 [SMILES: C#Cc1ccc(C(=O)N(C)Cc2cccc3cn[nH]c23)cc1OCC] | 185 |
| 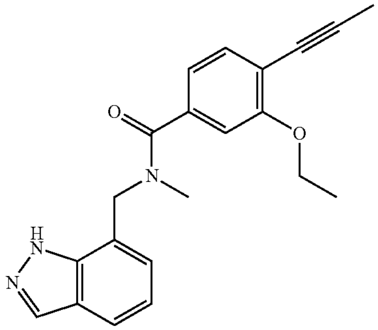 [SMILES: CC#Cc1ccc(C(=O)N(C)Cc2cccc3cn[nH]c23)cc1OCC] | 186 |
| 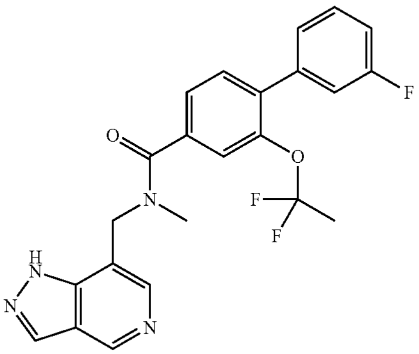 [SMILES: CN(Cc1cncc2cn[nH]c12)C(=O)c1ccc(-c2cccc(F)c2)c(OC(C)(F)F)c1] | 187 |
TABLE 8-continued
| Structure | No. |
| --- | --- |
| 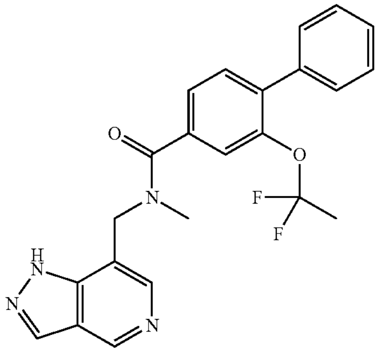 [SMILES: CN(Cc1cncc2cn[nH]c12)C(=O)c1ccc(-c2ccccc2)c(OC(C)(F)F)c1] | 188 |
| 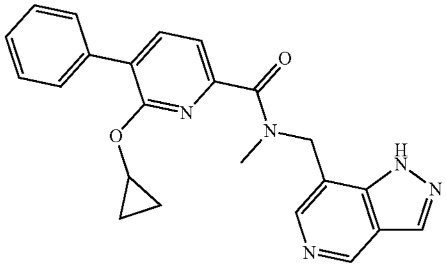 [SMILES: CN(Cc1cncc2cn[nH]c12)C(=O)c1ccc(-c2ccccc2)c(OC2CC2)n1] | 189 |
| 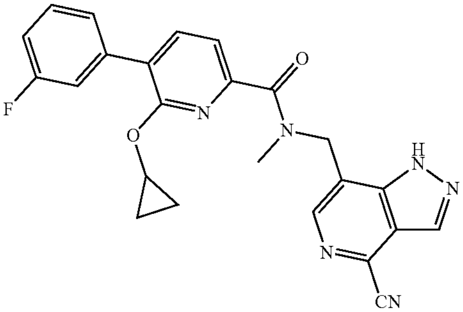 [SMILES: CN(Cc1cnc(C#N)c2cn[nH]c12)C(=O)c1ccc(-c2cccc(F)c2)c(OC2CC2)n1] | 190 |
| 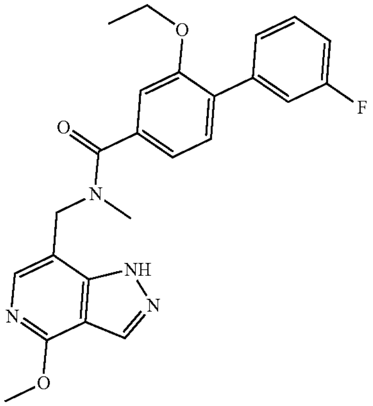 [SMILES: CCOc1cc(C(=O)N(C)Cc2cnc(OC)c3cn[nH]c23)ccc1-c1cccc(F)c1] | 191 |

TABLE 8-continued
| Structure | No. |
|---|---|
| 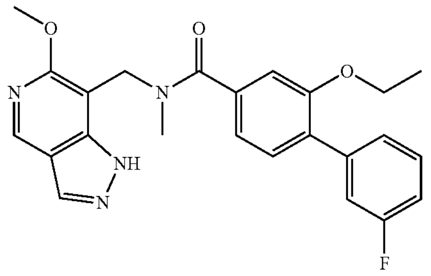 [SMILES: CCOc1cc(C(=O)N(C)Cc2c(OC)ncc3cn[nH]c23)ccc1-c1cccc(F)c1] | 192 |
| 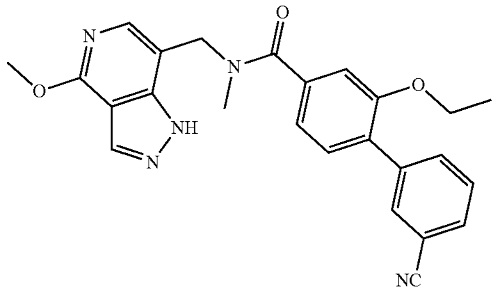 [SMILES: CCOc1cc(C(=O)N(C)Cc2cnc(OC)c3cn[nH]c23)ccc1-c1cccc(C#N)c1] | 193 |
| 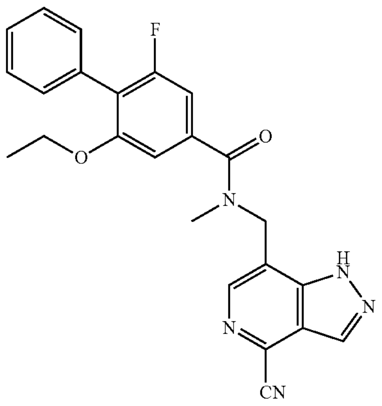 [SMILES: CCOc1cc(C(=O)N(C)Cc2cnc(C#N)c3cn[nH]c23)cc(F)c1-c1ccccc1] | 194 |
| 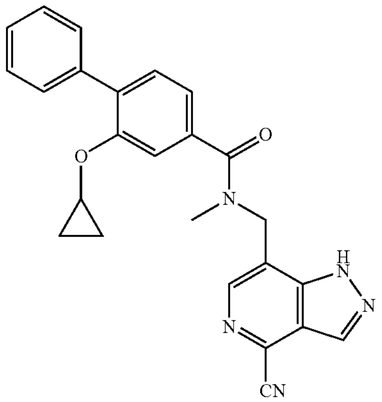 [SMILES: CN(Cc1cnc(C#N)c2cn[nH]c12)C(=O)c1ccc(-c2ccccc2)c(OC2CC2)c1] | 195 |
TABLE 8-continued
| Structure | No. |
|---|---|
| 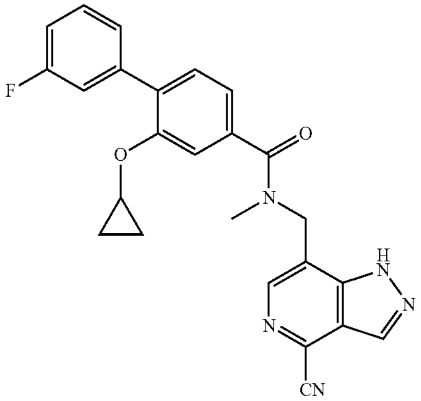 [SMILES: CN(Cc1cnc(C#N)c2cn[nH]c12)C(=O)c1ccc(-c2cccc(F)c2)c(OC2CC2)c1] | 196 |
| 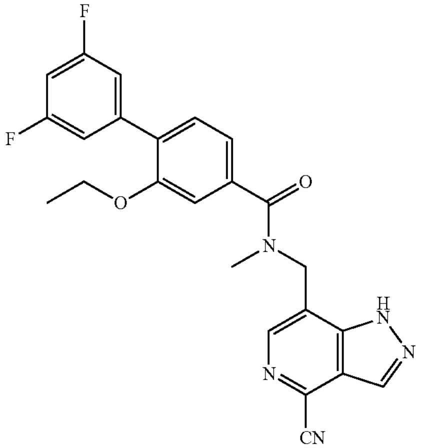 [SMILES: CCOc1cc(C(=O)N(C)Cc2cnc(C#N)c3cn[nH]c23)ccc1-c1cc(F)cc(F)c1] | 197 |
| 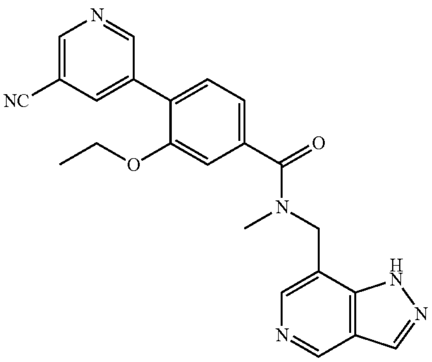 [SMILES: CCOc1cc(C(=O)N(C)Cc2cncc3cn[nH]c23)ccc1-c1cncc(C#N)c1] | 198 |

TABLE 8-continued
| Structure | No. |
|---|---|
| 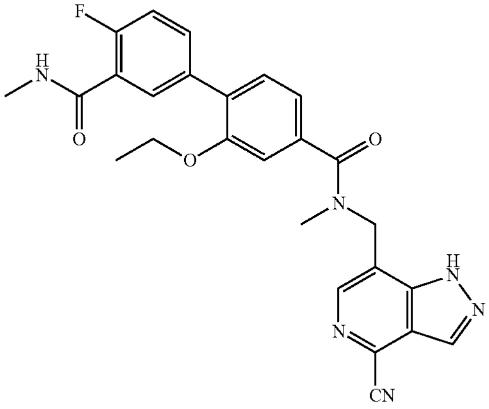 | 199 |
| 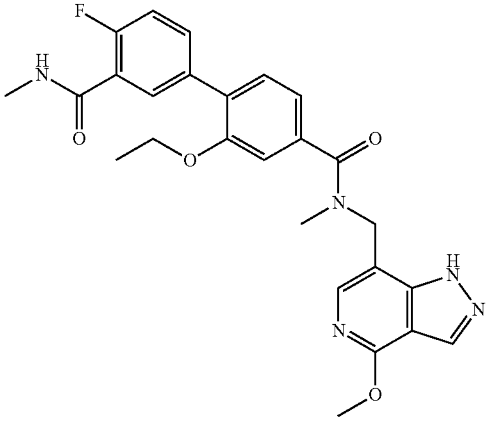 [SMILES: CCOc1cc(C(=O)N(C)Cc2cnc(OC)c3cn[nH]c23)ccc1-c1ccc(F)c(C(=O)NC)c1] | 200 |
| 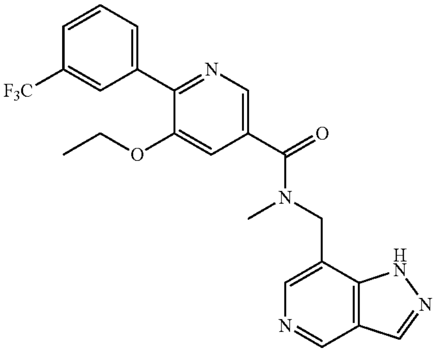 [SMILES: CCOc1cc(C(=O)N(C)Cc2cncc3cn[nH]c23)cnc1-c1cccc(C(F)(F)F)c1] | 201 |
| 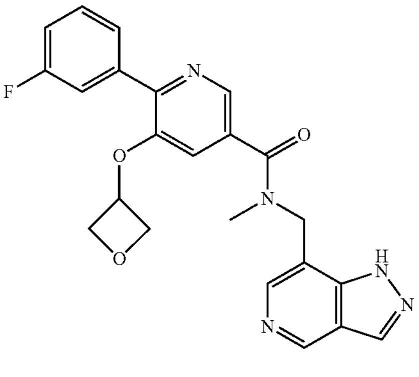 [SMILES: CN(Cc1cncc2cn[nH]c12)C(=O)c1cnc(-c2cccc(F)c2)c(OC2COC2)c1] | 202 |
TABLE 8-continued
| Structure | No. |
|---|---|
| 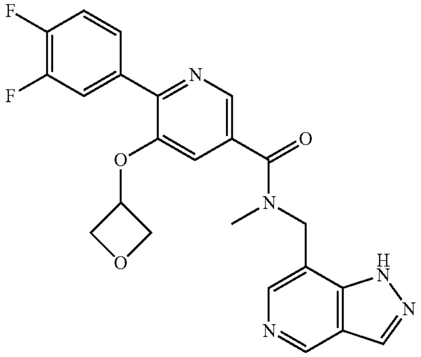 [SMILES: CN(Cc1cncc2cn[nH]c12)C(=O)c1cnc(-c2ccc(F)c(F)c2)c(OC2COC2)c1] | 203 |
| 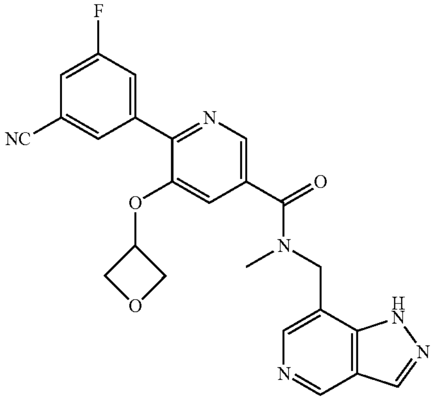 [SMILES: CN(Cc1cncc2cn[nH]c12)C(=O)c1cnc(-c2cc(F)cc(C#N)c2)c(OC2COC2)c1] | 204 |
| 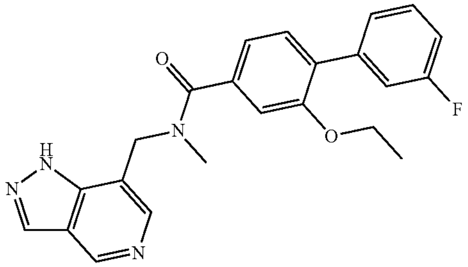 [SMILES: CCOc1cc(C(=O)N(C)Cc2cncc3cn[nH]c23)ccc1-c1cccc(F)c1] | 205 |
| 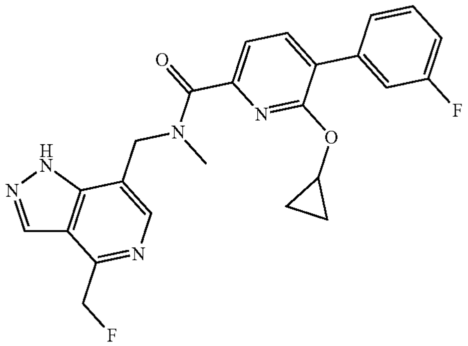 [SMILES: CN(Cc1cnc(CF)c2cn[nH]c12)C(=O)c1ccc(-c2cccc(F)c2)c(OC2CC2)n1] | 206 |

TABLE 8-continued
| Structure | No. |
| --- | --- |
| 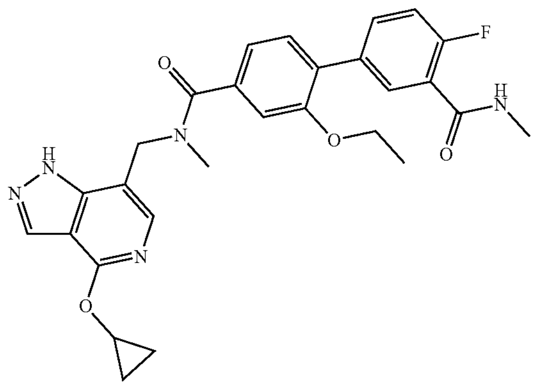 [SMILES: CCOc1cc(C(=O)N(C)Cc2cnc(OC3CC3)c3cn[nH]c23)ccc1-c1ccc(F)c(C(=O)NC)c1] | 207 |
| 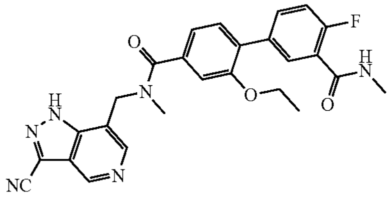 [SMILES: CCOc1cc(C(=O)N(C)Cc2cncc3c(C#N)n[nH]c23)ccc1-c1ccc(F)c(C(=O)NC)c1] | 208 |
| 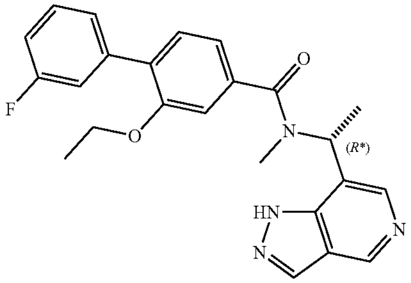 [SMILES: CCOc1cc(C(=O)N(C)[C@H](C)c2cncc3cn[nH]c23)ccc1-c1cccc(F)c1] | 209 |
| 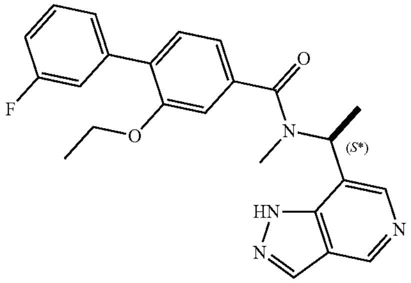 [SMILES: CCOc1cc(C(=O)N(C)[C@@H](C)c2cncc3cn[nH]c23)ccc1-c1cccc(F)c1] | 210 |
| 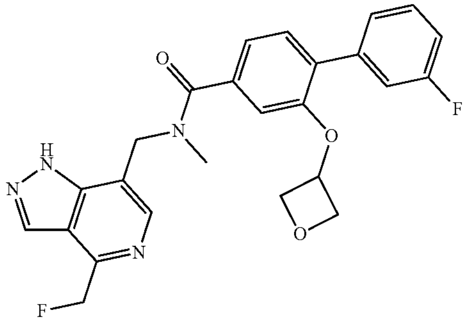 [SMILES: CN(Cc1cnc(CF)c2cn[nH]c12)C(=O)c1ccc(-c2cccc(F)c2)c(OC2COC2)c1] | 211 |
TABLE 8-continued
| Structure | No. |
| --- | --- |
| 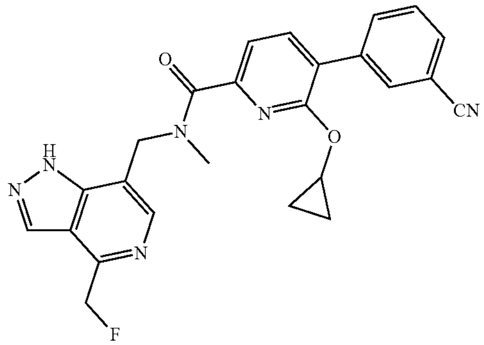 [SMILES: CN(Cc1cnc(CF)c2cn[nH]c12)C(=O)c1ccc(-c2cccc(C#N)c2)c(OC2CC2)n1] | 212 |
| 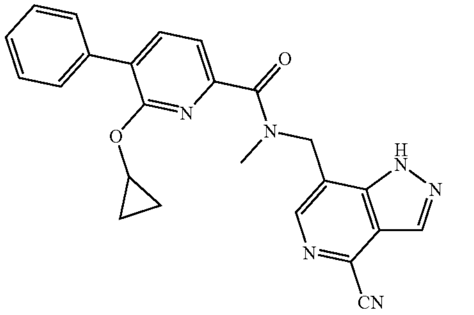 [SMILES: CN(Cc1cnc(C#N)c2cn[nH]c12)C(=O)c1ccc(-c2ccccc2)c(OC2CC2)n1] | 213 |
| 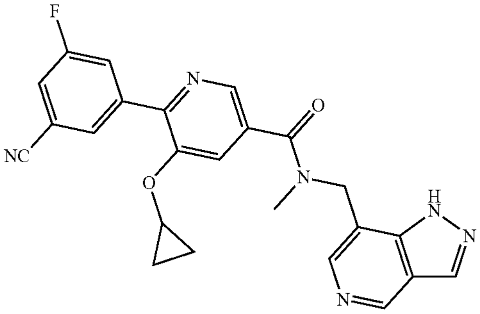 [SMILES: CN(Cc1cncc2cn[nH]c12)C(=O)c1cnc(-c2cc(F)cc(C#N)c2)c(OC2CC2)c1] | 214 |
| 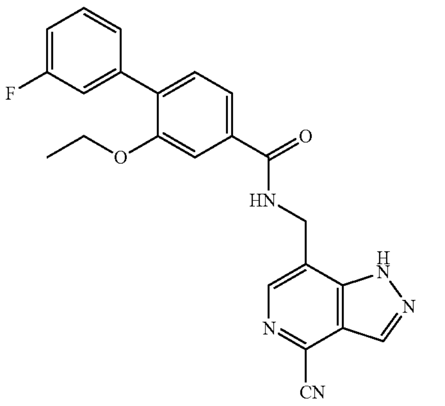 [SMILES: CCOc1cc(C(=O)NCc2cnc(C#N)c3cn[nH]c23)ccc1-c1cccc(F)c1] | 215 |

TABLE 8-continued
| Structure | No. |
|---|---|
| 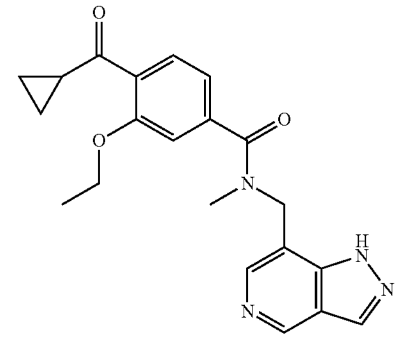 [SMILES: CCOc1cc(C(=O)N(C)Cc2cncc3cn[nH]c23)ccc1C(=O)C1CC1] | 216 |
| 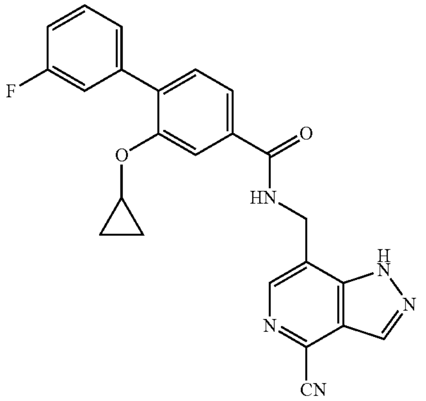 [SMILES: N#Cc1ncc(CNC(=O)c2ccc(-c3cccc(F)c3)c(OC3CC3)c2)c2[nH]ncc12] | 217 |
| 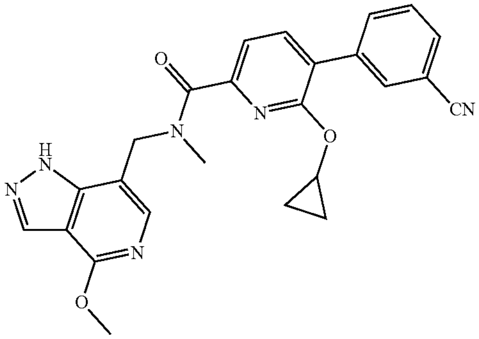 [SMILES: COc1ncc(CN(C)C(=O)c2ccc(-c3cccc(C#N)c3)c(OC3CC3)n2)c2[nH]ncc12] | 218 |
| 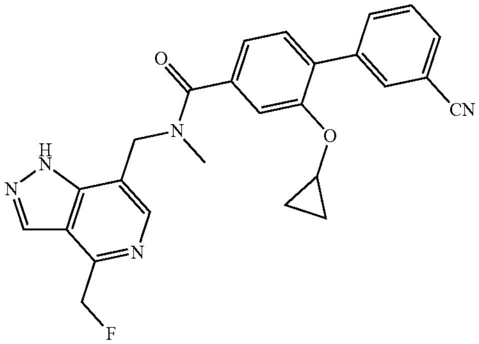 [SMILES: CN(Cc1cnc(CF)c2cn[nH]c12)C(=O)c1ccc(-c2cccc(C#N)c2)c(OC2CC2)c1] | 219 |
TABLE 8-continued
| Structure | No. |
|---|---|
| 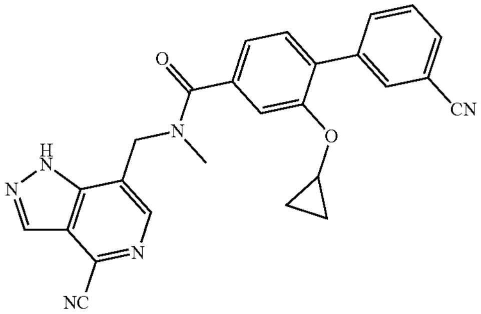 [SMILES: CN(Cc1cnc(C#N)c2cn[nH]c12)C(=O)c1ccc(-c2cccc(C#N)c2)c(OC2CC2)c1] | 220 |
| 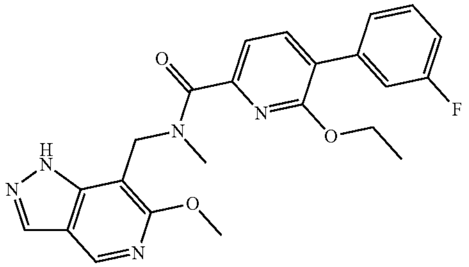 [SMILES: CCOc1nc(C(=O)N(C)Cc2c(OC)ncc3cn[nH]c23)ccc1-c1cccc(F)c1] | 221 |
| 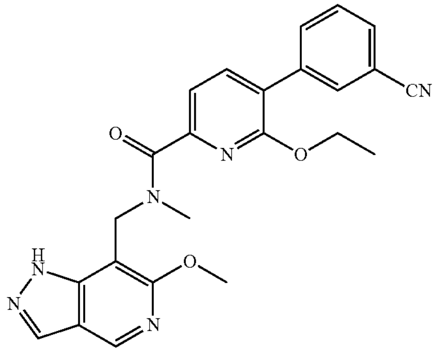 [SMILES: CCOc1nc(C(=O)N(C)Cc2c(OC)ncc3cn[nH]c23)ccc1-c1cccc(C#N)c1] | 222 |
| 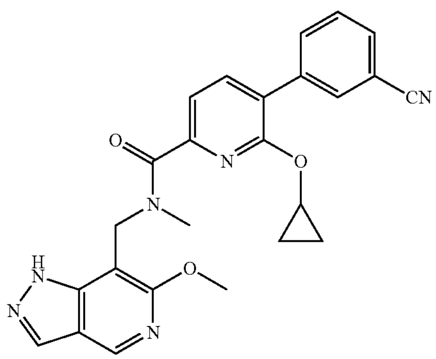 [SMILES: COc1ncc2cn[nH]c2c1CN(C)C(=O)c1ccc(-c2cccc(C#N)c2)c(OC2CC2)n1] | 223 |

TABLE 8-continued
| Structure | No. |
| --- | --- |
| 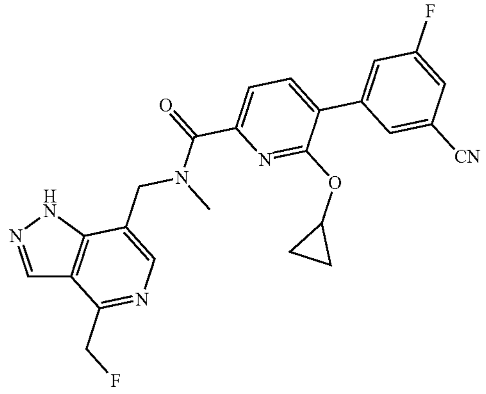 [SMILES: CN(Cc1cnc(CF)c2cn[nH]c12)C(=O)c1ccc(-c2cc(F)cc(C#N)c2)c(OC2CC2)n1] | 224 |
| 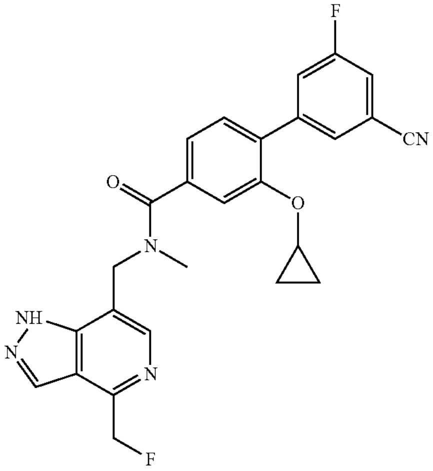 [SMILES: CN(Cc1cnc(CF)c2cn[nH]c12)C(=O)c1ccc(-c2cc(F)cc(C#N)c2)c(OC2CC2)c1] | 225 |
| 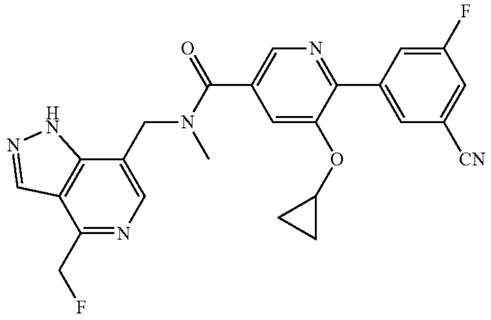 [SMILES: CN(Cc1cnc(CF)c2cn[nH]c12)C(=O)c1cnc(-c2cc(F)cc(C#N)c2)c(OC2CC2)c1] | 226 |
| 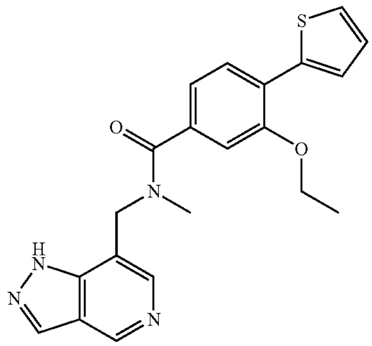 [SMILES: CCOc1cc(C(=O)N(C)Cc2cncc3cn[nH]c23)ccc1-c1cccs1] | 227 |
TABLE 8-continued
| Structure | No. |
| --- | --- |
| 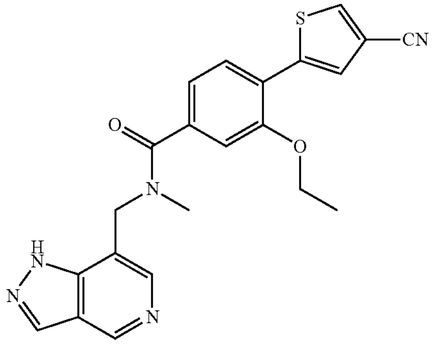 [SMILES: CCOc1cc(C(=O)N(C)Cc2cncc3cn[nH]c23)ccc1-c1cc(C#N)cs1] | 228 |
| 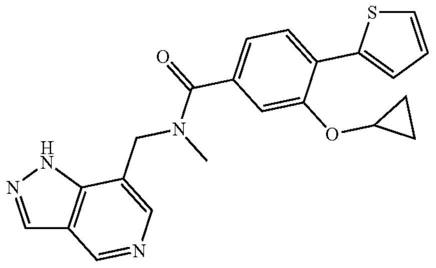 [SMILES: CN(Cc1cncc2cn[nH]c12)C(=O)c1ccc(-c2cccs2)c(OC2CC2)c1] | 229 |
| 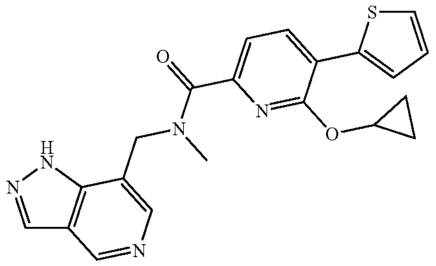 [SMILES: CN(Cc1cncc2cn[nH]c12)C(=O)c1ccc(-c2cccs2)c(OC2CC2)n1] | 230 |
| 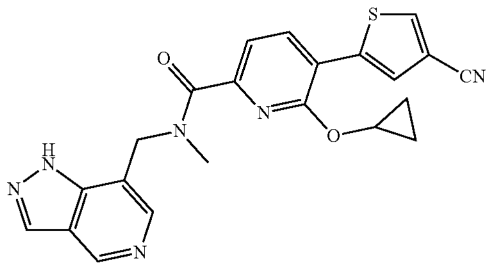 | 231 |
| 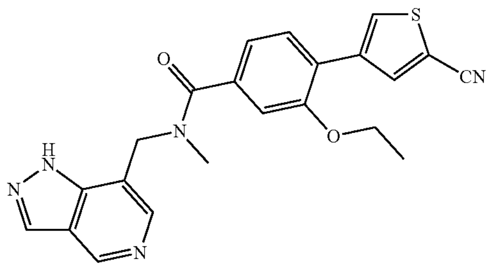 [SMILES: CCOc1cc(C(=O)N(C)Cc2cncc3cn[nH]c23)ccc1-c1csc(C#N)c1] | 232 |

TABLE 8-continued
| Structure | No. |
| --- | --- |
| 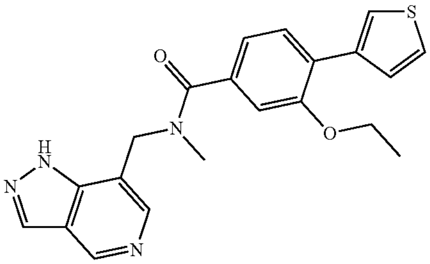 [SMILES: CCOc1cc(C(=O)N(C)Cc2cncc3cn[nH]c23)ccc1-c1ccsc1] | 233 |
| 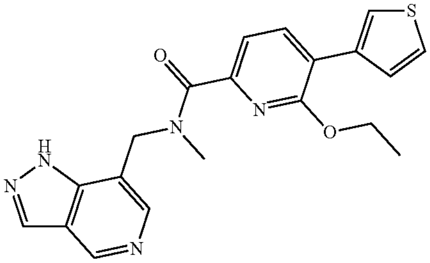 [SMILES: CCOc1nc(C(=O)N(C)Cc2cncc3cn[nH]c23)ccc1-c1ccsc1] | 234 |
| 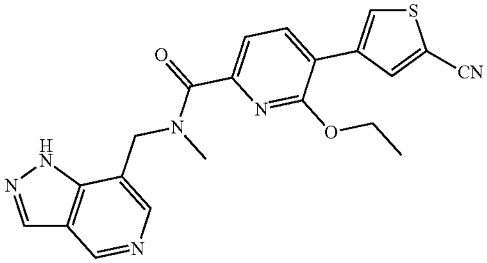 | 235 |
| 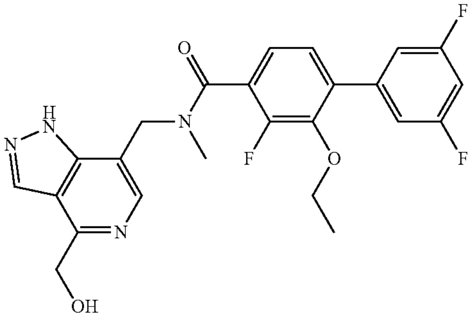 [SMILES: CCOc1c(-c2cc(F)cc(F)c2)ccc(C(=O)N(C)Cc2cnc(CO)c3cn[nH]c23)c1F] | 236 |
| 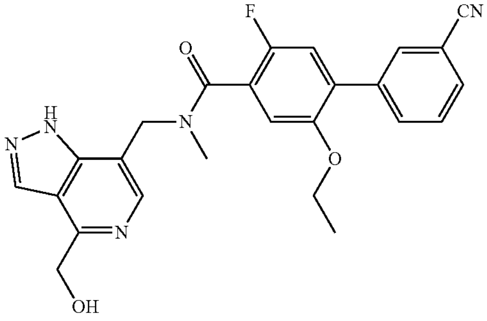 [SMILES: CCOc1cc(C(=O)N(C)Cc2cnc(CO)c3cn[nH]c23)c(F)cc1-c1cccc(C#N)c1] | 237 |
TABLE 8-continued
| Structure | No. |
| --- | --- |
| 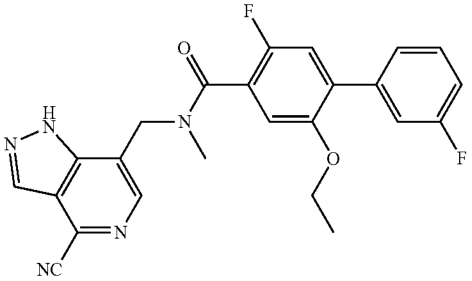 [SMILES: CCOc1cc(C(=O)N(C)Cc2cnc(C#N)c3cn[nH]c23)c(F)cc1-c1cccc(F)c1] | 238 |
| 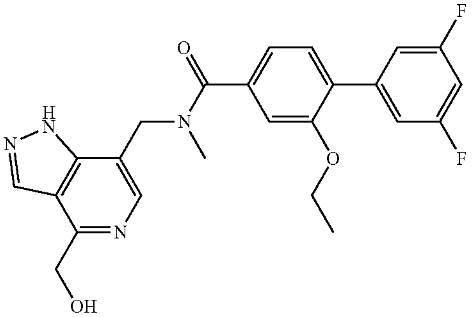 [SMILES: CCOc1cc(C(=O)N(C)Cc2cnc(CO)c3cn[nH]c23)ccc1-c1cc(F)cc(F)c1] | 239 |
| 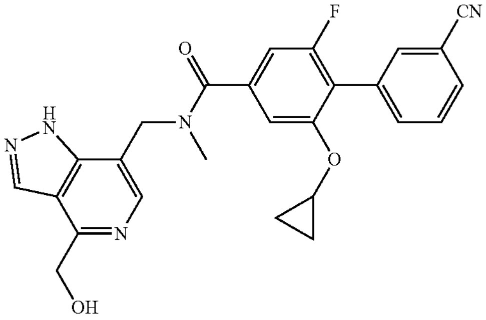 [SMILES: CN(Cc1cnc(CO)c2cn[nH]c12)C(=O)c1cc(F)c(-c2cccc(C#N)c2)c(OC2CC2)c1] | 240 |
| 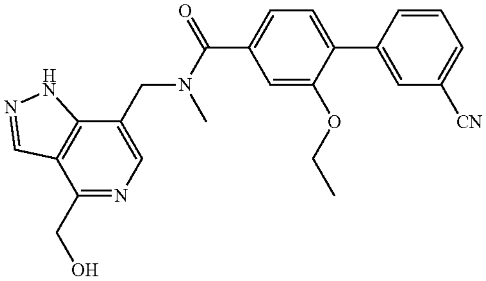 | 241 |
| 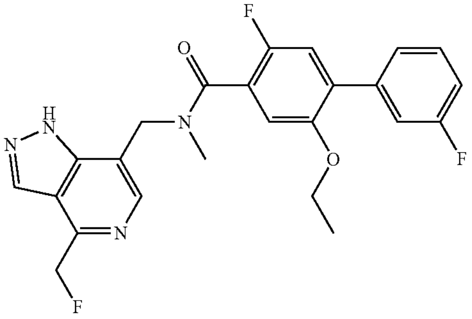 [SMILES: CCOc1cc(C(=O)N(C)Cc2cnc(CF)c3cn[nH]c23)c(F)cc1-c1cccc(F)c1] | 242 |

TABLE 8-continued
| Structure | No. |
| --- | --- |
| 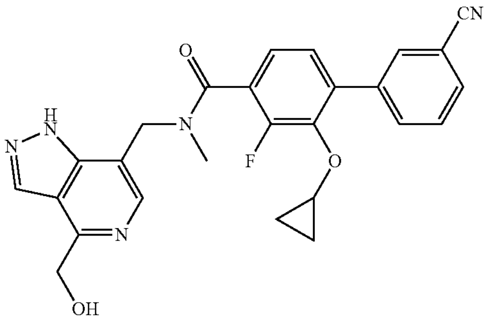 [SMILES: CN(Cc1cnc(CO)c2cn[nH]c12)C(=O)c1ccc(-c2cccc(C#N)c2)c(OC2CC2)c1F] | 243 |
| 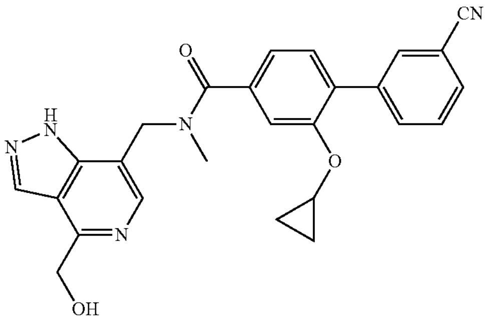 [SMILES: CN(Cc1cnc(CO)c2cn[nH]c12)C(=O)c1ccc(-c2cccc(C#N)c2)c(OC2CC2)c1] | 244 |
| 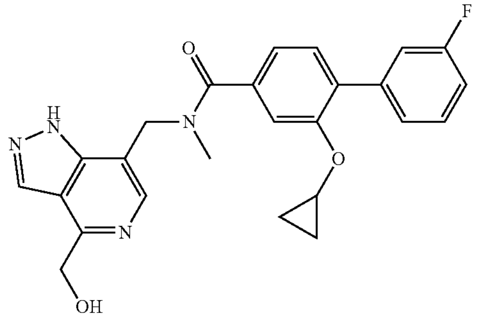 | 245 |
| 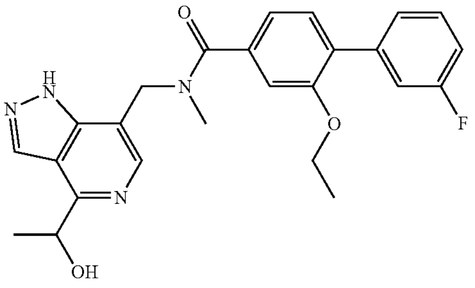 [SMILES: CCOc1cc(C(=O)N(C)Cc2cnc(C(C)O)c3cn[nH]c23)ccc1-c1cccc(F)c1] | 246 |
| 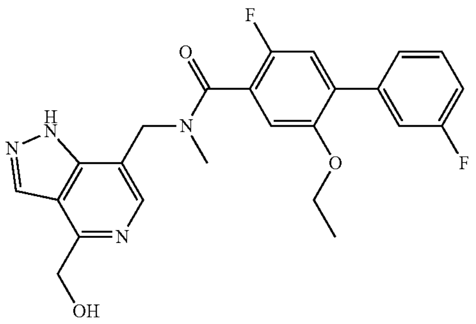 [SMILES: CCOc1cc(C(=O)N(C)Cc2cnc(CO)c3cn[nH]c23)c(F)cc1-c1cccc(F)c1] | 247 |
TABLE 8-continued
| Structure | No. |
| --- | --- |
| 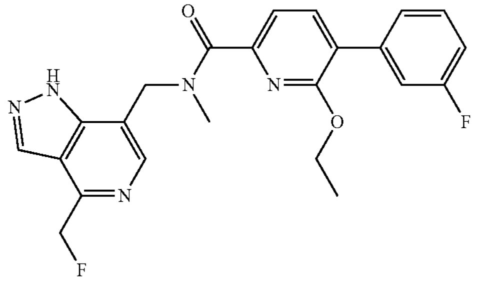 [SMILES: CCOc1nc(C(=O)N(C)Cc2cnc(CF)c3cn[nH]c23)ccc1-c1cccc(F)c1] | 248 |
| 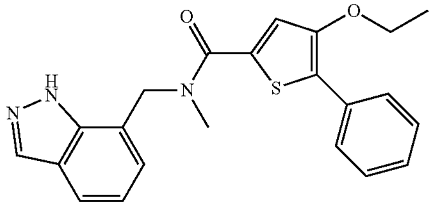 [SMILES: CCOc1cc(C(=O)N(C)Cc2cccc3cn[nH]c23)sc1-c1ccccc1] | 249 |
| 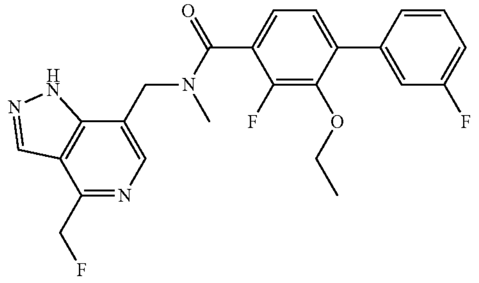 [SMILES: CCOc1c(-c2cccc(F)c2)ccc(C(=O)N(C)Cc2cnc(CF)c3cn[nH]c23)c1F] | 250 |
| 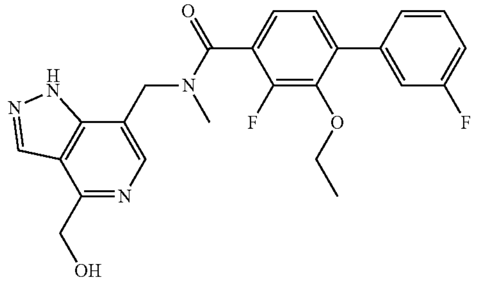 | 251 |
| 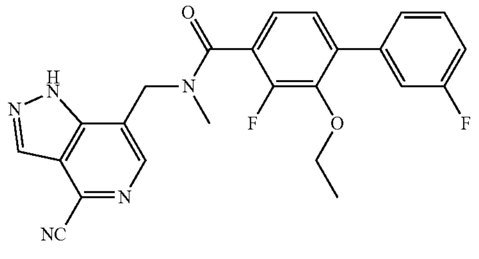 [SMILES: CCOc1c(-c2cccc(F)c2)ccc(C(=O)N(C)Cc2cnc(C#N)c3cn[nH]c23)c1F] | 252 |
| 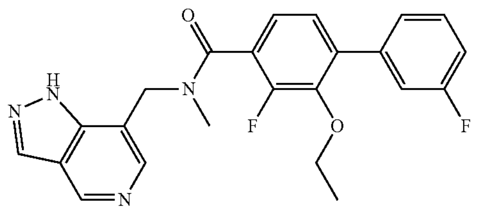 [SMILES: CCOc1c(-c2cccc(F)c2)ccc(C(=O)N(C)Cc2cncc3cn[nH]c23)c1F] | 253 |

TABLE 8-continued
| Structure | No. |
|---|---|
| 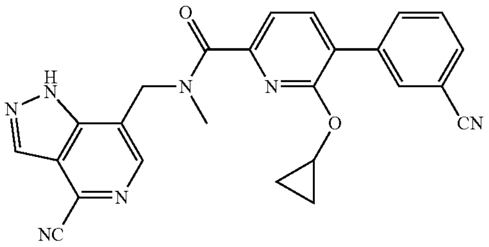 [SMILES: CN(Cc1cnc(C#N)c2cn[nH]c12)C(=O)c1ccc(-c2cccc(C#N)c2)c(OC2CC2)n1] | 254 |
| 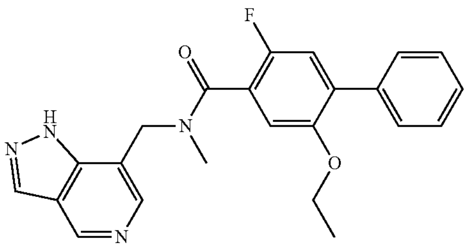 [SMILES: CCOc1cc(C(=O)N(C)Cc2cncc3cn[nH]c23)c(F)cc1-c1ccccc1] | 255 |
| 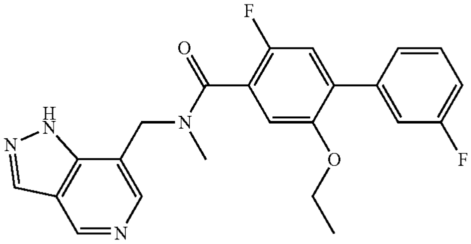 [SMILES: CCOc1cc(C(=O)N(C)Cc2cncc3cn[nH]c23)c(F)cc1-c1cccc(F)c1] | 256 |
| 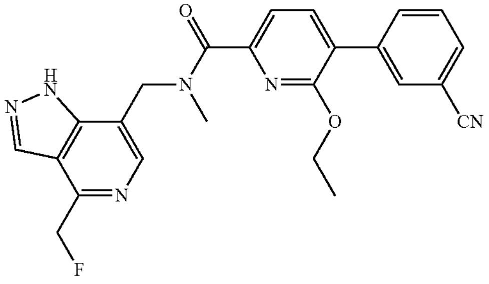 [SMILES: CCOc1nc(C(=O)N(C)Cc2cnc(CF)c3cn[nH]c23)ccc1-c1cccc(C#N)c1] | 257 |
| 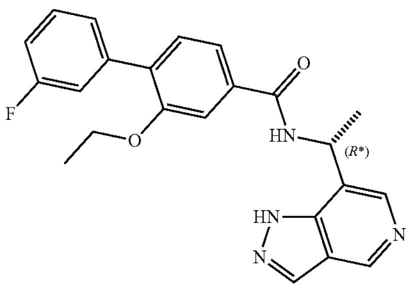 [SMILES: CCOc1cc(C(=O)N[C@H](C)c2cncc3cn[nH]c23)ccc1-c1cccc(F)c1] | 258 |
TABLE 8-continued
| Structure | No. |
|---|---|
| 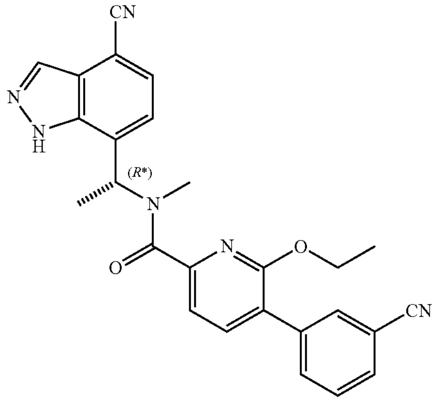 [SMILES: CCOc1nc(C(=O)N(C)[C@H](C)c2ccc(C#N)c3cn[nH]c23)ccc1-c1cccc(C#N)c1] | 259 |
| 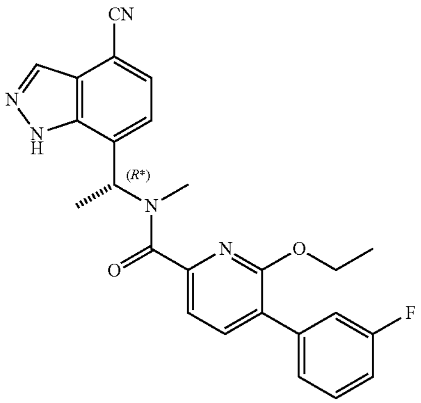 [SMILES: CCOc1nc(C(=O)N(C)[C@H](C)c2ccc(C#N)c3cn[nH]c23)ccc1-c1cccc(F)c1] | 260 |
| 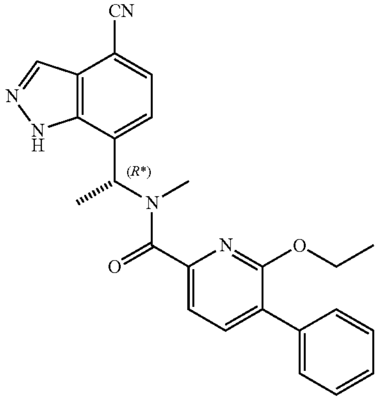 [SMILES: CCOc1nc(C(=O)N(C)[C@H](C)c2ccc(C#N)c3cn[nH]c23)ccc1-c1ccccc1] | 261 |
| 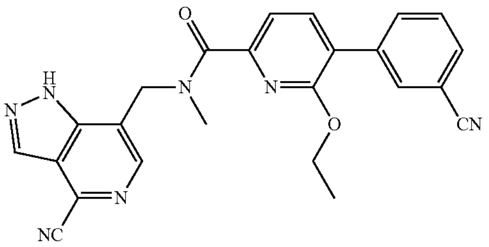 | 262 |

TABLE 8-continued
| Structure | No. |
| --- | --- |
| 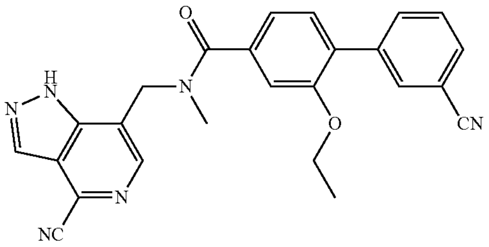 [SMILES: CCOc1cc(C(=O)N(C)Cc2cnc(C#N)c3cn[nH]c23)ccc1-c1cccc(C#N)c1] | 263 |
| 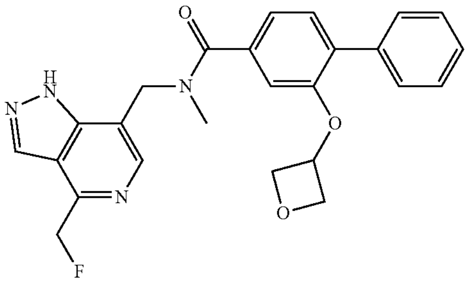 [SMILES: CN(Cc1cnc(CF)c2cn[nH]c12)C(=O)c1ccc(-c2ccccc2)c(OC2COC2)c1] | 264 |
| 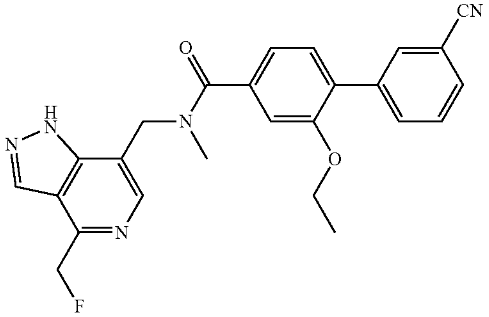 [SMILES: CCOc1cc(C(=O)N(C)Cc2cnc(CF)c3cn[nH]c23)ccc1-c1cccc(C#N)c1] | 265 |
| 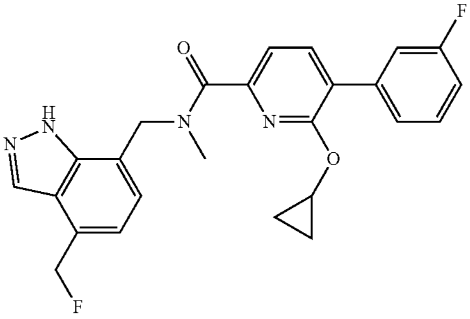 [SMILES: CN(Cc1ccc(CF)c2cn[nH]c12)C(=O)c1ccc(-c2cccc(F)c2)c(OC2CC2)n1] | 266 |
| 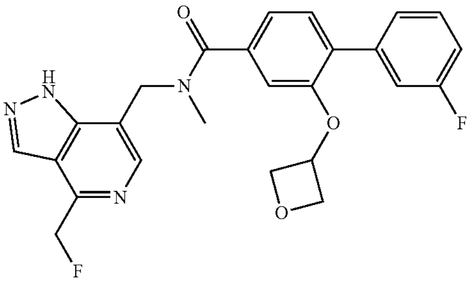 [SMILES: CN(Cc1cnc(CF)c2cn[nH]c12)C(=O)c1ccc(-c2cccc(F)c2)c(OC2COC2)c1] | 267 |
TABLE 8-continued
| Structure | No. |
| --- | --- |
| 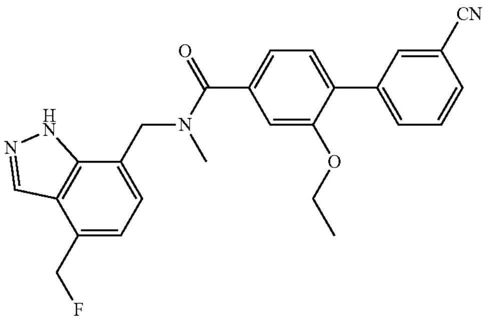 [SMILES: CCOc1cc(C(=O)N(C)Cc2ccc(CF)c3cn[nH]c23)ccc1-c1cccc(C#N)c1] | 268 |
| 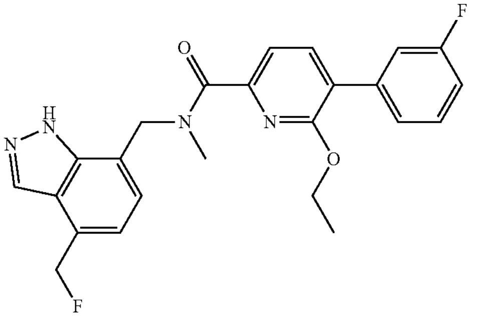 [SMILES: CCOc1nc(C(=O)N(C)Cc2ccc(CF)c3cn[nH]c23)ccc1-c1cccc(F)c1] | 269 |
| 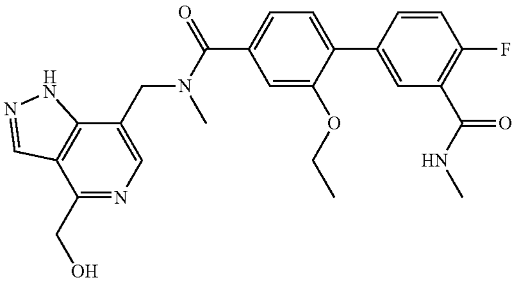 [SMILES: CCOc1cc(C(=O)N(C)Cc2cnc(CO)c3cn[nH]c23)ccc1-c1ccc(F)c(C(=O)NC)c1] | 270 |
| 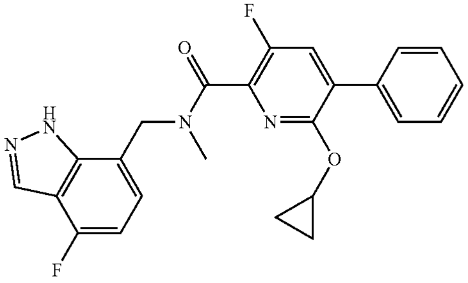 [SMILES: CN(Cc1ccc(F)c2cn[nH]c12)C(=O)c1nc(OC2CC2)c(-c2ccccc2)cc1F] | 271 |
| 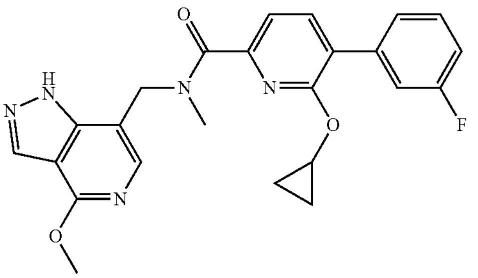 [SMILES: COc1ncc(CN(C)C(=O)c2ccc(-c3cccc(F)c3)c(OC3CC3)n2)c2[nH]ncc12] | 272 |

TABLE 8-continued
| Structure | No. |
|---|---|
| 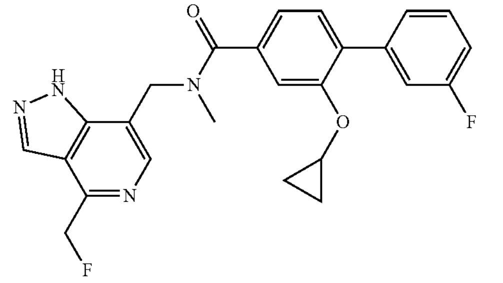 [SMILES: CN(Cc1cnc(CF)c2cn[nH]c12)C(=O)c1ccc(-c2cccc(F)c2)c(OC2CC2)c1] | 273 |
| 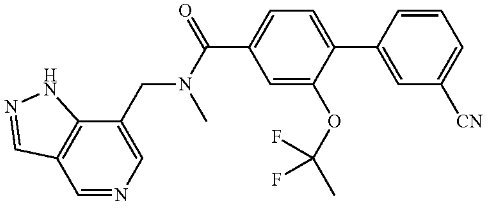 [SMILES: CN(Cc1cncc2cn[nH]c12)C(=O)c1ccc(-c2cccc(C#N)c2)c(OC(C)(F)F)c1] | 274 |
| 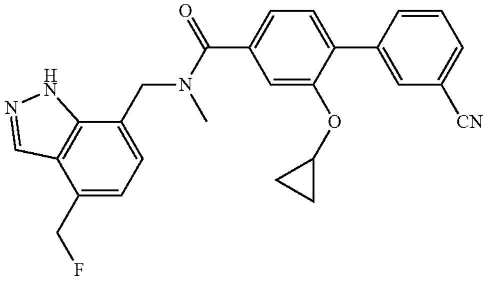 [SMILES: CN(Cc1ccc(CF)c2cn[nH]c12)C(=O)c1ccc(-c2cccc(C#N)c2)c(OC2CC2)c1] | 275 |
| 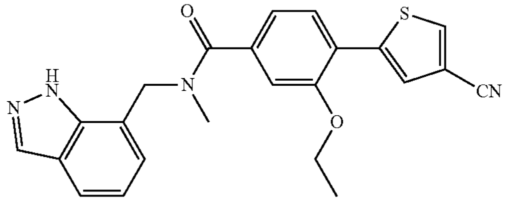 [SMILES: CCOc1cc(C(=O)N(C)Cc2cccc3cn[nH]c23)ccc1-c1cc(C#N)cs1] | 276 |
| 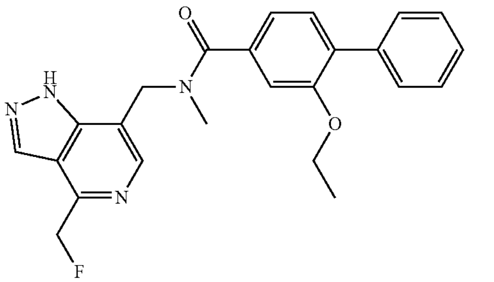 [SMILES: CCOc1cc(C(=O)N(C)Cc2cnc(CF)c3cn[nH]c23)ccc1-c1ccccc1] | 277 |
| 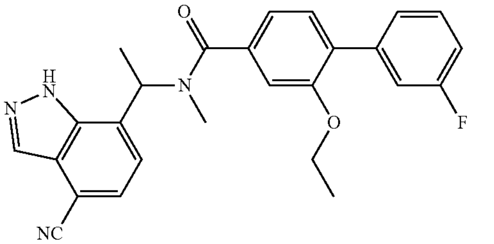 [SMILES: CCOc1cc(C(=O)N(C)C(C)c2ccc(C#N)c3cn[nH]c23)ccc1-c1cccc(F)c1] | 278 |
TABLE 8-continued
| Structure | No. |
|---|---|
| 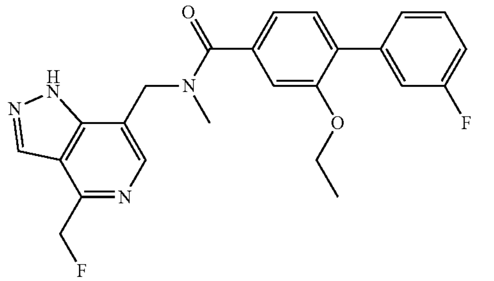 [SMILES: CCOc1cc(C(=O)N(C)Cc2cnc(CF)c3cn[nH]c23)ccc1-c1cccc(F)c1] | 279 |
| 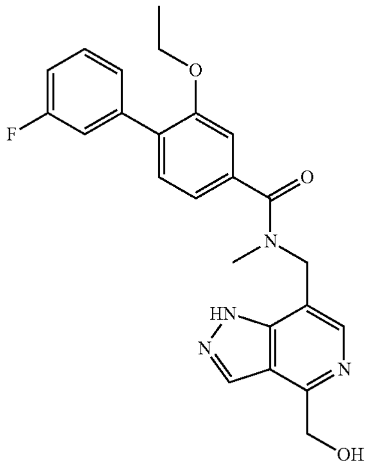 [SMILES: CCOc1cc(C(=O)N(C)Cc2cnc(CO)c3cn[nH]c23)ccc1-c1cccc(F)c1] | 280 |
| 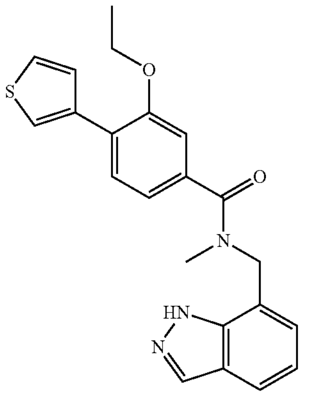 [SMILES: CCOc1cc(C(=O)N(C)Cc2cccc3cn[nH]c23)ccc1-c1ccsc1] | 281 |
| 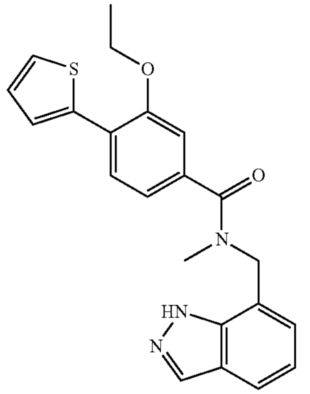 [SMILES: CCOc1cc(C(=O)N(C)Cc2cccc3cn[nH]c23)ccc1-c1cccs1] | 282 |

TABLE 8-continued
| Structure | No. |
| --- | --- |
| 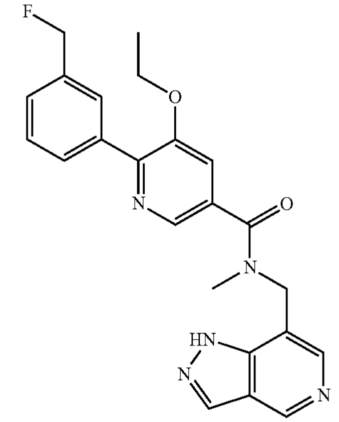 [SMILES: CCOc1cc(C(=O)N(C)Cc2cncc3cn[nH]c23)cnc1-c1cccc(CF)c1] | 283 |
| 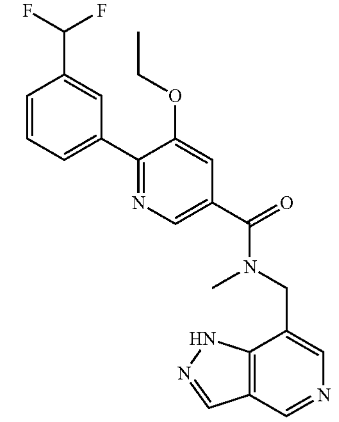 [SMILES: CCOc1cc(C(=O)N(C)Cc2cncc3cn[nH]c23)cnc1-c1cccc(C(F)F)c1] | 284 |
| 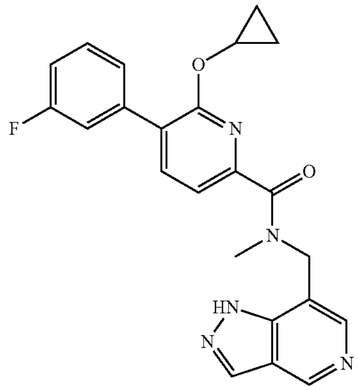 | 285 |
TABLE 8-continued
| Structure | No. |
| --- | --- |
| 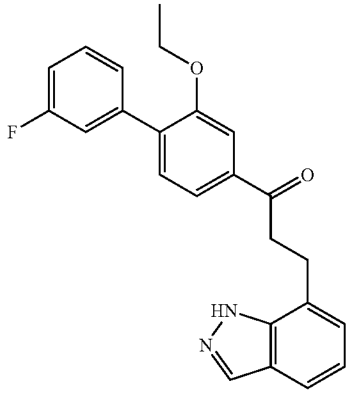 [SMILES: CCOc1cc(C(=O)CCc2cccc3cn[nH]c23)ccc1-c1cccc(F)c1] | 286 |
| 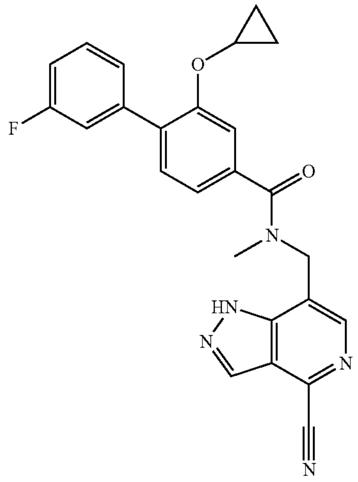 [SMILES: CN(Cc1cnc(C#N)c2cn[nH]c12)C(=O)c1ccc(-c2cccc(F)c2)c(OC2CC2)c1] | 287 |
| 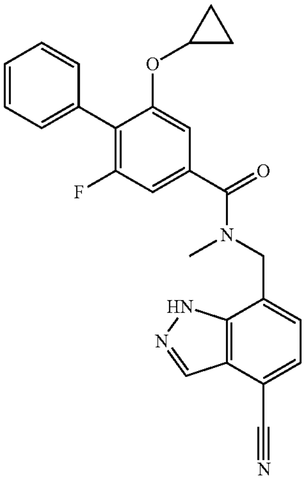 [SMILES: CN(Cc1ccc(C#N)c2cn[nH]c12)C(=O)c1cc(F)c(-c2ccccc2)c(OC2CC2)c1] | 288 |

TABLE 8-continued
| Structure | No. |
|---|---|
| 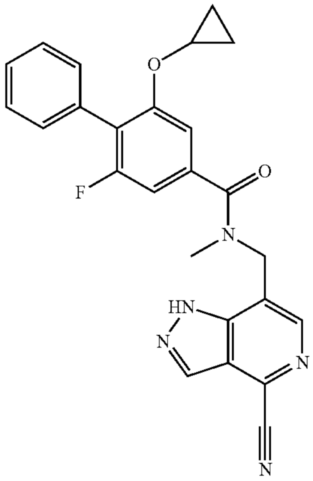 [SMILES: CN(Cc1cnc(C#N)c2cn[nH]c12)C(=O)c1cc(F)c(-c2ccccc2)c(OC2CC2)c1] | 289 |
| 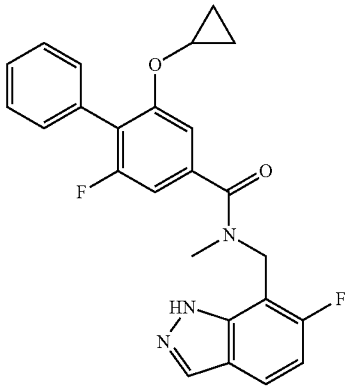 [SMILES: CN(Cc1c(F)ccc2cn[nH]c12)C(=O)c1cc(F)c(-c2ccccc2)c(OC2CC2)c1] | 290 |
| 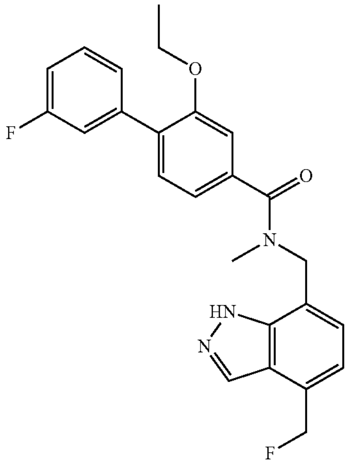 [SMILES: CCOc1cc(C(=O)N(C)Cc2ccc(CF)c3cn[nH]c23)ccc1-c1cccc(F)c1] | 291 |
TABLE 8-continued
| Structure | No. |
|---|---|
| 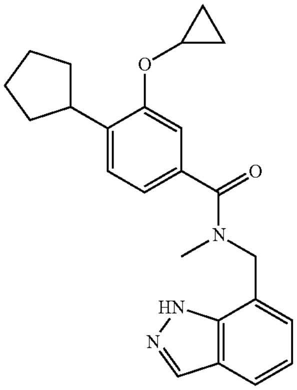 [SMILES: CN(Cc1cccc2cn[nH]c12)C(=O)c1ccc(C2CCCC2)c(OC2CC2)c1] | 292 |
| 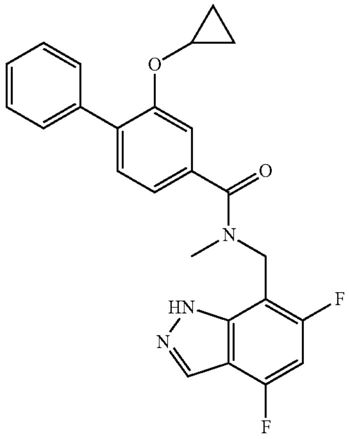 [SMILES: CN(Cc1c(F)cc(F)c2cn[nH]c12)C(=O)c1ccc(-c2ccccc2)c(OC2CC2)c1] | 293 |
| 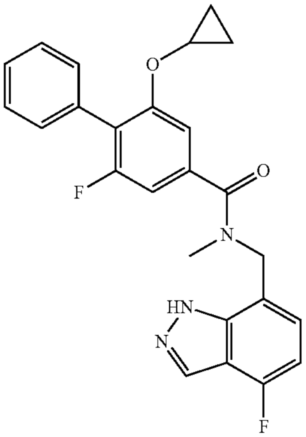 [SMILES: CN(Cc1ccc(F)c2cn[nH]c12)C(=O)c1cc(F)c(-c2ccccc2)c(OC2CC2)c1] | 294 |

TABLE 8-continued
| Structure | No. |
| --- | --- |
| 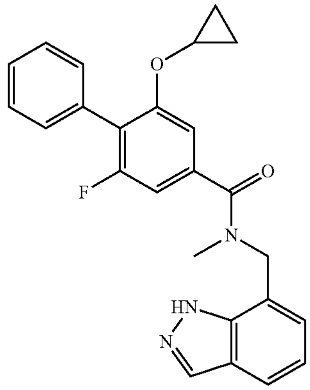 [SMILES: CN(Cc1cccc2cn[nH]c12)C(=O)c1cc(F)c(-c2ccccc2)c(OC2CC2)c1] | 295 |
| 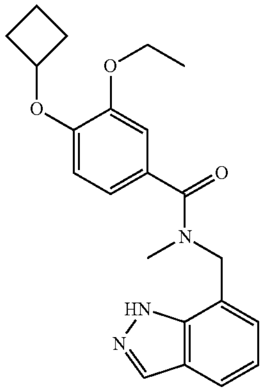 [SMILES: CCOc1cc(C(=O)N(C)Cc2cccc3cn[nH]c23)ccc1OC1CCC1] | 296 |
| 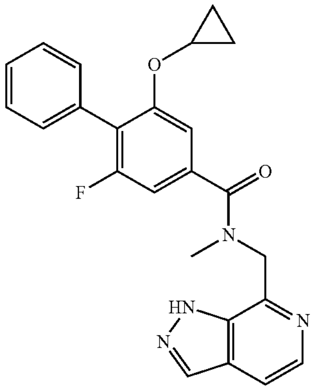 [SMILES: CN(Cc1nccc2cn[nH]c12)C(=O)c1cc(F)c(-c2ccccc2)c(OC2CC2)c1] | 297 |
| 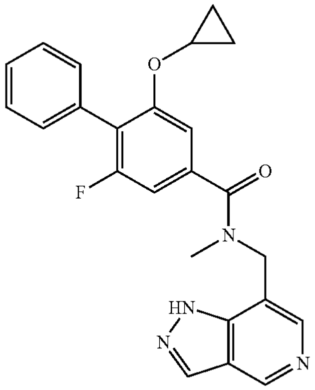 [SMILES: CN(Cc1cncc2cn[nH]c12)C(=O)c1cc(F)c(-c2ccccc2)c(OC2CC2)c1] | 298 |
| 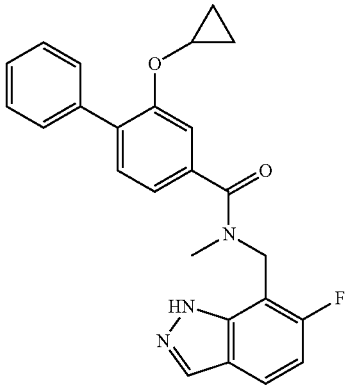 [SMILES: CN(Cc1c(F)ccc2cn[nH]c12)C(=O)c1ccc(-c2ccccc2)c(OC2CC2)c1] | 299 |
| 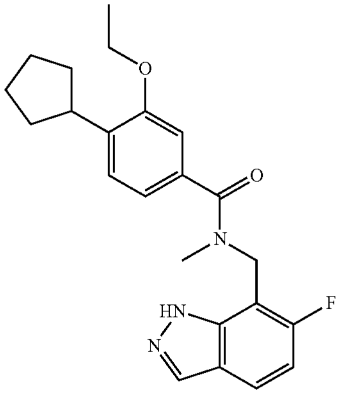 [SMILES: CCOc1cc(C(=O)N(C)Cc2c(F)ccc3cn[nH]c23)ccc1C1CCCC1] | 300 |
| 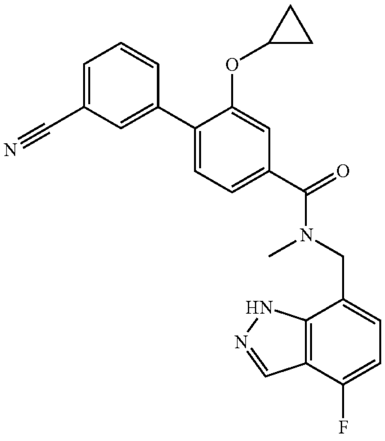 [SMILES: CN(Cc1ccc(F)c2cn[nH]c12)C(=O)c1ccc(-c2cccc(C#N)c2)c(OC2CC2)c1] | 301 |

TABLE 8-continued
| Structure | No. |
|---|---|
| 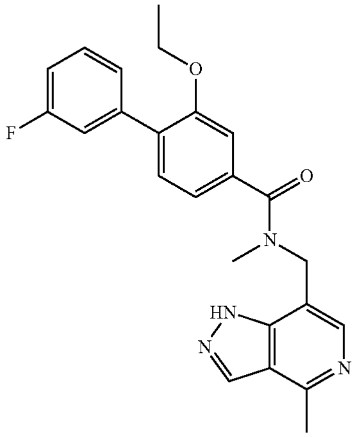 [SMILES: CCOc1cc(C(=O)N(C)Cc2cnc(C)c3cn[nH]c23)ccc1-c1cccc(F)c1] | 302 |
| 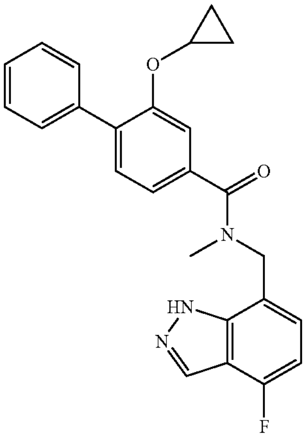 [SMILES: CN(Cc1ccc(F)c2cn[nH]c12)C(=O)c1ccc(-c2ccccc2)c(OC2CC2)c1] | 303 |
| 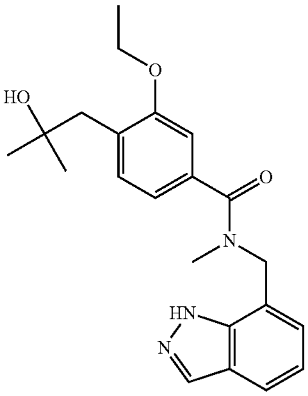 [SMILES: CCOc1cc(C(=O)N(C)Cc2cccc3cn[nH]c23)ccc1CC(C)(C)O] | 304 |
| 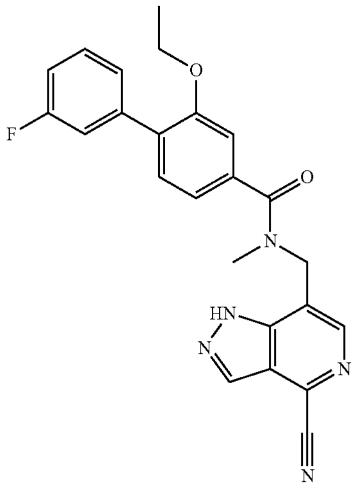 [SMILES: CCOc1cc(C(=O)N(C)Cc2cnc(C#N)c3cn[nH]c23)ccc1-c1cccc(F)c1] | 305 |
| 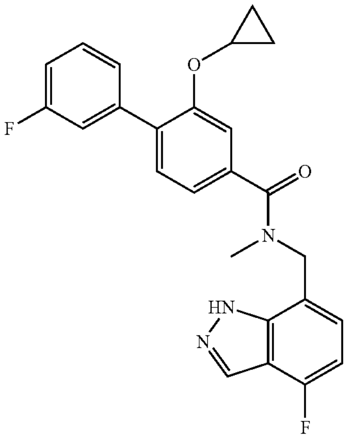 [SMILES: CN(Cc1ccc(F)c2cn[nH]c12)C(=O)c1ccc(-c2cccc(F)c2)c(OC2CC2)c1] | 306 |
| 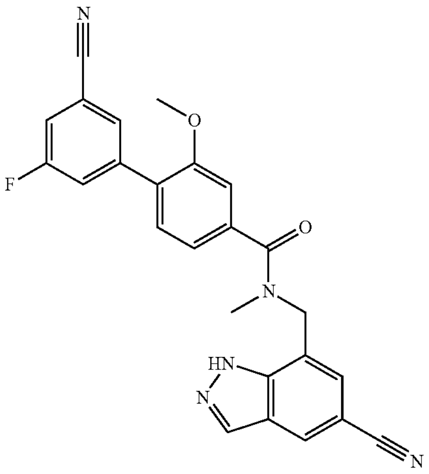 [SMILES: COc1cc(C(=O)N(C)Cc2cc(C#N)cc3cn[nH]c23)ccc1-c1cc(F)cc(C#N)c1] | 307 |

TABLE 8-continued
| Structure | No. |
|---|---|
| 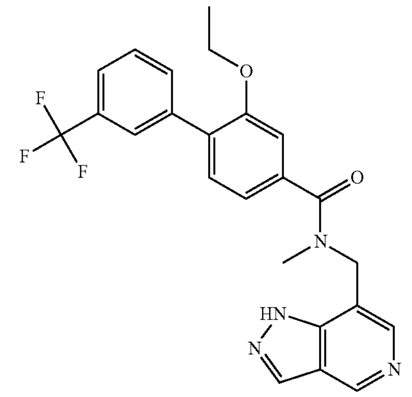 [SMILES: CCOc1cc(C(=O)N(C)Cc2cncc3cn[nH]c23)ccc1-c1cccc(C(F)(F)F)c1] | 308 |
| 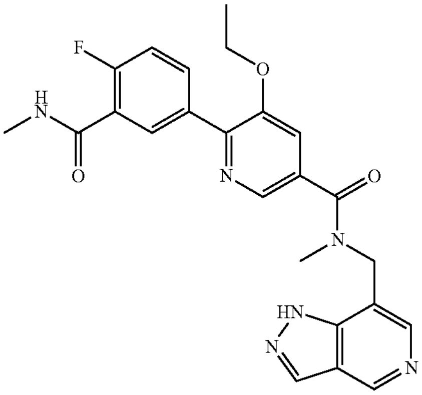 [SMILES: CCOc1cc(C(=O)N(C)Cc2cncc3cn[nH]c23)cnc1-c1ccc(F)c(C(=O)NC)c1] | 309 |
| 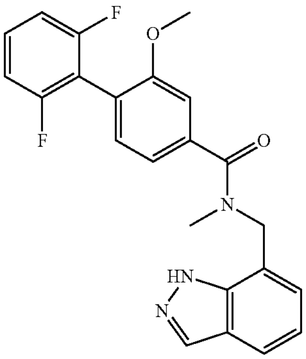 [SMILES: COc1cc(C(=O)N(C)Cc2cccc3cn[nH]c23)ccc1-c1c(F)cccc1F] | 310 |
| 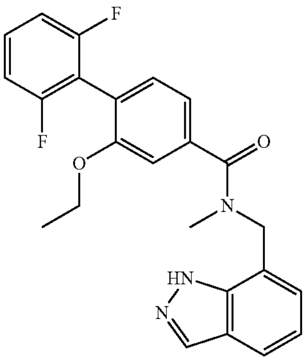 [SMILES: CCOc1cc(C(=O)N(C)Cc2cccc3cn[nH]c23)ccc1-c1c(F)cccc1F] | 311 |
TABLE 8-continued
| Structure | No. |
|---|---|
| 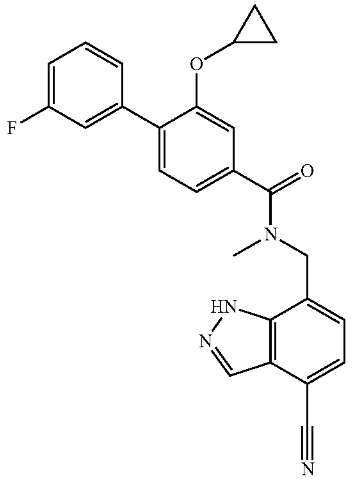 [SMILES: CN(Cc1ccc(C#N)c2cn[nH]c12)C(=O)c1ccc(-c2cccc(F)c2)c(OC2CC2)c1] | 312 |
| 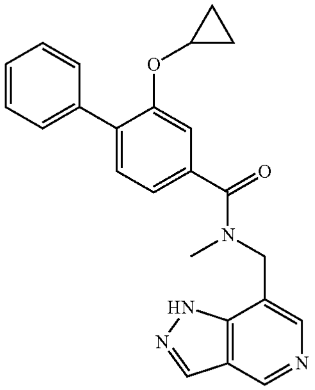 [SMILES: CN(Cc1cncc2cn[nH]c12)C(=O)c1ccc(-c2ccccc2)c(OC2CC2)c1] | 313 |
| 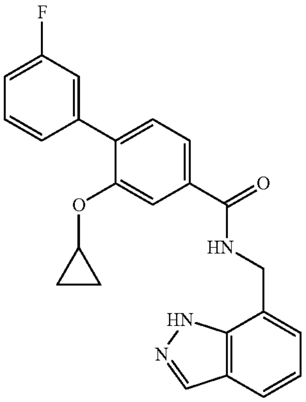 [SMILES: O=C(NCc1cccc2cn[nH]c12)c1ccc(-c2cccc(F)c2)c(OC2CC2)c1] | 314 |

TABLE 8-continued
| Structure | No. |
| --- | --- |
| 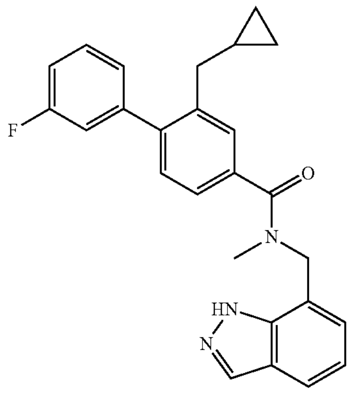 [SMILES: CN(Cc1cccc2cn[nH]c12)C(=O)c1ccc(-c2cccc(F)c2)c(CC2CC2)c1] | 315 |
| 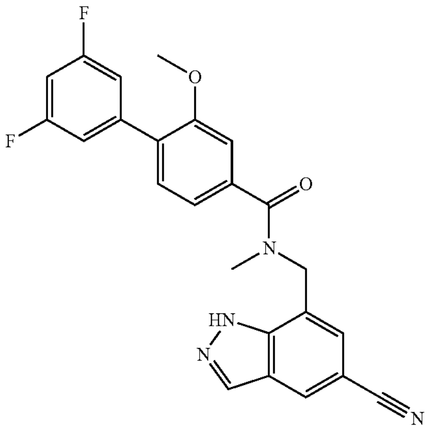 [SMILES: COc1cc(C(=O)N(C)Cc2cc(C#N)cc3cn[nH]c23)ccc1-c1cc(F)cc(F)c1] | 316 |
| 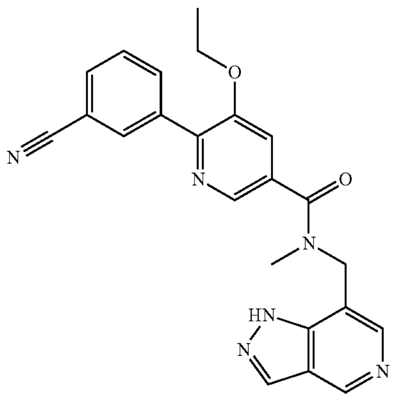 | 317 |
TABLE 8-continued
| Structure | No. |
| --- | --- |
| 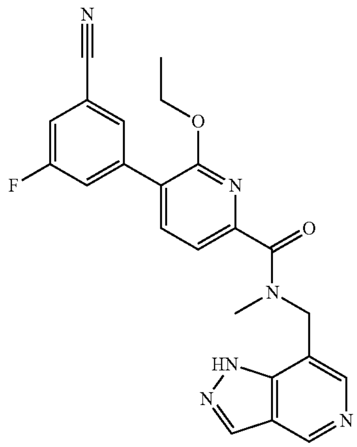 [SMILES: CCOc1nc(C(=O)N(C)Cc2cncc3cn[nH]c23)ccc1-c1cc(F)cc(C#N)c1] | 318 |
| 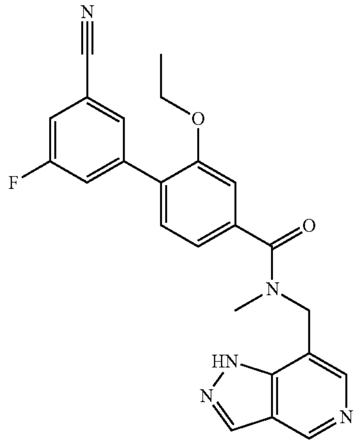 [SMILES: CCOc1cc(C(=O)N(C)Cc2cncc3cn[nH]c23)ccc1-c1cc(F)cc(C#N)c1] | 319 |
| 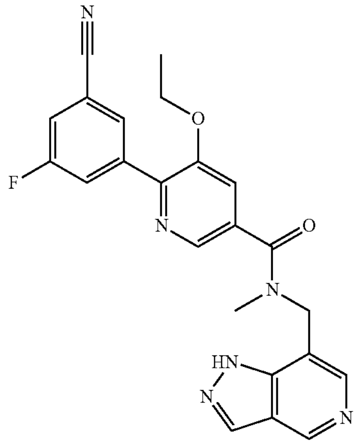 [SMILES: CCOc1cc(C(=O)N(C)Cc2cncc3cn[nH]c23)cnc1-c1cc(F)cc(C#N)c1] | 320 |

TABLE 8-continued
| Structure | No. |
|---|---|
| 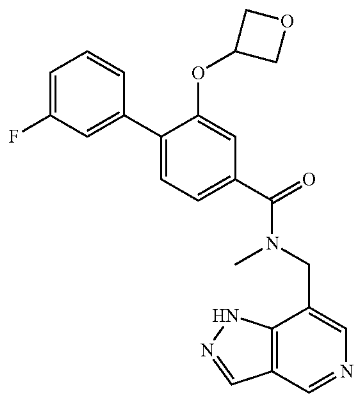 [SMILES: CN(Cc1cncc2cn[nH]c12)C(=O)c1ccc(-c2cccc(F)c2)c(OC2COC2)c1] | 321 |
| 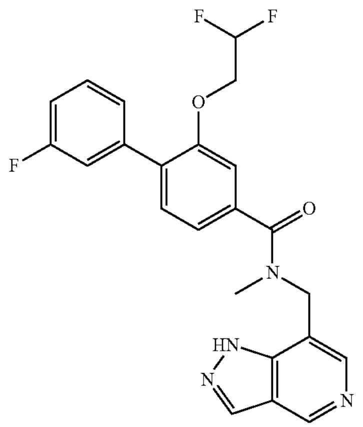 [SMILES: CN(Cc1cncc2cn[nH]c12)C(=O)c1ccc(-c2cccc(F)c2)c(OCC(F)F)c1] | 322 |
| 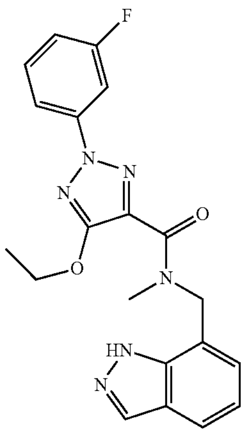 [SMILES: CCOc1nn(-c2cccc(F)c2)nc1C(=O)N(C)Cc1cccc2cn[nH]c12] | 323 |
TABLE 8-continued
| Structure | No. |
|---|---|
| 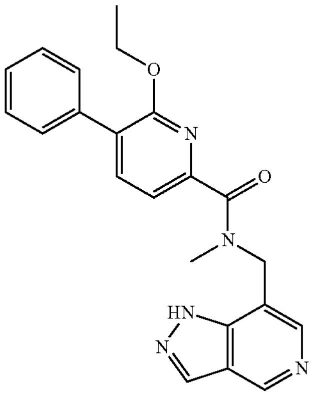 [SMILES: CCOc1nc(C(=O)N(C)Cc2cncc3cn[nH]c23)ccc1-c1ccccc1] | 324 |
| 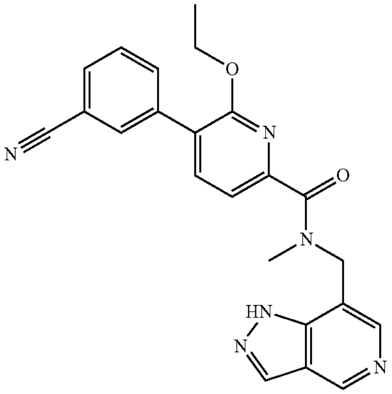 [SMILES: CCOc1nc(C(=O)N(C)Cc2cncc3cn[nH]c23)ccc1-c1cccc(C#N)c1] | 325 |
| 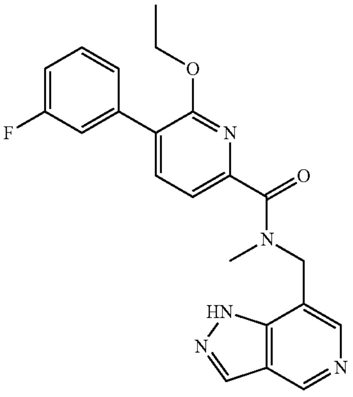 [SMILES: CCOc1nc(C(=O)N(C)Cc2cncc3cn[nH]c23)ccc1-c1cccc(F)c1] | 326 |
| 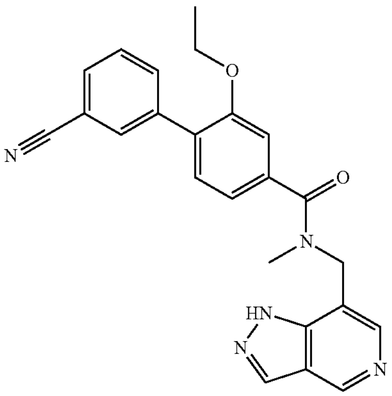 [SMILES: CCOc1cc(C(=O)N(C)Cc2cncc3cn[nH]c23)ccc1-c1cccc(C#N)c1] | 327 |

TABLE 8-continued
| Structure | No. |
|---|---|
| 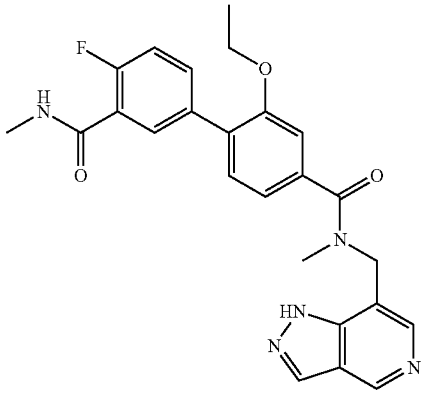 | 328 |
| 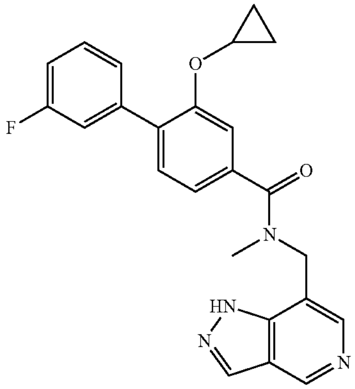 [SMILES: CN(Cc1cncc2cn[nH]c12)C(=O)c1ccc(-c2cccc(F)c2)c(OC2CC2)c1] | 329 |
| 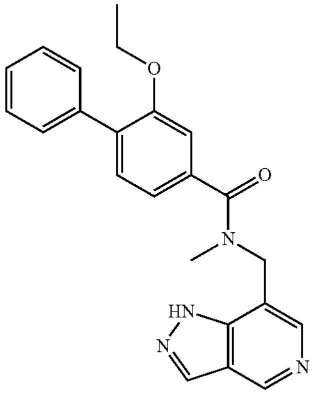 [SMILES: CCOc1cc(C(=O)N(C)Cc2cncc3cn[nH]c23)ccc1-c1ccccc1] | 330 |
TABLE 8-continued
| Structure | No. |
|---|---|
| 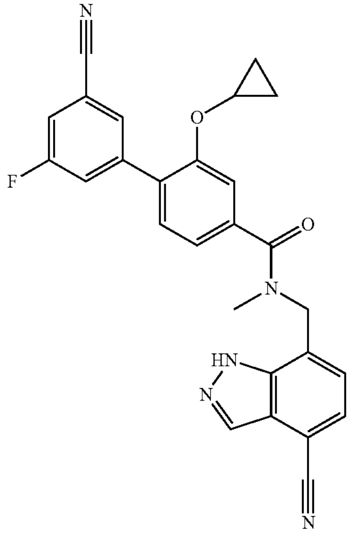 [SMILES: CN(Cc1ccc(C#N)c2cn[nH]c12)C(=O)c1ccc(-c2cc(F)cc(C#N)c2)c(OC2CC2)c1] | 331 |
| 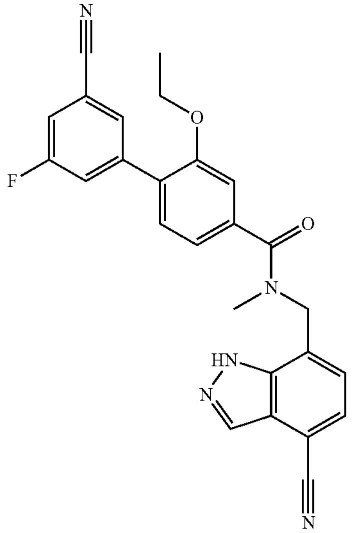 [SMILES: CCOc1cc(C(=O)N(C)Cc2ccc(C#N)c3cn[nH]c23)ccc1-c1cc(F)cc(C#N)c1] | 332 |
| 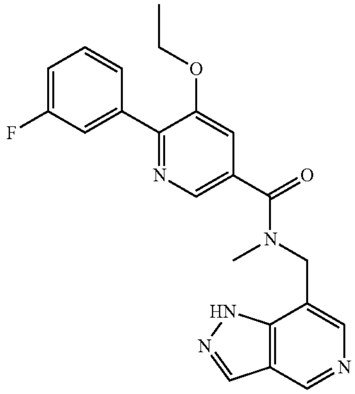 [SMILES: CCOc1cc(C(=O)N(C)Cc2cncc3cn[nH]c23)cnc1-c1cccc(F)c1] | 333 |

TABLE 8-continued
| Structure | No. |
| --- | --- |
| 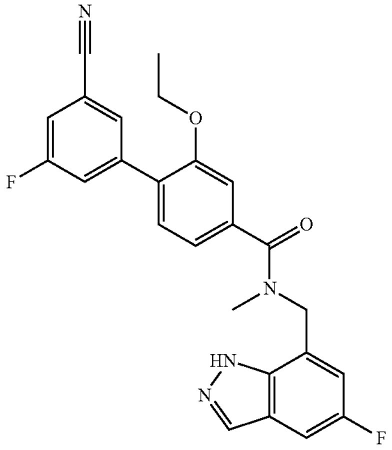 [SMILES: CCOc1cc(C(=O)N(C)Cc2cc(F)cc3cn[nH]c23)ccc1-c1cc(F)cc(C#N)c1] | 334 |
| 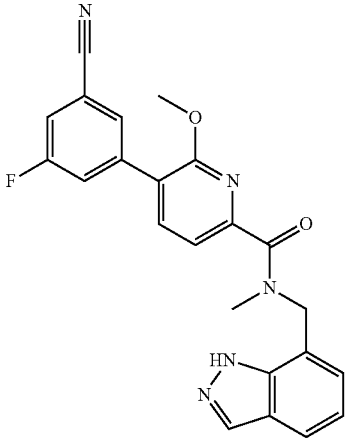 [SMILES: COc1nc(C(=O)N(C)Cc2cccc3cn[nH]c23)ccc1-c1cc(F)cc(C#N)c1] | 335 |
| 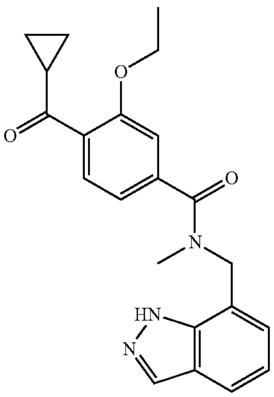 [SMILES: CCOc1cc(C(=O)N(C)Cc2cccc3cn[nH]c23)ccc1C(=O)C1CC1] | 336 |
TABLE 8-continued
| Structure | No. |
| --- | --- |
| 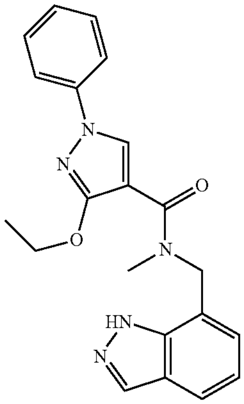 [SMILES: CCOc1nn(-c2ccccc2)cc1C(=O)N(C)Cc1cccc2cn[nH]c12] | 337 |
| 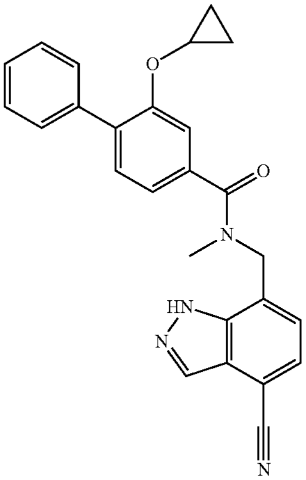 [SMILES: CN(Cc1ccc(C#N)c2cn[nH]c12)C(=O)c1ccc(-c2ccccc2)c(OC2CC2)c1] | 338 |
| 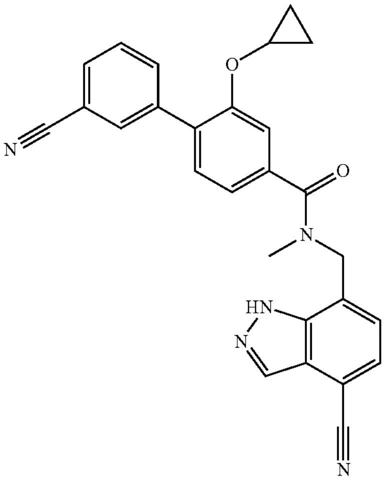 [SMILES: CN(Cc1ccc(C#N)c2cn[nH]c12)C(=O)c1ccc(-c2cccc(C#N)c2)c(OC2CC2)c1] | 339 |

TABLE 8-continued
| Structure | No. |
|---|---|
| 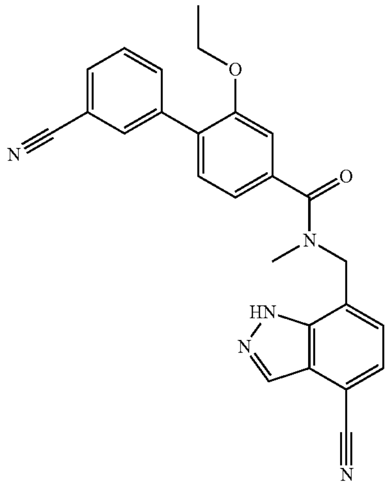 [SMILES: CCOc1cc(C(=O)N(C)Cc2ccc(C#N)c3cn[nH]c23)ccc1-c1cccc(C#N)c1] | 340 |
| 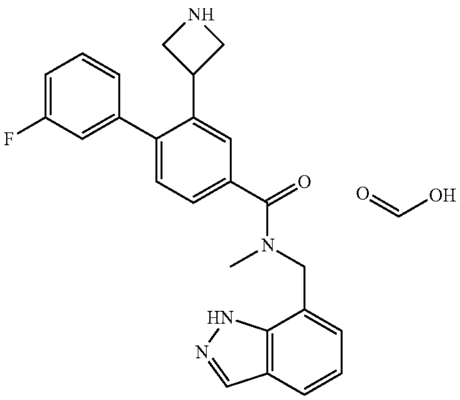 | 341 |
| 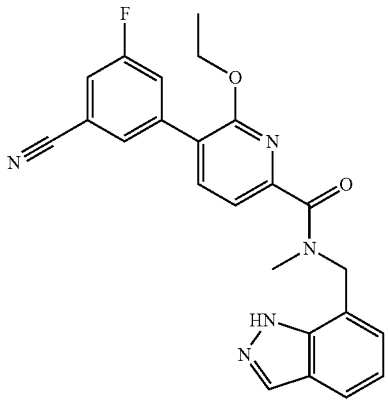 [SMILES: CCOc1nc(C(=O)N(C)Cc2cccc3cn[nH]c23)ccc1-c1cc(F)cc(C#N)c1] | 342 |
TABLE 8-continued
| Structure | No. |
|---|---|
| 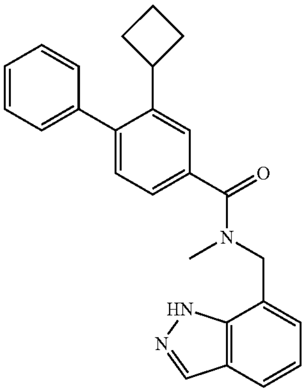 [SMILES: CN(Cc1cccc2cn[nH]c12)C(=O)c1ccc(-c2ccccc2)c(C2CCC2)c1] | 343 |
| 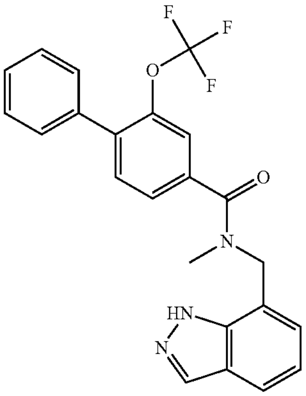 [SMILES: CN(Cc1cccc2cn[nH]c12)C(=O)c1ccc(-c2ccccc2)c(OC(F)(F)F)c1] | 344 |
| 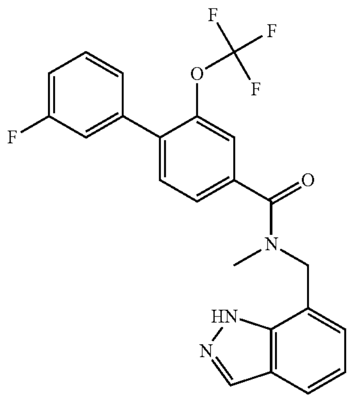 [SMILES: CN(Cc1cccc2cn[nH]c12)C(=O)c1ccc(-c2cccc(F)c2)c(OC(F)(F)F)c1] | 345 |

TABLE 8-continued
| Structure | No. |
|---|---|
| 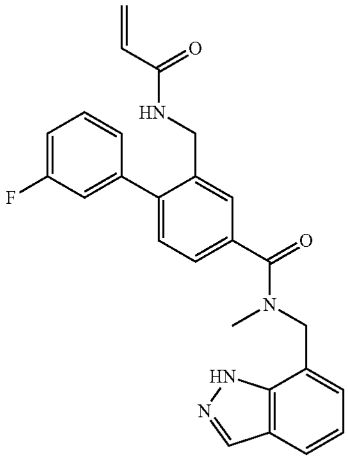 [SMILES: C=CC(=O)NCc1cc(C(=O)N(C)Cc2cccc3cn[nH]c23)ccc1-c1cccc(F)c1] | 346 |
| 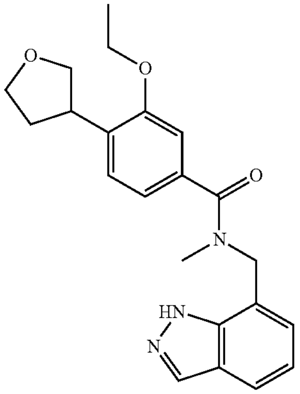 [SMILES: CCOc1cc(C(=O)N(C)Cc2cccc3cn[nH]c23)ccc1C1CCOC1] | 347 |
| 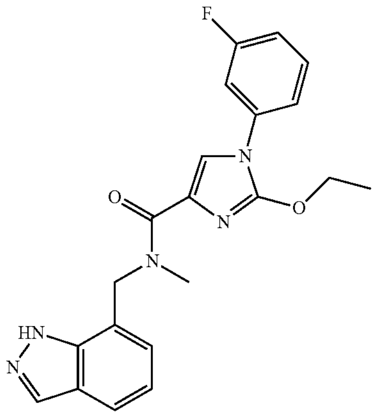 [SMILES: CCOc1nc(C(=O)N(C)Cc2cccc3cn[nH]c23)cn1-c1cccc(F)c1] | 348 |
TABLE 8-continued
| Structure | No. |
|---|---|
| 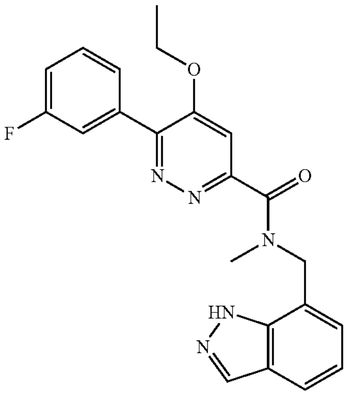 [SMILES: CCOc1cc(C(=O)N(C)Cc2cccc3cn[nH]c23)nnc1-c1cccc(F)c1] | 349 |
| 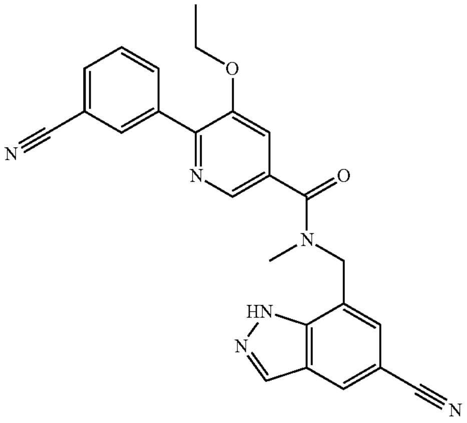 [SMILES: CCOc1cc(C(=O)N(C)Cc2cc(C#N)cc3cn[nH]c23)cnc1-c1cccc(C#N)c1] | 350 |
| 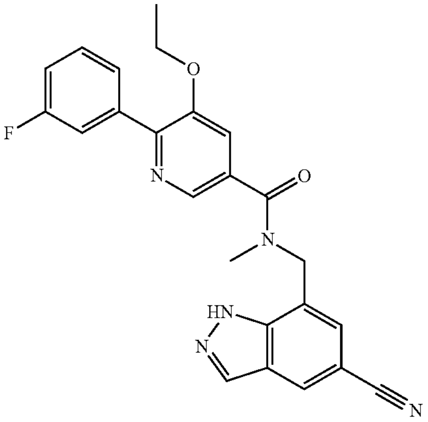 [SMILES: CCOc1cc(C(=O)N(C)Cc2cc(C#N)cc3cn[nH]c23)cnc1-c1cccc(F)c1] | 351 |
| 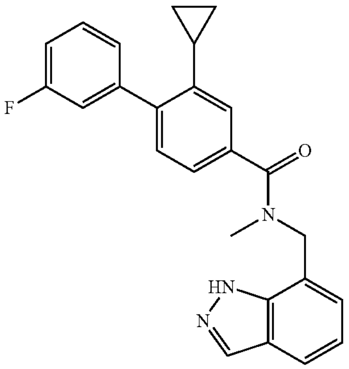 [SMILES: CN(Cc1cccc2cn[nH]c12)C(=O)c1ccc(-c2cccc(F)c2)c(C2CC2)c1] | 352 |

TABLE 8-continued
| Structure | No. |
|---|---|
| 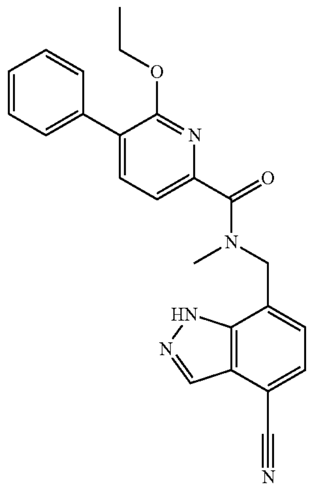 [SMILES: CCOc1nc(C(=O)N(C)Cc2ccc(C#N)c3cn[nH]c23)ccc1-c1ccccc1] | 353 |
| 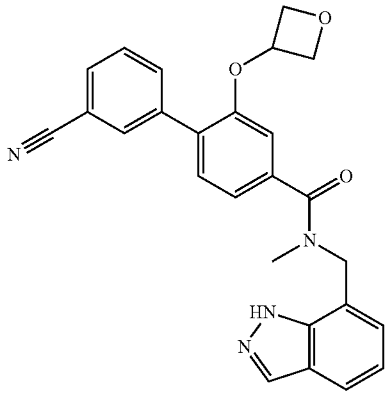 [SMILES: CN(Cc1cccc2cn[nH]c12)C(=O)c1ccc(-c2cccc(C#N)c2)c(OC2COC2)c1] | 354 |
| 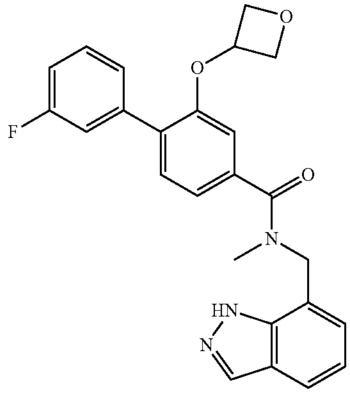 [SMILES: CN(Cc1cccc2cn[nH]c12)C(=O)c1ccc(-c2cccc(F)c2)c(OC2COC2)c1] | 355 |
TABLE 8-continued
| Structure | No. |
|---|---|
| 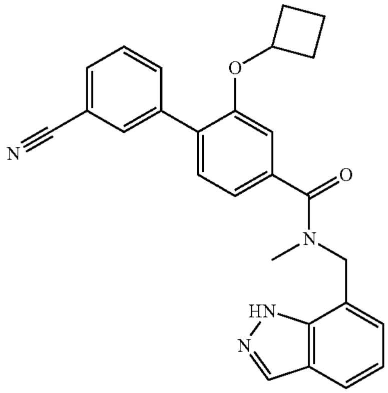 | 356 |
| 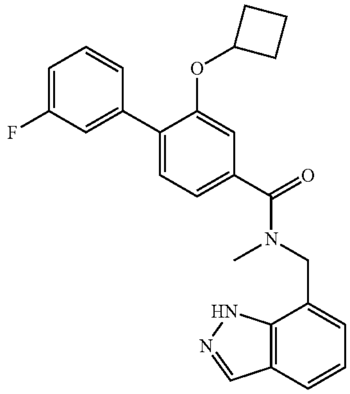 [SMILES: CN(Cc1cccc2cn[nH]c12)C(=O)c1ccc(-c2cccc(F)c2)c(OC2CCC2)c1] | 357 |
| 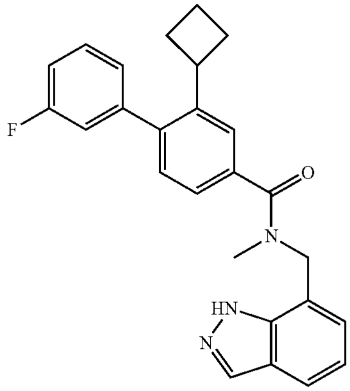 [SMILES: CN(Cc1cccc2cn[nH]c12)C(=O)c1ccc(-c2cccc(F)c2)c(C2CCC2)c1] | 358 |
| 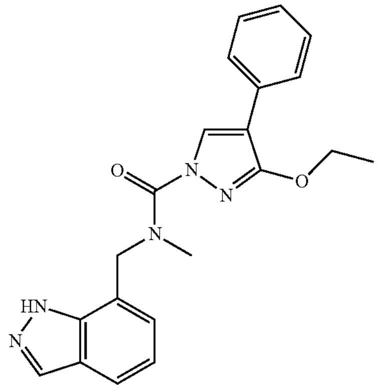 [SMILES: CCOc1nn(C(=O)N(C)Cc2cccc3cn[nH]c23)cc1-c1ccccc1] | 359 |

TABLE 8-continued
| Structure | No. |
|---|---|
| 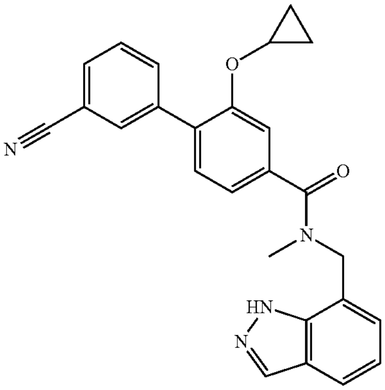 [SMILES: CN(Cc1cccc2cn[nH]c12)C(=O)c1ccc(-c2cccc(C#N)c2)c(OC2CC2)c1] | 360 |
| 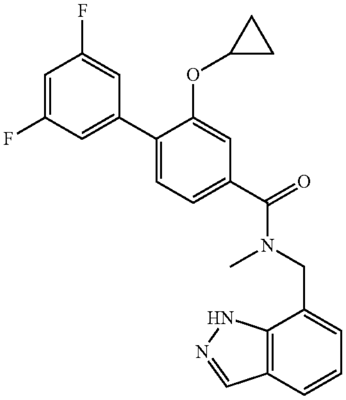 [SMILES: CN(Cc1cccc2cn[nH]c12)C(=O)c1ccc(-c2cc(F)cc(F)c2)c(OC2CC2)c1] | 361 |
| 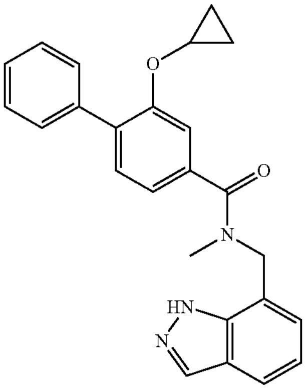 [SMILES: CN(Cc1cccc2cn[nH]c12)C(=O)c1ccc(-c2ccccc2)c(OC2CC2)c1] | 362 |
| 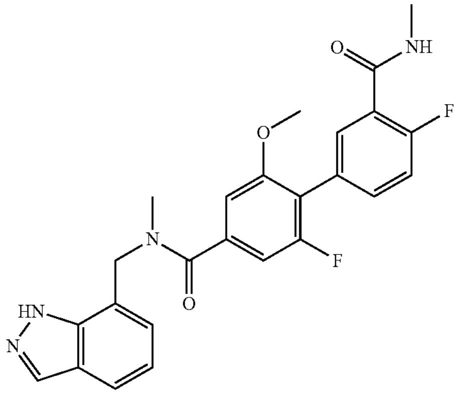 [SMILES: CNC(=O)c1cc(-c2c(F)cc(C(=O)N(C)Cc3cccc4cn[nH]c34)cc2OC)ccc1F] | 363 |
TABLE 8-continued
| Structure | No. |
|---|---|
| 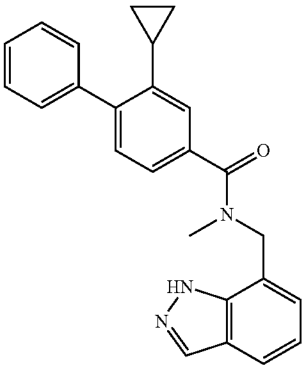 [SMILES: CN(Cc1cccc2cn[nH]c12)C(=O)c1ccc(-c2ccccc2)c(C2CC2)c1] | 364 |
| 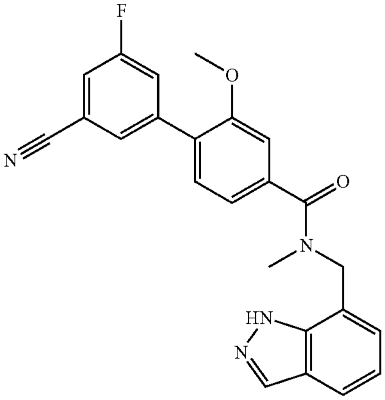 [SMILES: COc1cc(C(=O)N(C)Cc2cccc3cn[nH]c23)ccc1-c1cc(F)cc(C#N)c1] | 365 |
| 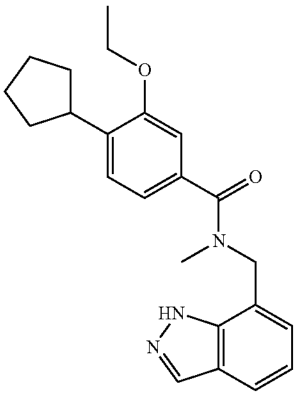 [SMILES: CCOc1cc(C(=O)N(C)Cc2cccc3cn[nH]c23)ccc1C1CCCC1] | 366 |
| 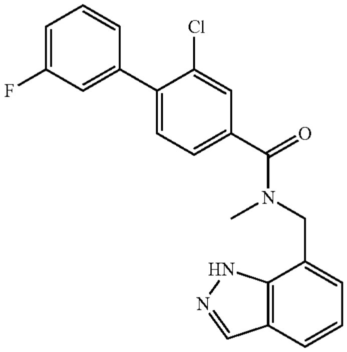 [SMILES: CN(Cc1cccc2cn[nH]c12)C(=O)c1ccc(-c2cccc(F)c2)c(Cl)c1] | 367 |

TABLE 8-continued
| Structure | No. |
|---|---|
| 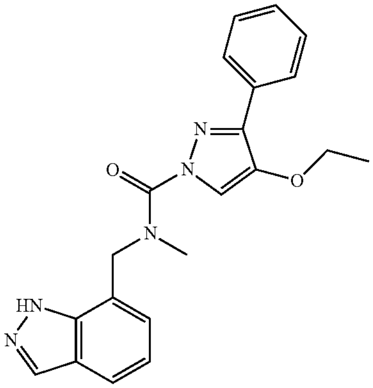 [SMILES: CCOc1cn(C(=O)N(C)Cc2cccc3cn[nH]c23)nc1-c1ccccc1] | 368 |
| 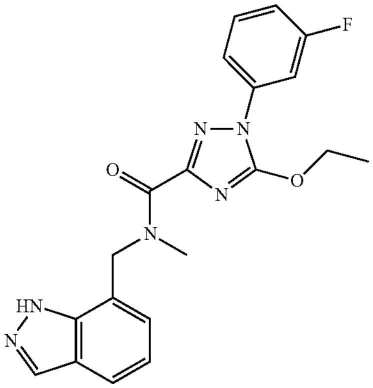 [SMILES: CCOc1nc(C(=O)N(C)Cc2cccc3cn[nH]c23)nn1-c1cccc(F)c1] | 369 |
| 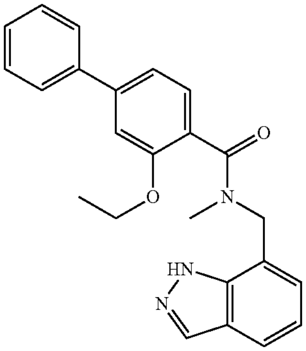 [SMILES: CCOc1cc(-c2ccccc2)ccc1C(=O)N(C)Cc1cccc2cn[nH]c12] | 370 |
| 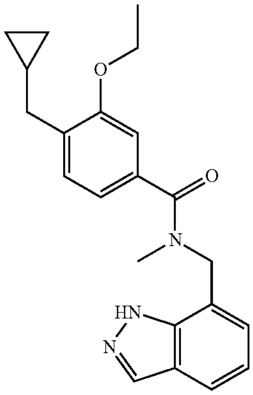 [SMILES: CCOc1cc(C(=O)N(C)Cc2cccc3cn[nH]c23)ccc1CC1CC1] | 371 |
TABLE 8-continued
| Structure | No. |
|---|---|
| 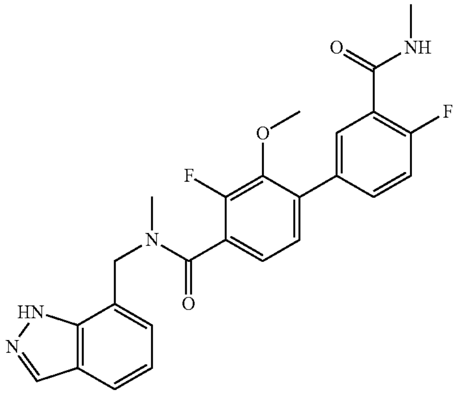 [SMILES: CNC(=O)c1cc(-c2ccc(C(=O)N(C)Cc3cccc4cn[nH]c34)c(F)c2OC)ccc1F] | 372 |
| 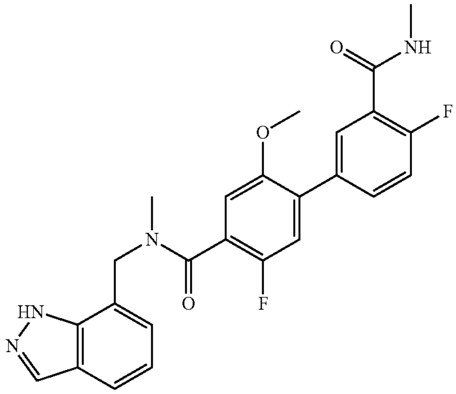 [SMILES: CNC(=O)c1cc(-c2cc(F)c(C(=O)N(C)Cc3cccc4cn[nH]c34)cc2OC)ccc1F] | 373 |
| 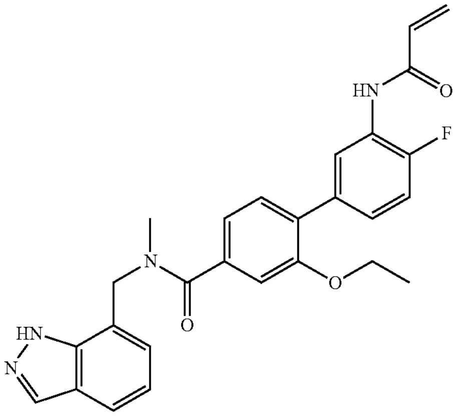 [SMILES: C=CC(=O)Nc1cc(-c2ccc(C(=O)N(C)Cc3cccc4cn[nH]c34)cc2OCC)ccc1F] | 374 |
| 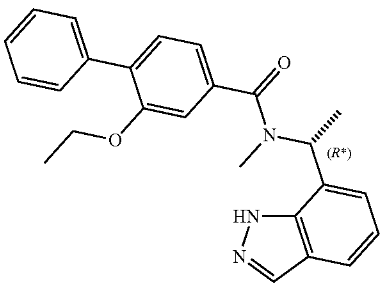 [SMILES: CCOc1cc(C(=O)N(C)[C@H](C)c2cccc3cn[nH]c23)ccc1-c1ccccc1] | 375 |

TABLE 8-continued
| Structure | No. |
|---|---|
| 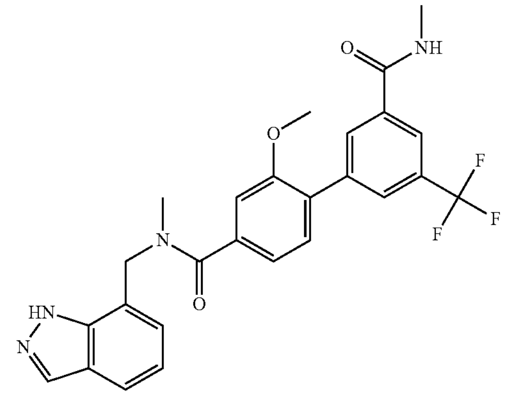 [SMILES: CNC(=O)c1cc(-c2ccc(C(=O)N(C)Cc3cccc4cn[nH]c34)cc2OC)cc(C(F)(F)F)c1] | 376 |
| 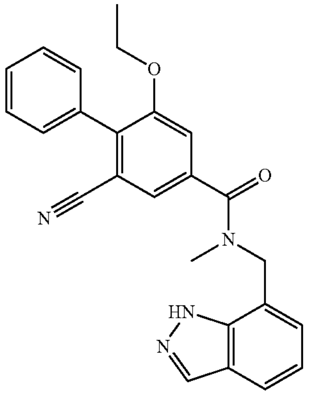 [SMILES: CCOc1cc(C(=O)N(C)Cc2cccc3cn[nH]c23)cc(C#N)c1-c1ccccc1] | 377 |
| 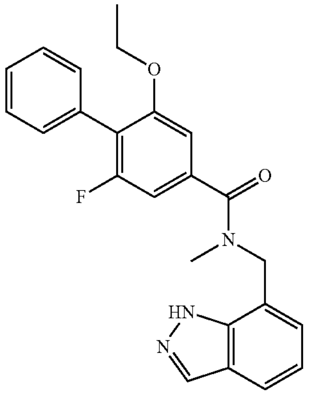 [SMILES: CCOc1cc(C(=O)N(C)Cc2cccc3cn[nH]c23)cc(F)c1-c1ccccc1] | 378 |
| 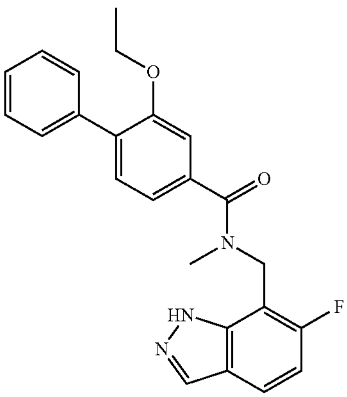 [SMILES: CCOc1cc(C(=O)N(C)Cc2c(F)ccc3cn[nH]c23)ccc1-c1ccccc1] | 379 |
TABLE 8-continued
| Structure | No. |
|---|---|
| 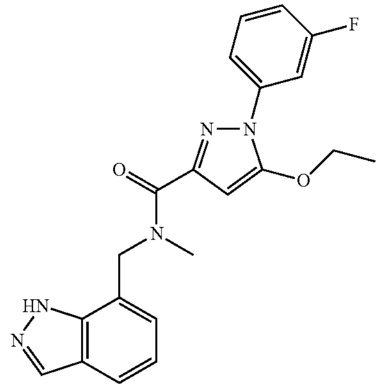 [SMILES: CCOc1cc(C(=O)N(C)Cc2cccc3cn[nH]c23)nn1-c1cccc(F)c1] | 380 |
| 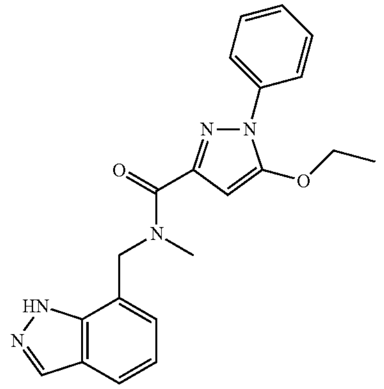 [SMILES: CCOc1cc(C(=O)N(C)Cc2cccc3cn[nH]c23)nn1-c1ccccc1] | 381 |
| 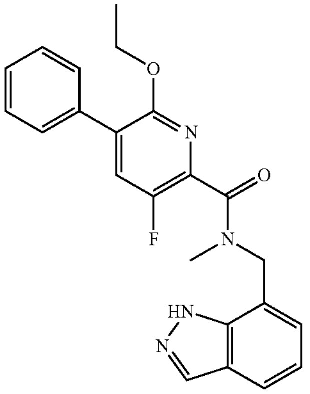 [SMILES: CCOc1nc(C(=O)N(C)Cc2cccc3cn[nH]c23)c(F)cc1-c1ccccc1] | 382 |
| 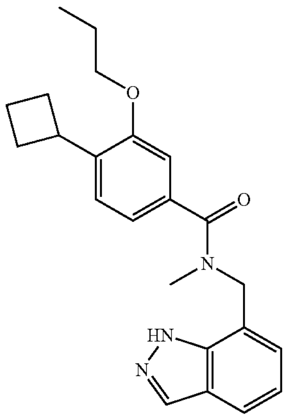 [SMILES: CCCOc1cc(C(=O)N(C)Cc2cccc3cn[nH]c23)ccc1C1CCC1] | 383 |

TABLE 8-continued

| Structure | No. |
| --- | --- |
| 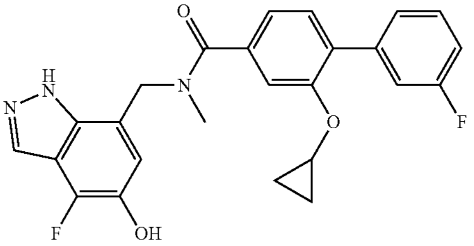 [SMILES: CN(Cc1cc(O)c(F)c2cn[nH]c12)C(=O)c1ccc(-c2cccc(F)c2)c(OC2CC2)c1] | 384 |
| 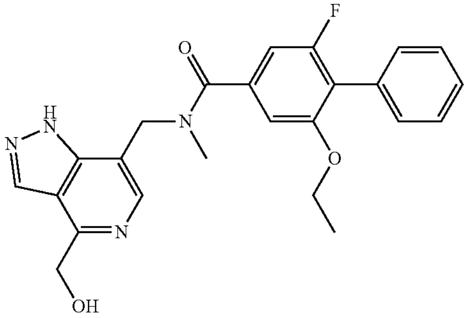 [SMILES: CCOc1cc(C(=O)N(C)Cc2cnc(CO)c3cn[nH]c23)cc(F)c1-c1ccccc1] | 385 |
| 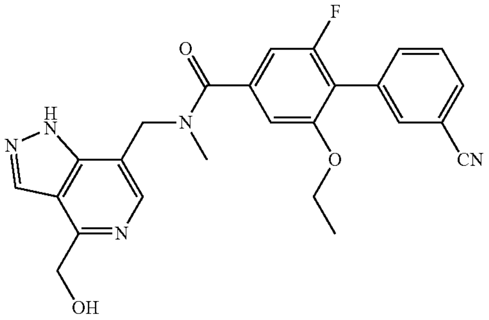 [SMILES: CCOc1cc(C(=O)N(C)Cc2cnc(CO)c3cn[nH]c23)cc(F)c1-c1cccc(C#N)c1] | 386 |
| 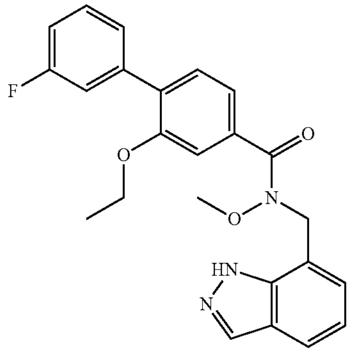 [SMILES: CCOc1cc(C(=O)N(Cc2cccc3cn[nH]c23)OC)ccc1-c1cccc(F)c1] | 387 |
| 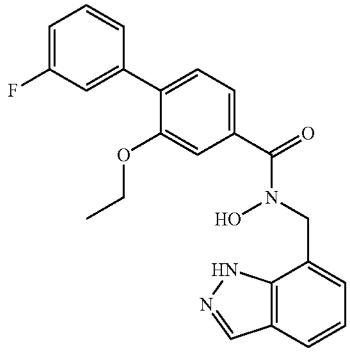 [SMILES: CCOc1cc(C(=O)N(O)Cc2cccc3cn[nH]c23)ccc1-c1cccc(F)c1] | 388 |

TABLE 8-continued

| Structure | No. |
| --- | --- |
| 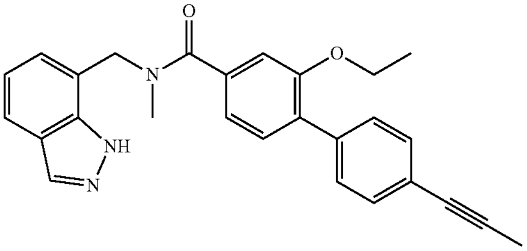 [SMILES: CC#Cc1ccc(-c2ccc(C(=O)N(C)Cc3cccc4cn[nH]c34)cc2OCC)cc1] | 389 |
| 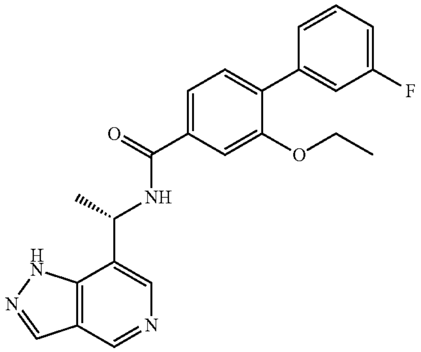 [SMILES: CCOc1cc(C(=O)N[C@@H](C)c2cncc3cn[nH]c23)ccc1-c1cccc(F)c1] | 390 |

or a pharmaceutically acceptable salt thereof.

In an embodiment, the compound of the formulae herein has one of the following core structures:

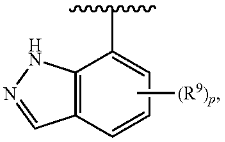,
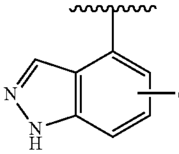, and
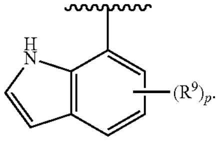.

In another aspect, provided herein is a pharmaceutical composition comprising a compound described herein, or a pharmaceutically acceptable salt thereof, and a pharmaceutically acceptable carrier.

The compounds disclosed herein may exist as tautomers and optical isomers (e.g., enantiomers, diastereomers, diastereomeric mixtures, racemic mixtures, and the like). The absolute stereochemistry is specified according to the Cahn-Ingold-Prelog R—S system. Chiral centers, of which the absolute configurations are known, are labelled by prefixes R and S, assigned by the standard sequence-rule procedure, and preceded when necessary by the appropriate locants (*Pure & Appl. Chem.* 45, 1976, 11-30). Certain examples contain chemical structures that are depicted or labelled as an (R*) or (S*). When (R*) or (S*) is used in the name of a compound or in the chemical representation of the compound, it is intended to convey that the compound is a pure single isomer at that stereocenter; however, absolute configuration of that stereocenter has not been established. Thus, a compound designated as (R*) refers to a compound that is a pure single isomer at that stereocenter with an absolute configuration of either (R) or (S), and a compound designated as (S*) refers to a compound that is a pure single isomer at that stereocenter with an absolute configuration of either (R) or (S).

It is generally well known in the art that any compound that will be converted in vivo to provide a compound disclosed herein is a prodrug within the scope of the present disclosure.

Compounds provided herein can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

In the compounds provided herein, any atom not specifically designated as a particular isotope is meant to represent any stable isotope of that atom. Unless otherwise stated, when a position is designated specifically as "H" or "hydrogen," the position is understood to have hydrogen at its natural abundance isotopic composition. Also, unless otherwise stated, when a position is designated specifically as "D" or "deuterium", the position is understood to have deuterium at an abundance that is at least 3000 times greater than the natural abundance of deuterium, which is 0.015% (i.e., at least 45% incorporation of deuterium).

In embodiments, the compounds provided herein have an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Methods of Treatment

In an aspect, provided herein is a method of inhibiting NLRP3 inflammasome in a subject in need thereof, comprising administering to the individual a therapeutically effective amount of a compound disclosed herein.

In another aspect, provided herein is a method of treating inflammation in a subject in need thereof, comprising administering to the individual a therapeutically effective amount of a compound disclosed herein.

In another aspect, provided herein is a method of treating inflammaging in a subject in need thereof, comprising administering to the individual a therapeutically effective amount of a compound disclosed herein.

In another aspect, provided herein is a method of treating cryopyrin-associated periodic syndrome (CAPS) in a subject in need thereof, comprising administering to the individual a therapeutically effective amount of a compound disclosed herein.

In an embodiment, the CAPS is selected from the group consisting of familial cold autoinflammatory syndrome, Muckle-Wells syndrome, and neonatal-onset multisystem inflammatory disease.

In another aspect, provided herein is a method of treating a dermatologic disease in a subject in need thereof, comprising administering to the individual a therapeutically effective amount of a compound disclosed herein.

In an embodiment, the dermatologic disease is selected from the group consisting of psoriasis, urticaria, skin photoaging, and eczema.

Also provided herein is a method of using the compounds provided herein for treatment or amelioration of aging or an aging-related condition negatively impacting longevity or quality of life, wherein the aging-related condition negatively impacting longevity or quality of life is selected from the group consisting of inflammation, anemia, hyperglycemia, dyslipidemia, hyperinsulinemia, insulin resistance, immunosuppression, liver disease, iron overload, hypertrigliceridemia, impaired skin integrity, wound healing, scarring, pain, allergies, sleep disorders and problems, gastrointestinal disorders and problems, Th1-type inflammation, Th2-type inflammation, an inflammatory disease involving T-cell dependent B cell proliferation, T-cell dependent B cell proliferation, allergy, asthma, atherosclerosis, autoimmunity, hypercholesterolemia, chronic inflammation, chronic obstructive pulmonary disease (COPD), Crohn's disease, cutaneous responses to tissue damage, fibrosis, hematological oncology, metabolic diseases, cardiovascular disease, organ transplantation, psoriasis, liver fibrosis, dermatitis, pulmonary fibrosis, pulmonary responses to respiratory infections, restenosis, rheumatoid arthritis, sarcoidosis, stromal biology in tumors, systemic lupus erythematosus (SLE), ulcerative colitis, vascular inflammation, and diseases that are driven or exacerbated by one or more factors selected from the group consisting of alpha smooth muscle actin (αSMA), CD40, CD69, collagen I, collagen Ill, decorin, e-selectin, eotaxin 3 (CCL26), fibroblast proliferation, human leukocyte antigen-DR isotype (HLA-DR), immunoglobulin G, interferon gamma-induced protein 10 (IP-10/CXCL10), interferon-inducible T cell alpha chemoattractant (I-TAC/CXCL11), interleukin (IL)-1, IL-1.alpha., IL-2, IL-6, IL-8 (CXCL8), IL-10, IL-17A, IL-17F, keratin 8/81, macrophage colony-stimulating factor (M-CSF), matrix metalloproteinase (MMP)-1, MMP-9, monocyte chemoattractant protein 1 (MCP-1), monokine induced by gamma interferon (MIG/CXCL9), plasminogen activation inhibitor 1 (PAI-1), prostaglandin E2 (PGE2), serum amyloid A, T or B cell proliferation, tissue plasminogen activator (tPA), tumor necrosis factor alpha (TNF.alpha.), vascular cell adhesion molecule (VCAM-1), and vascular endothelial growth factor 2 (VEGFR2), comprising: administering to a subject in need thereof a compound provided herein.

In an aspect, provided herein is a method of reversing a normal aging process in subject comprising administering to the subject a therapeutically effective amount of a compound provided herein or a pharmaceutically acceptable salt thereof.

In another aspect, provided herein is a method of reversing a normal aging process in subject comprising administering to the subject a pharmaceutical composition comprising a therapeutically effective amount of a compound provided herein or a pharmaceutically acceptable salt thereof.

In yet another aspect, provided herein is a method of extending lifespan of a subject comprising administering to the subject a therapeutically effective amount of a compound provided herein or a pharmaceutically acceptable salt thereof.

In still another aspect, provided herein is a method of extending lifespan of a subject comprising administering to the subject a pharmaceutical composition comprising a therapeutically effective amount of a compound provided herein or a pharmaceutically acceptable salt thereof.

In another aspect, provided herein is a method to slow down and mitigate the aging process in a subject comprising administering to the subject a therapeutically effective amount of a compound provided herein or a pharmaceutically acceptable salt thereof.

In another aspect, provided herein is a method of inhibiting or modulating the pro-inflammatory pathway in a cell comprising contacting the cell with a compound provided herein, or a pharmaceutically acceptable salt thereof. In yet another aspect, provided herein is a method of inhibiting or modulating NLRP3 in a cell comprising contacting the cell with a compound provided herein, or a pharmaceutically acceptable salt thereof.

Treatment of a cell (in vitro or in vivo) that expresses a NLRP3 inflammasome with a compound provided herein can result in inhibiting the pro-inflammatory pathway and inhibiting downstream events related to the signaling pathway such as inflammation or inflammaging.

In another aspect, provided herein is a method of treating a neurosensory disease in a subject in need thereof, comprising administering to the individual a therapeutically effective amount of a compound disclosed herein.

In an embodiment, the neurosensory disease is selected from the group consisting of hearing loss, hearing injury, and ocular disease. In an embodiment, the ocular disease is retinal and optic nerve injury.

In yet another aspect, provided herein is a method of treating an inflammatory disorder in a subject in need thereof, comprising administering to the individual a therapeutically effective amount of a compound disclosed herein.

In an embodiment, the inflammatory disorder is selected from the group consisting of allergy, asthma, atopic dermatitis, atherosclerosis, autoimmune diseases, coeliac disease, chronic inflammation, glomerulonephritis, hepatitis, inflammatory bowel disease, preperfusion injury, SARS-CoV-2 infection, transplant rejection, heart disease, diabetes, arthritis, Crohn's disease, ulcerative colitis, non-alcoholic steatohepatitis (NASH), gout, coronary artery disease, rheumatoid arthritis, intestinal disorders, and acute respiratory distress syndrome (ARDS).

In another embodiment, the inflammatory disorder is a neuroinflammatory disease. In yet another embodiment, the inflammatory disorder is inner ear inflammation.

In an embodiment, a chronic inflammation comprises a tissue inflammation. Tissue inflammation is a chronic inflammation that is confined to a particular tissue or organ. In an embodiment, a tissue inflammation comprises, e.g., a skin inflammation, ocular inflammation, a muscle inflammation, a tendon inflammation, a ligament inflammation, a bone inflammation, a cartilage inflammation, a lung inflammation, a heart inflammation, a liver inflammation, a pancreatic inflammation, a kidney inflammation, a bladder inflammation, a stomach inflammation, an intestinal inflammation, a neuron inflammation, and a brain inflammation.

In another embodiment, a chronic inflammation comprises a systemic inflammation. Although the processes involved are identical to tissue inflammation, systemic inflammation is not confined to a particular tissue but in fact overwhelms the body, involving the endothelium and other organ systems. When it is due to infection, the term sepsis is applied, with the terms bacteremia being applied specifically for bacterial sepsis and viremia specifically to viral sepsis. Vasodilation and organ dysfunction are serious problems associated with widespread infection that may lead to septic shock and death.

In yet another embodiment, a chronic inflammation comprises an arthritis. Arthritis includes a group of conditions involving damage to the joints of the body due to the inflammation of the synovium including, without limitation osteoarthritis, rheumatoid arthritis, juvenile idiopathic arthritis, spondyloarthropathies like ankylosing spondylitis, reactive arthritis (Reiter's syndrome), psoriatic arthritis, enteropathic arthritis associated with inflammatory bowel disease, Whipple disease and Behcet disease, septic arthritis, gout (also known as gouty arthritis, crystal synovitis, metabolic arthritis), pseudogout (calcium pyrophosphate deposition disease), and Still's disease. Arthritis can affect a single joint (monoarthritis), two to four joints (oligoarthritis) or five or more joints (polyarthritis) and can be either an auto-immune disease or a non-autoimmune disease.

In still another aspect, provided herein is a method of treating an age-related disorder in a subject in need thereof, comprising administering to the individual a therapeutically effective amount of a compound disclosed herein.

In an embodiment, the age-related disorder is selected from the group consisting of neurodegeneration, cardiovascular disease, insulin resistance, diabetes, osteoporosis, osteoarthritis, cognitive decline, dementia, frailty, cataracts, arthritis, obesity, hypertension, angina, congestive heart failure, dyslipidemia, myocardial infarction, vascular disease, respiratory disease, kidney disease, cerebrovascular disease, peripheral vascular disease, Alzheimer's disease, cardiac diastolic dysfunction, benign prostatic hypertrophy, aortic aneurysm, and emphysema.

In another aspect, provided herein is a method of treating a metabolic condition in a subject in need thereof, comprising administering to the individual a therapeutically effective amount of a compound disclosed herein.

In an embodiment, the metabolic condition is selected from the group consisting of diabetes, obesity, cystic fibrosis, and hyperthyroidism.

In yet another aspect, provided herein is a method of treating a neurodegenerative disease in a subject in need thereof, comprising administering to the individual a therapeutically effective amount of a compound disclosed herein.

In an embodiment, the neurodegenerative disease is selected from the group consisting of Alzheimer's disease, Parkinson's disease, Huntington's disease, multiple sclerosis (MS), amyotrophic lateral sclerosis (ALS), and Batten disease.

In an aspect, provided herein is a method of treating a disease or disorder of the inner ear in a subject in need thereof, comprising administering to the individual a therapeutically effective amount of a compound disclosed herein.

In an embodiment, the disease or disorder of the inner ear is selected from the group consisting of hearing loss, hearing impairment, vertigo, Meniere's disease, and tinnitus. In another embodiment, the disease of the inner ear is hearing loss. In yet another embodiment, the disease of the inner ear is hearing impairment.

In another embodiment, the hearing loss is age-related, noise-induced, or the result of a viral infection. In yet another embodiment, the viral infection is Zika virus or coronavirus.

Potency of the inhibitor can also be determined by $IC_{50}$ value. A compound with a lower $IC_{50}$ value, as determined under substantially similar conditions, is a more potent inhibitor relative to a compound with a higher $IC_{50}$ value.

In an embodiment of the methods, the subject is a human.

In another aspect, the disclosure provides a compound disclosed herein, or a pharmaceutically acceptable salt thereof, for use in the manufacture of a medicament for treating or preventing a disease in which NLRP3 inflammasome plays a role.

In an aspect, provided herein is a method of treating a condition selected from the group consisting of autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

One aspect of this disclosure provides compounds that are useful for the treatment of diseases, disorders, and conditions characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer.

Therefore, in an aspect, provided herein is a method of treating cancer in a subject in need thereof comprising administering to the subject a therapeutically effective amount of a compound disclosed herein, or a pharmaceutically acceptable salt thereof.

In an embodiment, the cancer is selected from the group consisting of breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, colorectal, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon, rectum, large intestine, rectum, brain and central nervous system, chronic myeloid leukemia (CML), and leukemia.

In another embodiment, the cancer is selected from the group consisting of myeloma, lymphoma, or a cancer selected from gastric, renal, head and neck, oropharangeal, non-small cell lung cancer (NSCLC), endometrial, hepatocarcinoma, non-Hodgkin's lymphoma, and pulmonary.

In an embodiment, the cancer is selected from the group consisting of prostate cancer, colon cancer, lung cancer, squamous cell cancer of the head and neck, esophageal cancer, hepatocellular carcinoma, melanoma, sarcoma, gastric cancer, pancreatic cancer, ovarian cancer, breast cancer.

In an embodiment, the cancer is selected from the group consisting of tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodysplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in treating are, for example, colon carcinoma, familial adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

In another aspect, provided herein is the use of one or more compounds of the disclosure in the manufacture of a medicament for the treatment of cancer, including without limitation the various types of cancer disclosed herein.

In some embodiments, the compounds of this disclosure are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the compounds of this disclosure are useful for treating hematopoietic disorders, in particular, acute-myelogenous leukemia (AML), chronic-myelogenous leukemia (CML), acute-promyelocytic leukemia, and acute lymphocytic leukemia (ALL).

Administration/Dosages/Formulations

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, com, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations (for example, sterile injectable aqueous or oleaginous suspensions) may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility.

The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this disclosure with suitable non-irritating excipients or carriers such as cocoa butter, polyethylene glycol, or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this disclosure.

The ointments, pastes, creams and gels may contain, in addition to an active compound of this disclosure, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this disclosure, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds of the present disclosure can be administered intratympanically, wherein a long, narrow, bore needle is passed through the ear canal and through the eardrum to administer medications into the middle ear space where they are absorbed by the inner ear.

According to the methods of treatment of the present disclosure, disorders are treated or prevented in a subject, such as a human or other animal, by administering to the subject a therapeutically effective amount of a compound of the disclosure, in such amounts and for such time as is necessary to achieve the desired result. The term "therapeutically effective amount" of a compound of the disclosure, as used herein, means a sufficient amount of the compound so as to decrease the symptoms of a disorder in a subject. As is well understood in the medical arts a therapeutically effective amount of a compound of this disclosure will be at a reasonable benefit/risk ratio applicable to any medical treatment.

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 100 mg, conveniently administered, e.g., in divided doses up to four times a day or in retard form. Suitable unit dosage forms for oral administration comprise from ca. 1 to 50 mg active ingredient.

In certain embodiments, a therapeutic amount or dose of the compounds of the present disclosure may range from about 0.1 mg/Kg to about 500 mg/Kg, alternatively from about 1 to about 50 mg/Kg. In general, treatment regimens according to the present disclosure comprise administration to a patient in need of such treatment from about 10 mg to about 1000 mg of the compound(s) of this disclosure per day in single or multiple doses. Therapeutic amounts or doses will also vary depending on route of administration, as well as the possibility of co-usage with other agents.

Upon improvement of a subject's condition, a maintenance dose of a compound, composition or combination of this disclosure may be administered, if necessary. Subsequently, the dosage or frequency of administration, or both, may be reduced, as a function of the symptoms, to a level at which the improved condition is retained; when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present disclosure will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The disclosure also provides for a pharmaceutical combination, e.g., a kit, comprising a) a first agent which is a compound of the disclosure as disclosed herein, in free form or in pharmaceutically acceptable salt form, and b) at least one co-agent. The kit can comprise instructions for its administration.

Some examples of materials which can serve as pharmaceutically acceptable carriers include, but are not limited to, ion exchangers; alumina; aluminum stearate; lecithin; serum proteins, such as human serum albumin; buffer substances such as phosphates, glycine, sorbic acid, or potassium sorbate; partial glyceride mixtures of saturated vegetable fatty acids; water; salts or electrolytes, such as protamine sulfate; disodium hydrogen phosphate; potassium hydrogen phosphate; sodium chloride; zinc salts; colloidal silica; magnesium trisilicate; polyvinyl pyrrolidone; polyacrylates; waxes; polyethylenepolyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols, such a propylene glycol or polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; and phosphate buffer solutions. Further, non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are other embodiments of the present disclosure.

Kits

In an aspect, provided herein is a kit comprising a compound capable of inhibiting NLRP3 inflammasome activity selected from one or more compounds of disclosed herein, or pharmaceutically acceptable salts thereof, and instructions for use in treating a disorder associated with NLRP3 inflammasomes.

In another aspect, the disclosure provides a kit comprising a compound capable of inhibiting NLRP3 inflammasome activity selected from a compound disclosed herein, or a pharmaceutically acceptable salt thereof.

In yet another aspect, provided herein is a kit comprising a compound disclosed herein, or a pharmaceutically acceptable salt thereof for the treatment of any of the indications disclosed herein.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings of the present disclosure as set forth.

EXAMPLES

The compounds and methods disclosed herein are further illustrated by the following examples, which should not be construed as further limiting. The practice of the present disclosure will employ, unless otherwise indicated, conventional techniques of organic synthesis, cell biology, cell culture, and molecular biology, which are within the skill of the art.

Abbreviations

ACN acetonitrile
AcOH acetic acid
DCM dichloromethane
DMAP 4-dimethylaminopyridine
DMF dimethylformamide
DMSO dimethylsulfoxide
dppf 1,1'-bis(diphenylphosphino)ferrocene
EDCl 1-ethyl-3-(3-dimethylaminopropyl)carbodiimide
EtOAc ethyl acetate
EtOH ethanol
HPLC high-performance liquid chromatography LCMS liquid chromatography-mass spectrometry
MeOH methanol
NMR nuclear magnetic resonance
PE petroleum ether
THF tetrahydrofuran
TLC thin layer chromatography

Example 1: Synthetic Procedures

Scheme 1.

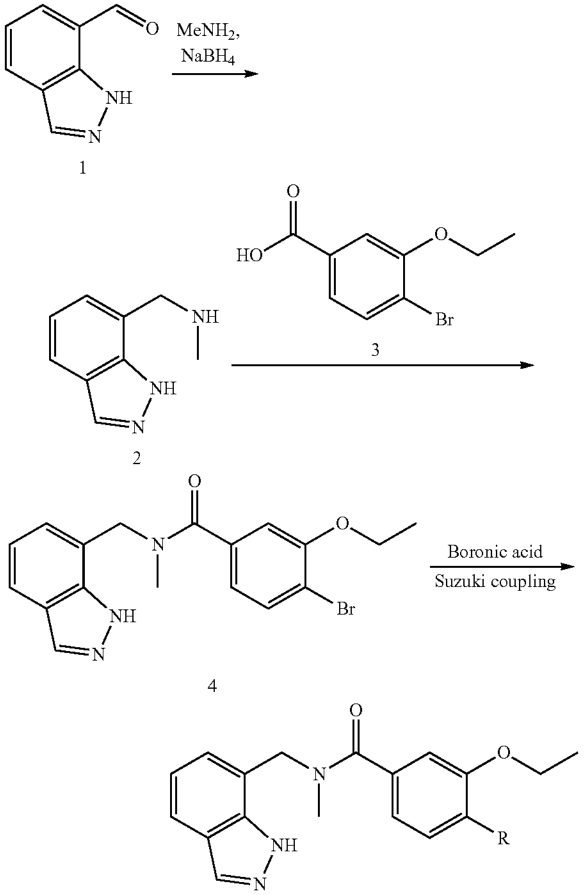

To a solution of compound 1 (4 g, 27.37 mmol, 1 eq) in MeOH (20 mL) was added AcOH (164.36 mg, 2.74 mmol, 156.54 uL, 0.1 eq) and $MeNH_2$ in MeOH (2 M, 41.05 mL, 3 eq), the mixture was stirred at 15° C. for 2 h, then $NaBH_4$ (1.14 g, 30.11 mmol, 1.1 eq) was added in portions at 0° C., then the reaction was stirred at 30° C. for 16 h. LCMS showed the reaction was completed. After the reaction was completed, the mixture was poured into $NH_4Cl$ (200 mL) and extracted with EtOAc (200 mL×3), the combined organic phase was washed with brine (200 mL), dried over anhydrous $Na_2SO_4$, and concentrated to give a crude product. The crude product used for next reaction without further purification. Compound 2 (5 g, crude) was obtained as yellow oil. LCMS: m/z=162.2 (M+H$^+$).

To a solution of compound 3 (1 g, 4.08 mmol, 1 eq) in DCM (20 mL) was added EDCl (1.02 g, 5.30 mmol, 1.3 eq), DMAP (49.85 mg, 408.05 umol, 0.1 eq) and compound 2 (1.97 g, 12.24 mmol, 3 eq), the mixture was stirred at 30° C. for 12 h. LCMS showed the reaction was completed. The mixture poured into water (50 mL) and extracted with DCM (50 mL×3), the combined organic phase was washed with brine (50 mL), dried over anhydrous $Na_2SO_4$, and concentrated to give a crude product. The crude product was purified by column chromatography ($SiO_2$, Petroleum ether/Ethyl acetate=10/1 to 1/1, desired product Rf=0.6). Compound 4 (1.2 g, 3.09 mmol, 75.74% yield, 100% purity) was obtained as white solid, confirmed by LCMS and H-NMR. LCMS: m/z=387.9 (M+H$^+$) $^1$H NMR (400 MHz, CHLOROFORM-d) δ=8.21-7.98 (m, 1H), 7.84-7.66 (m, 1H), 7.53-7.39 (m, 1H), 7.27-7.15 (m, 1H), 7.11-7.03 (m, 1H), 6.94-6.87 (m, 1H), 6.85-6.75 (m, 1H), 4.86 (s, 2H), 4.03 (d, J=7.0 Hz, 2H), 2.87 (s, 3H), 1.40 (t, J=7.0 Hz, 3H).

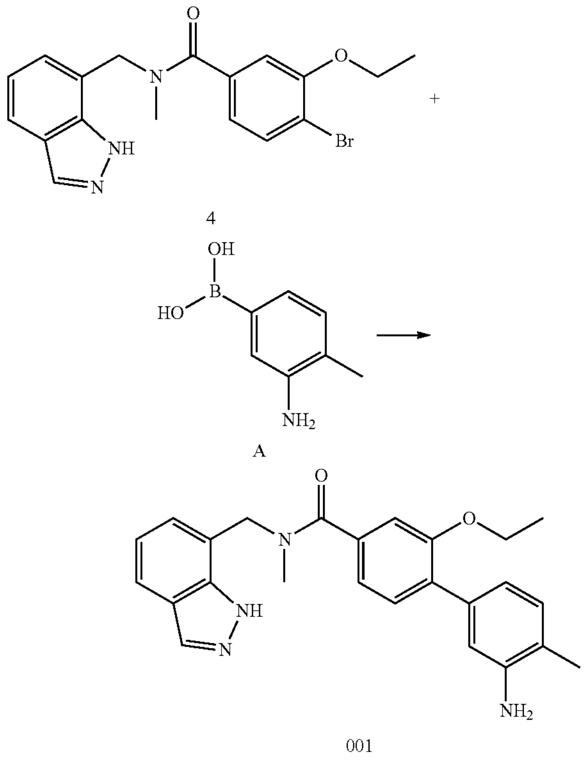

To a mixture of compound 4 (80 mg, 206.05 umol, 1 eq), compound A (46.34 mg, 247.26 umol, 1.2 eq, HCl), $K_2CO_3$ (85.43 mg, 618.15 umol, 3 eq) in dioxane (2 mL) and $H_2O$ (0.2 mL) was added $Pd(dppf)Cl_2CH_2Cl_2$ (33.65 mg, 41.21 umol, 0.2 eq) under $N_2$ atmosphere, then the reaction mixture was stirred at 100° C. for 12 h. LCMS: m/z=415.0 (M+H$^+$) showed 4 consumed completely and desired mass was detected. The reaction mixture was added thiourea resin, then the mixture was stirred for 4 hr. The crude product was purified by prep-HPLC (FA, column: Phenomenex luna C18 150*25 mm*10 um; mobile phase: [water (0.225% FA)-ACN]; B %: 30%-60%, 10 min), the purified solution was lyophilized to give a black brown solid. Compound 001 (21.2 mg, 50.64 umol, 24.58% yield, 99.02% purity) was obtained as a black brown solid. LCMS and $^1$H NMR confirmed. LCMS: m/z=415.5 (M+H$^+$). $^1$H NMR (400 MHz, METHANOL-d$_4$) δ=8.13 (br s, 1H), 7.78 (br d, J=7.2 Hz, 1H), 7.30 (br d, J=2.9 Hz, 2H), 7.20-6.98 (m, 6H), 4.97 (br s, 2H), 4.04 (br d, J=5.6 Hz, 2H), 3.01 (br s, 3H), 2.30 (br s, 3H), 1.35 (br s, 3H).

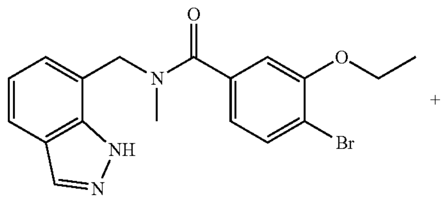

4

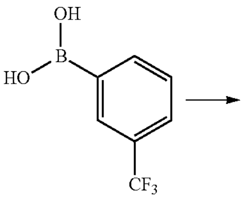

B

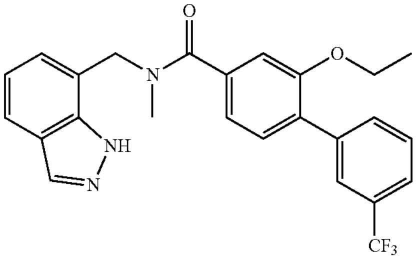

002

Compound 002 was prepared as described for the synthesis of compound 001 with Compound 4 and Compound B as the starting materials. Compound 002 (15.4 mg, 33.66 umol, 16.34% yield, 99.126% purity) was obtained as a yellow solid. LCMS: m/z=454.3 (M+H$^+$). $^1$H NMR (400 MHz, CHLOROFORM-d) δ=8.51-8.02 (m, 1H), 7.85 (br s, 1H), 7.79-7.66 (m, 2H), 7.65-7.46 (m, 3H), 7.40-7.28 (m, 2H), 7.22-7.02 (m, 3H), 4.98 (br s, 2H), 4.08 (br s, 2H), 3.03 (br s, 3H), 1.36 (br s, 3H).

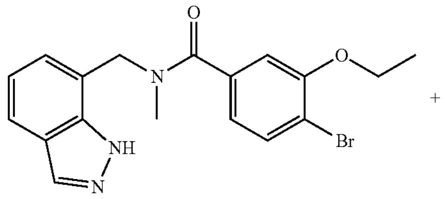

4

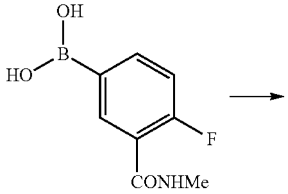

D

-continued

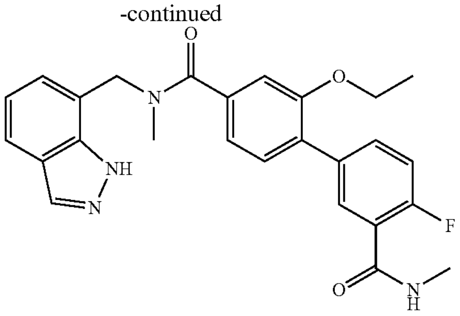

003

Compound 003 was prepared as described for the synthesis of Compound 001 with Compound 4 and Compound D as the starting materials. Compound 003 (54.3 mg, 114.51 umol, 55.57% yield, 97.112% purity) was obtained as a yellow solid. LCMS: m/z=461.3 (M+H$^+$). $^1$H NMR (400 MHz, CHLOROFORM-d) δ=8.33-8.12 (m, 2H), 7.80 (br d, J=6.7 Hz, 1H), 7.68 (br d, J=2.1 Hz, 1H), 7.35 (br d, J=4.0 Hz, 2H), 7.21-7.06 (m, 4H), 6.83-6.72 (m, 1H), 4.99 (br s, 2H), 4.18-3.99 (m, 2H), 3.06 (br d, J=4.6 Hz, 3H), 3.02 (br s, 3H), 1.37 (br s, 3H).

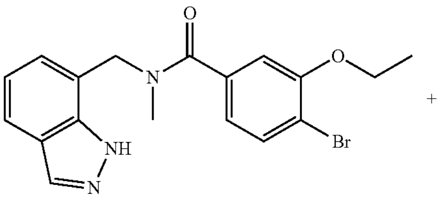

4

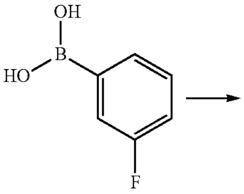

F

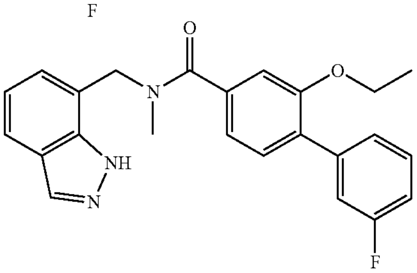

004

Compound 004 was prepared as described for the synthesis of Compound 001 with Compound 4 and Compound F as the starting materials. Compound 004 (14.8 mg, 36.51 umol, 17.72% yield, 99.518% purity) was obtained as a yellow solid. LCMS: m/z=404.3 (M+H$^+$). $^1$H NMR (400 MHz, CHLOROFORM-d) δ=8.35-7.99 (m, 1H), 7.76 (br s, 1H), 7.31 (br d, J=6.6 Hz, 5H), 7.22-6.98 (m, 4H), 4.98 (br s, 2H), 4.07 (br d, J=2.0 Hz, 2H), 3.02 (br s, 3H), 1.37 (br s, 3H).

Compound 004 was also prepared by the following protocol.

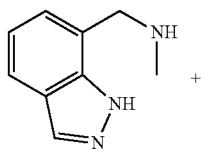

2

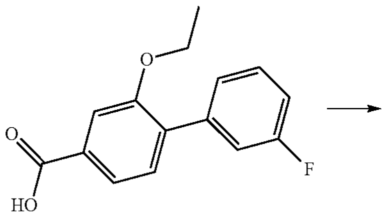

5

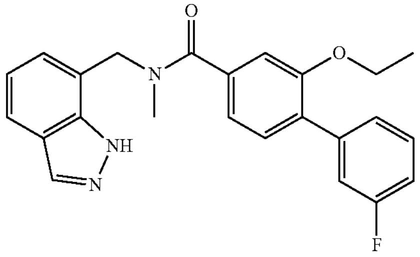

004

Compound 004 was prepared as described for the synthesis of Compound 4 with Compound 2 and Compound 5 as the starting materials and step 1 at 30° C. for 4 h. Compound 004 (130.32 mg, 552.74 umol, 59.40% yield, 100% purity) was obtained as a white solid. LCMS: m/z=404.0 (M+H$^+$). $^1$H NMR (400 MHz, CHLOROFORM-d) δ=8.14 (s, 1H), 7.79 (d, J=8.1 Hz, 1H), 7.30 (s, 5H), 7.18-7.11 (m, 1H), 7.07 (br dd, J=2.7, 3.9 Hz, 3H), 4.98 (s, 2H), 4.18-3.99 (m, 2H), 3.01 (s, 3H), 1.37 (s, 3H).

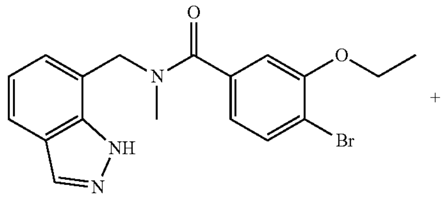

4

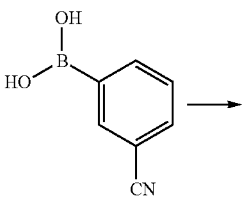

E

-continued

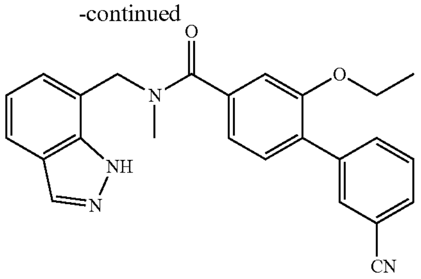

005

Compound 005 was prepared as described for the synthesis of Compound 001 with Compound 4 and Compound E as the starting materials, however step 1 was conducted at 100° C. for 12 h and step 2 was conducted at 15° C. for 12 h. Compound 005 (10.0 mg, 24.36 umol, 11.82% yield, 100% purity) was obtained as a gray solid. LCMS: m/z=411.0 (M+H$^+$). $^1$H NMR (400 MHz, CHLOROFORM-d) δ=8.37-8.01 (m, 1H), 7.87 (s, 1H), 7.83-7.70 (m, 2H), 7.64 (br d, J=7.6 Hz, 1H), 7.54 (br d, J=7.6 Hz, 1H), 7.32 (br s, 3H), 7.28-7.00 (m, 3H), 4.99 (br s, 2H), 4.10 (br d, J=5.4 Hz, 2H), 3.04 (br s, 3H), 1.38 (br s, 3H).

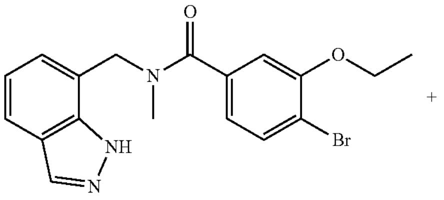

4

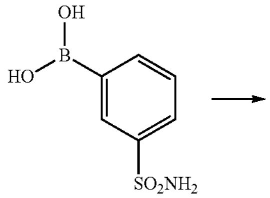

G

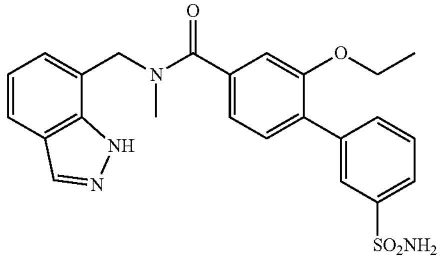

006

Compound 006 was prepared as described for the synthesis of Compound 001 with Compound 4 and Compound G as the starting materials, however, step 1 was conducted at 100° C. for 16 h and step 2 was conducted at 15° C. for 12 h. Compound 006 (34.2 mg, 72.66 umol, 35.27% yield, 98.7% purity) was obtained as white solid. LCMS: m/z=465.1 (M+H$^+$). $^1$H NMR (400 MHz, CHLOROFORM-d) δ=8.34-8.10 (m, 2H), 7.97-7.88 (m, 1H), 7.80 (br s, 2H), 7.66-7.53 (m, 1H), 7.43-7.29 (m, 2H), 7.24-7.00 (m, 3H), 5.00 (br s, 4H), 4.26-3.90 (m, 2H), 3.03 (br s, 3H), 1.38 (br s, 3H).

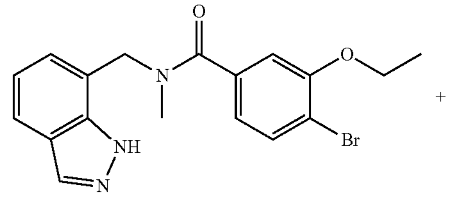

4

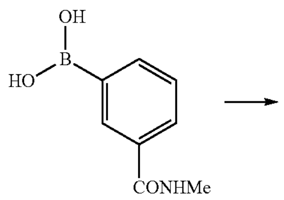

C

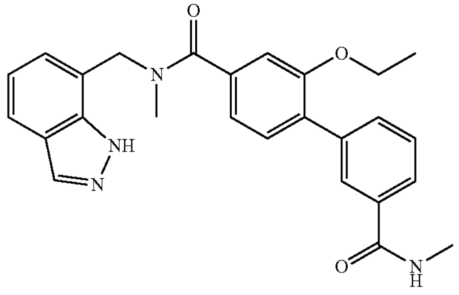

007

Compound 007 was prepared as described for the synthesis of Compound 001 with Compound 4 and Compound C as the starting materials. Also, step 1 was conducted at 100° C. for 16 h and step 2 was conducted at 100° C. for 16 h. Compound 007 (13.8 mg, 30.25 umol, 14.68% yield, 97.0% purity) was obtained as a gray solid. LCMS: m/z=443.1 ($M+H^+$). $^1H$ NMR (400 MHz, CHLOROFORM-d) δ=8.20-8.08 (m, 1H), 7.94 (s, 1H), 7.85-7.77 (m, 1H), 7.77-7.64 (m, 2H), 7.54-7.44 (m, 1H), 7.37 (br d, J=7.7 Hz, 1H), 7.31 (br d, J=6.6 Hz, 1H), 7.22-7.01 (m, 3H), 6.36-6.03 (m, 1H), 4.99 (s, 2H), 4.07 (br d, J=6.4 Hz, 2H), 3.24-2.89 (m, 6H), 1.36 (br t, J=6.2 Hz, 3H)

Scheme 2.

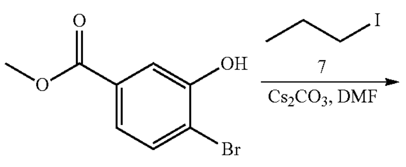

6

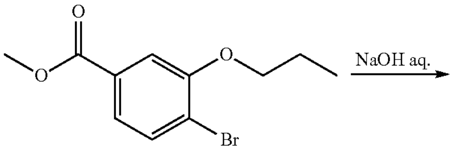

8

-continued

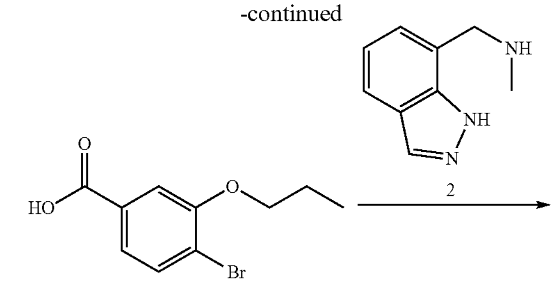

9

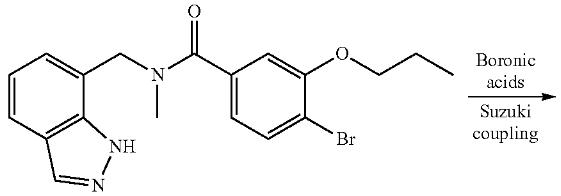

10

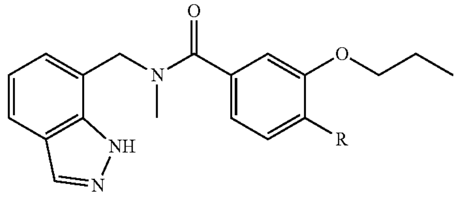

To a solution of compound 6 (5 g, 21.64 mmol, 1 eq) in DMF (50 mL) was added compound 7 (5.52 g, 32.46 mmol, 3.17 mL, 1.5 eq) and $Cs_2CO_3$ (7.05 g, 21.64 mmol, 1 eq), the mixture was stirred at 50° C. for 1 hr. TLC (PE:EtOAc=10:1, Rf=0.5) showed the starting material was consumed completely and a new point was detected. The mixture was filtered and the filtrate was collected. The filtrate was poured into water (50 mL). The aqueous phase was extracted with ethyl acetate (50 mL×3). The combined organic phase was washed with brine (50 mL×4), dried with anhydrous $Na_2SO_4$, filtered and concentrated to give a crude product in vacuum. The crude product used for next step without further purification. Compound 8 (5.14 g, 18.39 mmol, 84.96% yield, 97.7% purity) was obtained as black brown solid, confirmed by LCMS and $^1H$ NMR. LCMS: m/z=273.0 ($M+H^+$). 1H NMR (400 MHz, DMSO-d6) δ=7.72 (d, J=8.1 Hz, 1H), 7.50 (d, J=1.8 Hz, 1H), 7.44 (dd, J=1.9, 8.1 Hz, 1H), 4.09-4.03 (m, 2H), 3.86 (s, 3H), 1.77 (sxt, J=7.0 Hz, 2H), 1.02 (t, J=7.4 Hz, 3H).

To a solution of methyl compound 8 (5.14 g, 18.39 mmol, 97.7% purity, 1 eq) in MeOH (60 mL) and THF (60 mL) was added NaOH in water (2 M, 60 mL, 6.53 eq), the mixture was stirred at 50° C. for 1 hr. The mixture was adjusted to pH=2 with HCl (1 mol/L). Then there was a lot of solid separated out, the mixture was filtered and the white solid was collected and dried in vacuo. The crude product used for next step without further purification. Compound 9 (4.37 g, 16.83 mmol, 91.55% yield, 99.8% purity) was obtained as white solid, confirmed by LCMS and $^1H$ NMR. LCMS: m/z=256.9 (M+H+). 1H NMR (400 MHz, DMSO-d6) δ=13.22 (s, 1H), 7.71 (d, J=8.1 Hz, 1H), 7.52 (s, 1H), 7.47-7.42 (m, 1H), 4.07 (t, J=6.3 Hz, 2H), 1.77 (sxt, J=6.9 Hz, 2H), 1.02 (t, J=7.4 Hz, 3H).

Compound 10 was prepared as described for the synthesis of compound 4 with compound 9 and compound 2 as the starting materials. Compound 10 (1 g, 2.49 mmol, 80.51% yield, 100% purity) was obtained as a white solid. LCMS:

m/z=401.9 (M+H+). $^1$H NMR (400 MHz, CHLOROFORM-d) δ=8.13-7.96 (m, 1H), 7.81-7.63 (m, 1H), 7.53-7.37 (m, 1H), 7.22-7.15 (m, 1H), 7.08-7.00 (m, 1H), 6.92-6.87 (m, 1H), 6.83-6.76 (m, 1H), 4.85 (s, 2H), 3.91 (s, 2H), 2.86 (s, 3H), 1.88-1.69 (m, 2H), 0.99 (t, J=7.4 Hz, 3H).

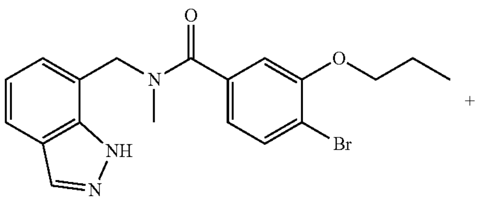

10

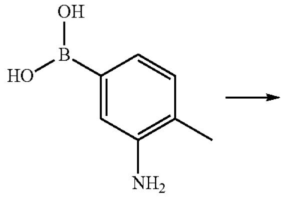

A

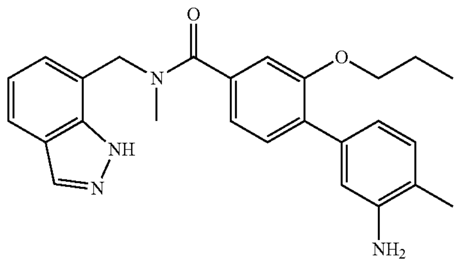

008

Compound 008 was prepared as described for the synthesis of Compound 001 with Compound 10 and Compound A as the starting materials and step 2 at 20° C. for 12 hr. Compound 008 (19.8 mg, 44.91 umol, 25.81% yield, 97.2% purity) was obtained as a red solid. LCMS: m/z=429.2 ($M+H^+$). 1H NMR (400 MHz, DMSO-d6) δ=12.95-12.64 (m, 1H), 8.15-8.08 (m, 1H), 7.78-7.70 (m, 1H), 7.29 (dd, J=7.4, 15.2 Hz, 2H), 7.22-7.15 (m, 1H), 7.11-7.05 (m, 2H), 6.94 (d, J=7.6 Hz, 1H), 6.82-6.76 (m, 1H), 6.66 (d, J=7.3 Hz, 1H), 4.94 (s, 2H), 4.83-4.36 (m, 2H), 3.78 (s, 2H), 3.04 (s, 3H), 2.10 (s, 3H), 1.60 (d, J=7.0 Hz, 2H), 0.87 (t, J=7.1 Hz, 3H).

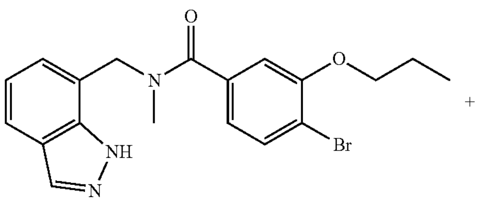

10

-continued

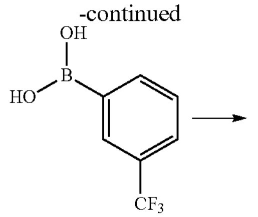

B

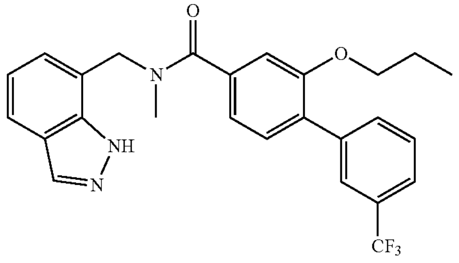

009

Compound 009 was prepared as described for the synthesis of Compound 001 with Compound 10 and Compound B as the starting materials and step 2 at 20° C. for 12 h. Compound 009 (10.2 mg, 21.69 umol, 12.46% yield, 99.4% purity) was obtained as a white solid. LCMS: m/z=468.2 ($M+H^+$). $^1$H NMR (400 MHz, CHLOROFORM-d) δ=8.31-8.11 (m, 1H), 7.92-7.78 (m, 2H), 7.77-7.67 (m, 1H), 7.65-7.49 (m, 3H), 7.44-7.30 (m, 2H), 7.26-7.02 (m, 3H), 5.01 (br s, 2H), 4.15-3.83 (m, 2H), 3.17-2.90 (m, 3H), 1.83-1.70 (m, 2H), 0.99 (br s, 3H).

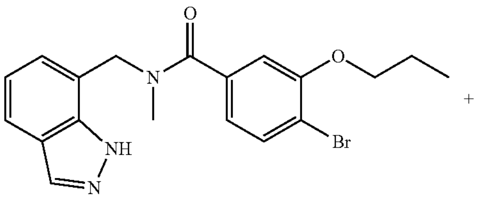

10

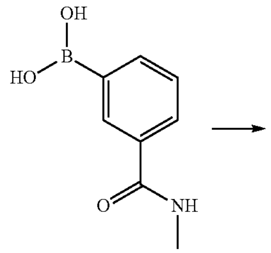

C

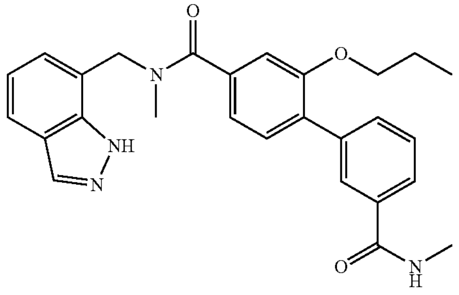

010

Compound 010 was prepared as described for the synthesis of Compound 001 with Compound 10 and Compound C as the starting materials and step 2 at 20° C. for 12 h. Compound 010 (20.3 mg, 44.33 umol, 25.48% yield, 99.7% purity) was obtained as a white solid. LCMS: m/z=457.2 (M+H+). $^1$H NMR (400 MHz, CHLOROFORM-d) δ=11.92 (s, 1H), 8.05 (s, 1H), 7.84 (s, 1H), 7.75-7.56 (m, 3H), 7.45-7.35 (m, 1H), 7.29-7.24 (m, 1H), 7.21 (d, J=6.9 Hz, 1H), 7.06 (t, J=7.5 Hz, 1H), 6.99 (t, J=3.1 Hz, 2H), 6.10 (s, 1H), 4.90 (s, 2H), 3.86 (t, J=6.3 Hz, 2H), 3.06-2.84 (m, 6H), 1.74-1.61 (m, 2H), 0.87 (t, J=7.4 Hz, 3H).

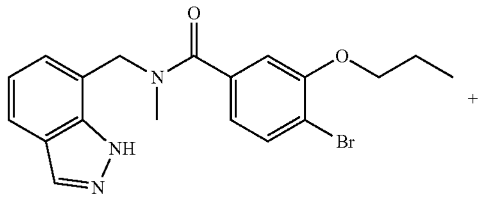

10

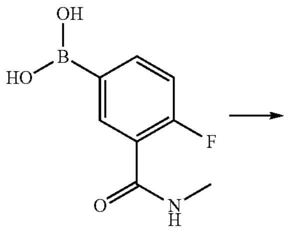

D

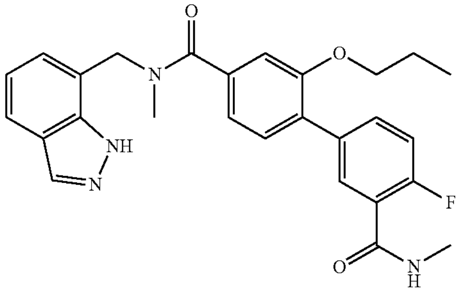

011

Compound 011 was prepared as described for the synthesis of Compound 001 with Compound 10 and Compound D as the starting materials and step 2 at 20° C. for 12 h. Compound 011 (18.1 mg, 37.00 umol, 21.26% yield, 97% purity) was obtained as a white solid. LCMS: m/z=475.3 (M+H+). $^1$H NMR (400 MHz, CHLOROFORM-d) δ=8.26 (d, J=6.97 Hz, 1H) 8.22-8.11 (m, 1H) 7.80 (d, J=3.55 Hz, 1H) 7.68 (s, 1H) 7.35 (s, 1H) 7.32 (s, 1H) 7.19-7.04 (m, 4H) 6.78-6.75 (m, 1H) 4.99 (s, 2H) 4.04-3.88 (m, 2H) 3.08-3.01 (m, 6H) 1.75 (s, 2H) 0.97 (s, 3H).

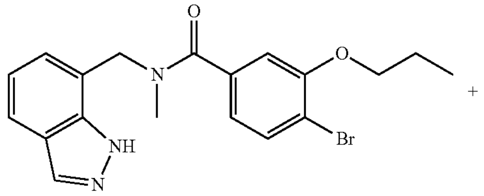

10

-continued

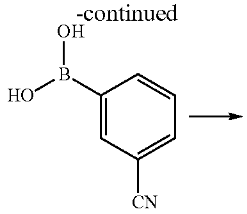

E

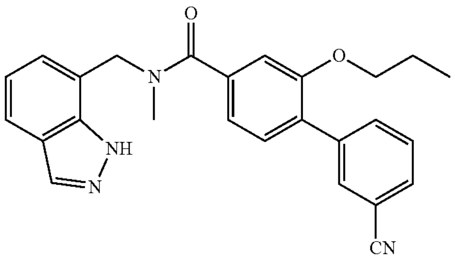

012

Compound 012 was prepared as described for the synthesis of compound 001 with compound 10 and compound E as the starting materials and step 2 at 20° C. for 12 h. Compound 012 (12.5 mg, 28.86 umol, 16.58% yield, 98% purity) was obtained as a white solid. LCMS: m/z=425.2 (M+H+). $^1$H NMR (400 MHz, CHLOROFORM-d) δ=8.27-8.05 (m, 1H), 7.85 (s, 1H), 7.77 (d, J=7.7 Hz, 2H), 7.62 (d, J=7.6 Hz, 1H), 7.55-7.48 (m, 1H), 7.31 (s, 2H), 7.23-6.97 (m, 3H), 5.07-4.90 (m, 2H), 4.11-3.84 (m, 2H), 3.02 (s, 3H), 1.75 (s, 2H), 0.97 (s, 3H).

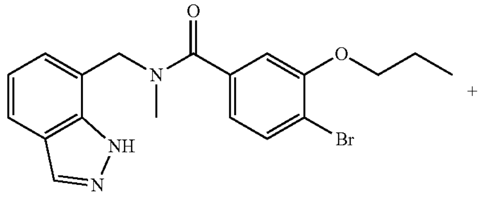

10

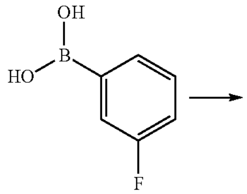

F

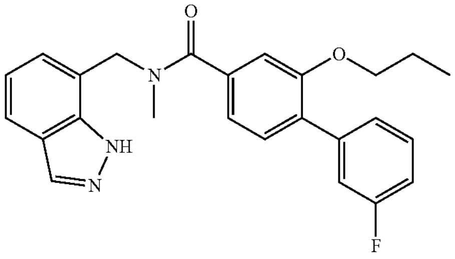

013

Compound 013 was prepared as described for the synthesis of compound 001 with compound 10 and compound F as the starting materials and step 2 at 20° C. for 12 h.

Compound 013 (39.8 mg, 94.38 umol, 54.24% yield, 99% purity) was obtained as a white solid. LCMS: m/z=418.2 ($M+H^+$). $^1H$ NMR (400 MHz, CHLOROFORM-d) δ=8.23 (s, 1H) 7.80 (d, J=6.50 Hz, 1H) 7.65 7.44 m, 1H) 7.33 (s, 5H) 7.17 (s, 1H) 7.09 (s, 3H) 4.99 (s, 2H) 3.97 (s, 2H) 3.03 (s, 3H) 1.78 (d, J=5.63 Hz, 2H) 1.00 (s, 3H).

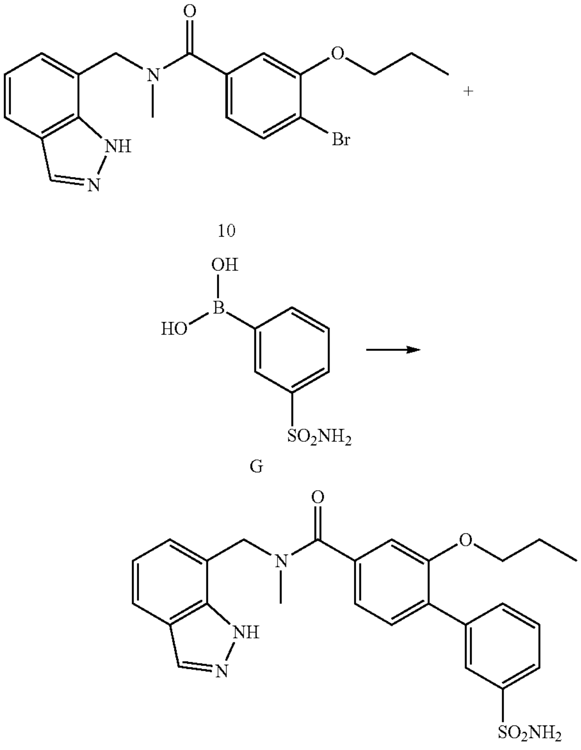

10

G

014

Compound 014 was prepared as described for the synthesis of compound 001 with compound 10 and compound G as the starting materials and step 2 at 20° C. for 12 h. Compound 014 (21.2 mg, 44.21 umol, 25.41% yield, 99.8% purity) was obtained as a white solid. LCMS: m/z=479.3 ($M+H^+$). $^1H$ NMR (400 MHz, CHLOROFORM-d) δ=8.27-8.17 (m, 1H) 8.14 (s, 1H) 7.90 (d, J=6.72 Hz, 1H) 7.81 (d, J=1.83 Hz, 1H) 7.77 (d, J=7.09 Hz, 1H) 7.56 (d, J=5.99 Hz, 1H) 7.44-7.30 (m, 2H) 7.17 (s, 1H) 7.13-7.06 (m, 1H) 5.00 (s, 2H) 4.39-4.75 (m, 2H) 4.12-3.82 (m, 2H) 3.12-2.93 (m, 3H) 1.83-1.64 (m, 2H) 0.97 (s, 3H).

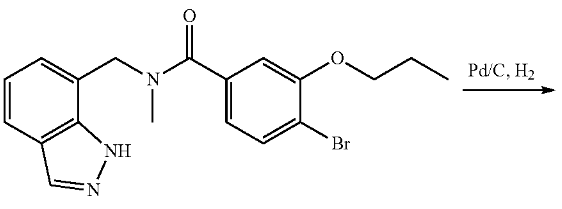

10

-continued

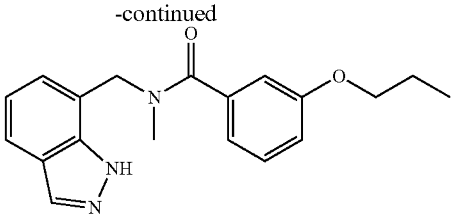

015

To a solution of compound 10 (50 mg, 124.29 umol, 1 eq) in THF (5 mL) was added Pd/C (20 mg, 18.80 umol, 10% purity, 1.51e-1 eq) under $N_2$ atmosphere, the mixture was stirred at 30° C. for 12 hr in $H_2$ (250.55 ug, 124.29 umol, 1 eq) atmosphere. LCMS showed the starting material was consumed completely and there was 70% desired mass. The reaction mixture was filtered under $N_2$ atmosphere, the filtrate was concentrated to give a crude product. The crude product was purified by prep-HPLC (FA, column: Phenomenex luna C18 150*25 mm*10 um; mobile phase: [water (0.225% FA)-ACN]; B %: 46%-76%, 10 min). The purified solution was lyophilized. Compound 015 (21.5 mg, 66.48 umol, 53.49% yield, 100% purity) was obtained as colorless oil, confirmed by LCMS and $^1H$ NMR. LCMS: m/z=324.1 ($M+H^+$). $^1H$ NMR (400 MHz, CHLOROFORM-d) δ=8.17 (s, 1H), 7.80 (d, J=8.1 Hz, 1H), 7.37-7.29 (m, 2H), 7.21-7.12 (m, 1H), 7.04-6.94 (m, 3H), 4.97 (s, 2H), 3.94 (t, J=6.5 Hz, 2H), 2.96 (s, 3H), 1.86-1.76 (m, 2H), 1.05 (t, J=7.4 Hz, 3H).

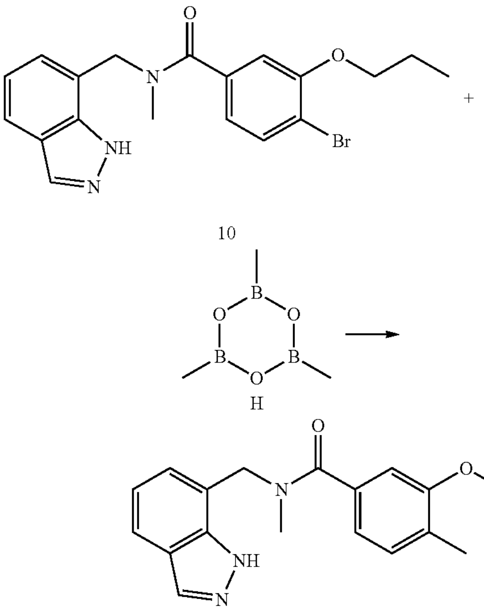

10

H

016

Compound 016 was prepared as described for the synthesis of compound 001 with compound 10 and compound H as the starting materials and step 2 at 20° C. for 3 hr. Compound 016 (24.7 mg, 72.40 umol, 41.61% yield, 98.9% purity) was obtained as a black brown oil. LCMS: m/z=338.1 ($M+H^+$). $^1H$ NMR (400 MHz, CHLOROFORM-d) δ=8.17 (s, 1H), 7.80 (d, J=8.1 Hz, 1H), 7.31 (d, J=6.7 Hz, 1H), 7.15 (d, J=6.6 Hz, 2H), 6.94 (s, 2H), 4.97 (s, 2H), 3.96 (s, 2H), 2.99 (s, 3H), 2.26 (s, 3H), 1.85 (d J=7.0 Hz, 2H), 1.07 (t, J=7.2

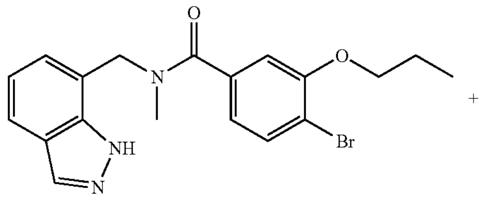

10

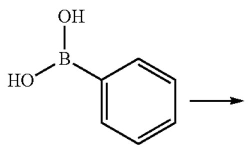

I

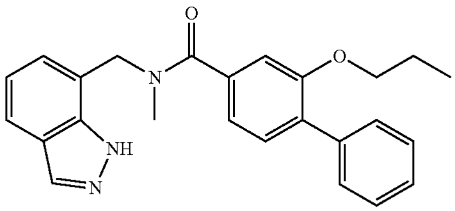

017

Compound 017 was prepared as described for the synthesis of compound 001 with compound 10 and compound I as the starting materials and step 2 at 20° C. for 3 hr. Compound 017 (15.9 mg, 38.81 umol, 22.30% yield, 97.5% purity) was obtained as a yellow solid. LCMS: m/z=400.2 ($M+H^+$). $^1H$ NMR (400 MHz, CHLOROFORM-d) δ=8.37-8.02 (m, 1H), 7.92-7.75 (m, 1H), 7.59-7.53 (m, 2H), 7.45-7.40 (m, 2H), 7.39-7.30 (m, 3H), 7.24-6.99 (m, 3H), 5.17-4.89 (m, 2H), 3.99 (td, J=1.3, 2.7 Hz, 2H), 3.07 (s, 3H), 1.77 (d, J=1.2 Hz, 2H), 1.06-0.93 (m, 3H).

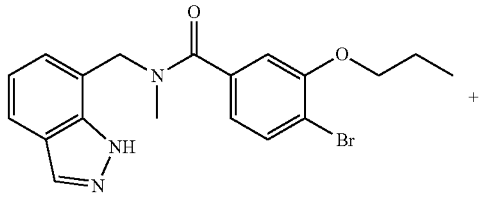

10

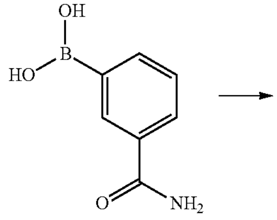

J

-continued

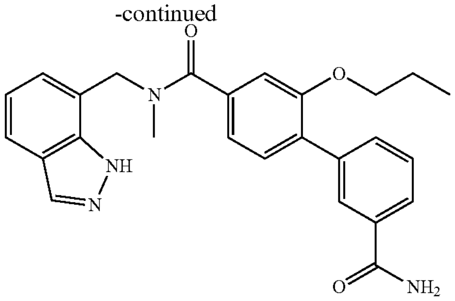

018

Compound 018 was prepared as described for the synthesis of compound 001 with compound 10 and compound J as the starting materials and step 2 at 20° C. for 12 h. Compound 018 (17.5 mg, 39.55 umol, 22.73% yield, 100% purity) was obtained as a white solid. LCMS: m/z=443.3 ($M+H^+$). $^1H$ NMR (400 MHz, CHLOROFORM-d) δ=8.18 (s, 1H) 8.00 (s, 1H) 7.84-7.76 (m, 2H) 7.73 (d, J=7.46 Hz, 1H) 7.50 (t, J=7.40 Hz, 1H) 7.40-7.30 (m, 2H) 7.17 (t, J=6.85 Hz, 1H) 7.09 (s, 2H) 6.33-6.02 (m, 1H) 6.01-5.72 (m, 1H) 5.06-4.92 (m, 2H) 3.96 (s, 2H) 3.03 (s, 3H) 1.74 (d, J=5.75 Hz, 2H) 0.96 (t, J=6.91 Hz, 3H).

Scheme 3.

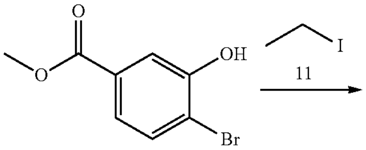

6

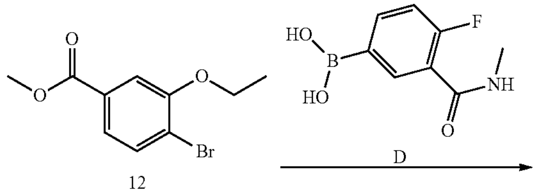

12

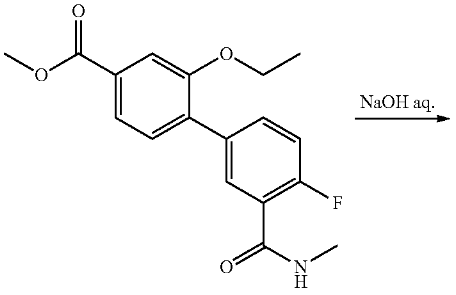

13

-continued

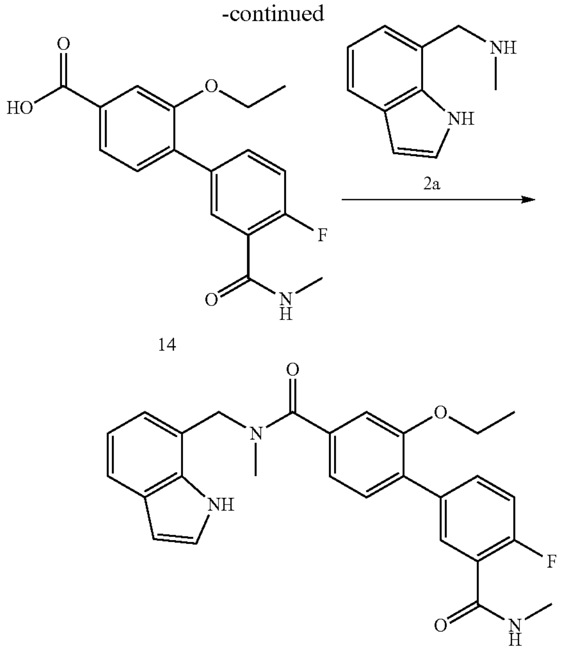

14

2a

019

Compound 12 was prepared as described for the synthesis of compound 8 with compound 6 and compound 11 as the starting materials. Compound 12 (950 mg, 3.47 mmol, 80.14% yield, 94.6% purity) was obtained as a yellow solid. LCMS: m/z=260.9 ($M+H^+$). $^1H$ NMR (400 MHz, DMSO-$d_6$) δ=7.78 (d, J=8.3 Hz, 1H), 7.56 (d, J=1.8 Hz, 1H), 7.50 (dd, J=1.9, 8.1 Hz, 1H), 4.22 (q, J=7.0 Hz, 2H), 3.91 (s, 3H), 1.43 (t, J=6.9 Hz, 3H).

Compound 13 was prepared as described for the synthesis of compound 001 with compound 12 and compound D as the starting materials and step 1 at 90° C. for 12 hr. The mixture was poured into water (20 ml) and the aqueous phase was extracted with ethyl acetate (20 mL×3). The combined organic phase was washed with brine (20 mL×4), dried with anhydrous $Na_2SO_4$, filtered and concentrated to give a crude product in vacuum. The crude product was purified by column chromatography on silica gel eluted with PE:EtOAc=8:1 to 4:1. Compound 13 (480 mg, 1.43 mmol, 78.24% yield, 98.6% purity) was obtained as yellow solid. LCMS: m/z=332.1 ($M+H^+$). $^1H$ NMR (400 MHz, DMSO-$d_6$) δ=8.36 (d, J=2.3 Hz, 1H), 7.83 (dd, J=2.3, 6.9 Hz, 1H), 7.77 (ddd, J=2.4, 5.0, 8.5 Hz, 1H), 7.69 (dd, J=1.4, 7.9 Hz, 1H), 7.64 (d, J=1.4 Hz, 1H), 7.55 (d, J=7.9 Hz, 1H), 7.40 (dd, J=8.7, 10.3 Hz, 1H), 4.18 (q, J=6.9 Hz, 2H), 3.93 (s, 3H), 2.84 (d, J=4.5 Hz, 3H), 1.34 (t, J=6.9 Hz, 3H).

Compound 14 was prepared as described for the synthesis of compound 9 with compound 13 as the starting material and step 1 at 30° C. for 1 h. The crude product used for next step without further purification. Compound 14 (315 mg, 962.94 umol, 66.47% yield, 97.0% purity) was obtained as a yellow solid. LCMS: m/z=318.1 (M+H+). $^1H$ NMR (400 MHz, DMSO-$d_6$) δ=13.09 (s, 1H), 8.32 (s, 1H), 7.78 (d, J=5.3 Hz, 1H), 7.72 (d, J=2.8 Hz, 1H), 7.64-7.57 (m, 2H), 7.47 (d, J=7.7 Hz, 1H), 7.34 (t, J=9.4 Hz, 1H), 4.12 (q, J=6.7 Hz, 2H), 2.79 (d, J=4.3 Hz, 3H), 1.29 (t, J=6.8 Hz, 3H).

Compound 019 was prepared as described for the synthesis of compound 4 with compound 14 and compound 2a as the starting materials. The mixture was concentrated to give a crude product. The crude product was purified by prep-HPLC (FA, column: Phenomenex luna C18 150*25 mm*10 um; mobile phase: [water(0.225% FA)-ACN]; B %: 49%-79%, 10 min), the purified solution was lyophilized. Compound 019 (21.7 mg, 47.04 umol, 21.32% yield, 99.6% purity) was obtained as a white solid. LCMS: m/z=460.2 (M+H+). $^1H$ NMR (400 MHz, CHLOROFORM-d) δ=10.44 (s, 1H), 8.28 (dd, J=2.3, 7.6 Hz, 1H), 7.75-7.65 (m, 2H), 7.39-7.32 (m, 2H), 7.21-7.15 (m, 1H), 7.15-7.07 (m, 2H), 7.06-6.98 (m, 2H), 6.84-6.72 (m, 1H), 6.65-6.58 (m, 1H), 5.06-4.93 (m, 2H), 4.13-4.00 (m, 2H), 3.14-2.97 (m, 6H), 1.37 (t, J=6.9 Hz, 3H).

Scheme 4

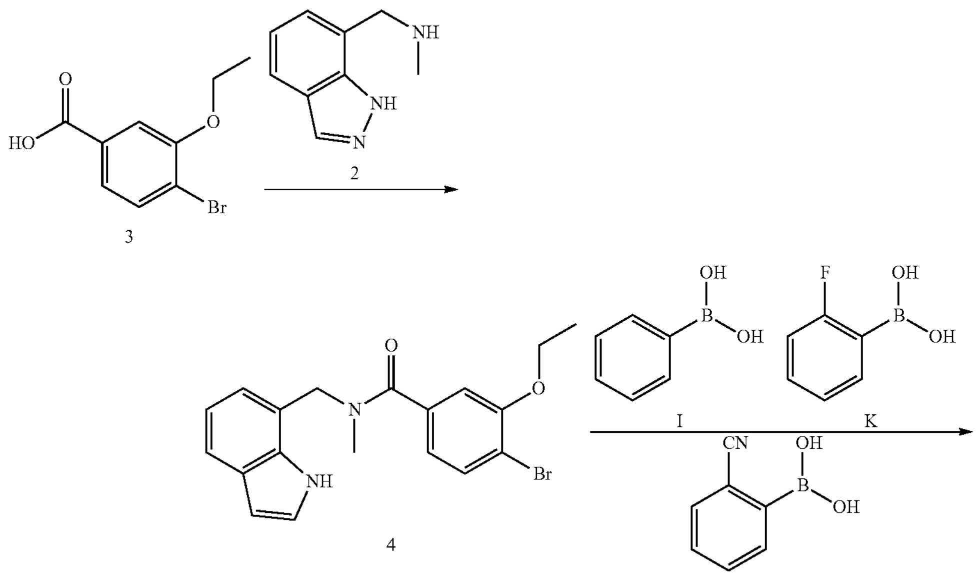

2

3

4

I

K

L

-continued

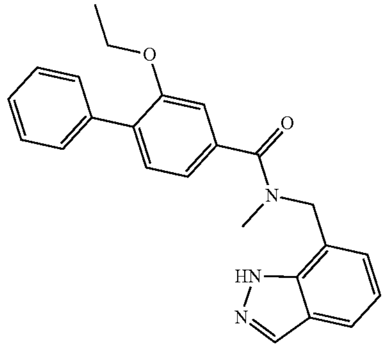

036

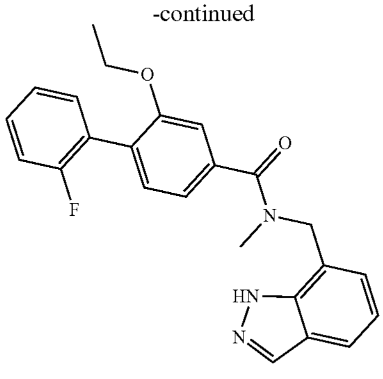

035

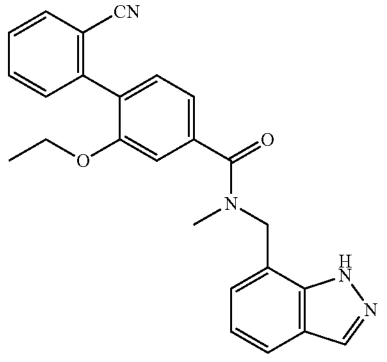

034

To a solution of compound 2 and compound 3 (456.13 mg, 2.32 mmol, 1.2 eq) in dioxane (5 mL) and $H_2O$ (0.6 mL) was added $Pd(dppf)Cl_2 \cdot CH_2Cl_2$ (315.19 mg, 385.96 umol, 0.2 eq), the mixture stirred at 90° C. for 12 h. LCMS showed most of the starting material was remained, then $K_2CO_3$ (533.42 mg, 3.86 mmol, 2 eq) was added, the mixture was stirred at 90° C. for 4 h. LCMS (showed the starting material was consumed completely. After the reaction was completed, the mixture was poured into water (100 mL) and extracted with EtOAc (100 mL×3), the combined organic phase was washed with brine (100 mL), dried over anhydrous $Na_2SO_4$, and concentrated to give a crude product. The crude product was purified by column chromatography ($SiO_2$, Petroleum ether/Ethyl acetate=1/0 to 1/1, desired product Rf=0.6). Compound 4 (630 mg, crude) was obtained as yellow oil. LCMS: m/z=331.9 ($M+H^+$)

Compound 036 was prepared as described for the synthesis of compound 001 with compound 4 and compound I as the starting materials. Also, step 1 was conducted at 90° C. for 12 hr and step 2 was conducted at 15° C. for 12 h. Compound 036 (16.71 mg, 43.35 umol, 42.08% yield, 100% purity) obtained as a white solid. LCMS: m/z=386.1 ($M+H^+$). $^1H$ NMR (400 MHz, CHLOROFORM-d) δ=8.10-8.03 (m, 1H), 7.74-7.67 (m, 1H), 7.50-7.43 (m, 2H), 7.37-7.30 (m, 2H), 7.29-7.20 (m, 3H), 7.10-6.97 (m, 3H), 4.97-4.84 (m, 2H), 4.07-3.91 (m, 2H), 3.02-2.88 (m, 3H), 1.34-1.21 (m, 3H).

Compound 035 was prepared as described for the synthesis of Compound 001 with compound 4 and compound K as the starting materials. Also, step 1 was conducted at 90° C. for 12 hr and step 2 was conducted at 15° C. for 12 h. Compound 035 (5.48 mg, 13.58 umol, 13.18% yield, 100% purity) obtained as a white solid. LCMS: m/z=404.1 ($M+H^+$). $^1H$ NMR (400 MHz, CHLOROFORM-d) δ=8.11-8.03 (m, 1H), 7.75-7.66 (m, 1H), 7.32-7.20 (m, 4H), 7.16-6.92 (m, 5H), 4.96-4.86 (m, 2H), 4.04-3.91 (m, 2H), 2.99-2.90 (m, 3H), 1.26-1.19 (m, 3H)

Compound 034 was prepared as described for the synthesis of compound 001 with compound 4 and compound L as the starting materials. Also, step 1 was conducted at 90° C. for 12 hr and step 2 was conducted at 15° C. for 12 h. Compound 034 (8.62 mg, 21.00 umol, 20.38% yield, 100% purity) obtained as a white solid. LCMS: m/z=411.1 ($M+H^+$). $^1H$ NMR (400 MHz, CHLOROFORM-d) δ=8.28-8.04 (m, 1H), 7.90-7.71 (m, 2H), 7.70-7.61 (m, 1H), 7.54-7.39 (m, 2H), 7.37-7.29 (m, 2H), 7.24-7.06 (m, 3H), 5.13-4.90 (m, 2H), 4.21-4.04 (m, 2H), 3.11-2.99 (m, 3H), 1.41-1.30 (m, 3H).

Scheme 5.

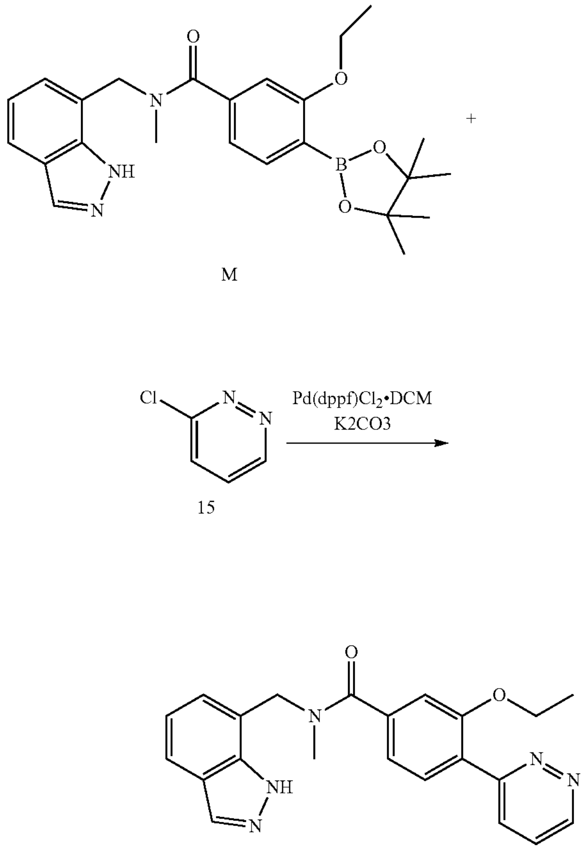

M

15

037

Compound 037 was prepared as described for the synthesis of compound 001 with compound M and compound 15 as the starting materials. Also, step 1 was conducted at 90° C. for 12 hr and step 2 was conducted at 15° C. for 12 h. Compound 037 (6.46 mg, 16.67 umol, 18.15% yield, 100% purity) was obtained as a red solid. LCMS: m/z=388.1 ($M+H^+$), $^1H$ NMR (400 MHz, CHLOROFORM-d) δ=9.11-9.02 (m, 1H), 8.08-8.04 (m, 1H), 8.03-7.97 (m, 1H), 7.96-7.92 (m, 1H), 7.73-7.68 (m, 1H), 7.44-7.39 (m, 1H), 7.23-7.20 (m, 1H), 7.11-7.03 (m, 3H), 4.97-4.84 (m, 2H), 4.11-3.98 (m, 2H), 2.97-2.86 (m, 3H), 1.34-1.26 (m, 3H).

Scheme 6.

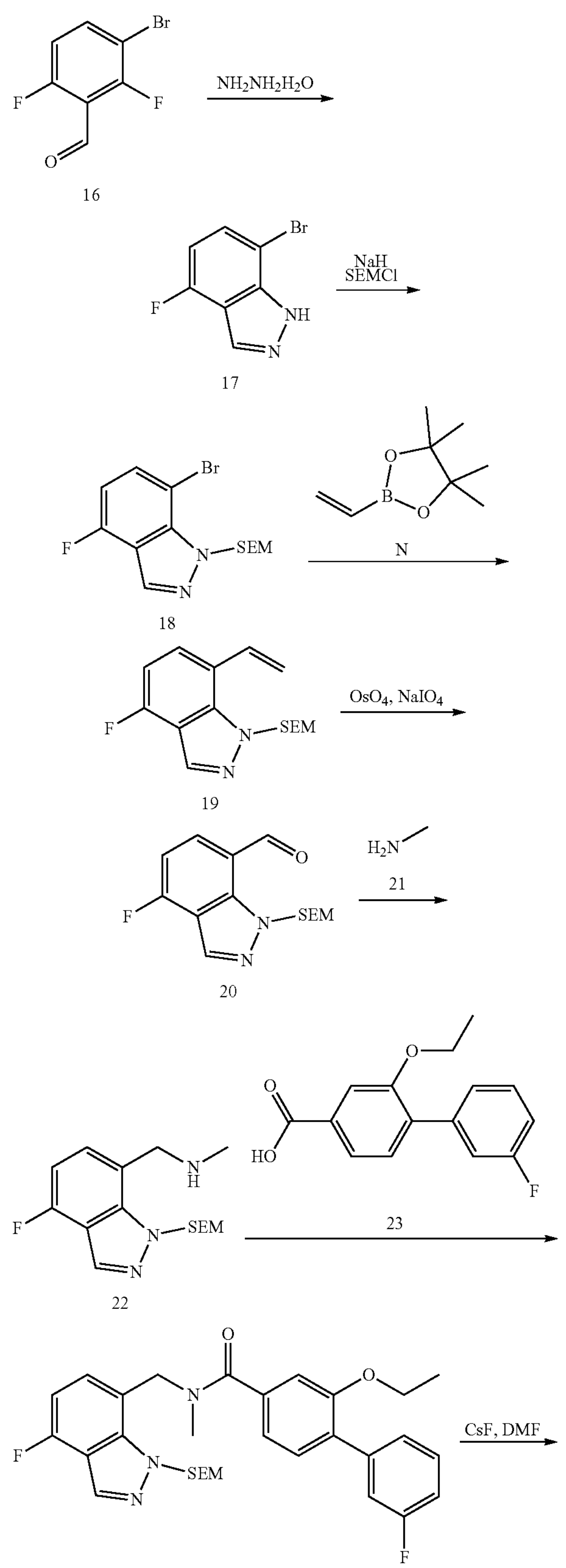

-continued

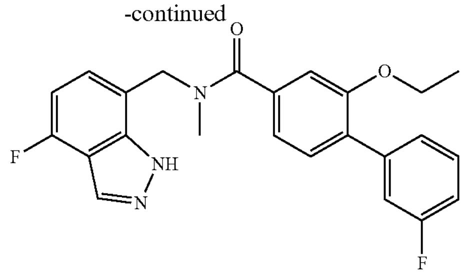

038

To a solution of compound 16 (5 g, 22.62 mmol, 1 eq) in DMSO (50 mL) was added $NH_2NH_2 \cdot H_2O$ (4.53 g, 90.50 mmol, 4.40 mL, 4 eq), the mixture was stirred at 130° C. for 12 hr. LCMS showed there was desired mass. The mixture was cooled to room temperature and poured into water (200 mL). The aqueous phase was extracted with ethyl acetate (200 mL*3). The combined organic phase was washed with brine (200 mL*4), dried with anhydrous $Na_2SO_4$, filtered and concentrated to give a crude product in vacuum. The crude product was purified by column chromatography on silica gel eluted with petroleum ether/ethyl acetate=6:1 to 4:1. Compound 17 (1.05 g, 4.51 mmol, 19.94% yield, 92.4% purity) was obtained as white solid, confirmed by LCMS and $^1H$ NMR. LCMS: m/z=215.0 ($M+H^+$). $^1H$ NMR (400 MHz, DMSO-$d_6$) δ=13.84 (s, 1H), 8.35 (s, 1H), 7.58 (dd, J=4.3, 8.2 Hz, 1H), 6.90 (dd, J=8.5, 9.6 Hz, 1H)

To a solution of compound 17 (1.05 g, 4.88 mmol, 1 eq) in THF (15 mL) was added SEM-Cl (1.22 g, 7.32 mmol, 1.30 mL, 1.5 eq) and NaH (390.62 mg, 9.77 mmol, 60% purity, 2 eq) at 0° C., the mixture was stirred at 20° C. for 12 hr. LCMS showed there was desired mass. The mixture was neutralized with saturated $NH_4Cl$ solution (50 mL) at 0° C. and extracted with Ethyl acetate (3×50 mL). The combined organic layer was dried over $Na_2SO_4$ and concentrated under reduced pressure to give a residue. The crude product was purified by column chromatography on silica gel eluted with petroleum ether/ethyl acetate=6:1 to 5:1. Compound 18 (1.5 g, crude) was obtained as colorless oil, confirmed by LCMS. LCMS: m/z=347.0 ($M+2+H^+$)

Compound 19 was prepared as described for the synthesis of compound 19 with compound 18 and compound N as the starting materials and $Cs_2CO_3$ as the base. The mixture was filtered, and the filtrate was concentrated in vacuo. The crude product was purified by column chromatography on silica gel eluted with petroleum ether/ethyl acetate=15:1 to 14:1. Compound 19 was obtained as colorless oil. LCMS: m/z=293.0 ($M+H^+$). $^1H$ NMR (400 MHz, CHLOROFORM-d) δ=8.15-8.09 (m, 1H), 7.57-7.41 (m, 2H), 6.86 (dd, J=8.2, 9.2 Hz, 1H), 5.87-5.81 (m, 2H), 5.74 (dd, J=1.3, 17.2 Hz, 1H), 5.46 (dd, J=1.1, 10.9 Hz, 1H), 3.65 (dd, J=7.7, 8.8 Hz, 2H), 0.99-0.93 (m, 2H), 0.01--0.04 (m, 9H) To a solution of compound 19 (220 mg, 752.33 umol, 1 eq) in acetone (10 mL) and $H_2O$ (2 mL) was added $OsO_4$ (19.13 mg, 75.23 umol, 3.90 uL, 0.1 eq) and $NaIO_4$ (804.58 mg, 3.76 mmol, 208.44 uL, 5 eq), the mixture was stirred at 20° C. for 3 hr. TLC (PE:EtOAc=5:1, $R_f$=0.6) showed the starting material was consumed completely and there was a new point. The reaction mixture was poured into saturated aqueous $Na_2SO_3$ (40 mL), the combined mixture was stirred for 2 h, the resulting solution was extracted by dichloromethane (2×20 mL), the organic phase was dried and concentrated under vacuo to give a residue. The crude product was purified by prep-TLC (PE:EtOAc=5:1). Compound 20 (80 mg, 244.57 umol, 32.51% yield, 90% purity) was obtained as yellow oil, confirmed by $^1$H NMR. $^1$H NMR (400 MHz, CHLOROFORM-d) δ=10.36 (s, 1H), 8.31 (s, 1H), 8.09 (dd, J=5.4, 8.1 Hz, 1H), 7.09 (t, J=8.4 Hz, 1H), 6.25 (s, 2H), 3.60 (t, J=8.1 Hz, 2H), 0.94 (t, J=8.1 Hz, 2H), 0.00 (s, 9H)

To a solution of compound 20 (70 mg, 237.77 umol, 1 eq) in MeOH (2 mL) was added compound 21 in MeOH (2 M, 356.66 uL, 3 eq) and AcOH (1.43 mg, 23.78 umol, 1.36 uL, 0.1 eq), the mixture was stirred at 20° C. for 2 hr, then the mixture was added $NaBH_4$ (13.49 mg, 356.66 umol, 1.5 eq), the mixture was stirred at 20° C. for 2 hr. LCMS showed there was desired mass. The reaction mixture was poured into $NH_4Cl$ (5 mL), then the mixture was added $Na_2CO_3$ (0.05 g), the solution was filtered, the filtrate was concentrated under reduced pressure to give a residue. Then the solution was triturated in DCM and MeOH and collected by filtration, the filtrate was concentrated under reduced pressure to give a residue. The crude product was purified by prep-HPLC (HCl, column: 3_Phenomenex Luna C18 75*30 mm*3 um; mobile phase: [water(0.05% HCl)-ACN]; B %: 26%-46%, 9 min), the purified solution was lyophilized. Compound 22 (50 mg, 161.58 umol, 67.95% yield, 100% purity) was obtained as white oil, confirmed by LCMS. LCMS: m/z=310.1 ($M+H^+$)

Compound 24 was prepared as described for the synthesis of compound 4 with compound 22 and compound 23 as the starting materials and step 1 at 20° C. for 12 hr. The mixture was concentrated to give a crude product. The crude product was purified by prep-TLC (PE:EtOAc=2:1). Compound 24 was obtained as a white oil. LCMS: m/z=574.3 (M+Na). $^1$H NMR (400 MHz, CHLOROFORM-d) δ=8.02 (s, 1H), 7.36-7.20 (m, 4H), 7.16-6.81 (m, 5H), 5.88-5.51 (m, 2H), 5.27-5.00 (m, 2H), 3.63 (s, 2H), 3.53-3.29 (m, 2H), 3.16-2.90 (m, 3H), 1.16-1.00 (m, 2H), 0.85-0.56 (m, 3H), −0.17 (s, 9H)

The solution of compound 24 (15 mg, 26.56 umol, 97.7% purity, 1 eq) in DMF (1 mL) was added CsF (40.35 mg, 265.63 umol, 9.79 uL, 10 eq), the mixture was stirred at 80° C. for 48 hr. LCMS showed there was desired mass. The mixture was filtered and the filtrate was concentrated in vacuo. The crude product was purified by prep-HPLC (FA, column: Phenomenex luna C18 150*25 mm*10 um; mobile phase: [water(0.225% FA)-ACN]; B %: 50%-80%, 10 min), the purified solution was lyophilized. Compound 038 (5.2 mg, 12.34 umol, 46.45% yield, 100% purity) was obtained as white solid, confirmed by LCMS and $^1$H NMR. LCMS: m/z=422.2 ($M+H^+$). $^1$H NMR (400 MHz, CHLOROFORM-d) δ=12.36-11.90 (m, 1H), 8.10 (s, 1H), 7.35-7.19 (m, 4H), 7.11 (dd, J=4.6, 7.6 Hz, 1H), 7.00-6.91 (m, 3H), 6.66 (dd, J=7.8, 9.6 Hz, 1H), 4.83 (s, 2H), 3.98 (q, J=7.0 Hz, 2H), 2.92 (s, 3H), 1.28 (t, J=7.0 Hz, 3H).

Compound 147 was prepared in a similar manner to 038 and was obtained as a white solid (9.3 mg, 20.39 umol, 24.72% yield, 99% purity). LCMS: m/z=452.2 ($M+H^+$) $^1$H NMR (400 MHz, CHLOROFORM-d) δ=12.24-11.86 (m, 1H), 8.20-8.18 (m, 1H), 7.39-7.28 (m, 4H), 7.20 (d, J=7.6 Hz, 1H), 7.07-7.02 (m, 3H), 6.73 (d, J=7.6 Hz, 1H), 5.97 (s, 1H), 5.83 (s, 1H), 4.91 (s, 2H), 4.06 (q, J=7.0 Hz, 2H), 3.02-2.97 (m, 3H), 1.36 (t, J=7.0 Hz, 3H).

Compound 148 was prepared in a similar manner to 038 and was obtained as an off-white solid (11.3 mg, 25.48 umol, 36.55% yield, 100% purity). LCMS: m/z=444.3 (M+H+) $^1$H NMR (400 MHz, CHLOROFORM-d) δ=12.60-11.41 (m, 1H), 8.24 (s, 1H), 7.32 (br t, J=7.9 Hz, 4H), 7.17 (br d, J=7.0 Hz, 1H), 7.09-7.00 (m, 3H), 6.71 (br d, J=7.0 Hz, 1H), 4.92 (s, 2H), 4.12-4.02 (m, 2H), 2.99 (s, 3H), 2.29 (br d, J=4.8 Hz, 1H), 1.36 (br t, J=6.9 Hz, 3H), 1.11 (br d, J=6.8 Hz, 2H), 0.93 (br d, J=3.4 Hz, 2H).

Compound 149 was prepared in a similar manner to 038 and was obtained as brown solid (3.4 mg, 7.46 umol, 21.55% yield, 98.2% purity). LCMS: m/z=448.2 (M+H+) $^1$H NMR (400 MHz, CHLOROFORM-d) δ=1.37 (br t, J=6.88 Hz, 3H) 2.99 (s, 3H) 3.48 (s, 3H) 4.06 (br d, J=7.00 Hz, 2H) 4.82 (s, 2H) 4.96 (s, 2H) 7.01-7.11 (m, 4H) 7.25 (br d, J=7.00 Hz, 1H) 7.29-7.40 (m, 4H) 8.23 (s, 1H) 11.87-12.21 (m, 1H).

Scheme 7.

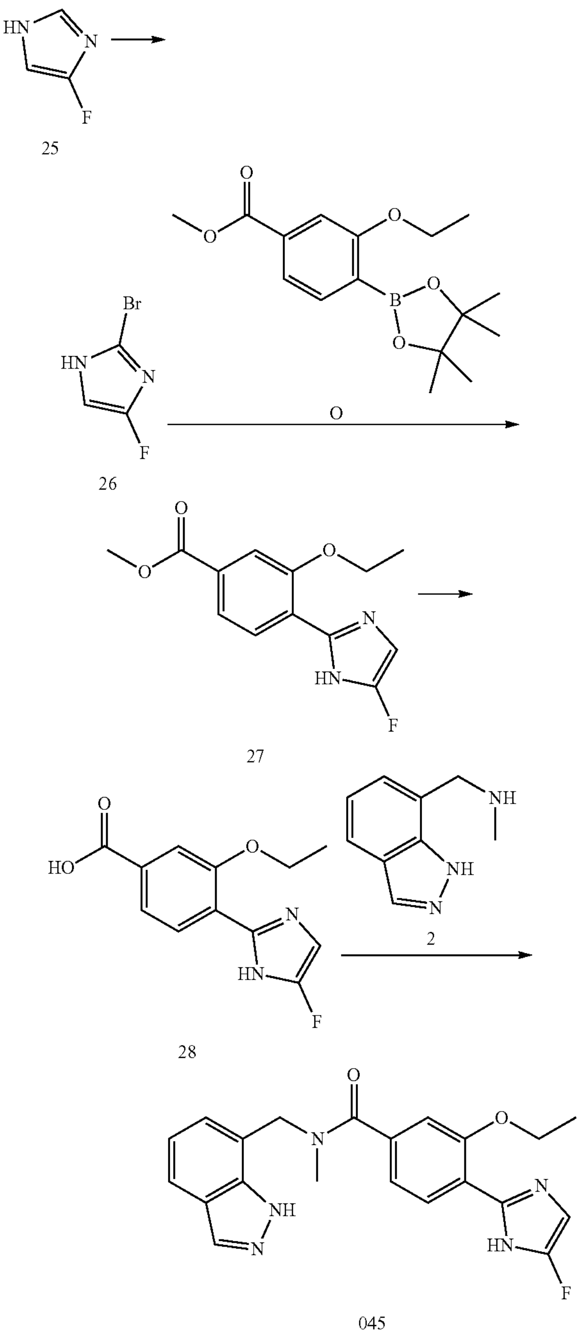

25

26

27

2

28

045

To a solution of compound 25 (200 mg, 2.32 mmol, 1 eq) in $CH_3CN$ (5 mL) and $H_2O$ (5 mL) was added NaBr (239.10 mg, 2.32 mmol, 74.72 uL, 1 eq) and $PhI(OAc)_2$ (748.47 mg, 2.32 mmol, 1 eq) at 20° C. under $N_2$. The reaction was poured into water (20 mL), and extracted by EA (20 mL*3). The organic layers was combined and washed by brine (20 ml) dried over $Na_2SO_4$, filtered and concentrated under vacuum. The residue was purified by silica column (PE: EA=10:1, 5:1) to give Compound 26 (350 mg, 2.04 mmol, 87.65% yield, 96% purity) as a light yellow solid, confirmed by LCMS. LCMS: m/z=166.9 ($M+H^+$)

Compound 27 was prepared as described for the synthesis of 001 with compound 26 and compound O as the starting materials, [2-(2-aminophenyl)phenyl]palladium(1+);bis(1-adamantyl)-butyl-phosphane;methanesulfonate as the catalyst, and $K_3PO_4$ as the base. Also, step 1 was conducted at 100° C. for 4 hours. The reaction mixture was concentrated under vacuum. The residue was purified by silica column (PE/EA=10:1, 3:1) to give Compound 27 (32.76% yield, 91.6% purity) as a light yellow solid. LCMS: m/z=265.0 ($M+H^+$)

Compound 28 was prepared as described for the synthesis of compound 9 with compound 27 as the starting material, LiOH as the base, and step 1 at 50° C. for 2 hr. Also, the pH of the resulting solution was adjusted to 7. Compound 28 (88.54% yield, 96% purity) was obtained as a white solid. LCMS: m/z=250.9 ($M+H^+$)

To a solution of compound 28 (60 mg, 230.53 umol, 96.14% purity, 1 eq) in DMF (4 mL) was added compound 2 (74.32 mg, 461.06 umol, crude purity, 2 eq) and HATU (113.95 mg, 299.69 umol, 1.3 eq); DIEA (59.59 mg, 461.06 umol, 80.31 uL, 2 eq). The mixture was stirred at 20° C. for 2 hours. The reaction was poured into water (20 mL), and extracted by EA (20 mL*3), the organic layers was combined and washed by brine (20 mL), dried over $Na_2SO_4$, filtered and concentrated under vacuum. The residue was purified by Prep-HPLC to give 045 (25.28 mg, 64.26 umol, 27.87% yield, 100% purity) as white solid, confirmed by LCMS and 1H NMR. LCMS: m/z=250.9 ($M+H^+$). 1H NMR (400 MHz, CDCl3) δ ppm 12.00 (s, 1H), 10.39 (s, 1H), 8.13 (s, 1H) 7.75-7.85 (m, 2H), 7.27-7.31 (m, 2H), 7.05-7.19 (m, 3H), 4.96 (s, 2H), 4.24 (q, J=7.2 Hz, 2H), 3.00 (s, 3H) 1.54-1.57 (m, 3H).

Scheme 8.

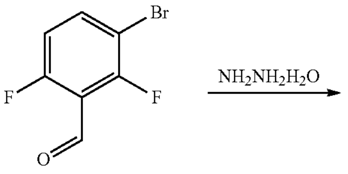

29

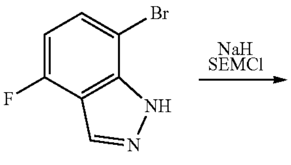

30

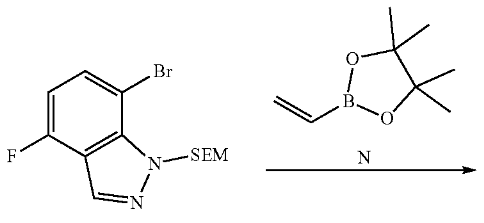

31

-continued

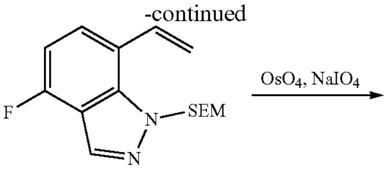

32

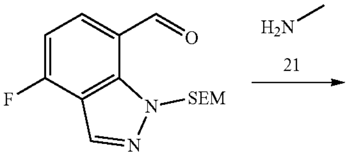

33

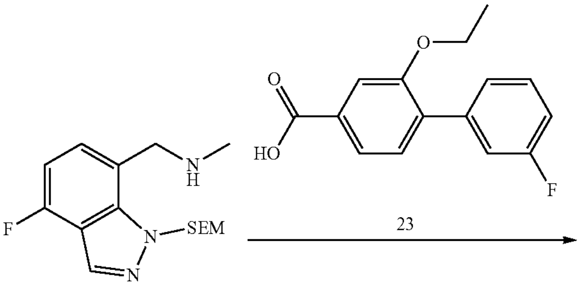

34

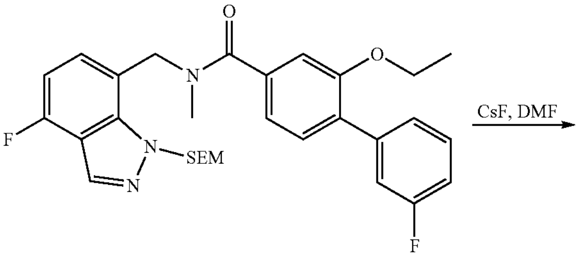

35

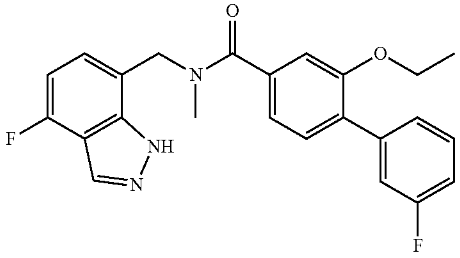

046

To a solution of compound 29 (5 g, 22.62 mmol, 1 eq) in DMSO (50 mL) was added $NH_2NH_2 \cdot H_2O$ (4.53 g, 90.50 mmol, 4.40 mL, 4 eq), the mixture was stirred at 130° C. for 12 hr. LCMS showed there was desired mass. The mixture was cooled to room temperature and poured into water (200 mL). The aqueous phase was extracted with ethyl acetate (200 mL*3). The combined organic phase was washed with brine (200 mL*4), dried with anhydrous $Na_2SO_4$, filtered and concentrated to give a crude product in vacuum. The crude product was purified by column chromatography on silica gel eluted with petroleum ether/ethyl acetate=6:1 to 4:1. Compound 30 (1.05 g, 4.51 mmol, 19.94% yield, 92.4% purity) was obtained as white solid, confirmed by LCMS and $^1H$ NMR. LCMS: m/z=215.0 ($M+H^+$), $^1H$ NMR (400 MHz, DMSO-$d_6$) δ=13.84 (s, 1H), 8.35 (s, 1H), 7.58 (dd, J=4.3, 8.2 Hz, 1H), 6.90 (dd, J=8.5, 9.6 Hz, 1H)

To a solution of compound 30 (1.05 g, 4.88 mmol, 1 eq) in THF (15 mL) was added SEM-Cl (1.22 g, 7.32 mmol, 1.30 mL, 1.5 eq) and NaH (390.62 mg, 9.77 mmol, 60% purity, 2 eq) at 0° C., the mixture was stirred at 20° C. for 12 hr. LCMS showed there was desired mass. The mixture was neutralized with saturated $NH_4Cl$ solution (50 mL) at 0° C. and extracted with Ethyl acetate (3×50 mL). The combined organic layer was dried over $Na_2SO_4$ and concentrated under reduced pressure to give a residue. The crude product was purified by column chromatography on silica gel eluted with petroleum ether/ethyl acetate=6:1 to 5:1. Compound 31 (1.5 g, crude) was obtained as colorless oil, confirmed by LCMS. LCMS: m/z=347.0 ($M+2+H^+$)

Compound 32 was prepared as described for the synthesis of compound 001 with compound 31 and compound N as the starting materials and $Cs_2CO_3$ as the base. The mixture was filtered and the filtrate was concentrated in vacuo. The crude product was purified by column chromatography on silica gel eluted with petroleum ether/ethyl acetate=15:1 to 14:1. Compound 32 was obtained as colorless oil. LCMS: m/z=293.0 ($M+H^+$). $^1H$ NMR (400 MHz, CHLOROFORM-d) δ=8.15-8.09 (m, 1H), 7.57-7.41 (m, 2H), 6.86 (dd, J=8.2, 9.2 Hz, 1H), 5.87-5.81 (m, 2H), 5.74 (dd, J=1.3, 17.2 Hz, 1H), 5.46 (dd, J=1.1, 10.9 Hz, 1H), 3.65 (dd, J=7.7, 8.8 Hz, 2H), 0.99-0.93 (m, 2H), 0.01--0.04 (m, 9H).

Compound 33 was prepared as described for the synthesis of compound 20 with compound 32 as the starting material. Compound 33 (32.51% yield, 90% purity) was obtained as a yellow oil. $^1H$ NMR (400 MHz, CHLOROFORM-d) δ=10.36 (s, 1H), 8.31 (s, 1H), 8.09 (dd, J=5.4, 8.1 Hz, 1H), 7.09 (t, J=8.4 Hz, 1H), 6.25 (s, 2H), 3.60 (t, J=8.1 Hz, 2H), 0.94 (t, J=8.1 Hz, 2H), 0.00 (s, 9H)

To a solution of compound 33 (70 mg, 237.77 umol, 1 eq) in MeOH (2 mL) was added compound 21 in MeOH (2 M, 356.66 uL, 3 eq) and AcOH (1.43 mg, 23.78 umol, 1.36 uL, 0.1 eq), the mixture was stirred at 20° C. for 2 hr, then the mixture was added $NaBH_4$ (13.49 mg, 356.66 umol, 1.5 eq), the mixture was stirred at 20° C. for 2 hr. LCMS showed there was desired mass. The reaction mixture was poured into $NH_4Cl$ (5 mL), then the mixture was added $Na_2CO_3$ (0.05 g), the solution was filtered, the filtrate was concentrated under reduced pressure to give a residue. Then the solution was triturated in DCM and MeOH and collected by filtration, the filtrate was concentrated under reduced pressure to give a residue. The crude product was purified by prep-HPLC (HCl, column: 3_Phenomenex Luna C18 75*30 mm*3 um; mobile phase: [water(0.05% HCl)-ACN]; B %: 26%-46%, 9 min), the purified solution was lyophilized. Compound 34 (50 mg, 161.58 umol, 67.95% yield, 100% purity) was obtained as white oil, confirmed by LCMS. LCMS: m/z=310.1 ($M+H^+$)

Compound 35 was prepared as described for the synthesis of compound 4 with compound 34 and compound 23 as the starting materials and step 1 at 20° C. for 12 hr. The crude product was purified by prep-TLC (PE:EtOAc=2:1). Compound 35 was obtained as a white oil. LCMS: m/z=574.3 (M+Na). $^1H$ NMR (400 MHz, CHLOROFORM-d) δ=8.02 (s, 1H), 7.36-7.20 (m, 4H), 7.16-6.81 (m, 5H), 5.88-5.51 (m, 2H), 5.27-5.00 (m, 2H), 3.63 (s, 2H), 3.53-3.29 (m, 2H), 3.16-2.90 (m, 3H), 1.16-1.00 (m, 2H), 0.85-0.56 (m, 3H), −0.17 (s, 9H)

Compound 046 was prepared as described for the synthesis of compound 038 with compound 35 as the starting material. Compound 046 (5.2 mg, 12.34 umol, 46.45% yield, 100% purity) was obtained as a white solid. LCMS: m/z=422.2 ($M+H^+$) $^1H$ NMR (400 MHz, CHLOROFORM-d) δ=12.36-11.90 (m, 1H), 8.10 (s, 1H), 7.35-7.19 (m, 4H), 7.11 (dd, J=4.6, 7.6 Hz, 1H), 7.00-6.91 (m, 3H), 6.66 (dd, J=7.8, 9.6 Hz, 1H), 4.83 (s, 2H), 3.98 (q, J=7.0 Hz, 2H), 2.92 (s, 3H), 1.28 (t, J=7.0 Hz, 3H).

Scheme 9.

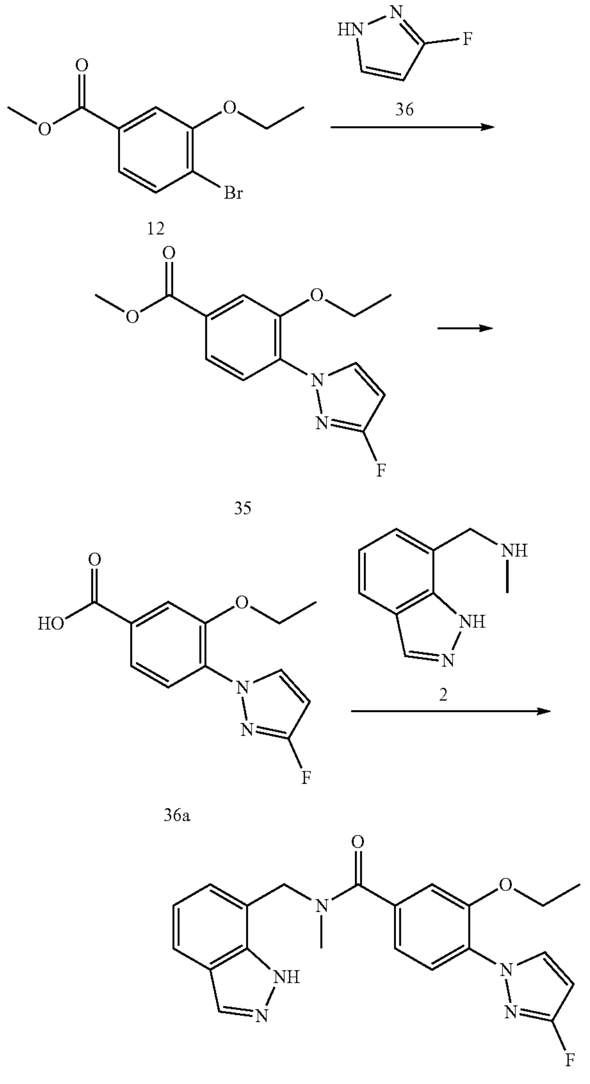

12

36

35

36a

2

047

To a solution of compound 12 (200 mg, 764.20 umol, 99% purity, 1 eq) and compound 36 (197.32 mg, 2.29 mmol, 3 eq) in DMF (6 mL) was added (1R,2R)—N1,N2-dimethylcyclohexane-1,2-diamine (21.74 mg, 152.84 umol, 0.2 eq) and CuI (14.55 mg, 76.42 umol, 0.1 eq) and $K_2CO_3$ (211.24 mg, 1.53 mmol, 2 eq) under $N_2$, the the mixture was stirred at 110° C. for 12 hours. The reaction solution was poured into water (20 mL), and then extracted by EA (10 mL*3). The organic layers were combined and washed with brine (30 mL), dried over $Na_2SO_4$, filtered and concentrated under vacuum to give a residue. The residue was purified by silica column (PE:EA=20:1, 10:1 UV 254 nm) (TLC, PE:EA=10:1, UV 254 nm) to give Compound 35 (50 mg, 189.21 umol, 24.76% yield, 100% purity) as a white solid, confirmed by LCMS and HNMR and 2D-NMR-LCMS(HMBC-NOE). LCMS: m/z=265.2 ($M+H^+$). $^1H$ NMR (400 MHz, CDCl3) δ ppm 8.20-8.19 (m, 1H), 7.87 (d, J=8.4 Hz, 1H), 7.70-7.74 (m, 2H) 6.02-6.00 (m, 1H), 4.23 (q, J=6.8 Hz, 3H), 3.94 (s, 3H), 1.50 (t, J=6.8 Hz, 3H).

Compound 36a was prepared as described for the synthesis of compound 9 with compound 35 as the starting material, step 1 at 20° C. for 1 h. Also, the pH of the resulting solution was adjusted to 5. Compound 36a (98.57% yield) was obtained as a white solid. LCMS: m/z=251.1 (M+H+).

To a solution of compound 36 (30 mg, 119.89 umol, 1 eq) and compound 2 (38.65 mg, 239.78 umol, 2 eq) in DMF (3 mL) was added DIEA (46.49 mg, 359.68 umol, 62.65 uL, N/A purity, 3 eq) and HATU (68.38 mg, 179.84 umol, N/A purity, 1.5 eq) at 20° C. The mixture was stirred at 20° C. for 1 hour. The reaction solution was poured into water (20 mL), then extracted by EA (20 mL*2). The organic layers was combined and washed by brine (20 mL), dried over anhydrous $Na_2SO_4$, filtered and concentrated under vacuum to give a residue. The residue was purified by prep-HPLC (base): column: Waters Xbridge 150*25 mm*5 um; mobile phase: [water (0.05% ammonia hydroxide v/v)-ACN]; B %: 34%-64%, 9 min and lyophilization to give 047 (40.03 mg, 101.75 umol, 84.87% yield, 100% purity) as a white solid, confirmed by LCMS (220 nm) and HNMR. LCMS: m/z=394.2 (M+H+). $^1$H NMR (400 MHz, CDCl3) δ ppm 8.14 (s, 1H) 8.10-8.09 (m, 1H) 7.79 (d, J=8.4 Hz, 2H) 7.27 (d, J=6.8 Hz, 1H) 7.12-7.17 (m, 3H) 5.98-6.00 (m, 1H) 4.96 (s, 2H) 4.14-4.19 (m, 2H) 2.98 (s, 3H) 1.46 (t, J=6.8 Hz, 3H).

Scheme 10.

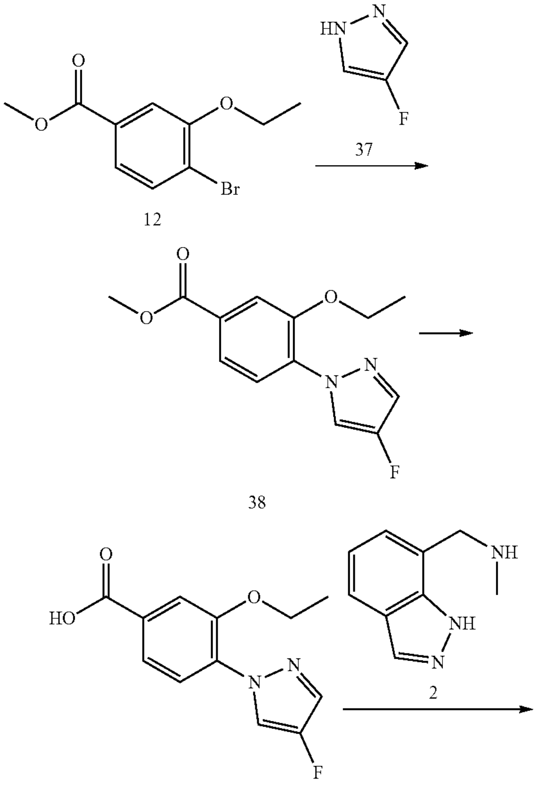

12

37

38

2

39

-continued

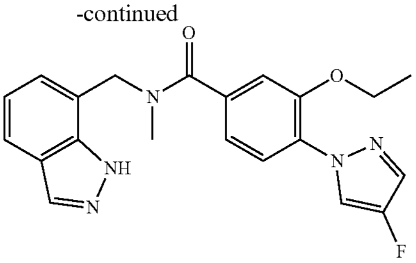

048

Compound 38 was prepared as described for the synthesis of compound 35 with compound 12 and compound 37 as the starting materials. Compound 38 (44.57% yield, 100% purity) was obtained as a white solid. LCMS: m/z=265.1 (M+H+). $^1$H NMR (400 MHz, $CDCl_3$) δ ppm 8.23 (s, 1H) 7.92 (d, J=8.4 Hz, 1H) 7.70-7.75 (m, 2H) 7.60 (d, J=4.0 Hz, 1H) 4.20-4.25 (m, 2H) 3.94 (s, 3H) 1.51 (t, J=6.8 Hz, 3H).

Compound 39 was prepared as described for the synthesis of compound 9 with compound 38 as the starting material, step 1 at 20° C. for 1 h. Also, the pH of the resulting solution was adjusted to 5. Compound 39 (79.20% yield) was obtained as a white solid.

To a solution of compound 39 (50.00 mg, 199.82 umol, 1 eq) and compound 2 (64.42 mg, 399.64 umol, 2 eq) in DMF (3 mL) was added DI ETOAC (77.47 mg, 599.46 umol, 104.41 uL, 3 eq) and HATU (113.97 mg, 299.73 umol, 1.5 eq) at 20° C., the mixture was stirred at 20° C. The reaction solution was poured into water (20 mL), then extracted by EtOAc (20 mL*2), the organic layers was combined and washed by brine (20 mL), dried over anhydrous $Na_2SO_4$, filtered and concentrated under vacuum to give a residue. The residue was purified by prep-HPLC(base): column: Waters Xbridge 150*25 mm*5 um; mobile phase: [water (0.05% ammonia hydroxide v/v)-ACN]; B %: 30%-60%, 9 min and lyophilization to give 048 (53.67 mg, 136.42 umol, 68.27% yield, 100% purity) as a white solid, confirmed by LCMS and HNMR. LCMS: m/z=394.2 (M+H+). $^1$H NMR (400 MHz, $CDCl_3$-$d_6$) δ ppm 8.16 (s, 1H), 8.13 (d, J=4.4 Hz, 1H), 7.85-7.78 (m, 2H), 7.57 (d, J=4.0 Hz, 1H), 7.28 (d, J=13.6 Hz, 1H), 7.18-7.14 (m, 3H), 4.96 (s, 2H), 4.17 (q, J=7.2 Hz, 2H), 2.99 (s, 3H), 1.47 (t, J=7.2 Hz, 3H).

Scheme 11.

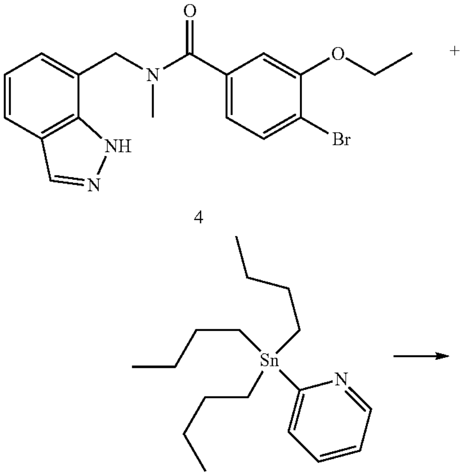

4

40

-continued

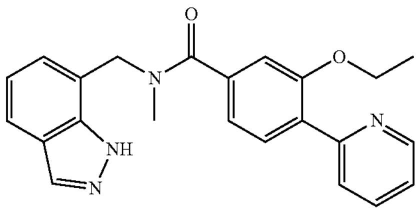

052

To a mixture of compound 4 (50 mg, 128.78 umol, 1 eq), compound 40 (56.89 mg, 154.54 umol, 1.2 eq), LiCl (54.60 mg, 1.29 mmol, 26.37 uL, 10 eq) in DMF (2 mL) was added $Pd(PPh_3)_4$ (14.88 mg, 12.88 umol, 0.1 eq) under $N_2$ atmosphere, then the reaction mixture was stirred at 110° C. for 12 hr. LCMS: m/z=387.1 ($M+H^+$) showed compound 4 consumed completely and desired mass was detected. The reaction mixture was concentrated to give a residue. The solution was purified by prep-HPLC (column: Waters Xbridge 150*25 mm*5 um; mobile phase: [wate (10 mM $NH_4HCO_3$)-ACN]; B %: 33%-63%, 2 min), the purified solution was lyophilized to give a white solid. Compound 052 (15.8 mg, 39.80 umol, 30.90% yield, 97.342% purity) was obtained as a white solid. LCMS and $^1H$ NMR confirmed. LCMS: m/z=387.3 ($M+H^+$). $^1H$ NMR (400 MHz, CHLOROFORM-d) δ=12.29-11.70 (m, 1H), 8.78-8.70 (m, 1H), 8.16-8.09 (m, 1H), 7.98-7.91 (m, 1H), 7.86 (d, J=7.8 Hz, 1H), 7.78 (d, J=8.0 Hz, 2H), 7.33-7.27 (m, 2H), 7.10 (s, 3H), 4.97 (s, 2H), 4.19-4.06 (m, 2H), 2.99 (s, 3H), 1.40 (s, 3H).

Scheme 12.

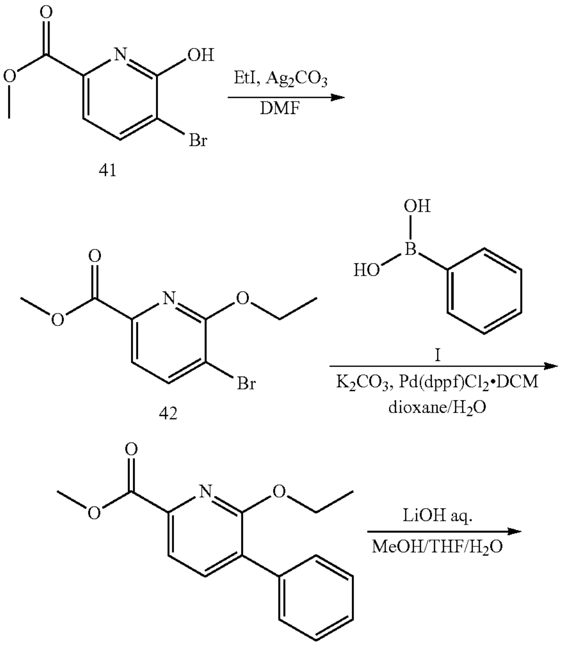

41

42

43

-continued

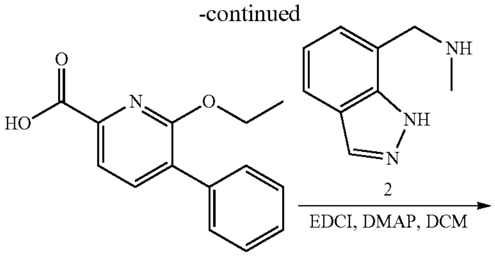

44

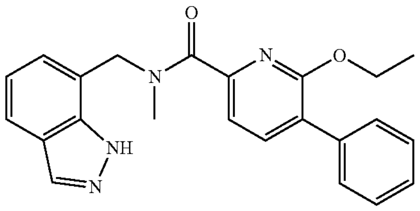

053

Compound 42 was prepared as described for the synthesis of compound 8 with compound 41 and EtI as the starting materials, $Ag_2CO_2$ as the base, and step 1 at 60° C. for 12 hr. The residue was purified on silica gel column chromatography (PE:EA=9:1 to 5:1) to give the product. The product compound 42 (35.69% yield) was obtained as yellow solid.

Compound 43 was prepared as described for the synthesis of compound 001 with compound 42 and compound I as the starting materials. LCMS: m/z=258.2 ($M+H^+$) showed Compound 42 was consumed completely and a main peak with desired mass was detected. The mixture was filtered and the filtrate was poured into water (10 mL). The suspension was extracted with EtOAc (10 mL×3). The combined organic layer was dried over $Na_2SO_4$, filtered and the filtrate was concentrated in vacuo. The residue was purified by prep-TLC (PE:EA=5:1) to give the product ($R_f$=0.7). The product compound 43 (80.49% yield, 98% purity) was obtained as a yellow solid. LCMS: m/z=258.2 ($M+H^+$)

Compound 44 was prepared as described for the synthesis of compound 9 with compound 43 as the starting material, $LiOH{\cdot}H_2O$ as the base, and step 1 at 30° C. for 12 h. Also, the pH of the resulting solution was adjusted to 4-5. The crude product compound 44 was obtained as a white solid. LCMS: m/z=244.1 ($M+H^+$) Compound 053 was prepared as described for the synthesis of compound 4 with compound 44 and compound 2 as the starting materials. The residue was purified by prep-HPLC (FA:column:Phenomenex luna C18 150*25 mm*10 um; mobile phase: [water(0.225% FA)-ACN]; B %: 51%-81%, 10 min), and the eluent was lyophilized to give the product. The product 053 (20 mg, 49.84 umol, 30.31% yield, 96.3% purity) was obtained as a white solid. LCMS: m/z=387.3 ($M+H^+$). 1H NMR (400 MHz, CHLOROFORM-d) δ=8.09 (s, 1H), 7.74 (d, J=8.1 Hz, 1H), 7.69 (d, J=7.6 Hz, 1H), 7.60-7.51 (m, 2H), 7.46-7.37 (m, 3H), 7.37-7.32 (m, 1H), 7.28-7.20 (m, 1H), 7.14-7.06 (m, 1H), 4.96 (s, 2H), 4.39 (q, J=7.0 Hz, 2H), 3.15 (s, 3H), 1.40-1.13 (m, 3H).

Scheme 13.

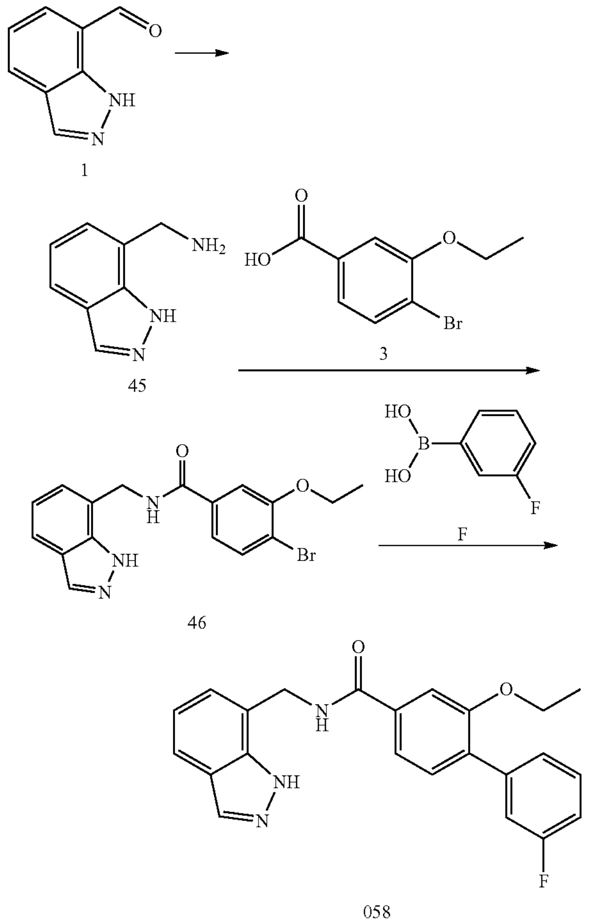

To a solution of compound 1 (100 mg, 684.25 umol, 1 eq) in MeOH (3 mL) and $NH_3 \cdot H_2O$ (3 mL) was added nickel (10 mg, 170.38 umol, 2.49e-1 eq) under $N_2$, the mixture was stirred at 40° C. under $H_2$ (50 Psi) for 12 h. LCMS showed there was no target mass. After the reaction was completed, the mixture was filtered under $N_2$ atmosphere, the filtrated was concentrated to give a crude product. The crude product used for next step without further purification. Compound 45 (100 mg, crude) was obtained as yellow solid.

Compound 46 was prepared as described for the synthesis of compound 4 with compound 3 and compound 45 as the starting materials. The crude product was purified by prep-TLC (PE:EtOAc=1:1). Compound 46 (28.76% yield, 97.5% purity) was obtained as a yellow solid. LCMS: m/z=374.0 $(M+H^+)$.

Compound 058 was prepared as described for the synthesis of compound 001 using compound 46 and compound F as the starting materials and step to at 20° C. for 12 hr. The crude product was purified by prep-HPLC (Base, column: Waters Xbridge 150*25 mm*5 um; mobile phase: [water (0.05% ammonia hydroxide v/v)-ACN]; B %: 40%-70%, 8 min). The purified solution was lyophilized. Compound 058 (6.2 mg, 15.92 umol, 19.86% yield, 100% purity) was obtained as a white solid. LCMS: m/z=390.1 $(M+H^+)$. $^1H$ NMR (400 MHz, CHLOROFORM-d) δ=8.11 (s, 1H), 7.75 (d, J=8.1 Hz, 1H), 7.57 (s, 1H), 7.44-7.29 (m, 5H), 7.15-7.10 (m, 1H), 7.09-7.02 (m, 1H), 6.89-6.81 (m, 1H), 4.97 (d, J=6.7 Hz, 2H), 4.16 (q, J=7.0 Hz, 2H), 1.41 (t, J=7.0 Hz, 3H).

Scheme 14.

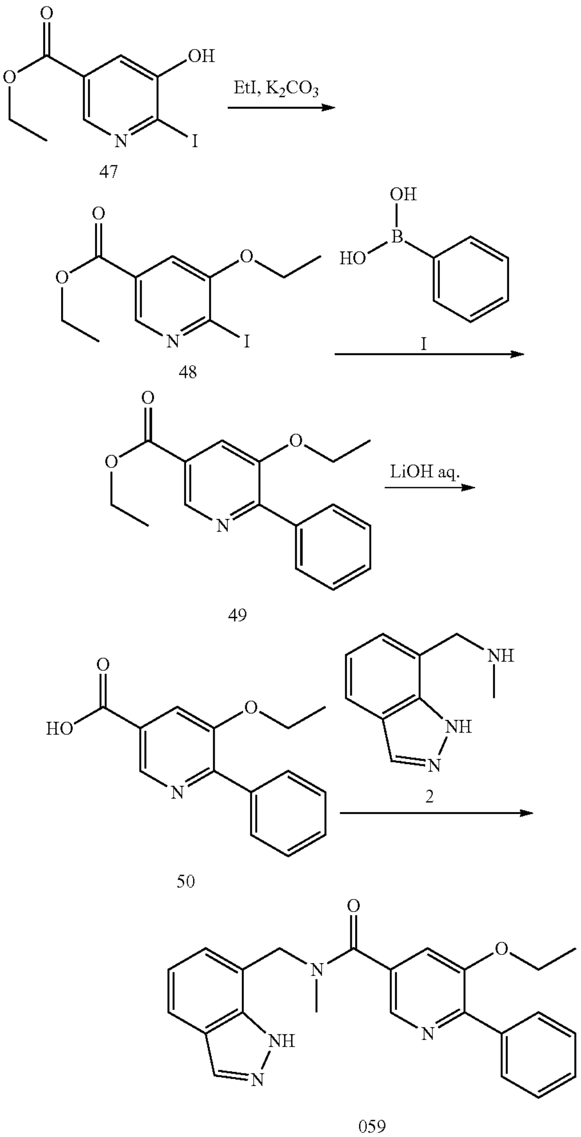

Compound 48 was prepared as described for the synthesis of compound 8 with compound 47 and EtI as the starting materials, $K_2CO_2$ as the base, and step 1 at 50° C. for 12 hr. Compound 48 (86.70% yield, 95% purity) was obtained as a white solid and used in the next step. LCMS: m/z=321.8 $(M+H^+)$. $^1H$ NMR (400 MHz, CHLOROFORM-d) δ=8.56 (d, J=1.6 Hz, 1H), 7.50 (d, J=1.7 Hz, 1H), 4.42 (d, J=7.1 Hz, 2H), 4.18 (d, J=7.0 Hz, 2H), 1.54 (t, J=7.0 Hz, 3H), 1.41 (t, J=7.1 Hz, 3H) Compound 49 was prepared as described for the synthesis of compound 001 with compound 48 and compound I as the starting materials. LCMS: m/z=272.0 $(M+H^+)$ showed 48 consumed completely and desired mass was detected. The reaction mixture was extracted with ethyl acetate and the organic phase was concentrated to give a residue. The solution was purified by prep-TLC (PE:EA=5:1, Rf=0.5) and the purified solution was concentrated to give a white solid. Compound 49 (58.24% yield, 98.418% purity) was obtained as a white solid and used in the next step. LCMS: m/z=272.0 $(M+H^+)$ Compound 50 was prepared as described for the synthesis of compound 9 with compound 49 as the starting material, LiOH as the base, and step 1 at 20° C. for 2 h. Compound 50 was obtained as a white solid and used to the next step. LCMS: m/z=244.2 (M+H$^+$)

Compound 059 was prepared as described for the synthesis of compound 4 with compound 50 and compound 2 as the starting materials and step 1 at 30° C. for 2 hr. The reaction mixture was concentrated to give a residue. The solution was purified by prep-HPLC (column: Waters Xbridge 150*25 mm*5 um; mobile phase: [water (10 mM $NH_4HCO_3$)-ACN]; B %: 39%-69%, 8 min), the purified solution was lyophilized to give a white solid. Compound 059 (21.8 mg, 56.41 umol, 27.45% yield, 100% purity) was obtained as a white solid. LCMS: m/z=387.0 (M+H$^+$). $^1$H NMR (400 MHz, CHLOROFORM-d) δ=12.21-11.57 (m, 1H), 8.44-8.32 (m, 1H), 8.16-8.05 (m, 1H), 7.86 (br s, 2H), 7.81-7.71 (m, 1H), 7.48-7.34 (m, 4H), 7.26-7.21 (m, 1H), 7.15-7.08 (m, 1H), 4.96 (s, 2H), 4.09 (d, J=6.9 Hz, 2H), 3.04 (s, 3H), 1.42 (t, J=6.9 Hz, 3H).

Scheme 15.

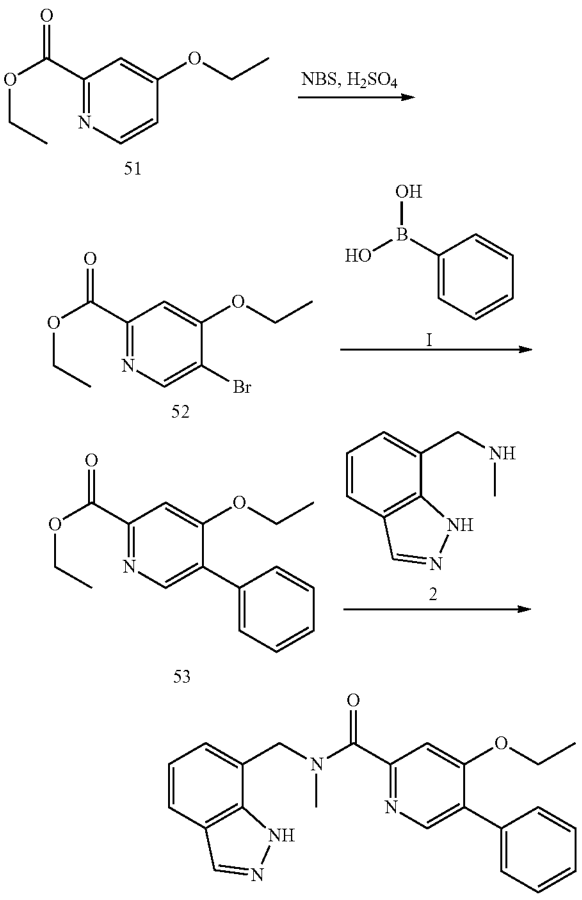

A mixture of compound 51 (230 mg, 1.18 mmol, 1 eq) and NBS (377.46 mg, 2.12 mmol, 1.8 eq) in $H_2SO_4$ (8 mL) was stirred at 25° C. for 12 hrs. TLC (petroleum ether/ethyl acetate=3/1, UV=254 nm) showed a spot was formed. The reaction mixture was added into saturated $NaHCO_3$ solution (200 mL) dropwised at 0° C. The mixture was extracted with ethyl acetate (80 mL×3). The combined organic phase was washed with brine (100 mL), dried over $Na_2SO_4$, filtered and concentrated under vacuum to give a residue. The residue was purified by column chromatography ($SiO_2$, PE/EA=10/1 to 3/1) to give compound 52 (270 mg, 935.75 umol, 79.42% yield, 95% purity) as a white solid. LCMS: m/z=274.1 (M+H$^+$). $^1$H NMR (400 MHz, DMSO-d6) δ=8.69 (s, 1H), 7.65 (s, 1H), 4.37-4.29 (m, 4H), 1.39 (t, J=7.2 Hz, 3H), 1.33 (t, J=7.2 Hz, 3H).

Compound 53 was prepared as described for the synthesis of compound 001 with compound 52 and compound I as the starting materials and step 1 at 100° C. for 4 hrs. The mixture was concentrated under vacuum to give a residue. The residue was dissolved into MeOH (10 mL) and filtered. The filtrate was purified by reversed phase (column: spherical C18 20-35 mm 100 A 80 g; mobile phase: [water (0.5% FA)-ACN]; B %: 45%-53%, 20 min) and concentrated under vacuum to give compound 53 (23.25% yield, 89% purity) as a white solid. LCMS: m/z=244.1 (M+H+)

Compound 066 was prepared as described for the synthesis of compound 4 with compound 53 and compound 2 as the starting materials and step 1 at 25° C. for 12 hrs. The mixture was concentrated under vacuum to give a residue. The residue was purified by prep-HPLC (column: Phenomenex Gemini-NX C18 75*30 mm*3 um; mobile phase: [water (0.225% FA)-ACN]; B %: 42%-72%, 7 min) and lyophilized to give compound 066 (25.3 mg, 65.34 umol, 35.32% yield, 99.8% purity) as a white solid. LCMS: m/z=387.1 (M+H+). $^1$H NMR (400 MHz, CHLOROFORM-d) δ=8.44 (br s, 1H), 8.15 (s, 1H), 7.80 (br d, J=8.0 Hz, 1H), 7.59 (br d, J=7.2 Hz, 2H), 7.51-7.36 (m, 4H), 7.28-7.20 (m, 1H), 7.18-7.09 (m, 1H), 5.05-4.82 (m, 2H), 4.34-4.17 (m, 2H), 3.20-2.87 (m, 3H), 1.51-1.42 (m, 3H).

Scheme 16.

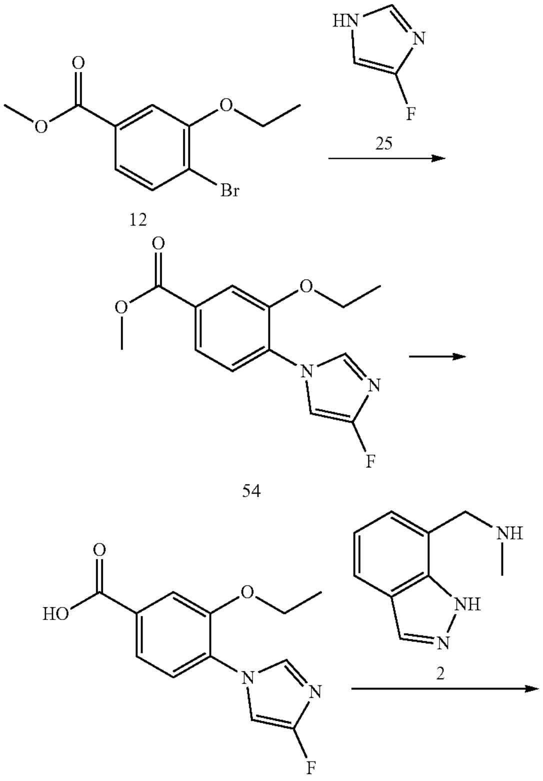

-continued

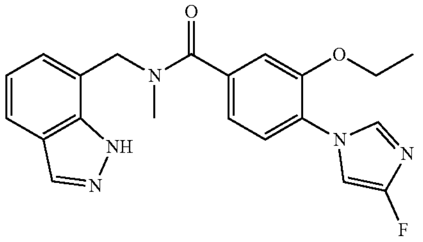

067

Compound 54 was prepared as described for the synthesis of compound 35 with compound 12 and compound 25 as the starting materials. The residue was purified by silica column (PE:EA=20:1, 51 UV254 nm) (TLC, PE:EA=5:1, UV254 nm) to give compound 54 (12.38% yield, 100% purity) as a white solid. LCMS: m/z=265.2 (M+H$^+$). $^1$H NMR (400 MHz, CDCl3) δ ppm 7.71-7.73 (m, 2H) 7.54 (d, J=1.6 Hz, 1H) 7.27-7.34 (m, 1H) 6.82-6.85 (m, 1H) 4.16-4.21 (m, 2H) 3.97 (s, 3H) 1.45 (t, J=6.8 Hz, 3H).

Compound 55 was prepared as described for the synthesis of compound 9 with compound 54 as the starting material and step 1 at 20° C. for 1 h. Also, the pH of the resulting solution was adjusted to 5. Compound 55 (99.80% yield) was obtained as a white solid. LCMS: m/z=251.1 (M+H$^+$).

To a solution of compound 55 (20 mg, 79.93 umol, 1 eq) and compound 2 (25.77 mg, 159.86 umol, N/A purity, 2 eq) in DMF (3 mL) was added DIEA (51.65 mg, 399.64 umol, 69.61 uL, 5 eq) and HATU (45.59 mg, 119.89 umol, 1.5 eq). The mixture was stirred at 20° C. for 1 hour. The reaction solution was poured into water (20 mL), then extracted by EA (20 mL*2), the organic layers was combined and washed by brine (20 mL), dried over anhydrous $Na_2SO_4$, filtered and concentrated under vacuum to give a residue. The residue was purified by prep-HPLC(base): column: Waters Xbridge 150*25 mm*5 um; mobile phase: [water (0.05% ammonia hydroxide v/v)-ACN]; B %: 32%-62%, 9 min and lyophilization to give 067 (13.17 mg, 33.48 umol, 41.88% yield, 100% purity) as a white solid, confirmed by LCMS and HNMR. LCMS: m/z=394.2 (M+H$^+$). $^1$H NMR (400 MHz, CDCl3) δ ppm 8.17 (s, 1H), 7.81 (d, J=8.0 Hz, 1H) 7.51 (s, 1H), 7.34-7.29 (m, 2H), 7.20-7.17 (m, 2H), 7.10 (d, J=7.6 Hz, 1H), 6.79 (d, J=8 Hz, 1H), 4.97 (s, 2H), 4.13 (q, J=6.8 Hz, 2H), 3.00 (s, 3H) 1.42 (t, J=6.8 Hz, 3H).

Scheme 17.

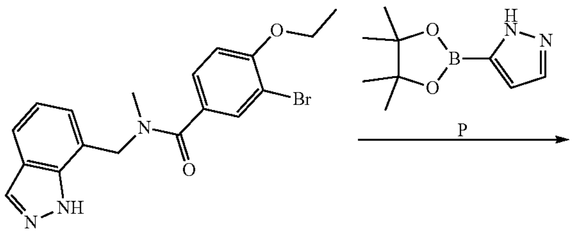

58

-continued

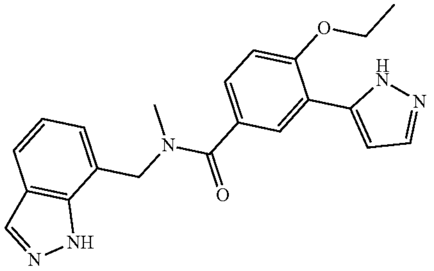

068

Compound 068 was prepared as described for the synthesis of compound 001 with compound 58 and compound P as the starting materials, $Cs_2CO_3$ as the base, and step 2 at 15° C. for 12 h. Compound 068 (10.34 mg, 27.54 umol, 21.39% yield, 100% purity) was obtained as a yellow solid. LCMS: m/z=376.0 (M+H$^+$). $^1$H NMR (400 MHz, CHLOROFORM-d) δ=8.14 (s, 1H), 7.97-7.86 (m, 1H), 7.84-7.76 (m, 1H), 7.73-7.59 (m, 1H), 7.47-7.42 (m, 1H), 7.30 (s, 1H), 7.18-7.11 (m, 1H), 7.07-6.99 (m, 1H), 6.89-6.53 (m, 1H), 4.98 (s, 2H), 4.39-4.22 (m, 2H), 3.02 (s, 4H), 1.60 (s, 3H).

Scheme 18.

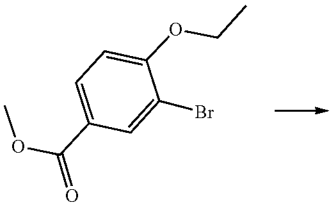

56

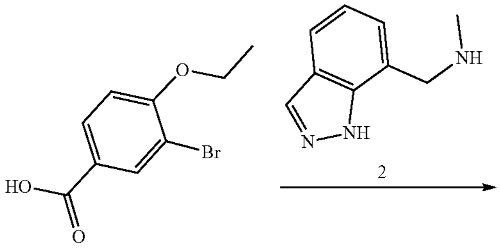

57

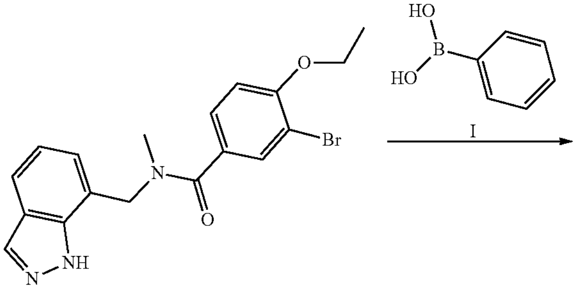

58

-continued

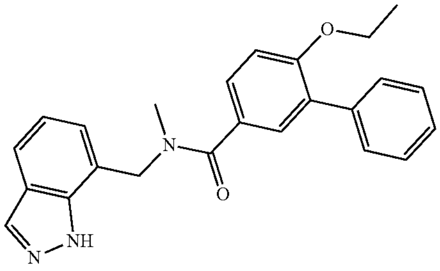

069

Compound 069 was prepared as described for the synthesis of compound 001 with compound 58 and compound I as the starting materials, $K_2CO_3$ as the base, step 1 at 90° C. for 12 h, and step 2 at 15° C. for 12 h. The crude product was purified by prep-HPLC (column: Waters Xbridge 150*25 mm*5 um; mobile phase: [water (0.05% ammonia hydroxide v/v)-ACN]; B %: 40%-70%, 9 min), and the purified solution was lyophilized. 069 (11.07 mg, 28.72 umol, 33.45% yield, 100% purity) was obtained as a white solid. LCMS: m/z=386.1 (M+H$^+$). $^1$H NMR (400 MHz, CHLOROFORM-d) δ=8.12 (s, 1H), 7.78 (d, J=8.1 Hz, 1H), 7.55 (br d, J=7.3 Hz, 2H), 7.50 (s, 2H), 7.42 (s, 2H), 7.38-7.31 (m, 1H), 7.28-7.25 (m, 1H), 7.17-7.08 (m, 1H), 7.03-6.95 (m, 1H), 4.97 (s, 2H), 4.18-4.02 (m, 2H), 3.03 (s, 3H), 1.39 (t, J=7.0 Hz, 3H).

Scheme 19.

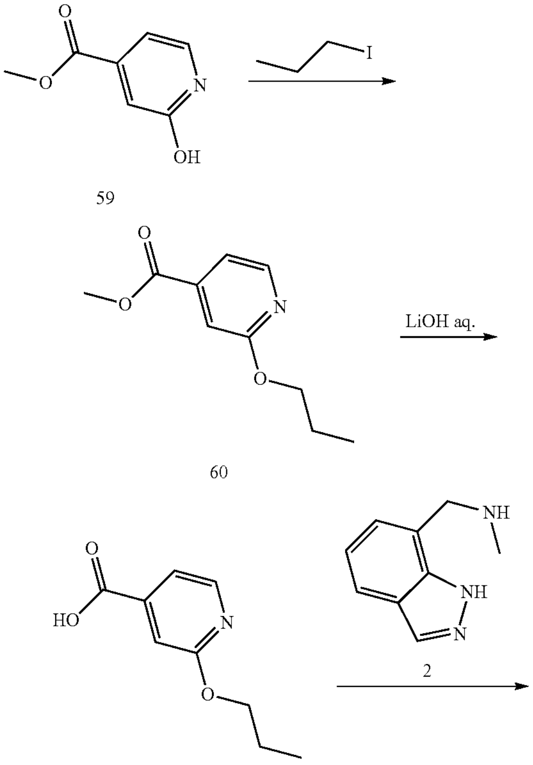

59

60

61

2

-continued

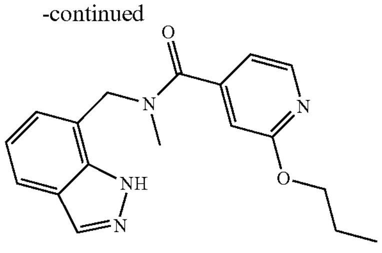

092

Compound 60 was prepared as described for the synthesis of compound 8 with compound 59 and 1-iodopropane as the starting materials, $Ag_2CO_2$ as the base, $CHCl_3$ and DMF as the solvent mixture, and step 1 at 30° C. for 12 hr. The residue was purified by prep-TLC (Petroleum ether:Ethyl acetate=2:1) to give Compound 60 (90 mg, 461.03 umol, 35.30% yield) as a colorless liquid. 1H NMR (400 MHz, METHANOL-d4) δ ppm 8.24 (d, J=5.13 Hz, 1H) 7.39 (d, J=5.26 Hz, 1H) 7.25 (s, 1H) 4.26 (t, J=6.54 Hz, 2H) 3.92 (s, 3H) 1.80 (m, J=7.07 Hz, 2H) 1.03 (t, J=7.46 Hz, 3H) Compound 61 was prepared as described for the synthesis of compound 9 with compound 60 as the starting material and $LiOH{\cdot}H_2O$ as the base. Also, the reagents were combined at 20° C. and step 1 was conducted at 30° C. for 2 h. Also, the pH of the resulting solution was adjusted to 3. Compound 61 (70 mg, 386.34 umol, 83.80% yield) was obtained as a white solid and used directly in the next step. LCMS: m/z=180.0 (M+H$^+$).

Compound 092 was prepared as described for the synthesis of compound 4 with compound 61 and compound 2 as the starting materials. The mixture was concentrated under vacuo to give a residue. The residue was purified by prep-HPLC (column: Phenomenex luna C18 150*25 mm*10 um; mobile phase: [water (0.225% FA)-ACN]; B %: 35%-65%, 10 min) to give a solution. The solution was lyophilized to give 092 (29 mg, 89.40 umol, 23.14% yield, 100% purity) as a white solid. LCMS: m/z=325.1 (M+H$^+$). 1H NMR (400 MHz, METHANOL-d4) δ=8.24-8.17 (m, 1H), 8.13-8.05 (m, 1H), 7.73 (s, 1H), 7.41-7.29 (m, 1H), 7.28-7.16 (m, 1H), 6.92 (m, J=4.6 Hz, 1H), 6.74 (s, 1H), 5.02 (s, 1H), 4.79 (s, 1H), 4.29-4.07 (m, 2H), 3.22-2.89 (m, 3H), 1.85-1.65 (m, 2H), 1.06-0.90 (m, 3H).

Scheme 20.

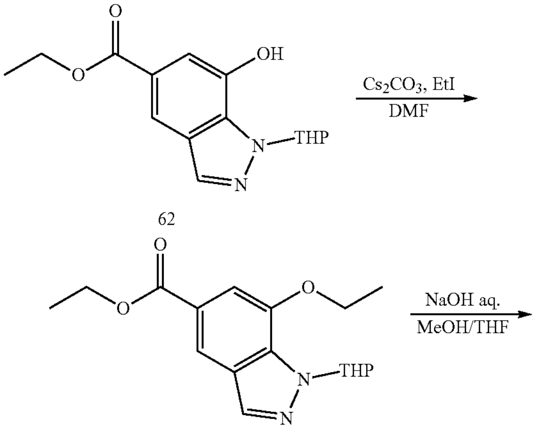

62

63

-continued

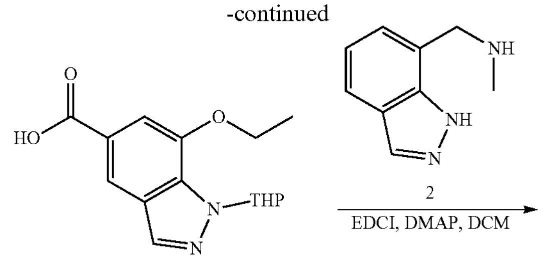

64

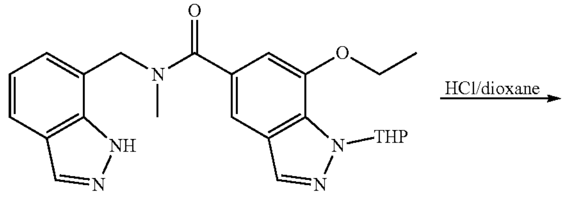

65

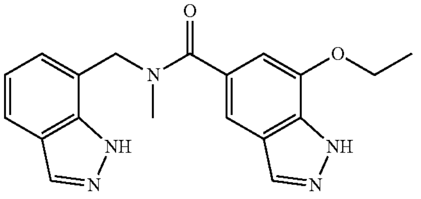

093

Compound 63 was prepared as described for the synthesis of compound 8 with compound 62 and EtI as the starting materials. The crude product compound 63 was obtained as yellow solid. LCMS: m/z=235.2 (M+H$^+$).

Compound 64 was prepared as described for the synthesis of compound 9 with compound 63 as the starting material and step 1 at 30° C. for 12 hr. Also, the pH of the resulting solution was adjusted to 4-5. The crude product compound 64 was obtained as a light yellow solid. LCMS: m/z=207.1 (M+H$^+$)

Compound 65 was prepared as described for the synthesis of compound 4 with compound 64 and compound 2 as the starting materials. The crude product compound 65 was obtained as a light yellow solid. LCMS: m/z=434.2 (M+H$^+$)

A solution of compound 65 (150 mg, 346.02 umol, 1 eq) in HCl/dioxane (10 mL) was stirred at 25° C. for 1 hr. LCMS: Rt=0.827 min, m/z=350.1 (M+H$^+$) showed compound 65 was consumed completely and a main peak with desired mass was detected. The mixture was concentrated in vacuo and the residue was based by TEA until pH=8-9. The mixture was purified by prep-HPLC (column: Waters Xbridge 150*25 mm*5 um; mobile phase: [water (10 mM NH4HCO3)-ACN]; B %: 22%-52%, 9 min), the eluent was lyophilized to give the product. The product 093 (20.63 mg, 58.15 umol, 16.81% yield, 98.49% purity) was obtained as white solid. LCMS and 1H NMR confirmed. LCMS: m/z=434.2 (M+H$^+$). 1H NMR (400 MHz, CHLOROFORM-d) δ=8.15 (s, 1H), 8.08 (s, 1H), 7.79 (d, J=7.8 Hz, 1H), 7.44 (s, 1H), 7.31 (br d, J=6.2 Hz, 1H), 7.15 (t, J=7.3 Hz, 1H), 6.89 (s, 1H), 4.99 (s, 2H), 4.26 (q, J=6.8 Hz, 2H), 3.03 (s, 3H), 1.53 (t, J=7.0 Hz, 3H).

Scheme 21.

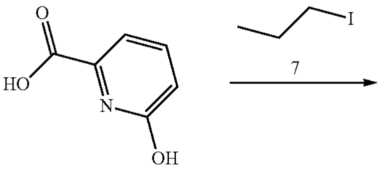

66

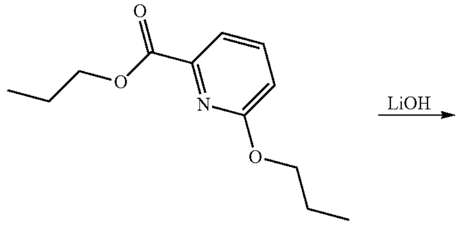

67

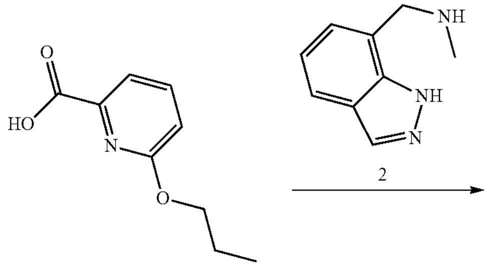

68

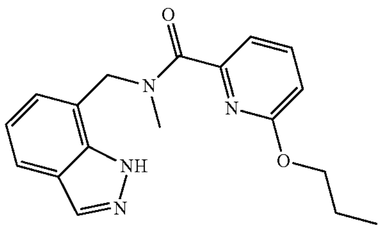

094

Compound 67 was prepared as described for the synthesis of compound 8 with compound 66 and 1-iodopropane as the starting materials, $Ag_2CO_2$ as the base, $CHCl_3$ as the solvent, and step 1 at 60° C. for 24 hr. The residue was purified by column chromatography on silica gel eluted with petroleum ether/ethyl acetate (1/0 to 6/1) and concentrated under reduced pressure to give Compound 67 (93.46% yield, 100% purity) as a colorless oil. LCMS: m/z=224.1 (M+H$^+$)

Compound 68 was prepared as described for the synthesis of compound 9 with compound 67 as the starting material, LiOH as the base, and step 1 at 50° C. for 1 hr. Also, the pH of the resulting solution was adjusted to 6. Compound 68 was obtained as a white solid and used for the next step without further purification. LCMS: m/z=179.8 (M+H$^+$)

Compound 094 was prepared as described for the synthesis of compound 4 with compound 68 and compound 2 as the starting materials. The residue was purified by prep-HPLC (column: Waters Xbridge 150*25 mm*5 um; mobile phase: [water(10 mM NH4HCO3)-ACN]; B %: 41%-71%, 9 min) and lyophilized to give Compound 094 (45.6 mg, 137.63 umol, 49.87% yield, 97.9% purity) as a colorless oil. LCMS: m/z=179.8 (M+H$^+$). $^1$H NMR: (400 MHz, CHLOROFORM-d) δ=8.03-7.98 (m, 1H), 7.67-7.62 (m, 1H), 7.57-7.50 (m, 1H), 7.11 (br d, J=6.8 Hz, 2H), 7.05-6.97 (m, 1H), 6.76 (br d, J=8.4 Hz, 1H), 4.90-4.64 (m, 2H), 4.19-3.97 (m, 2H), 2.76 (s, 3H), 1.73-1.55 (m, 2H), 0.96-0.73 (m, 3H).

Compound 172 was prepared in a similar manner to 094 and isolated as a white solid (8.1 mg, 18.39 umol, 13.67% yield, 100% purity). LCMS: m/z=441.0 $(M+H)^+$ 1H NMR (400 MHz, CHLOROFORM-d) δ ppm 11.62-12.36 (m, 1H) 8.14 (s, 1H) 8.03 (s, 1H) 7.78 (br d, J=8.00 Hz, 2H) 7.51 (d, J=7.88 Hz, 1H) 7.37 (d, J=8.13 Hz, 1H) 7.29 (br d, J=6.88 Hz, 1H) 7.14 (br t, J=7.50 Hz, 1H) 7.07-7.11 (m, 2H) 6.86 (br s, 1H) 4.94-5.04 (m, 2H) 4.45-4.56 (m, 2H) 4.07 (q, J=6.88 Hz, 2H) 2.98-3.07 (m, 3H) 1.35 (t, J=6.94 Hz, 3H).

Compound 173 was prepared in a similar manner to 094 and isolated as a yellow solid (2 mg, 4.14 umol, 2.86% yield, 94% purity). LCMS: m/z=455.2 (M+H)+1H NMR (CHLOROFORM-d, 400 MHz) δ=8.16 (s, 1H), 8.00 (s, 1H), 7.79 (d, J=8.0 Hz, 1H), 7.73 (dd, J=1.4, 7.9 Hz, 1H), 7.47 (d, J=7.9 Hz, 1H), 7.37 (d, J=8.0 Hz, 1H), 7.31 (br d, J=6.8 Hz, 1H), 7.16 (br t, J=7.4 Hz, 1H), 7.11-7.07 (m, 2H), 4.98 (s, 2H), 4.42 (s, 2H), 4.07 (q, J=7.0 Hz, 2H), 3.23 (s, 3H), 3.03 (s, 3H), 1.35 (t, J=6.9 Hz, 3H).

Compound 174 was prepared in a similar manner to 094 and isolated as a white solid (21.26 mg, 50.88 umol, 17.22% yield, 98% purity). LCMS: m/z=410.1 (M+H)+ 1H NMR (CHLOROFORM-d, 400 MHz) δ=8.14 (s, 1H) 7.79 (d, J=8.13 Hz, 1H) 7.48-7.56 (m, 4H) 7.31 (br dd, J=13.07, 7.44 Hz, 2H) 7.14 (br t, J=7.50 Hz, 1H) 7.05-7.10 (m, 2H) 4.98 (s, 2H) 4.01-4.10 (m, 2H) 3.12 (s, 1H) 3.01 (s, 3H) 1.35 (br t, J=6.88 Hz, 3H).

Compound 203 was prepared in a similar manner to 094 and isolated as a white solid (4.04 mg, 9.44 umol, 5.88% yield, 99% purity). LCMS: m/z=424.1 (M+H)+1H NMR (CHLOROFORM-d, 400 MHz) δ=8.14 (br s, 1H), 7.78 (br d, J=8.0 Hz, 1H), 7.50-7.40 (m, 4H), 7.35-7.29 (m, 2H), 7.14 (br t, J=7.5 Hz, 1H), 7.09-7.04 (m, 2H), 4.97 (s, 2H), 4.04 (q, J=6.8 Hz, 2H), 3.01 (s, 3H), 2.08 (s, 3H), 1.35 (br t, J=6.9 Hz, 3H).

Scheme 22

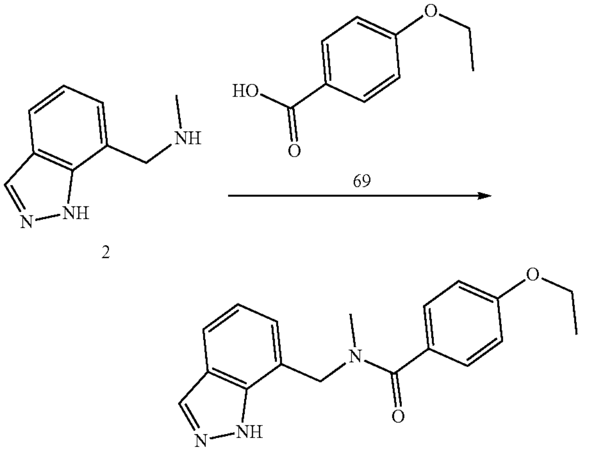

2

69

095

Compound 095 was prepared as described for the synthesis of compound 4 with compound 69 and compound 2 as the starting materials. The crude product was purified by prep-HPLC (FA, column: Phenomenex Luna C18 150*25 mm*10 um; mobile phase: [water(0.225% FA)-ACN]; B %: 33%-63%, 10 min). The purified solution was lyophilized. Compound 095 (62.8 mg, 203.00 umol, 67.47% yield, 100% purity) was obtained as a white oil. LCMS: m/z=310.1 $(M+H^+)$. $^1H$ NMR (400 MHz, METHANOL-$d_4$) δ=8.11 (s, 1H), 7.78 (d, J=8.1 Hz, 1H), 7.55-7.33 (m, 3H), 7.20 (s, 1H), 6.97 (s, 2H), 5.01 (s, 2H), 4.07 (s, 2H), 3.02 (s, 3H), 1.40 (s, 3H).

Scheme 23.

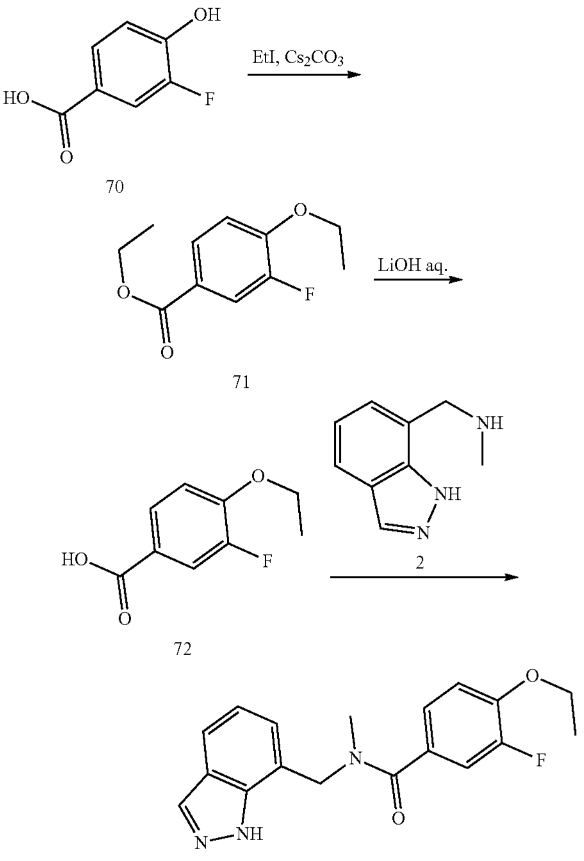

70

71

2

72

096

Compound 71 was prepared as described for the synthesis of compound 8 with compound 70 and EtI as the starting materials and step 1 at 50° C. for 12 hr. The crude product used for next step without further purification. Compound 71 was obtained as a yellow oil. LCMS: m/z=212.9 $(M+H^+)$ Compound 72 was prepared as described for the synthesis of compound 9 with compound 71 as the starting material, LiOH as the base, and step 1 at 30° C. for 12 hr. Also, the pH of the resulting solution was adjusted to 3. The crude product used for next step without further purification. Compound 72 obtained as a white solid. LCMS: m/z=183.05 $(M+H^+)$ Compound 096 was prepared as described for the synthesis of compound 4 with compound 72 and compound 2 as the starting materials. The crude product was purified by prep-HPLC (column: Phenomenex luna C18 150*25 mm*10 um; mobile phase: [water(0.225% FA)-ACN]; B %: 34%-64%, 10 min), and the purified solution was lyophilized. 096 (39.2 mg, 119.75 umol, 44.11% yield, 100% purity) was obtained as a colourless solid. Confirmed by LCMS and $^1H$ NMR. LCMS: m/z=328.0 $(M+H^+)$. $^1H$ NMR (400 MHz, METHANOL-$d_4$) δ=8.10 (s, 1H), 7.80-7.71 (m, 1H), 7.41-7.06 (m, 5H), 4.93 (br s, 2H), 4.30-3.97 (m, 2H), 3.13-2.93 (m, 3H), 1.50-1.34 (m, 3H).

Scheme 24.

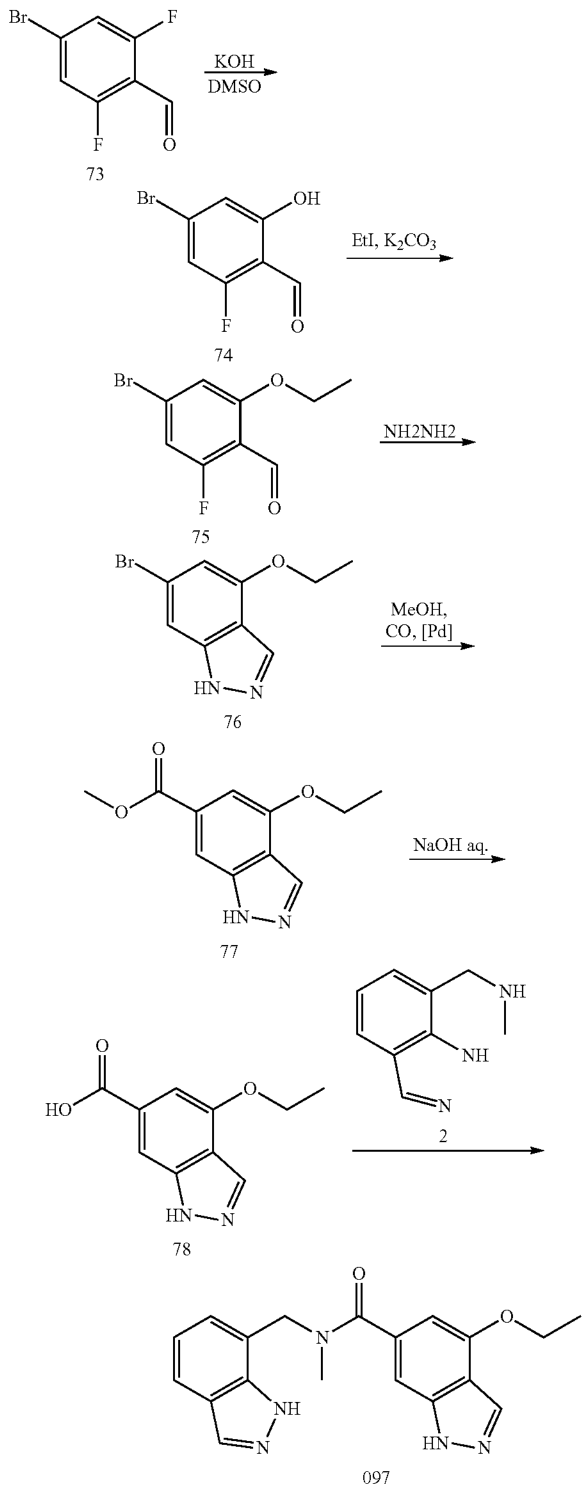

73, 74, 75, 76, 77, 2, 78, 097

To a solution of compound 74 (900 mg, 4.11 mmol, 1 eq) in DMF (10 mL) was added EtI (1.28 g, 8.22 mmol, 657.36 uL, 2 eq) and $K_2CO_3$ (1.42 g, 10.27 mmol, 2.5 eq), the mixture was stirred at 60° C. for 16 h. LCMS showed the reaction was completed. The mixture was poured into water (50 mL) and extracted with EtOAc (50 mL×3), the combined organic phase was washed with brine (50 mL), dried over anhydrous $Na_2SO_4$, and concentrated to give a crude product. The crude product was purified by column chromatography ($SiO_2$, Petroleum ether/Ethyl acetate=100/1 to 50/1, desired product Rf=0.7). Compound 75 (770 mg, 3.12 mmol, 75.84% yield, 100% purity) was obtained as white solid, confirmed by H-NMR. $^1$H NMR (400 MHz, CHLOROFORM-d) δ=10.51-10.21 (m, 1H), 6.95 (s, 2H), 4.25-4.04 (m, 2H), 1.51 (s, 3H).

Compound 76 was prepared as described for the synthesis of compound 17 with compound 75 as the starting material. The crude product used for next step without further purification. Compound 76 (99.06% yield) was obtained as a yellow solid. LCMS: m/z=241.0 (M+H+)

To a solution of compound 76 (290 mg, 1.20 mmol, 1 eq) in MeOH (10 mL) was added $Pd(OAc)_2$ (27.01 mg, 120.29 umol, 0.1 eq), DPPF (133.37 mg, 240.58 umol, 0.2 eq) and TEA (1.22 g, 12.03 mmol, 1.67 mL, 10 eq), the mixture was stirred at 80° C. under CO (50 Psi) for 12 h. LCMS showed the reaction was completed. After the reaction was completed, the mixture was filtered and the filtrated was concentrated to give a crude product. The crude product was purified by column chromatography ($SiO_2$, Petroleum ether/Ethyl acetate=10/1 to 1/1, desired product Rf=0.4). Compound 77 (220 mg, 998.98 umol, 83.05% yield, 100% purity) was obtained as white solid. LCMS: m/z=220.9 (M+H+). $^1$H NMR (400 MHz, CHLOROFORM-d) δ=8.36-8.18 (m, 1H), 7.88 (s, 1H), 7.17 (s, 1H), 4.29 (d, J=7.0 Hz, 2H), 3.98 (s, 3H), 1.55 (t, J=7.0 Hz, 3H)

Compound 78 was prepared as described for the synthesis of compound 9 with compound 77 as the starting material and LiOH as the base. Also, and step 1 was conducted at 15° C. for 1 hr and then at 30° C. for 12 h and the pH of the resulting solution was adjusted to 5. The crude product used for next step without further purification. 4-ethoxy-1H-indazole-6-carboxylic acid (78) was obtained as a white solid. LCMS: m/z=206.9 (M+H+).

Compound 097 was prepared as described for the synthesis of compound 4 with compound 78 and compound 2 as the starting materials. The crude product was purified by prep-HPLC (FA, column: Phenomenex luna C18 150*25 mm*10 um; mobile phase: [water(0.225% FA)-ACN]; B %: 29%-59%, 10 min) and the purified solution was lyophilized. 097 (15.0 mg, 42.93 umol, 17.71% yield, 100% purity) was obtained as a white solid. LCMS: m/z=350.0 (M+H+). $^1$H NMR (400 MHz, CHLOROFORM-d) δ=8.26-8.05 (m, 2H), 7.87-7.68 (m, 1H), 7.35-7.29 (m, 1H), 7.13 (s, 2H), 6.65-6.41 (m, 1H), 5.00 (s, 2H), 4.42-4.09 (m, 2H), 2.98 (s, 3H), 1.53 (s, 3H).

Compound 134 was prepared in a similar manner to 097 and was obtained as a white solid (5.3 mg, 12.55 umol, 16.31% yield, 100% purity). LCMS: m/z=423.1 (M−H+) $^1$H NMR (400 MHz, CHLOROFORM-d) δ=12.04 (s, br., 1H), 8.17 (d, J=1.5 Hz, 1H), 7.47-7.40 (m, 5H), 7.31-7.27 (m, 1H), 7.23-7.19 (m, 1H), 6.79-6.72 (m, 1H), 4.93 (s, 2H), 4.38 (d, J=7.0 Hz, 2H), 3.18 (s, 3H), 1.31 (t, J=7.1 Hz, 3H).

Compound 135 was prepared in a similar manner to 097 and was obtained as an off-white solid (7.8 mg, 17.81 umol, 33.73% yield, 100% purity). LCMS: m/z=438.1 (M−H+) $^1$H NMR (400 MHz, CHLOROFORM-d) δ=12.04 (br s, 1H), 8.08 (s, 1H), 7.28-7.16 (m, 4H), 7.08 (d, J=7.4 Hz, 1H), 6.99 (d, J=7.4 Hz, 1H), 6.96-6.89 (m, 3H), 4.82 (s, 2H), 3.95 (q, J=6.9 Hz, 2H), 2.89 (s, 3H), 1.25 (t, J=6.9 Hz, 3H).

Compound 136 was prepared in a similar manner to 097 and was obtained as an off-white solid (2.8 mg, 6.19 umol, 27.09% yield, 97% purity). LCMS: m/z=439.2 (M−H+) $^1$H NMR (400 MHz, CHLOROFORM-d) δ=12.08-11.89 (m, 1H), 8.05 (s, 1H), 7.60 (d, J=7.5 Hz, 1H), 7.33 (d, J=7.5 Hz, 1H), 7.30-7.20 (m, 3H), 7.07 (d, J=7.4 Hz, 1H), 6.98 (d, J=7.4 Hz, 1H), 6.96-6.91 (m, 1H), 4.81 (s, 2H), 4.28 (q, J=7.0 Hz, 2H), 3.03 (s, 3H), 1.25 (t, J=7.1 Hz, 3H).

Compound 137 was prepared in a similar manner to 097 and was obtained as an off-white solid (18.4 mg, 42.77 umol, 61.28% yield, 99.6% purity). LCMS: m/z=429.3 (M−H+) $^1$H NMR (400 MHz, CHLOROFORM-d) δ=12.53-12.19 (m, 1H), 8.34 (s, 1H), 7.56 (br d, J=7.4 Hz, 1H), 7.48-7.36 (m, 6H), 6.90-6.84 (m, 2H), 5.02 (s, 2H), 4.04 (q, J=7.0 Hz, 2H), 3.06 (s, 3H), 1.31 (br t, J=6.9 Hz, 3H).

Compound 167 was prepared in a similar manner to 097 and was obtained as a white solid (44.9 mg, 101.71 umol, 38.77% yield, 100% purity). LCMS: m/z=441.9 (M−H+) $^1$H NMR (400 MHz, CHLOROFORM-d) δ=8.43 (d, 1H, J=1.5 Hz), 8.27 (s, 1H), 8.2-8.2 (m, 2H), 7.84 (d, 1H, J=1.6 Hz), 7.68 (d, 1H, J=7.8 Hz), 7.5-7.6 (m, 1H), 7.23 (dd, 1H, J=4.5, 7.6 Hz), 6.77 (dd, 1H, J=7.8, 9.6 Hz), 4.95 (s, 2H), 3.86 (td, 1H, J=3.0, 5.8 Hz), 3.08 (s, 3H), 0.8-1.0 (m, 4H).

Compound 194 was prepared in a similar manner to 097 and was obtained as a white solid (1.6 mg, 3.60 umol, 4.96% yield, 96.7% purity). $^1$H NMR (400 MHz, CHLOROFORM-d) δ=12.48 (br s, 1H), 8.47 (s, 2H), 7.46-7.38 (m, 5H), 6.91-6.86 (m, 2H), 5.01 (s, 2H), 4.09-4.00 (m, 2H), 3.11 (s, 3H), 1.32 (t, J=6.9 Hz, 3H), 1.28-1.28 (m, 1H).

Compound 204 was prepared in a similar manner to 097 and was obtained as an off-white solid (10.97 mg, 21.20 umol, 10.68% yield, and 100% purity). $^1$H NMR (400 MHz, CHLOROFORM-d) δ=12.04 (br s, 1H), 8.22-8.16 (m, 1H), 8.09-8.05 (m, 1H), 7.84-7.79 (m, 1H), 7.63-7.57 (m, 1H), 7.31-7.26 (m, 1H), 7.11-7.04 (m, 1H), 7.02-6.99 (m, 1H), 6.99-6.97 (m, 1H), 6.76-6.63 (m, 1H), 4.79-4.74 (m, 2H), 4.48-4.39 (m, 1H), 4.02-3.95 (m, 2H), 3.00-2.97 (m, 3H), 2.97-2.93 (m, 3H), 1.31-1.26 (m, 3H), 0.86-0.81 (m, 4H).

Compound 214 was prepared in a similar manner to 097 and was obtained as a white solid (16.95 mg, 38.19 umol, 54.69% yield, 99.7% purity). $^1$H NMR (400 MHz, CHLOROFORM-d) δ=9.26 (br s, 1H), 8.51 (br s, 1H), 8.4-8.5 (m, 2H), 8.16 (s, 1H), 8.01 (br d, 1H, J=9.4 Hz), 7.84 (s, 1H), 7.3-7.4 (m, 1H), 5.03 (s, 2H), 3.88 (br d, 1H, J=2.8 Hz), 3.14 (s, 3H), 0.8-1.0 (m, 4H).

Compound 216 was prepared in a similar manner to 097 and was obtained as a white solid (16.34 mg, 41.88 umol, 15.22% yield, 97% purity). LCMS: m/z=378.9 (M+H+). $^1$H NMR (400 MHz, CHLOROFORM-d) δ=12.12 (br s, 1H), 9.08 (s, 1H), 8.26 (d, J=16.1 Hz, 2H), 7.50 (d, J=7.6 Hz, 1H), 6.99-6.87 (m, 2H), 4.87 (s, 2H), 4.07 (q, J=6.9 Hz, 2H), 2.92 (s, 3H), 2.70-2.56 (m, 1H), 1.39 (t, J=6.9 Hz, 3H), 1.17 (td, J=3.7, 7.7 Hz, 2H), 0.94 (qd, J=3.6, 7.5 Hz, 2H).

Scheme 25.

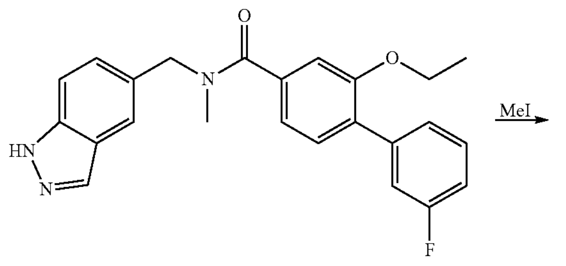

101

-continued

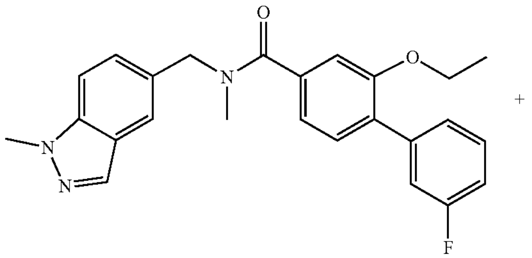

099

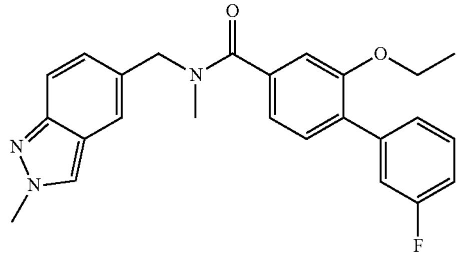

100

To a mixture of compound 101 (20 mg, 49.57 umol, 1 eq) in DMF (2 mL) was added NaH (3.97 mg, 99.15 umol, 60% purity, 2 eq) at 0° C. under $N_2$ atmosphere, then the mixture was stirred at 0° C. for 0.5 hr, $CH_3I$ (10.55 mg, 74.36 umol, 4.63 uL, 1.5 eq) was added, then the mixture was stirred at 20° C. for 12 hr. LCMS: Rt=0.945, 0.977 min, m/z=418.1 ($M+H^+$) showed 101 consumed completely and desired mass was detected. The reaction mixture was quenched by saturated sodium carbonate solution (5 mL) and extracted by ethyl acetate (3*5 mL), the organic phase was concentrated under reduced pressure to give a residue.

The solution was purified by prep-HPLC (column: Phenomenex luna C18 150*25 mm*10 um; mobile phase: [water (0.225% FA)-ACN]; B %: 46%-76%, 10 min), the solution was lyophilized to give a white solid. Compound 099 (2.2 mg, 5.27 umol, 10.63% yield, 100% purity) was obtained as a white solid. Compound 100 (1.2 mg, 2.75 umol, 5.54% yield, 95.593% purity) was obtained as a white solid. LCMS: m/z=418.3 ($M+H^+$). LCMS: m/z=418.3 ($M+H^+$). $^1$H NMR (400 MHz, DMSO-$d_6$) δ=8.11-7.96 (m, 1H), 7.63 (br s, 2H), 7.24 (br s, 5H), 7.20-7.06 (m, 3H), 4.91-4.53 (m, 2H), 4.16-3.88 (m, 5H), 2.97-2.82 (m, 3H), 1.34-1.13 (m, 3H) $^1$H NMR (400 MHz, DMSO-$d_6$) δ=8.39-8.22 (m, 1H), 7.74-7.55 (m, 2H), 7.52-7.21 (m, 5H), 7.15 (br s, 3H), 4.80-4.52 (m, 2H), 4.16 (s, 3H), 4.09-3.84 (m, 2H), 2.95-2.84 (m, 3H), 1.42-1.26 (m, 3H).

Scheme 26.

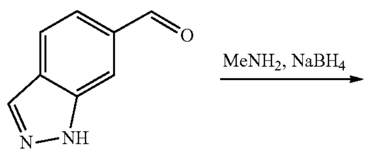

79

-continued

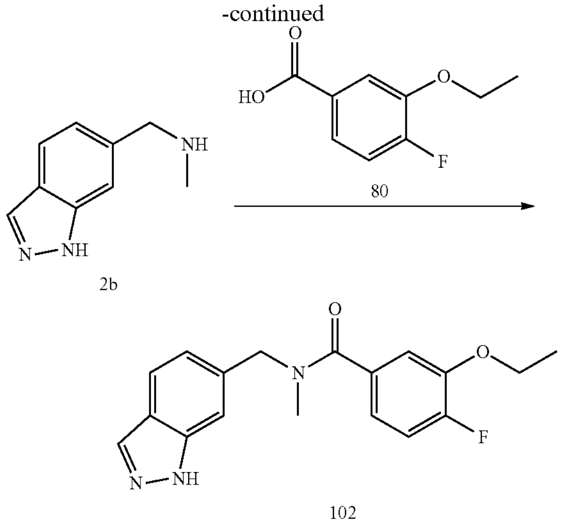

Compound 2b was prepared as described for the synthesis of compound 2 with compound 79 as the starting material, step 1 at 20° C. for 2 hr, and step 2 at 20° C. for 12 hr. The crude was purified by prep-HPLC (column: Waters Xbridge 150*25 mm*5 um; mobile phase: [water (10 mM $NH_4HCO_3$)-ACN]; B %: 0%-17%, min), the purified solution was lyophilized to give a white solid. Compound 2b was obtained as a white solid and used in the next step. LCMS: m/z=160.2 (M−H$^+$). $^1$H NMR (400 MHz, CHLOROFORM-d) δ=8.05 (s, 1H), 7.76-7.66 (m, 1H), 7.48 (s, 1H), 7.14 (s, 1H), 3.90 (s, 2H), 2.54 (s, 3H) Compound 102 was prepared as described for the synthesis of compound 4 with compound 80 and compound 2b as the starting materials. The solution was purified by prep-HPLC (column: Phenomenex luna C18 150*25 mm*10 um; mobile phase: [water (0.225% FA)-ACN]; B %: 29%-59%, 10 min) and the purified solution was lyophilized to give a white solid. Compound 102 (24.83 mg, 75.85 umol, 46.56% yield, 100% purity) was obtained as a white solid. LCMS: m/z=327.9 (M+H$^+$). $^1$H NMR (400 MHz, CHLOROFORM-d) δ=7.92-7.79 (m, 1H), 7.43-7.31 (m, 1H), 4.05 (s, 2H), 3.17 (br s, 4H), 3.01 (br s, 4H), 2.24-2.12 (m, 4H).

Scheme 27.

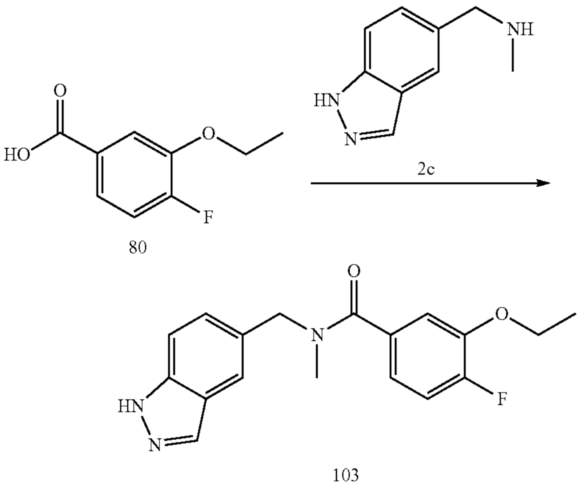

Compound 103 was prepared as described for the synthesis of compound 4 with compound 80 and compound 2c as the starting materials. The solution was purified by prep-HPLC (column: Phenomenex luna C18 150*25 mm*10 um; mobile phase: [water (0.225% FA)-ACN]; B %: 28%-58%, 10 min) and the purified solution was lyophilized to give a white solid. Compound 103 (30.06% yield, 100% purity) was obtained as a white solid. LCMS: m/z=382.0 (M+H$^+$). $^1$H NMR (400 MHz, METHANOL-$d_4$) δ=8.10-8.02 (m, 1H), 7.83-7.58 (m, 1H), 7.58-7.51 (m, 1H), 7.48-6.98 (m, 4H), 4.85-4.59 (m, 2H), 4.20-3.82 (m, 2H), 3.11-2.86 (m, 3H), 1.47-1.21 (m, 3H).

Scheme 28.

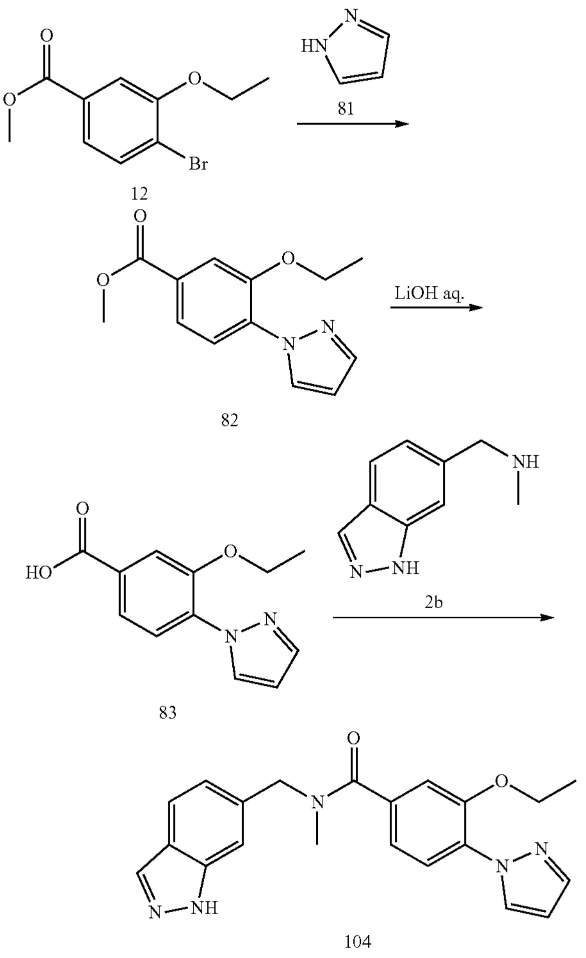

Compound 82 was prepared as described for the synthesis of compound 35 with compound 12 and compound 81 as the starting materials, N,N'-dimethylethane-1,2-diamine as the ligand, and step 1 at 110° C. for 16 hr. The residue was purified by column chromatography ($SiO_2$, Petroleum ether: Ethyl acetate=5:1) and the solution was concentrated to give a white solid. Compound 82 was obtained as a white solid. LCMS: m/z=247.2 (M+H$^+$). $^1$H NMR (400 MHz, CHLOROFORM-d) δ=8.58-8.19 (m, 1H), 8.04-7.92 (m, 1H), 7.83-7.65 (m, 3H), 6.63-6.35 (m, 1H), 4.24 (q, J=6.6 Hz, 2H), 3.95 (s, 3H), 1.49 (t, J=6.8 Hz, 3H)

Compound 83 was prepared as described for the synthesis of compound 9 with compound 82 as the starting material, $LiOH{\cdot}H_2O$ as the base, and step 1 at 30° C. for 2 hr. Also, the pH of the resulting solution was adjusted to 6-7. Compound 83 was obtained as a white solid.

Compound 104 was prepared as described for the synthesis of compound 4 with compound 83 and compound 2b as the starting materials. The residue was purified by prep-HPLC (column: Unisil 3-100 C18 Ultra 150*50 mm*3 um; mobile phase: [water (0.225% FA)-ACN]; B %: 30%-60%, 10 min) and the solution was lyophilized to give a white solid. 104 (45.48% yield, 100% purity) was obtained as a white solid. LCMS: m/z=376.2 $(M+H^+)$. $^1H$ NMR (400 MHz, CHLOROFORM-d) δ=8.31-8.13 (m, 1H), 8.09 (s, 1H), 7.96-7.74 (m, 2H), 7.71 (s, 1H), 7.61-7.31 (m, 1H), 7.27-6.93 (m, 3H), 6.52-6.35 (m, 1H), 5.02-4.59 (m, 2H), 4.30-3.77 (m, 2H), 3.28-2.87 (m, 3H), 1.62-1.15 (m, 3H).

Scheme 29.

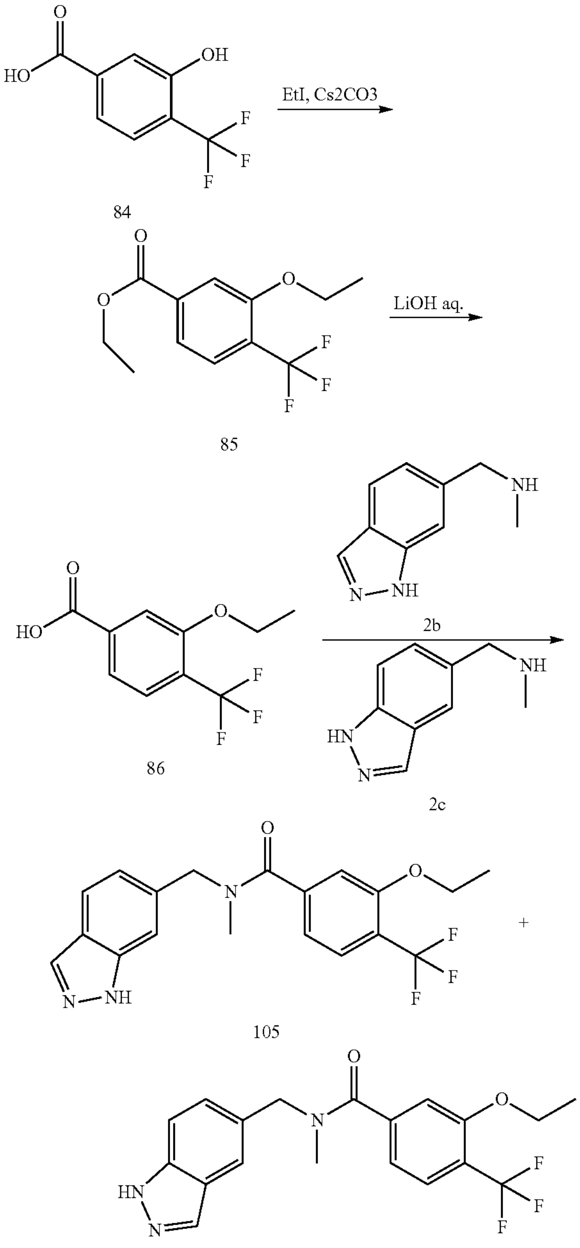

84

85

86

2b

2c

105

106

Compound 85 was prepared as described for the synthesis of compound 8 with compound 84 and EtI as the starting materials and step 1 at 50° C. for 12 hr. The crude product used for next step without further purification. Compound 85 was obtained as a white solid. LCMS: m/z=262.8 $(M+H^+)$ Compound 86 was prepared as described for the synthesis of compound 9 with compound 85 as the starting material, LiOH as the base, and step 1 at 30° C. for 12 hr. Also, the pH of the resulting solution was adjusted to 3. The crude product used for next step without further purification. Compound 86 was obtained as a yellow solid. LCMS: m/z=233.05 $(M+H^+)$ Compound 105 was prepared as described for the synthesis of compound 4 with compound 86 and compound 2b as the starting materials. The crude product was purified by prep-HPLC (column: Phenomenex Luna C18 150*25 mm*10 um; mobile phase: [water(0.225% FA)-ACN]; B %: 37%-67%, 10 min) and the purified solution was lyophilized. Compound 105 (18.7 mg, 49.55 umol, 29.01% yield, 100% purity) obtained as a white solid. LCMS: m/z=377.9 $(M+H^+)$. $^1H$ NMR (400 MHz, CHLOROFORM-d) δ=8.30-7.98 (m, 1H), 7.89-7.73 (m, 1H), 7.40 (br s, 1H), 7.43-7.29 (m, 1H), 7.25 (br s, 3H), 4.95-4.62 (m, 2H), 4.24-3.92 (m, 2H), 3.15-2.91 (m, 3H), 1.54-1.30 (m, 3H) Compound 106 was prepared as described for the synthesis of compound 4 with compound 86 and compound 2c as the starting materials. The crude product was purified by prep-HPLC (column: Phenomenex Luna C18 150*25 mm*10 um; mobile phase: [water(0.225% FA)-ACN]; B %: 36%-66%, 10 min) and the purified solution was lyophilized. 106 (14.7 mg, 38.95 umol, 22.81% yield, 100% purity) obtained as white solid. LCMS: m/z=377.9 $(M+H^+)$. $^1H$ NMR (400 MHz, CHLOROFORM-d) δ=8.28-8.00 (m, 1H), 7.60 (br s, 3H), 7.29 (s, 3H), 5.00-4.52 (m, 2H), 4.28-3.91 (m, 2H), 2.90 (br s, 3H), 1.63-1.16 (m, 3H).

Scheme 30.

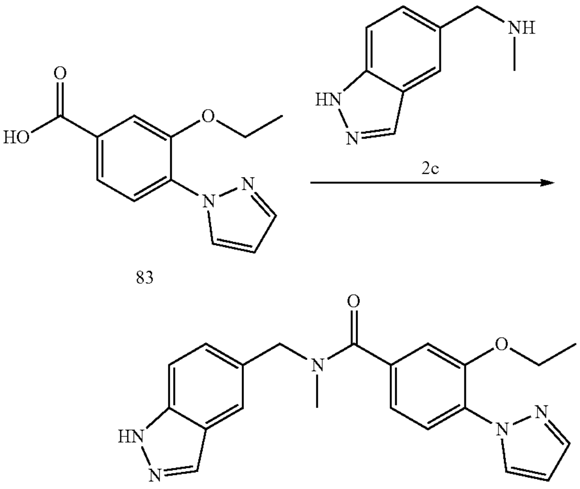

83

107

Compound 107 was prepared as described for the synthesis of compound 4 with compound 83 and compound 2c as the starting materials. The residue was purified by prep-HPLC (column: Phenomenex Synergi C18 150*25 mm*10 um; mobile phase: [water (0.225% FA)-ACN]; B %: 25%-55%, 10 min) and the solution was lyophilized to give a white solid. 107 (32 mg, 85.24 umol, 39.59% yield, 100% purity) was obtained as a white solid. LCMS: m/z=376.2 (M+H$^+$). $^1$H NMR (400 MHz, CHLOROFORM-d) δ=8.27-8.12 (m, 1H), 8.08 (s, 1H), 7.84 (s, 1H), 7.71 (s, 1H), 7.66-7.42 (m, 2H), 7.27-7.06 (m, 3H), 6.44 (s, 1H), 4.98-4.58 (m, 2H), 4.25-3.90 (m, 2H), 3.16-2.88 (m, 3H), 1.49-1.23 (m, 3H).

Scheme 31.

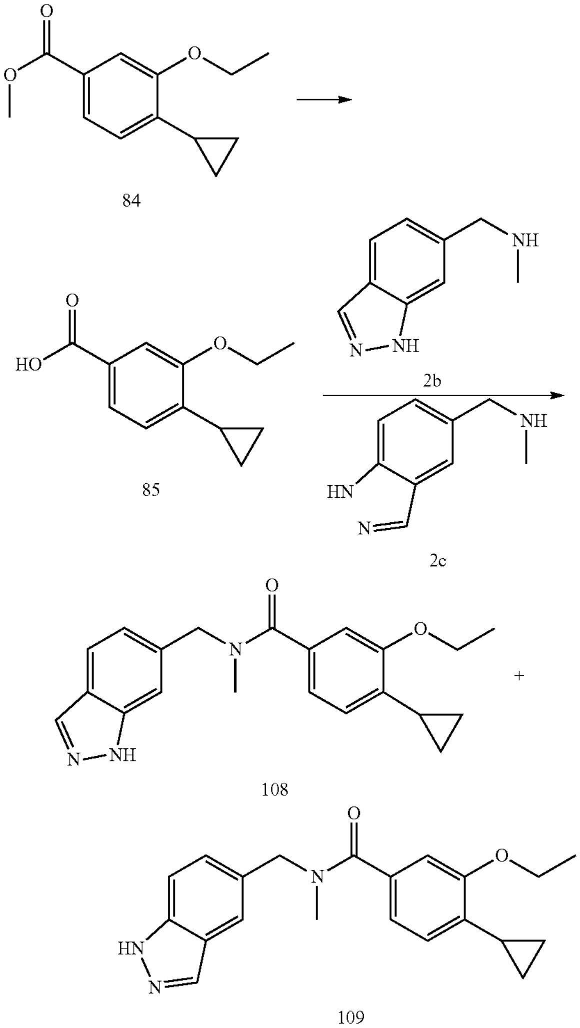

84

85

2c

108

\+

109

Compound 85 was prepared as described for the synthesis of compound 9 with compound 84 as the starting material, LiOH as the base, and step 1 at 30° C. for 12 hr. Also, the pH of the resulting solution was adjusted to 3. The crude product used for next step without further purification. Compound 85 was obtained as a white solid. LCMS: m/z=205.1 (M+H$^+$).

Compound 108 was prepared as described for the synthesis of compound 4 with compound 85 and compound 2b as the starting materials. The crude product was purified by prep-HPLC (column: Phenomenex Luna C18 150*25 mm*10 um; mobile phase: [water(0.225% FA)-ACN]; B %: 38%-68%, 10 min) and the purified solution was lyophilized. Compound 108 (12.57 mg, 35.97 umol, 12.37% yield, 100% purity) was obtained as a white solid. LCMS m/z=350.0 (M+H$^+$). $^1$H NMR (400 MHz, CHLOROFORM-d) δ=8.18-8.00 (m, 1H), 7.84-7.70 (m, 1H), 7.60-7.34 (m, 1H), 6.98 (br s, 3H), 6.89-6.70 (m, 1H), 4.98-4.59 (m, 2H), 4.22-3.77 (m, 2H), 3.19-2.83 (m, 3H), 2.30-2.13 (m, 1H), 1.54-1.24 (m, 3H), 1.07-0.85 (m, 2H), 0.74-0.57 (m, 2H).

Compound 109 was prepared as described for the synthesis of compound 4 with compound 85 and compound 2c as the starting materials. The crude product was purified by prep-HPLC (column: Phenomenex Luna C18 150*25 mm*10 um; mobile phase: [water(0.225% FA)-ACN]; B %: 37%-67%, 10 min) and the purified solution was lyophilized. 109 (43.01 mg, 123.09 umol, 42.31% yield, 100% purity) obtained as a white solid. LCMS: m/z=350.0 (M+H$^+$). $^1$H NMR (400 MHz, CHLOROFORM-d) δ=8.01 (s, 1H), 7.76-7.50 (m, 1H), 7.43 (br d, J=7.4 Hz, 1H), 7.19 (s, 1H), 6.89 (s, 2H), 6.77-6.61 (m, 1H), 4.85-4.51 (m, 2H), 4.11-3.75 (m, 2H), 3.12-2.73 (m, 3H), 2.26-2.05 (m, 1H), 1.48-1.15 (m, 3H), 0.87 (br d, J=7.4 Hz, 2H), 0.59 (br s, 2H).

Scheme 32.

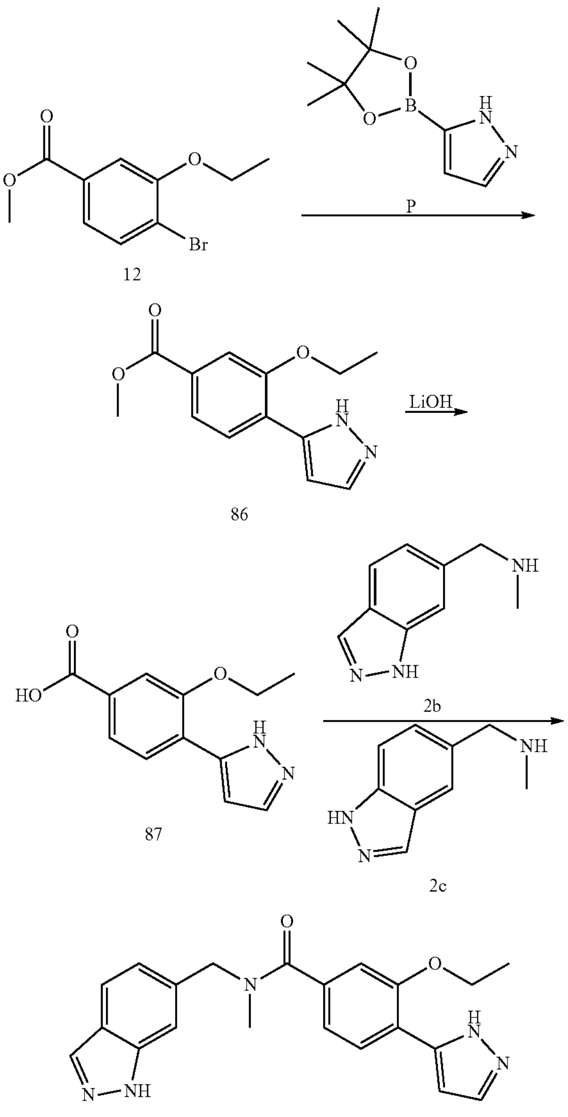

12

86

87

2c

110

-continued

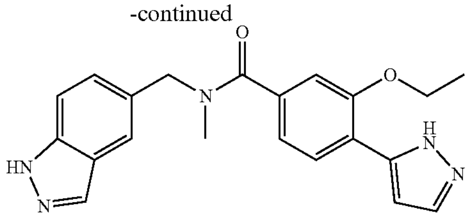

111

Compound 86 was prepared as described for the synthesis of compound 001 with compound 12 and compound P as the starting materials. The mixture was filtered and the filtrate was concentrated to give a crude product. The crude product was purified by column chromatography ($SiO_2$, Petroleum ether/Ethyl acetate=100/1 to 20/1, desired product Rf=0.3). Compound 86 (84.17% yield) was obtained as a yellow oil. LCMS: m/z=246.9 $(M+H^+)$ Compound 87 was prepared as described for the synthesis of compound 9 with compound 86 as the starting material, LiOH as the base, and step 1 at 30° C. for 12 hr. Also, the pH of the resulting solution was adjusted to 3. The crude product used for next step without further purification. Compound 87 (30.73% yield, 61% purity) was obtained as a white solid. LCMS: m/z=231.1 $(M+H^+)$ Compound 110 was prepared as described for the synthesis of compound 4 with compound 87 and compound 2b as the starting materials. The crude product was purified by prep-HPLC (column: Phenomenex luna C18 150*25 mm*10 um; mobile phase: [water(0.225% FA)-ACN]; B %: 24%-54%, 10 min) and the purified solution was lyophilized. 110 (13.94 mg, 36.39 umol, 16.90% yield, 98% purity) obtained as a white solid. LCMS: m/z=376.0 $(M+H^+)$. $^1$H NMR (400 MHz, METHANOL-$d_4$) δ=8.12-8.01 (m, 1H), 7.91-7.73 (m, 2H), 7.69-7.38 (m, 2H), 7.28-7.18 (m, 1H), 7.02 (br d, J=7.4 Hz, 2H), 6.93-6.72 (m, 1H), 4.76 (br s, 2H), 4.30-4.14 (m, 1H), 3.98-3.86 (m, 1H), 3.20-2.96 (m, 3H), 1.58-1.22 (m, 3H)

Compound 111 was prepared as described for the synthesis of compound 4 with compound 87 and compound 2c as the starting materials. The crude product was purified by prep-HPLC (column: Phenomenex luna C18 150*25 mm*10 um; mobile phase: [water(0.225% FA)-ACN]; B %: 22%-52%, 10 min) and the purified solution was lyophilized. Compound 111 (23.70% yield, 100% purity) was obtained as a white solid. LCMS: m/z=376.0 $(M+H^+)$. $^1$H NMR (400 MHz, CHLOROFORM-d) δ=8.06-7.97 (m, 1H), 7.77-7.33 (m, 4H), 7.19 (s, 1H), 7.16-6.95 (m, 2H), 6.74-6.51 (m, 1H), 4.91-4.51 (m, 2H), 4.30-3.89 (m, 2H), 3.10-2.78 (m, 3H), 1.64-1.22 (m, 3H).

Compound 150 was prepared in a similar manner to 111 and was obtained as a white solid (4.83 mg, 9.74 umol, 12.37% yield, 96.7% purity). LCMS: m/z=480.0 $(M-H^+)$ $^1$H NMR (400 MHz, CHLOROFORM-d) δ=12.31-12.04 (m, 1H), 8.50-8.28 (m, 1H), 8.19 (s, 1H), 7.75 (s, 2H), 7.53-7.39 (m, 1H), 7.24-7.12 (m, 2H), 6.84-6.66 (m, 2H), 4.95 (s, 2H), 4.50-4.28 (m, 2H), 3.17 (s, 3H), 3.08 (dd, J=0.9, 4.8 Hz, 3H), 1.38 (t, J=7.1 Hz, 3H).

Compound 151 was prepared in a similar manner to 111 and was obtained as a white solid (5.96 mg, 12.28 umol, 15.43% yield, 100% purity). LCMS: m/z=486.41 $(M-H^+)$ $^1$H NMR (400 MHz, CHLOROFORM-d) δ=12.59-12.20 (m, 1H), 8.40-8.19 (m, 2H), 7.74-7.62 (m, 1H), 7.59-7.48 (m, 1H), 7.40-7.31 (m, 2H), 7.20-7.10 (m, 1H), 7.10-7.02 (m, 2H), 6.83-6.69 (m, 1H), 5.01 (br s, 2H), 4.11-4.02 (m, 2H), 3.09-3.00 (m, 6H), 1.36 (td, J=3.6, 6.9 Hz, 3H).

Compound 152 was prepared in a similar manner to 111 and was obtained as a white solid (4.5 mg, 8.70 umol, 28.23% yield, 94% purity). LCMS: m/z=487.1 $(M-H^+)$ $^1$H NMR (400 MHz, CHLOROFORM-d) δ=12.65-12.04 (m, 1H), 8.42-8.22 (m, 2H), 7.90-7.68 (m, 2H), 7.58-7.53 (m, 1H), 7.52-7.47 (m, 1H), 7.39-7.35 (m, 1H), 7.23-7.16 (m, 1H), 6.88-6.58 (m, 1H), 5.04 (s, 2H), 4.52-4.16 (m, 2H), 3.29-3.14 (m, 3H), 3.08 (s, 3H), 1.43-1.35 (m, 3H).

Compound 153 was prepared in a similar manner to 111 and was obtained as a white solid (23.50 mg, 47.47 umol, 41.82% yield, 98.27% purity). LCMS: m/z=487.4 $(M-H^+)$ $^1$H NMR (400 MHz, CHLOROFORM-d) δ=12.52-12.19 (m, 1H), 8.86 (dd, J=2.4, 7.8 Hz, 1H), 8.44-8.31 (m, 2H), 8.20-8.11 (m, 1H), 7.57 (d, J=7.1 Hz, 1H), 7.46-7.34 (m, 2H), 7.22 (dd, J=8.7, 11.6 Hz, 1H), 6.84-6.70 (m, 1H), 5.05 (s, 2H), 4.17 (q, J=6.9 Hz, 2H), 3.16-3.02 (m, 6H), 1.52 (t, J=7.0 Hz, 3H).

Compound 170 was prepared in a similar manner to 111 and was obtained as a white solid (4.37 mg, 10.42 umol, 7.38% yield, 100% purity). LCMS: m/z=420.0 $(M-H^+)$ $^1$H NMR (400 MHz, CHLOROFORM-d) δ=8.22-8.17 (m, 1H), 7.40-7.35 (m, 1H), 7.35-7.29 (m, 3H), 7.11 (br d, J=7.5 Hz, 1H), 7.08-7.04 (m, 2H), 7.04-7.00 (m, 1H), 6.44 (d, J=7.4 Hz, 1H), 4.88 (s, 2H), 4.06 (q, J=6.9 Hz, 2H), 2.99 (s, 3H), 1.36 (t, J=6.9 Hz, 3H).

Compound 199 was prepared in a similar manner to 111 and was obtained as a white solid (6.82 mg, 13.40 umol, 15.03% yield, 95% purity). LCMS: m/z=487.2 $(M-H^+)$ $^1$H NMR (400 MHz, CHLOROFORM-d) δ=8.50-8.40 (m, 2H), 8.30-8.25 (m, 1H), 7.71-7.64 (m, 1H), 7.38 (d, J=7.6 Hz, 1H), 7.19-7.13 (m, 1H), 7.11-7.05 (m, 2H), 6.84-6.72 (m, 1H), 5.03-4.97 (m, 2H), 4.11-4.03 (m, 2H), 3.09-3.04 (m, 6H), 1.39-1.34 (m, 3H).

Scheme 33.

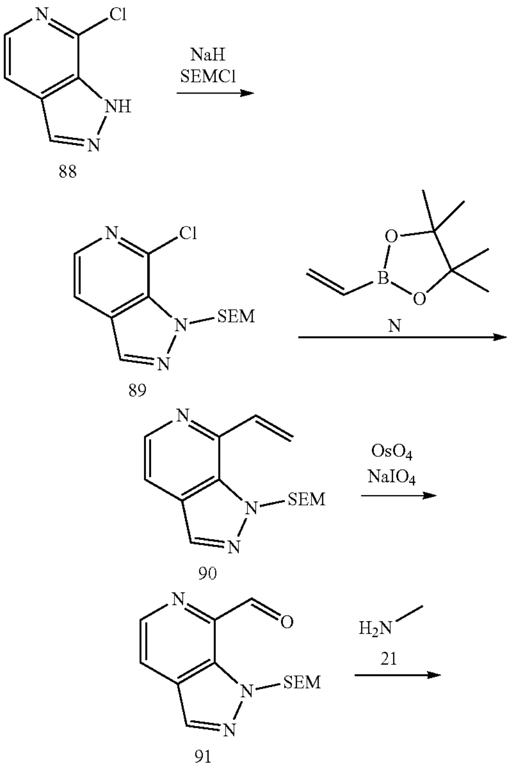

88

89

90

91

-continued

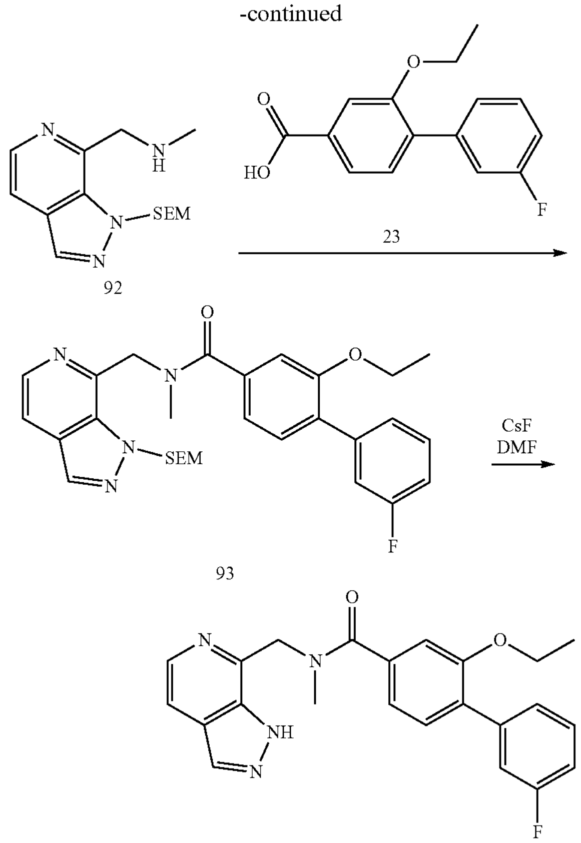

92

23

93

118

Compound 89 was prepared as described for the synthesis of compound 18 with compound 88 as the starting material. The crude product was purified by prep-TLC (PE:EtOAc=2:1). Compound 89 was obtained as a yellow oil. LCMS: m/z=284.0 (M+$H^+$). $^1$H NMR (400 MHz, CHLOROFORM-d) δ=8.20-8.10 (m, 2H), 7.61 (d, J=5.4 Hz, 1H), 6.09 (s, 2H), 3.68-3.56 (m, 2H), 0.99-0.87 (m, 2H), −0.05 (s, 9H).

Compound 90 was prepared as described for the synthesis of compound 001 with compound 89 and compound N as the starting materials and $Cs_2CO_3$ as the base. The mixture was filtered and the filtrate was concentrated in vacuo. The crude product was purified by column chromatography on silica gel eluted with petroleum ether/ethyl acetate=14:1 to 12:1. Compound 90 was obtained as a yellow oil. LCMS: m/z=276.1 (M+$H^+$). $^1$H NMR (400 MHz, CHLOROFORM-d) δ=8.41 (d, J=5.4 Hz, 1H), 8.09 (s, 1H), 7.73-7.58 (m, 2H), 6.59 (dd, J=1.8, 16.8 Hz, 1H), 5.94 (s, 2H), 5.75 (dd, J=1.9, 10.8 Hz, 1H), 3.70-3.55 (m, 2H), 1.00-0.87 (m, 2H), 0.02--0.06 (m, 9H).

Compound 91 was prepared as described for the synthesis of compound 20 with compound 90 as the starting material. Compound 91 was obtained as a colorless oil. $^1$H NMR (400 MHz, CHLOROFORM-d) δ=10.29 (s, 1H), 8.62 (d, J=5.3 Hz, 1H), 8.26 (s, 1H), 7.95 (d, J=5.3 Hz, 1H), 6.32 (s, 2H), 3.54-3.44 (m, 2H), 0.87-0.77 (m, 2H), −0.09 (s, 9H)

Compound 92 was prepared as described for the synthesis of compound 2 with compound 91 as the starting material, step 1 at 20° C. for 2 hr, and step 2 at 20° C. for 2 hr. The crude product was purified by prep-HPLC (HCl, column: 3_Phenomenex Luna C18 75*30 mm*3 um; mobile phase: [water(0.05% HCl)-ACN]; B %: 23%-43%, 9 min) and the purified solution was lyophilized. Compound 92 (33.73% yield, 100% purity, HCl) was obtained as a white solid. LCMS: m/z=293.1 (M+$H^+$)

Compound 93 was prepared as described for the synthesis of compound 4 with compound 92 and compound 23 as the starting materials and step 1 at 20° C. for 12 hr. The crude product was purified by prep-HPLC (FA, column: Phenomenex luna C18 150*25 mm*10 um; mobile phase: [water (0.225% FA)-ACN]; B %: 63%-93%, 10 min) and the purified solution was lyophilized. Compound 93 (15 mg, 24.80 umol, 40.78% yield, 88.4% purity) was obtained as a black oil. LCMS: m/z=535.3 (M+$H^+$)

Compound 118 was prepared as described for the synthesis of compound 038 with compound 93 as the starting material and step 1 at 80° C. for 12 hr. The crude product was purified by prep-HPLC (FA, column: Phenomenex Luna C18 150*25 mm*10 um; mobile phase: [water (0.225% FA)-ACN]; B %: 32%-62%, 10 min) and the purified solution was lyophilized. Compound 118 (2.4 mg, 5.93 umol, 23.93% yield, 100% purity) was obtained as a yellow solid. LCMS: m/z=405.2 (M+$H^+$) $^1$H NMR (400 MHz, CHLOROFORM-d) δ=8.10 (d, J=5.6 Hz, 1H), 8.06-8.00 (m, 1H), 7.53 (d, J=5.6 Hz, 1H), 7.25-7.12 (m, 4H), 6.99-6.87 (m, 3H), 5.01 (s, 2H), 3.92 (q, J=6.9 Hz, 2H), 2.96 (s, 3H), 1.22 (t, J=7.0 Hz, 3H).

Compound 158 was prepared in a similar manner to 038 and was obtained as a white solid (5.27 mg, 10.97 umol, 31.68% yield, 93.12% purity). LCMS: m/z=448.1 (M+$H^+$) $^1$H NMR (400 MHz, CHLOROFORM-d) δ=8.50-8.24 (m, 1H), 7.36 (br dd, J=8.9, 16.7 Hz, 6H), 7.14-7.01 (m, 3H), 5.02 (s, 2H), 4.18-4.01 (m, 2H), 3.07 (s, 3H), 1.42-1.35 (m, 3H).

Compound 159 was prepared in a similar manner to 038 and was obtained as a white solid (7.71 mg, 17.15 umol, 24.78% yield, 99.56% purity). LCMS: m/z=448.1 (M+$H^+$) $^1$H NMR (400 MHz, CHLOROFORM-d) δ=8.68 (s, 1H), 8.00 (d, J=7.3 Hz, 1H), 7.40-7.34 (m, 3H), 7.31 (br d, J=7.6 Hz, 2H), 7.09-7.02 (m, 3H), 5.05 (s, 2H), 4.07 (q, J=7.0 Hz, 2H), 3.03 (s, 3H), 1.37 (t, J=6.9 Hz, 3H).

Compound 191 was prepared in a similar manner to 038 and was obtained as a white solid (9.7 mg, 22.19 umol, 62.66% yield, 99.4% purity). LCMS: m/z=435.2 (M−$H^+$) $^1$H NMR (400 MHz, CHLOROFORM-d) δ=12.27-11.78 (m, 1H), 8.17 (s, 1H), 7.81 (s, 1H), 7.39-7.28 (m, 4H), 7.08-7.00 (m, 3H), 4.83 (s, 2H), 4.12 (s, 3H), 4.06 (q, J=7.0 Hz, 1H), 4.03-4.02 (m, 1H), 3.02 (s, 3H), 1.36 (t, J=6.9 Hz, 3H).

Compound 192 was prepared in a similar manner to 038 and was obtained as a white solid (21.8 mg, 49.37 umol, 58.82% yield, 98.4% purity). LCMS: m/z=435.2 (M−$H^+$) $^1$H NMR (400 MHz, CHLOROFORM-d) δ=12.18-11.95 (m, 1H), 8.17 (s, 1H), 7.82 (s, 1H), 7.41-7.28 (m, 4H), 7.11-7.00 (m, 3H), 4.84 (s, 2H), 4.12 (s, 3H), 4.07 (q, J=6.9 Hz, 2H), 3.03 (s, 3H), 1.37 (t, J=7.0 Hz, 3H).

Compound 193 was prepared in a similar manner to 038 and was obtained as a white solid (20 mg, 45.17 umol, 51.65% yield, 99.7% purity). LCMS: m/z=442.1 (M−$H^+$) $^1$H NMR (400 MHz, CHLOROFORM-d) δ=12.08-11.98 (m, 1H), 8.17 (s, 1H), 7.85 (t, J=1.5 Hz, 1H), 7.81 (s, 1H), 7.76 (td, J=1.4, 7.9 Hz, 1H), 7.62 (td, J=1.3, 7.8 Hz, 1H), 7.53-7.48 (m, 1H), 7.31 (d, J=7.8 Hz, 1H), 7.10-7.06 (m, 2H), 4.83 (s, 2H), 4.12 (s, 3H), 4.07 (q, J=6.9 Hz, 2H), 3.02 (s, 3H), 1.36 (t, J=6.9 Hz, 3H).

Compound 208 was prepared in a similar manner to 038 and was obtained as a white solid (2.4 mg, 4.83 umol, 21.29% yield, 97.94% purity). LCMS: m/z=487.3 (M−$H^+$) $^1$H NMR (400 MHz, CHLOROFORM-d) δ=13.14-12.94 (m, 1H), 9.47-8.45 (m, 1H), 8.28 (dd, J=2.4, 7.6 Hz, 1H), 7.71-7.65 (m, 1H), 7.39 (d, J=7.8 Hz, 1H), 7.16 (dd, J=8.6, 11.7 Hz, 1H), 7.12-7.08 (m, 1H), 7.06 (s, 1H), 6.83-6.73 (m, 1H), 4.97 (s, 2H), 4.07 (q, J=6.9 Hz, 2H), 3.10 (s, 3H), 3.06 (d, J=4.5 Hz, 3H), 1.38 (s, 3H).

Scheme 34.

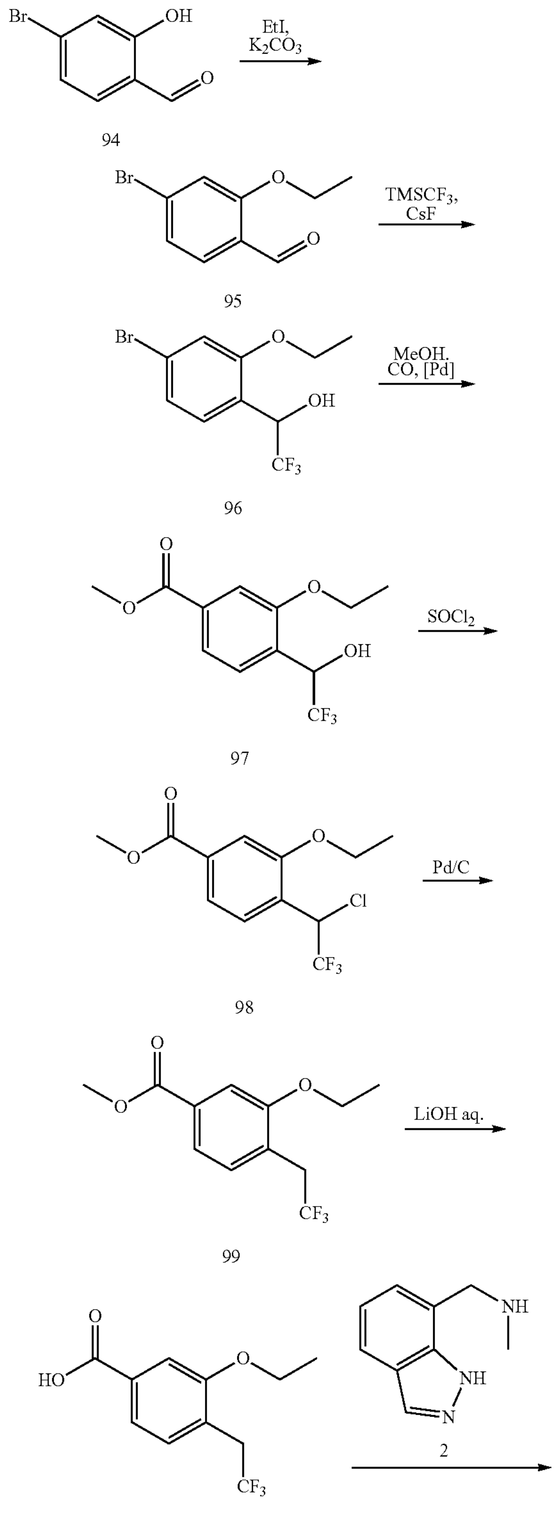

94

95

96

97

98

99

1a

2

-continued

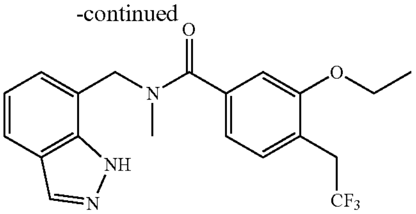

121

Compound 97 was prepared as described for the synthesis of compound 77 with compound 96 as the starting material. The crude product was purified by column on silica (petroleum ether:ethyl acetate=2:1, Rf=0.6) and concentrated under reduced pressure to give a yellow solid. Compound 97 (34.83% yield, 90% purity) was obtained as a yellow solid and used to the next step. LCMS: m/z=277.0 $(M-H^+)$ To a mixture of compound 97 (180 mg, 646.96 umol, 1 eq), Py (5.12 mg, 64.70 umol, 5.22 uL, 0.1 eq) in toluene (5 mL) was added $SOC_2$ (153.94 mg, 1.29 mmol, 93.86 uL, 2 eq) at 0° C., then the mixture was stirred at 70° C. for 12 hr. TLC (PE:EA=5:1, Rf=0.6) showed compound 97 consumed completely and new spot observed. The solution was extracted by ethyl acetate (3*10 mL), the organic phase was concentrated to give a residue. The solution was purified by column on silica (petroleum ether:ethyl acetate=5:1, Rf=0.6) and concentrated under reduced pressure to give a yellow oil. Compound 98 (130 mg, 394.38 umol, 60.96% yield, 90% purity) was obtained as a yellow oil. $^1$H NMR (400 MHz, CHLOROFORM-d) δ=7.70 (s, 2H), 7.61-7.54 (m, 1H), 6.06-5.74 (m, 1H), 4.26-4.07 (m, 2H), 3.94 (s, 3H), 1.47 (s, 3H).

Compound 99 was prepared as described for the synthesis of compound 10 with compound 98 as the starting material, MeOH as the solvent, and step 1 at 45° C. for 12 hr. The reaction mixture was purified by prep-TLC (PE:EA=5:1, Rf=0.6), the purified solution was concentrated to give a white solid. Compound 99 (77.54% yield, 99% purity) was obtained as a white solid. LCMS: m/z=262.8 $(M+H^+)$ Compound 1a was prepared as described for the synthesis of compound 9 with compound 99 as the starting material, LiOH as the base, and step 1 at 30° C. for 1 hr. Also, the pH of the resulting solution was adjusted to 1. Compound 1a (64.56% yield, 100% purity) was obtained as a white solid. LCMS: m/z=247.1 $(M-H^+)$ Compound 121 was prepared as described for the synthesis of compound 4 with compound 1a and compound 2 as the starting materials. The solution was purified by prep-HPLC (column: Waters Xbridge 150*25 mm*5 um; mobile phase: [water (10 mM $NH_4HCO_3$)-ACN]; B %: 44%-74%, 9 min) and the purified solution was lyophilized to give a brown solid. Compound 121 (46.89 mg, 116.26 umol, 64.12% yield, 97.04% purity) was obtained as a brown solid. LCMS: m/z=392.0 $(M+H^+)$. $^1$H NMR (400 MHz, CHLOROFORM-d) δ=8.49-8.33 (m, 1H), 8.11-8.00 (m, 1H), 7.63-7.52 (m, 2H), 7.47-7.37 (m, 1H), 7.31-7.23 (m, 2H), 5.24 (s, 2H), 4.45-4.27 (m, 2H), 3.87-3.68 (m, 2H), 3.24 (s, 3H), 1.71 (s, 3H).

Compound 178 was prepared in a similar manner to 121 and was obtained as a white solid (8 mg, 17.40 umol, 6.23% yield, 93.4% purity). LCMS: m/z=430.1 $(M+H^+)$ $^1$H NMR: (400 MHz, CHLOROFORM-d) δ 8.18-8.07 (m, 1H), 8.02-7.97 (m, 1H), 7.95 (d, J=1.1 Hz, 1H), 7.80-7.74 (m, 1H), 7.73-7.67 (m, 1H), 7.60 (d, J=7.8 Hz, 1H), 7.30 (d, J=6.9 Hz, 1H), 7.18-7.11 (m, 1H), 5.00 (s, 2H), 4.47-4.21 (m, 1H), 3.23 (s, 3H), 0.88-0.62 (m, 4H).

Compound 179 was prepared in a similar manner to 121 and was obtained as a white solid (35 mg, 84.03 umol, 57.42% yield, 100% purity). LCMS: m/z=443.2 (M+H$^+$) $^1$H NMR: (400 MHz, CHLOROFORM-d) δ 8.14 (s, 1H), 7.98 (d, J=1.4 Hz, 1H), 7.90 (d, J=1.3 Hz, 1H), 7.79 (d, J=7.9 Hz, 1H), 7.46 (d, J=7.8 Hz, 1H), 7.30-7.28 (m, 1H), 7.17-7.12 (m, 1H), 7.09-7.05 (m, 2H), 4.97 (s, 2H), 4.13 (q, J=7.0 Hz, 2H), 2.99 (s, 3H), 1.46 (t, J=6.9 Hz, 3H)

Compound 180 was prepared in a similar manner to 121 and was obtained as a white solid (12 mg, 28.30 umol, 12.94% yield, 98.451% purity). LCMS: m/z=418.1 (M+H$^+$) $^1$H NMR: (400 MHz, CHLOROFORM-d) δ 8.12 (s, 1H), 8.02 (d, J=4.8 Hz, 2H), 7.86 (d, J=7.6 Hz, 1H), 7.78 (d, J=8.0 Hz, 1H), 7.48 (d, J=7.6 Hz, 1H), 7.29 (d, J=6.8 Hz, 1H), 7.16-7.11 (m, 1H), 4.98 (s, 2H), 4.48 (q, J=7.0 Hz, 2H), 3.15 (s, 3H), 1.45 (t, J=7.1 Hz, 3H).

Compound 181 was prepared in a similar manner to 121 and was obtained as a white solid (13.11 mg, 33.40 umol, 16.01% yield, 100% purity). LCMS: m/z=393.1 (M+H$^+$).

Compound 182 was prepared in a similar manner to 121 and was obtained as a white solid (14.8 mg, 37.33 umol, 17.23% yield, and 99% purity). LCMS: m/z=418.1 (M+H$^+$) $^1$H NMR: (400 MHz, CHLOROFORM-d) δ 8.97-8.95 (m, 1H), 8.92-8.89 (m, 1H), 8.21-8.16 (m, 1H), 7.85-7.78 (m, 1H), 7.61-7.55 (m, 1H), 7.36-7.30 (m, 1H), 7.22-7.14 (m, 1H), 7.14-7.08 (m, 2H), 5.02-4.97 (m, 2H), 4.21-4.12 (m, 2H), 3.06-2.98 (m, 3H), 1.51-1.46 (m, 3H)

Scheme 35.

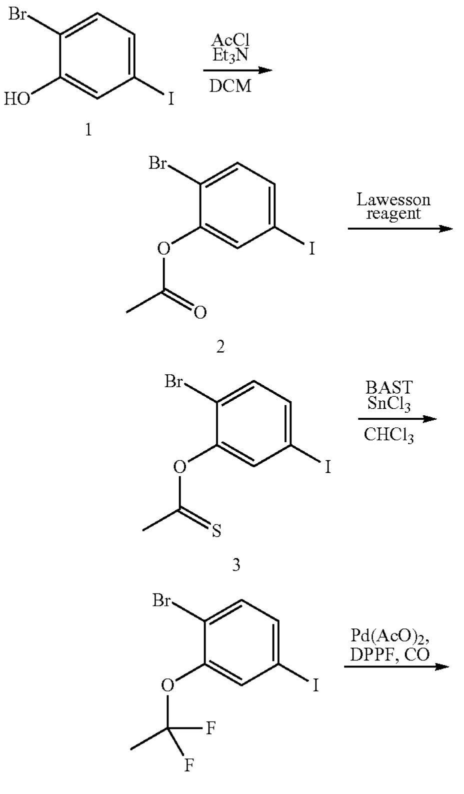

1 2 3 4

-continued

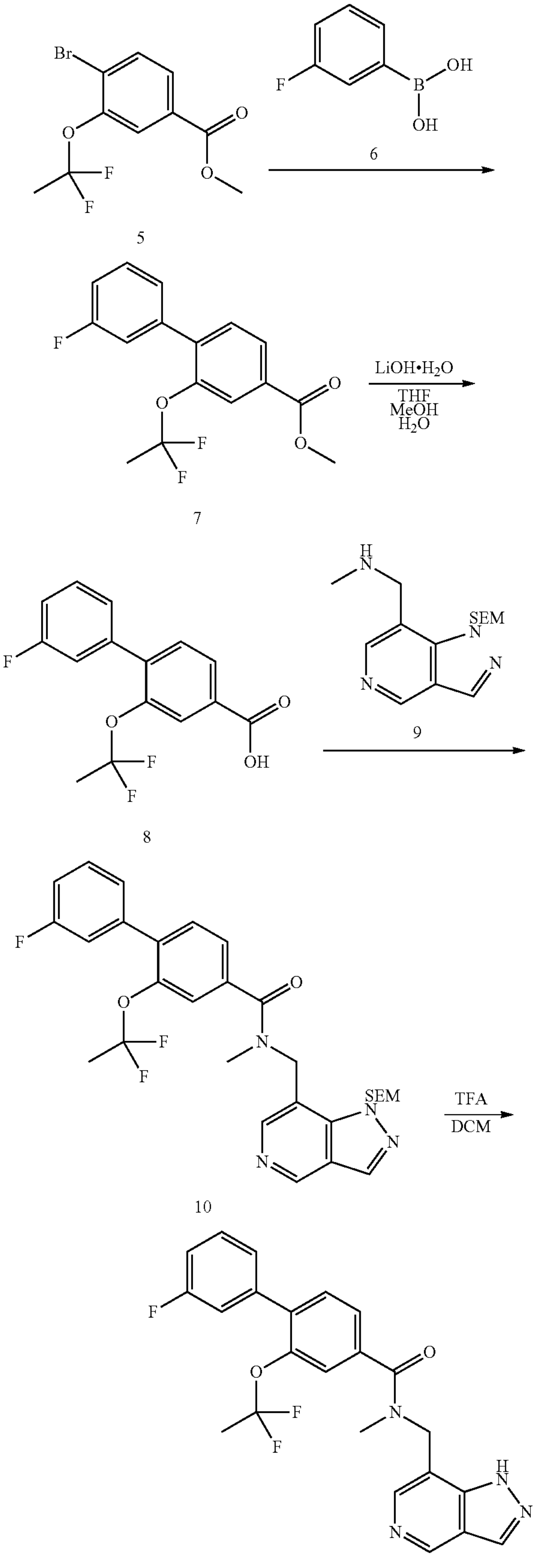

5 7 8 10 187

To a solution of compound 1 in DCM (35 mL) was added $Et_3N$ (1.40 g, 13.85 mmol, 1.93 mL, 1.2 eq) and acetyl chloride (1.09 g, 13.85 mmol, 988.40 uL, 1.2 eq), the reaction mixture was stirred at 0° C. for 12 hours under $N_2$. TLC (PE:EtOAc=10:1, product Rf=0.8) showed the starting material was consumed completely. The reaction mixture was filtered, the filtrate was concentrated to give a crude product. The crude product was purified by column chromatography on silica gel eluted with petroleum ether/ethyl acetate=100/1 to 20/1 (desired product Rf=0.8). Compound 2 was obtained as white solid. $^1H$ NMR: 1H NMR (400 MHz, CHLOROFORM-d) δ=7.42-7.34 (m, 2H), 7.28-7.20 (m, 1H), 2.37-2.21 (m, 3H).

To a solution of compound 2 (2.5 g, 7.33 mmol, 1 eq) in 108-67-8 (30 mL) was added Lawesson's reagent (8.90 g, 22.00 mmol, 3 eq), the mixture was stirred at 180° C. for 4 h. TLC (PE:EtOAc=10:1) showed most of the starting material was remained, and a new point was detected. After the reaction was completed, the mixture was cooled to room temperature, then the mixture was poured into water (80 mL), and extracted with EtOAc (80 mL×3), the combined organic phase was washed with brine (50 mL×3), dried over anhydrous $Na_2SO_4$, and concentrated to give a crude product. The crude product was purified by column chromatography ($SiO_2$, Petroleum ether/Ethyl acetate=100/1 to 80/1, desired product Rf=0.6). Compound 3 was obtained as yellow solid. $^1H$ NMR (400 MHz, CHLOROFORM-d) δ=7.41-7.34 (m, 1H), 7.30 (d, J=2.0 Hz, 1H), 7.26-7.21 (m, 1H), 2.71 (s, 3H)

To a solution of compound 3 (600 mg, 1.68 mmol, 1 eq) in CHCl3 (10 mL) was added $SbCl_3$ (1.15 g, 5.04 mmol, 3 eq) and BAST (1.12 g, 5.04 mmol, 1.10 mL, 3 eq) at 0° C., the mixture was stirred at 20° C. for 12 h. TLC (PE, staring material Rf=0.6, desired product Rf=0.9) showed the reaction was completed. After the reaction was completed, the mixture was poured into water (50 mL), and extracted with EtOAc (50 mL×3), the combined organic phase was washed with brine (50 mL×3), dried over anhydrous $Na_2SO_4$, and concentrated to give a crude product. The crude product was purified by column chromatography ($SiO_2$, Petroleum ether/Ethyl acetate=1/0). Compound 4 (170 mg, 468.40 umol, 27.87% yield, N/A purity) was obtained as colorless oil. $^1H$ NMR: $^1H$ NMR (400 MHz, CHLOROFORM-d) δ=7.68 (d, J=1.3 Hz, 1H), 7.40 (d, J=1.9 Hz, 1H), 7.30 (d, J=8.5 Hz, 1H), 1.99 (t, J=13.4 Hz, 3H).

To a solution of compound 4 (110 mg, 303.08 umol, 1 eq) in MeOH (20 mL) was added $Pd(OAc)_2$ (6.80 mg, 30.31 umol, 0.1 eq) and DPPF (33.60 mg, 60.62 umol, 0.2 eq), and TEA (153.34 mg, 1.52 mmol, 210.93 uL, 5 eq), the mixture was stirred at 40° C. for 12 hr under CO (50 Psi). After the reaction was completed, the mixture was filtered under $N_2$ and the filtrated was concentrated to give a crude product. The crude product was purified by prep-TLC (PE: EtOAc=10:1, desired product Rf=0.7). Compound 5 (70 mg, 237.23 umol, 78.27% yield, N/A purity) was obtained as colorless oil.

To a solution of compound 5 (30 mg, 101.67 umol, 1 eq) and compound 6 (21.34 mg, 152.50 umol, 1.5 eq) in 1,4-dioxane (2 mL) was added $K_2CO_3$ (28.10 mg, 203.34 umol, 2 eq) and $Pd(dppf)Cl_2$—$CH_2Cl_2$ (4.15 mg, 5.08 umol, 0.05 eq), the mixture was stirred at 100° C. for 12 hr under $N_2$. The mixture was filtered and the filtrate was concentrated to give a crude product. The crude product was purified by prep-TLC (Petroleum ether:Ethyl acetate=10:1, desired product Rf=0.6). Compound 7 (26 mg, 83.00 umol, 81.63% yield, 99.043% purity) was obtained as colorless oil. LCMS: m/z=311.1 ($M+H^+$).

To a solution of compound 7 (26 mg, 83.80 umol, 1 eq) in $H_2O$ (2 mL), THF (2 mL) and MeOH (2 mL) was added $LiOH{\cdot}H_2O$ (17.58 mg, 418.99 umol, 5 eq), the mixture was stirred at 25° C. for 12 hr. The reaction mixture was adjusted to pH=5 with HCl (1 M), then extracted with ethyl acetate (10 mL×3), and the combined organic phase was washed with saturated salt (10 mL×1), dried over sodium sulphate anhydrous. The organic phase was concentrated to give a crude product. The crude product was used for next step without purification. Compound 8 acid (20 mg, 67.51 umol, 80.57% yield) was obtained as white solid. LCMS: m/z=295.1 ($M-H^+$).

To a solution of compound 8 (20 mg, 67.51 umol, 1 eq) and compound 9 (29.62 mg, 101.27 umol, 1.5 eq) in DCM (2 mL) was added EDCl (19.41 mg, 101.27 umol, 1.5 eq) and DMAP (824.79 ug, 6.75 umol, 0.1 eq), the mixture was stirred at 20° C. for 3 hr. The reaction mixture was concentrated to give a crude product. The crude product was purified by prep-TLC (Petroleum ether:Ethyl acetate=0:1, desired product Rf=0.7). Compound 10 (45 mg, crude) was obtained as colorless oil. LCMS: m/z=571.2 ($M+H^+$).

A solution of compound 10 (45 mg, 78.85 umol, 1 eq) in TFA (2 mL) and DCM (2 mL) was stirred at 20° C. for 1 hr. The mixture was concentrated to give a crude product, the crude product was dissolved in MeOH (10 mL), and $Na_2CO_3$ (500 mg) was added to the mixture, the mixture was filtered and the filtrate was concentrated to give a crude product. The crude product was purified by prep-HPLC (FA, column: Phenomenex luna C18 150*25 mm*10 um; mobile phase: [water (FA)-ACN]; B %: 15%-45%, 9 min), the purified solution was lyophilized. Compound 187 (5.32 mg, 11.92 umol, 15.11% yield, 98.643% purity) was obtained as white solid. LCMS: m/z=441.1 ($M+H^+$) $^1H$ NMR: (400 MHz, CHLOROFORM-d) δ=9.29-9.17 (m, 1H), 8.47-8.37 (m, 2H), 7.58-7.50 (m, 1H), 7.48-7.35 (m, 3H), 7.24-7.15 (m, 2H), 7.13-7.06 (m, 1H), 5.04-4.95 (m, 2H), 4.95-4.89 (m, 1H), 3.08 (s, 3H), 1.73 (s, 3H).

Compound 126 was prepared in a similar manner to 187 and was obtained as a white solid (3 mg, 6.84 umol, 12.87% yield, 99% purity). LCMS: m/z=435.3 (M+H)+1H NMR (CHLOROFORM-d, 400 MHz) δ 12.0-12.3 (m, 1H), 8.1-8.2 (m, 1H), 7.7-7.8 (m, 1H), 7.4-7.6 (m, 1H), 7.3-7.4 (m, 1H), 7.3-7.3 (m, 1H), 7.1-7.3 (m, 2H), 7.0-7.1 (m, 1H), 6.7-6.8 (m, 1H), 4.8-5.0 (m, 2H), 4.1-4.4 (m, 1H), 3.1-3.4 (m, 2H), 2.8-2.9 (m, 1H), 0.5-0.8 (m, 4H).

Compound 133 was prepared in a similar manner to 187 and was obtained as a white solid (17 mg, 40.34 umol, 89.02% yield, 100% purity). LCMS: m/z=422.2 $(M+H)^+$1H NMR (CHLOROFORM-d, 400 MHz) δ 12.01 (br s, 1H), 8.11 (s, 1H), 7.37-7.32 (m, 4H), 7.31-7.26 (m, 1H), 7.12 (dd, J=4.6, 7.6 Hz, 1H), 6.77 (t, J=3.9 Hz, 2H), 6.68 (dd, J=7.8, 9.4 Hz, 1H), 4.83 (s, 2H), 3.94 (q, J=7.0 Hz, 2H), 2.94 (s, 3H), 1.21 (t, J=6.9 Hz, 3H).

Compound 160 was prepared in a similar manner to 187 and was obtained as a white solid. LCMS: m/z=461.2 $(M+H)^+$ 1H NMR (CHLOROFORM-d, 400 MHz) δ 12.36-11.98 (m, 1H), 8.52 (s, 1H), 8.59-8.39 (m, 1H), 7.41-7.33 (m, 2H), 7.30 (br d, J=5.5 Hz, 2H), 7.06 (s, 3H), 6.27-6.18 (m, 1H), 5.01 (s, 2H), 4.07 (q, J=6.8 Hz, 2H), 3.13 (d, J=4.9 Hz, 3H), 3.00 (s, 3H), 1.37 (t, J=6.9 Hz, 3H).

Compound 161 was prepared in a similar manner to 187 and was obtained as a white solid. LCMS: m/z=475.2 $(M+H)^+$ 1H NMR (CHLOROFORM-d, 400 MHz) δ 12.32-11.98 (m, 1H), 8.21 (s, 1H), 7.50-7.38 (m, 5H), 7.28 (d, J=7.0 Hz, 1H), 7.18-7.12 (m, 3H), 5.09 (s, 2H), 4.17 (q, J=6.9 Hz, 2H), 3.34 (br s, 3H), 3.11 (s, 6H), 1.47 (t, J=6.9 Hz, 3H).

Compound 165 was prepared in a similar manner to 187 and was obtained as colorless oil (5.16 mg, 11.65 umol, 16.66% yield, 99.7% purity). LCMS: m/z=442.2 $(M+H^+)$ $^1H$ NMR: (400 MHz, CHLOROFORM-d) δ=8.65-8.21 (m, 1H), 7.88-7.71 (m, 4H), 7.65-7.53 (m, 1H), 7.34-7.28 (m, 1H), 7.24-7.17 (m, 1H), 6.76 (br t, J=7.7 Hz, 1H), 5.04-4.74 (m, 2H), 3.98 (br s, 1H), 3.28-2.88 (m, 3H), 1.00-0.82 (m, 4H)

Compound 171 was prepared in a similar manner to 187 and was obtained as a white solid (13.42 mg, 31.38 umol, 12.48% yield, 99.7% purity). LCMS: m/z=427.2 $(M+H)^+$ 1H NMR (CHLOROFORM-d, 400 MHz) δ 12.57-11.40 (m, 1H), 8.15 (s, 1H), 7.94 (d, J=1.5 Hz, 1H), 7.78-7.73 (m, 1H), 7.71-7.65 (m, 1H), 7.65-7.58 (m, 1H), 7.54-7.45 (m, 1H), 7.39-7.33 (m, 1H), 7.33-7.28 (m, 1H), 7.22-7.16 (m, 1H), 6.92-6.82 (m, 1H), 6.77-6.68 (m, 1H), 4.95-4.87 (m, 2H), 3.89-3.82 (m, 1H), 0.94-0.85 (m, 2H), 0.78-0.70 (m, 2H).

Compound 188 was prepared in a similar manner to 187 and was obtained as colorless oil (5.76 mg, 12.82 umol, 13.63% yield, 94.046% purity). LCMS: m/z=423.1 $(M+H^+)$ $^1H$ NMR: (400 MHz, CHLOROFORM-d) δ=9.20 (s, 1H), 8.40 (d, J=11.3 Hz, 2H), 7.52 (s, 1H), 7.55-7.50 (m, 1H), 7.46 (s, 5H), 7.43-7.41 (m, 1H), 7.41-7.37 (m, 1H), 4.99 (s, 2H), 3.09 (s, 3H), 1.77 (br s, 3H).

Compound 189 was prepared in a similar manner to 187 and was obtained as a white solid (2.8 mg, 6.38 umol, 8.45% yield, 91% purity). LCMS: m/z=400.0 $(M+H)^+$ 1H NMR (CHLOROFORM-d, 400 MHz) δ 9.1-9.2 (m, 1H), 8.3-8.4 (m, 1H), 8.2-8.3 (m, 1H), 7.7-7.8 (m, 1H), 7.6-7.6 (m, 1H), 7.5-7.5 (m, 1H), 7.5-7.5 (m, 1H), 7.5-7.5 (m, 1H), 7.4-7.4 (m, 3H), 4.9-5.0 (m, 2H), 4.1-4.3 (m, 1H), 3.2-3.4 (m, 3H), 0.7-0.8 (m, 4H).

Compound 201 was prepared in a similar manner to 187 and was obtained as a white solid. LCMS: m/z=456.1 $(M+H)^+$ 1H NMR (CHLOROFORM-d, 400 MHz) δ 9.2-9.3 (m, 1H), 8.4-8.5 (m, 2H), 8.3-8.4 (m, 2H), 8.2-8.3 (m, 1H), 7.68 (d, 1H, J=7.9 Hz), 7.5-7.6 (m, 1H), 7.4-7.5 (m, 1H), 4.9-5.1 (m, 2H), 4.1-4.2 (m, 2H), 3.13 (s, 3H), 1.49 (t, 3H, J=6.9 Hz).

Compound 202 was prepared in a similar manner to 187 and was obtained as a white solid (8.34 mg, 19.15 umol, 33.73% yield, 99.50% purity). LCMS: m/z=434.2 $(M+H)^+$ 1H NMR (CHLOROFORM-d, 400 MHz) δ 12.07 (br dd, J=6.6, 9.6 Hz, 1H), 9.18 (s, 1H), 8.46 (d, J=1.6 Hz, 1H), 8.38 (s, 1H), 8.31 (s, 1H), 7.83 (d, J=7.9 Hz, 1H), 7.75 (d, J=9.9 Hz, 1H), 7.45 (dt, J=6.1, 8.0 Hz, 1H), 7.16 (t, J=8.0 Hz, 1H), 6.99 (d, J=1.6 Hz, 1H), 5.30 (t, J=5.7 Hz, 1H), 5.03 (t, J=6.9 Hz, 2H), 4.97 (s, 2H), 4.79 (dd, J=5.1, 7.8 Hz, 2H), 3.11 (s, 3H).

Compound 203 was prepared in a similar manner to 187 and was obtained as a white solid (20 mg, 44.30 umol, 25.77% yield, 100% purity). LCMS: m/z=451.1 $(M+H)^+$ 1H NMR (CHLOROFORM-d, 400 MHz) δ 13.08-11.63 (m, 1H), 9.33-9.19 (m, 1H), 8.52-8.46 (m, 1H), 8.46-8.43 (m, 1H), 8.43-8.39 (m, 1H), 8.02-7.89 (m, 1H), 7.88-7.78 (m, 1H), 7.30 (br s, 1H), 7.01-6.96 (m, 1H), 5.41-5.22 (m, 1H), 5.10-5.03 (m, 2H), 5.03-4.97 (m, 2H), 4.83-4.76 (m, 2H), 3.20-3.06 (m, 3H).

Compound 204 was prepared in a similar manner to 187 and was obtained as a white solid (6.9 mg, 14.60 umol, 25.28% yield, 97% purity). LCMS: m/z=459.1 $(M+H)^+$ 1H NMR (CHLOROFORM-d, 400 MHz) δ 11.9-12.0 (m, 1H), 9.1-9.2 (m, 1H), 8.4-8.5 (m, 1H), 8.3-8.4 (m, 1H), 8.3-8.3 (m, 1H), 8.2-8.3 (m, 1H), 8.1-8.1 (m, 1H), 7.4-7.5 (m, 1H), 7.02 (d, 1H, J=1.6 Hz), 5.34 (quin, 1H, J=5.4 Hz), 5.05 (t, 2H, J=6.9 Hz), 4.9-5.0 (m, 2H), 4.7-4.8 (m, 2H), 3.1-3.1 (m, 3H).

Compound 205 was prepared in a similar manner to 187 and was obtained as a white solid (64 mg, 156.92 umol, 93.22% yield, and 99.16% purity). LCMS: m/z=405.0 $(M+H)^+$ 1H NMR (CHLOROFORM-d, 400 MHz) δ 13.01-11.99 (m, 1H), 9.41-9.03 (m, 1H), 8.52-8.30 (m, 2H), 7.29 (td, J=2.9, 7.8 Hz, 2H), 7.26-7.20 (m, 2H), 7.06-6.94 (m, 3H), 4.93 (s, 2H), 4.00 (d, J=6.9 Hz, 2H), 3.02 (s, 3H), 1.31 (t, J=6.9 Hz, 3H).

Compound 215 was prepared in a similar manner to 187 and was obtained as a white solid (2.87 mg, 6.85 umol, 24.91% yield, 99.1% purity). LCMS: m/z=416.1 $(M+H)^+$ 1H NMR (CHLOROFORM-d, 400 MHz) δ 13.16-11.40 (m, 1H), 8.42 (s, 1H), 8.40 (s, 1H), 7.55 (d, J=1.3 Hz, 1H), 7.39-7.29 (m, 4H), 7.09-7.03 (m, 2H), 4.99 (d, J=6.6 Hz, 2H), 4.16 (q, J=6.9 Hz, 2H), 1.41 (t, J=6.9 Hz, 3H).

Compound 217 was prepared in a similar manner to 187 and was obtained as a white solid (5.8 mg, 13.46 umol, 15.01% yield, 99.2% purity). 1H NMR (CHLOROFORM-d, 400 MHz) δ 13.04-11.82 (m, 1H), 8.40 (d, J=6.9 Hz, 2H), 7.92 (s, 1H), 7.41-7.37 (m, 1H), 7.36-7.32 (m, 1H), 7.26-7.12 (m, 3H), 7.08-7.01 (m, 1H), 5.00 (d, J=6.6 Hz, 2H), 3.85 (tt, J=3.0, 5.9 Hz, 1H), 0.93-0.84 (m, 2H), 0.83-0.72 (m, 2H).

Compound 218 was prepared in a similar manner to 187 and was obtained as a white solid (9.8 mg, 21.56 umol, 22.93% yield, 100% purity). LCMS: m/z=455.2 $(M+H^+)$ 1H NMR (CHLOROFORM-d, 400 MHz) δ 12.33-11.77 (m, 1H), 8.14-8.05 (m, 1H), 7.82-7.71 (m, 2H), 7.70-7.63 (m, 2H), 7.58 (br d, J=7.8 Hz, 1H), 7.53 (d, J=7.6 Hz, 1H), 7.50-7.43 (m, 1H), 4.85-4.64 (m, 2H), 4.30-3.99 (m, 4H), 3.22-2.78 (m, 3H), 0.88-0.50 (m, 4H).

Scheme 36.

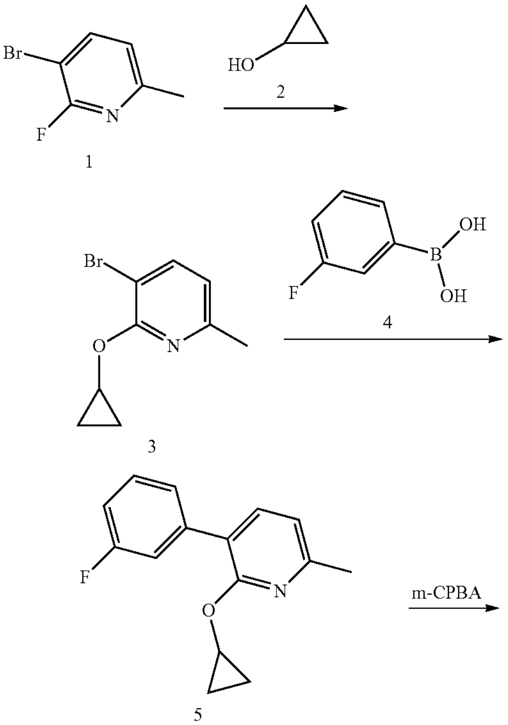

1
2
3
4
5

-continued

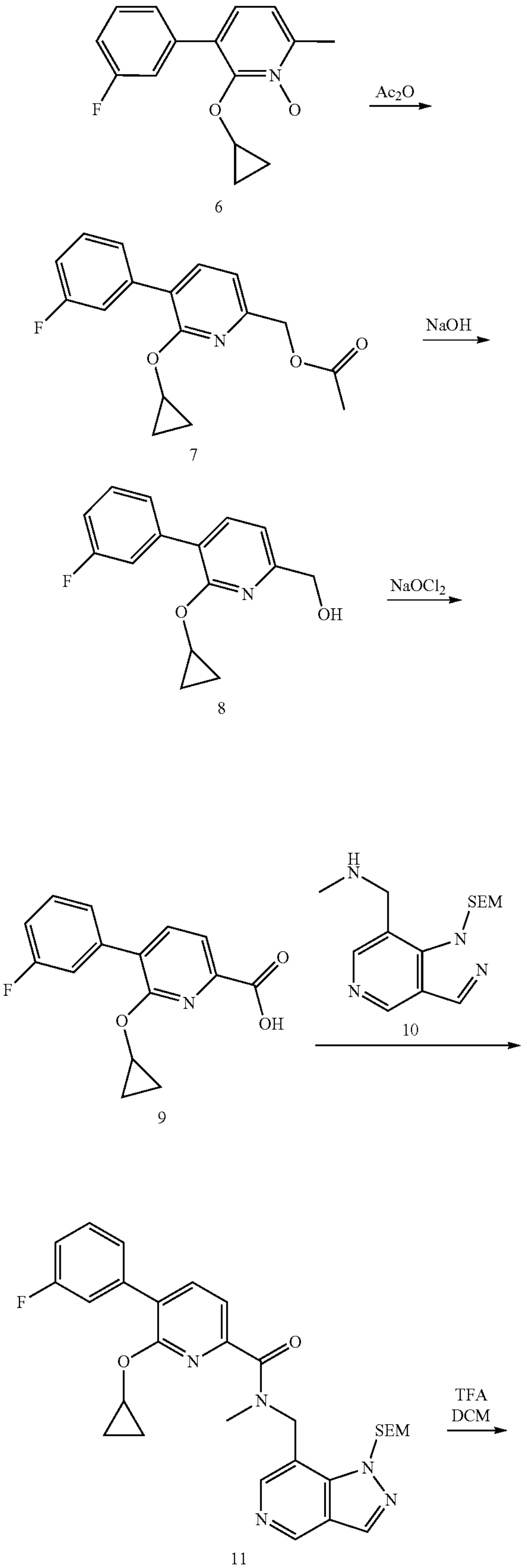

6
7
8
10
9
11

-continued

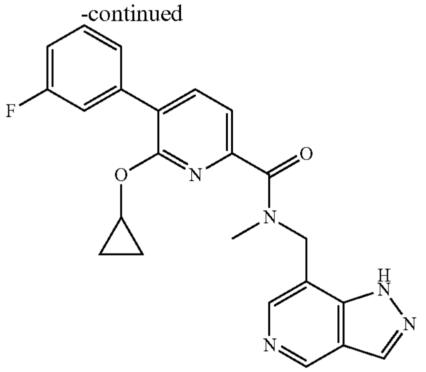

285

To a solution of compound 1 (2 g, 10.53 mmol, 1 eq) and compound 2 (916.97 mg, 15.79 mmol, 1.5 eq) in THF (20 mL) was added t-BuOK (2.36 g, 21.05 mmol, 2 eq) at 0° C., and then stirred at 50° C. for 2 h. The reaction was stirred at 50° C. for another 10 h. Cooled to room temperature, poured into 100 mL of water and extracted with EtOAc (100 mL×3). The combined organic layers were washed with brine (100 mL), dried over $Na_2SO_4$, filtered and concentrated to give crude product. The crude product was purified by silica gel column chromatography eluted with PE to give product. Compound 3 (2.17 g, 9.51 mmol, 90.39% yield) was obtained as colourless oil. LCMS: m/z=226.9 ($M+H^+$) $^1$HNMR: $^1$H NMR (400 MHz, CHLOROFORM-d) δ=7.62-7.64 (d, J=7.8 Hz, 1H), 6.65-6.32 (d, J=7.8 Hz, 1H), 4.41-4.38 (m, 1H), 2.44 (s, 3H), 0.80-0.78 (m, 4H)

To a solution of compound 3 (2.17 g, 9.51 mmol, 1 eq) and compound 4 (1.60 g, 11.42 mmol, 1.2 eq) in dioxane (25 mL)/$H_2O$ (2.5 mL) was added $K_2CO_3$ (2.63 g, 19.03 mmol, 2 eq) and Pd(dppf)$Cl_2$·$CH_2Cl_2$ (388.47 mg, 475.70 umol, 0.05 eq), and then the reaction was stirred at 100° C. for 12 h under $N_2$. After cooled to room temperature, 50 mL was added and extracted with EtOAc (50 mL×3). The combined organic layers was washed with brine (50 mL), dried over $Na_2SO_4$, filtered and concentrated. The residue was purified by silica gel column chromatography eluted with PE:EtOAc=1:0 to 20:1 to give product. Compound 5 (1.56 g, 6.41 mmol, 67.40% yield) was obtained as colourless oil. LCMS: m/z=244.0 ($M+H^+$) $^1$HNMR: $^1$H NMR (400 MHz, CHLOROFORM-d) δ=7.41 (d, J=7.4 Hz, 1H), 7.28-7.22 (m, 1H), 7.18-7.12 (m, 2H), 6.94-6.88 (m, 1H), 6.76 (d, J=7.5 Hz, 1H), 4.39-4.34 (m, 1H), 2.44 (s, 3H), 0.71-0.63 (m, 4H)

To a solution of compound 5 (800 mg, 3.29 mmol, 1 eq) in DCM (8 mL) was added m-CPBA (2.00 g, 9.87 mmol, 85% purity, 3 eq) at 0° C., the reaction mixture was stirred at 25° C. for 12 hours under $N_2$. After the reaction was completed, the mixture was poured into saturated $Na_2SO_3$ solution (100 mL), and extracted with EtOAc (50 mL×3), the combined organic phase was washed with brine (50 mL), dried over anhydrous $Na_2SO_4$, and concentrated to give a crude product. The crude product was purified by column chromatography ($SiO_2$, Petroleum ether/Ethyl acetate=1/1 to 1/5, desired product Rf=0.3). Compound 6 (350 mg, 1.35 mmol, 41.05% yield, N/A purity) was obtained as yellow oil. LCMS: m/z=260.1 ($M+H^+$)

A solution of compound 6 (338.68 mg, 1.31 mmol, 1 eq) in $Ac_2O$ (5.45 g, 53.38 mmol, 5.00 mL, 40.87 eq) was stirred at 120° C. for 12 hours under $N_2$ The reaction mixture was partitioned between EtOAc (150 ml) and water (150 ml). The separated organic layer was dried over ($Na_2SO_4$) and evaporated to dryness to give a crude product. The crude product was purified by column chromatography on silica gel eluted with petroleum ether:ethyl acetate=100/0 to 100/10 (desired mass Rf=0.4). Compound 7 (1.2 g, crude) was obtained as yellow liquid. LCMS: m/z=302.0 (M+H$^+$) 1H NMR (400 MHz, CHLOROFORM-d) δ=7.57-7.50 (m, 1H), 7.32-7.24 (m, 1H), 7.22-7.14 (m, 2H), 7.00-6.92 (m, 2H), 5.19-5.09 (m, 2H), 4.38-4.30 (m, 1H), 2.13-2.11 (m, 3H), 0.72-0.62 (m, 4H).

To a solution of compound 7 (1.2 g, 3.98 mmol, 1 eq) in THF (12 mL), MeOH (12 mL) and $H_2O$ (12 mL) was added NaOH (1.59 g, 39.83 mmol, 10 eq), the reaction mixture was stirred at 25° C. for 12 hours under $N_2$. The reaction mixture was partitioned between EtOAc (250 ml) ans water (250 ml), the combined organic layer was washed with saturated NaCl solution, dried over $Na_2SO_4$ and evaporated to give a crude product. The crude product was purified by column chromatography on silica gel eluted weigh petroleum ether: ethyl acetate=100/0 to 100/20 (desired product Rf=0.2). Compound 8 (169 mg, 644.00 umol, 16.17% yield, 98.8% purity) was obtained as yellow oil. LCMS: m/z=260.1 (M+H$^+$)

To a solution of compound 8 (140 mg, 539.97 umol, 1 eq) in ACN (5 mL) was added $NaH_2PO_4$ (2 M, 404.98 uL, 1.5 eq) and TEMPO (169.82 mg, 1.08 mmol, 2 eq), the mixture was stirred at 20° C. for 1 h, then sodium; chlorite (146.51 mg, 1.62 mmol, 3 eq) and NaClO (1.21 g, 1.62 mmol, 996.60 uL, 10% purity, 3 eq) was added, the mixture was stirred at 20° C. for 12 h. After the reaction was completed, the mixture was poured into saturated $Na_2SO_3$ solution (100 mL), and extracted with EtOAc (50 mL×3), the combined organic phase was washed with brine (50 mL), dried over anhydrous $Na_2SO_4$, and concentrated to give a crude product. LCMS: m/z=274.0 (M+H$^+$)

To a solution of compound 1 (40 mg, 146.38 umol, 1 eq) and compound 2 (42.81 mg, 146.38 umol, 1 eq) in DCM (2 mL) was added EDCl (42.09 mg, 219.57 umol, 1.5 eq) and DMAP (1.79 mg, 14.64 umol, 0.1 eq), the mixture was stirred at 20° C. for 12 h. Evaporate the solution on a water bath under reduced pressure using a rotary evaporator. The crude product was purified by Prep-TLC (Ethyl acetate, desired product Rf=0.8). Compound 3 (10 mg, 17.36 umol, 11.86% yield, 95.1% purity) was obtained as a colorless oil. LCMS: m/z=548.2 (M+H$^+$)

To a solution of compound 3 (10 mg, 18.26 umol, 1 eq) in DCM (2 mL) was added TFA (1.54 g, 13.51 mmol, 1 mL, 739.72 eq), the mixture was stirred at 20° C. for 1 h. The mixture was concentrated to give a crude product. The crude product was purified by prep-HPLC (FA, column: Phenomenex luna C18 150*25 mm*10 um; mobile phase: [water (FA)-ACN]; B %: 14%-44%, 9 min), the purified solution was lyophilized. Compound 285 (2.2 mg, 4.83 umol, 26.44% yield, 91.6% purity) was obtained as yellow solid. LCMS: m/z=418.2 (M+H$^+$) $^1$H NMR: $^1$H NMR (400 MHz, CHLOROFORM-d) δ=12.47-11.95 (m, 1H), 9.40-8.87 (m, 1H), 8.20 (s, 2H), 7.67 (d, J=7.5 Hz, 1H), 7.52 (d, J=7.6 Hz, 1H), 7.39 (br s, 1H), 7.21 (s, 1H), 7.16 (br s, 1H), 7.05-6.95 (m, 1H), 5.16-4.77 (m, 2H), 4.43-3.95 (m, 1H), 3.23 (s, 3H), 0.81-0.59 (m, 4H).

Compound 127 was prepared in a similar manner to 285 and was obtained as a light yellow solid (10.08 mg, 21.44 umol, 29.19% yield, 93.90% purity). LCMS: m/z=440.6 (M−H$^+$) $^1$H NMR (400 MHz, CHLOROFORM-d) δ=12.30-11.88 (m, 1H), 8.22-8.13 (m, 1H), 7.84-7.76 (m, 1H), 7.72 (s, 2H), 7.69-7.64 (m, 1H), 7.63-7.57 (m, 1H), 7.57-7.51 (m, 1H), 7.24-7.13 (m, 1H), 6.83-6.69 (m, 1H), 5.05-4.83 (m, 2H), 4.40-4.26 (m, 1H), 3.33-3.16 (m, 3H), 0.87-0.64 (m, 4H).

Compound 128 was prepared in a similar manner to 285 and was obtained as an off white solid (3.5 mg, 8.02 umol, 11.32% yield, 99.5% purity). LCMS: m/z=435.1 (M−H$^+$) $^1$H NMR (400 MHz, CHLOROFORM-d) δ=12.47-11.38 (m, 1H), 8.31 (s, 1H), 8.09 (s, 1H), 7.75-7.68 (m, 1H), 7.66-7.60 (m, 1H), 7.59-7.52 (m, 1H), 7.35-7.24 (m, 1H), 7.17-7.10 (m, 1H), 7.05-6.96 (m, 1H), 6.72-6.61 (m, 1H), 4.85 (s, 2H), 3.74 (br s, 1H), 3.03-2.93 (m, 3H), 0.88-0.77 (m, 2H), 0.76-0.64 (m, 2H).

Compound 129 was prepared in a similar manner to 285 and was obtained as a white solid (4 mg, 8.52 umol, 19.33% yield, 97.9% purity). LCMS: m/z=460.2 (M−H$^+$) $^1$H NMR (400 MHz, CHLOROFORM-d) δ=12.12-11.94 (m, 1H), 8.44-8.40 (m, 1H), 8.21-8.15 (m, 2H), 8.04-7.99 (m, 1H), 7.86-7.82 (m, 1H), 7.41-7.36 (m, 1H), 7.26-7.20 (m, 1H), 6.83-6.74 (m, 1H), 4.99-4.91 (m, 2H), 3.91-3.85 (m, 1H), 3.11-3.03 (m, 3H), 0.99-0.89 (m, 2H), 0.88-0.80 (m, 2H).

Compound 130 was prepared in a similar manner to 285 and was obtained as a white solid (3.4 mg, 7.21 umol, 16.81% yield, 96% purity). LCMS: m/z=453.3 (M−H$^+$) $^1$H NMR (400 MHz, CHLOROFORM-d) δ=12.12-12.03 (m, 1H), 8.40 (d, J=1.8 Hz, 1H), 8.20 (s, 1H), 7.82 (d, J=1.8 Hz, 1H), 7.59-7.52 (m, 2H), 7.23 (dd, J=4.5, 7.6 Hz, 1H), 6.85 (tt, J=2.4, 8.7 Hz, 1H), 6.77 (dd, J=7.8, 9.6 Hz, 1H), 4.96 (s, 2H), 3.86 (tt, J=3.0, 5.9 Hz, 1H), 3.07 (s, 3H), 0.94-0.90 (m, 2H), 0.87-0.83 (m, 2H).

Compound 131 was prepared in a similar manner to 285 and was obtained as a white solid (13.1 mg, 29.68 umol, 24.20% yield, 99.8% purity). LCMS: m/z=441.2 (M−H$^+$) $^1$H NMR (400 MHz, CHLOROFORM-d) δ=12.48 (br s, 1H), 8.28 (s, 1H), 7.49-7.32 (m, 8H), 7.10 (br d, J=7.8 Hz, 1H), 5.11 (s, 2H), 3.76 (br s, 1H), 3.13 (s, 3H), 0.88-0.69 (m, 4H).

Compound 143 was prepared in a similar manner to 285 and was obtained as an off-white solid (2.9 mg, 6.69 umol, 11.34% yield, 100% purity). LCMS: m/z=434.2 (M+H$^+$) $^1$H NMR (400 MHz, CHLOROFORM-d) δ=12.11-11.61 (m, 1H), 7.90-7.80 (m, 1H), 7.40-7.33 (m, 2H), 7.30 (br d, J=7.6 Hz, 3H), 7.21-7.11 (m, 1H), 7.09-7.00 (m, 3H), 5.11 (br s, 2H), 5.02-4.91 (m, 2H), 4.11-4.00 (m, 2H), 3.08-2.93 (m, 3H), 1.45-1.28 (m, 3H).

Compound 144 was prepared in a similar manner to 285 and was obtained as an off-white solid (10 mg, 23.93 umol, 32.77% yield, 99.9% purity). LCMS: m/z=418.3 (M+H$^+$) $^1$H NMR (400 MHz, CHLOROFORM-d) δ=11.62-11.54 (m, 1H), 7.71 (d, J=8.1 Hz, 1H), 7.41-7.31 (m, 4H), 7.15-7.01 (m, 5H), 4.97 (s, 2H), 4.07 (q, J=7.0 Hz, 2H), 3.00 (s, 3H), 2.65 (s, 3H), 1.38 (t, J=6.9 Hz, 3H).

Compound 145 was prepared in a similar manner to 285 and was obtained as a white solid (7.6 mg, 17.48 umol, 16.42% yield, 99.7% purity). LCMS: m/z=434.2 (M+H$^+$) $^1$H NMR (400 MHz, CHLOROFORM-d) δ=12.15-11.72 (m, 1H), 8.17 (s, 1H), 7.39-7.28 (m, 4H), 7.17 (d, J=7.6 Hz, 1H), 7.07-6.99 (m, 3H), 6.41 (d, J=7.6 Hz, 1H), 4.88 (s, 2H), 4.05 (q, J=7.0 Hz, 2H), 3.99 (s, 3H), 2.99-2.97 (m, 3H), 1.35 (t, J=6.9 Hz, 3H).

Compound 146 was prepared in a similar manner to 285 and was obtained as a white solid (11.4 mg, 26.24 umol, 37.04% yield, 100% purity). LCMS: m/z=435.1 (M+H$^+$) $^1$H NMR (400 MHz, CHLOROFORM-d) δ=1.38 (t, J=7.00 Hz, 3H) 3.14 (s, 3H) 3.99 (s, 3H) 4.39-4.45 (m, 2H) 4.90 (s, 2H) 6.42 (d, J=7.63 Hz, 1H) 7.04-7.10 (m, 1H) 7.18 (d, J=7.63 Hz, 1H) 7.35 (br d, J=7.38 Hz, 2H) 7.38-7.43 (m, 1H) 7.45 (d, J=7.63 Hz, 1H) 7.72 (d, J=7.50 Hz, 1H) 8.17 (s, 1H) 11.76-12.08 (m, 1H).

Compound 156 was prepared in a similar manner to 285 and was obtained as a white solid (4.79 mg, 10.30 umol, 24.35% yield, 99.048% purity). LCMS: m/z=613.3

(M+Na$^+$) $^1$H NMR (400 MHz, CHLOROFORM-d) δ=8.23 (br d, J=7.5 Hz, 1H), 7.54-7.21 (m, 6H), 7.18-6.83 (m, 3H), 5.21-4.95 (m, 2H), 4.67-4.47 (m, 1H), 4.23-3.49 (m, 2H), 3.27-2.90 (m, 6H), 1.46-1.22 (m, 3H), 1.09 (br s, 1H).

Compound 157 was prepared in a similar manner to 285 and was obtained as a white solid (15.6 mg, 32.87 umol, 50.98% yield, 100% purity). LCMS: m/z=475.2 (M+H$^+$) $^1$H NMR (400 MHz, CHLOROFORM-d) δ=12.25-12.07 (m, 1H), 8.11 (d, J=8.1 Hz, 1H), 7.39-7.20 (m, 5H), 7.17-7.10 (m, 2H), 7.05-6.77 (m, 3H), 5.05-4.75 (m, 2H), 4.13-3.73 (m, 2H), 3.51-3.32 (m, 3H), 3.21-3.10 (m, 3H), 2.93 (s, 3H), 1.29 (s, 3H).

Compound 164 was prepared in a similar manner to 285 and was obtained as a white solid (7.67 mg, 18.10 umol, 19.90% yield, 99% purity). LCMS: m/z=420.1 (M+H+) $^1$H NMR (400 MHz, CHLOROFORM-d) δ=7.98 (s, 1H), 7.40-7.33 (m, 2H), 7.33-7.28 (m, 2H), 7.12-7.01 (m, 4H), 6.97 (s, 1H), 4.92 (s, 2H), 4.05 (q, J=6.8 Hz, 2H), 3.02 (s, 3H), 1.36 (t, J=6.9 Hz, 3H).

Compound 168 was prepared in a similar manner to 285 and was obtained as a white solid (44.42 mg, 96.68 umol, 50.21% yield, 100% purity). LCMS: m/z=460.1 (M+H+) $^1$H NMR (400 MHz, CHLOROFORM-d) δ=12.28-11.94 (m, 1H), 8.29-8.06 (m, 1H), 7.74 (d, J=7.6 Hz, 1H), 7.66-7.56 (m, 2H), 7.52-7.47 (m, 1H), 7.40-7.34 (m, 1H), 7.17 (br d, J=2.3 Hz, 1H), 6.76 (dd, J=7.8, 9.6 Hz, 1H), 4.85 (s, 2H), 4.44-4.05 (m, 1H), 3.24 (s, 3H), 0.92-0.45 (m, 4H).

Compound 169 was prepared in a similar manner to 285 and was obtained as a white solid (2.54 mg, 4.59 umol, 32.63% yield, 90% purity). LCMS: m/z=453.0 (M+H+) $^1$H NMR (400 MHz, CHLOROFORM-d) δ=12.31-11.74 (m, 1H), 8.09 (s, 1H), 7.65 (d, J=7.6 Hz, 1H), 7.51 (d, J=7.6 Hz, 1H), 7.44-7.24 (m, 1H), 7.14 (dd, J=4.5, 7.6 Hz, 1H), 7.16-7.11 (m, 1H), 7.01-6.93 (m, 1H), 7.04-6.90 (m, 1H), 6.81-6.61 (m, 2H), 4.89-4.77 (m, 1H), 4.95-4.68 (m, 1H), 4.29-4.07 (m, 1H), 3.16 (s, 3H), 0.68 (br d, J=12.4 Hz, 4H).

Compound 190 was prepared in a similar manner to 285 and was obtained as a white solid (5.16 mg, 11.63 umol, 10.74% yield, 99.7% purity). LCMS: m/z=443.1 (M+H+) $^1$H NMR (400 MHz, CHLOROFORM-d) δ=8.49-8.45 (m, 1H), 8.44-8.42 (m, 1H), 7.81-7.76 (m, 1H), 7.66-7.61 (m, 1H), 7.45-7.37 (m, 1H), 7.31-7.29 (m, 1H), 7.27-7.24 (m, 1H), 7.13-7.07 (m, 1H), 5.08-5.05 (m, 2H), 4.38-4.30 (m, 1H), 3.38-3.35 (m, 3H), 0.81-0.75 (m, 4H).

Compound 195 was prepared in a similar manner to 285 and was obtained as a white solid (12 mg, 27.26 umol, 43.13% yield, 96.2% purity). LCMS: m/z=424.3 (M−H+) $^1$H NMR (400 MHz, CHLOROFORM-d) δ=12.62-12.52 (m, 1H), 8.44 (d, J=4.6 Hz, 2H), 7.47-7.42 (m, 3H), 7.42-7.37 (m, 2H), 7.36-7.33 (m, 2H), 7.13-7.08 (m, 1H), 5.01 (s, 2H), 3.78-3.74 (m, 1H), 3.10 (s, 3H), 0.79 (br t, J=5.3 Hz, 2H), 0.81-0.74 (m, 1H), 0.75 (dd, J=3.5, 4.3 Hz, 1H).

Compound 200 was prepared in a similar manner to 285 and was obtained as a white solid (12.9 mg, 26.25 umol, 36.26% yield, 100% purity). LCMS: m/z=492.1 (M−H+) $^1$H NMR (400 MHz, CHLOROFORM-d) δ=1.36 (t, J=6.94 Hz, 3H) 3.02 (s, 3H) 3.06 (d, J=4.25 Hz, 3H) 4.07 (q, J=7.00 Hz, 2H) 4.13 (s, 3H) 4.84 (s, 2H) 6.77 (dt, J=7.63, 4.57 Hz, 1H) 7.04-7.10 (m, 2H) 7.15 (dd, J=11.76, 8.63 Hz, 1H) 7.36 (d, J=7.50 Hz, 1H) 7.65-7.70 (m, 1H) 7.81-7.84 (m, 1H) 8.18 (s, 1H) 8.27 (dd, J=7.69, 2.44 Hz, 1H) 11.91-12.31 (m, 1H).

Compound 213 was prepared in a similar manner to 285 and was obtained as a white solid (2.34 mg, 5.24 umol, 5.70% yield, 95% purity). LCMS: m/z=425.0 (M−H+) $^1$H NMR (400 MHz, CHLOROFORM-d) δ=12.31-11.74 (m, 1H), 8.09 (s, 1H), 7.65 (d, J=7.6 Hz, 1H), 7.51 (d, J=7.6 Hz, 1H), 7.44-7.24 (m, 1H), 7.14 (dd, J=4.5, 7.6 Hz, 1H), 7.16-7.11 (m, 1H), 7.01-6.93 (m, 1H), 7.04-6.90 (m, 1H), 6.81-6.61 (m, 2H), 4.89-4.77 (m, 1H), 4.95-4.68 (m, 1H), 4.29-4.07 (m, 1H), 4.29-4.01 (m, 1H), 3.16 (s, 3H), 0.68 (br d, J=12.4 Hz, 4H).

Compound 232 was prepared in a similar manner to 285 and was obtained as a white solid (6 mg, 14.37 umol, 19.68% yield, 100% purity). LCMS: m/z=418.1 (M−H+) $^1$H NMR (400 MHz, CHLOROFORM-d) δ=12.54-12.40 (m, 1H), 9.20 (br s, 1H), 8.44 (br s, 1H), 8.39 (s, 1H), 7.99 (d, J=1.4 Hz, 1H), 7.91 (d, J=1.4 Hz, 1H), 7.49 (d, J=8.3 Hz, 1H), 7.11-7.08 (m, 2H), 4.99 (s, 2H), 4.15 (q, J=6.9 Hz, 2H), 3.06 (s, 3H), 1.48 (t, J=6.9 Hz, 3H)

Compound 233 was prepared in a similar manner to 285 and was obtained as a white solid (7 mg, 17.70 umol, 15.42% yield, 99% purity). LCMS: m/z=393.1 (M−H+) $^1$H NMR (400 MHz, CHLOROFORM-d) δ=12.26 (br s, 1H), 9.15 (br s, 1H), 8.46-8.17 (m, 2H), 7.74 (dd, J=1.3, 3.0 Hz, 1H), 7.55 (d, J=8.4 Hz, 1H), 7.48 (dd, J=1.3, 5.0 Hz, 1H), 7.36 (dd, J=3.0, 5.0 Hz, 1H), 7.10-7.02 (m, 2H), 4.95 (s, 2H), 4.13 (q, J=7.0 Hz, 2H), 3.05 (s, 3H), 1.48 (t, J=6.9 Hz, 3H)

Compound 234 was prepared in a similar manner to 285 and was obtained as a yellow solid (34 mg, 86.41 umol, 43.10% yield, 100% purity). LCMS: m/z=394.1 (M−H+) $^1$H NMR (400 MHz, CHLOROFORM-d) δ=13.40-12.56 (m, 1H), 9.66-9.07 (m, 1H), 8.61-8.39 (m, 2H), 8.06-7.77 (m, 2H), 7.57-7.46 (m, 2H), 7.40 (dd, J=3.1, 5.1 Hz, 1H), 5.23-4.85 (m, 2H), 4.47 (q, J=6.4 Hz, 2H), 3.39-3.18 (m, 3H), 1.67-1.36 (m, 3H)

Compound 235 was prepared in a similar manner to 285 and was obtained as a white solid (8 mg, 19.12 umol, 29.97% yield, 100% purity). LCMS: m/z=419.0 (M−H+) $^1$H NMR (400 MHz, CHLOROFORM-d) b=12.63-12.25 (m, 1H), 9.21 (br s, 1H), 8.45 (br s, 1H), 8.38 (s, 1H), 8.03 (d, J=0.9 Hz, 2H), 7.89 (d, J=7.6 Hz, 1H), 7.52 (d, J=7.8 Hz, 1H), 5.00 (s, 2H), 4.48 (q, J=7.1 Hz, 2H), 3.24 (s, 3H), 1.46 (t, J=7.1 Hz, 3H)

Scheme 37.

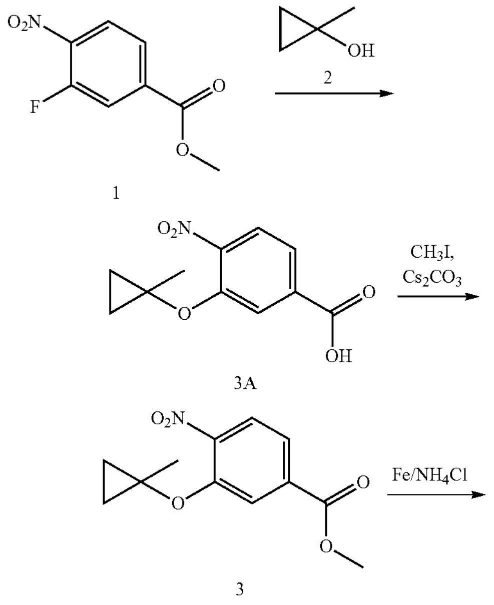

1

3A

3

-continued

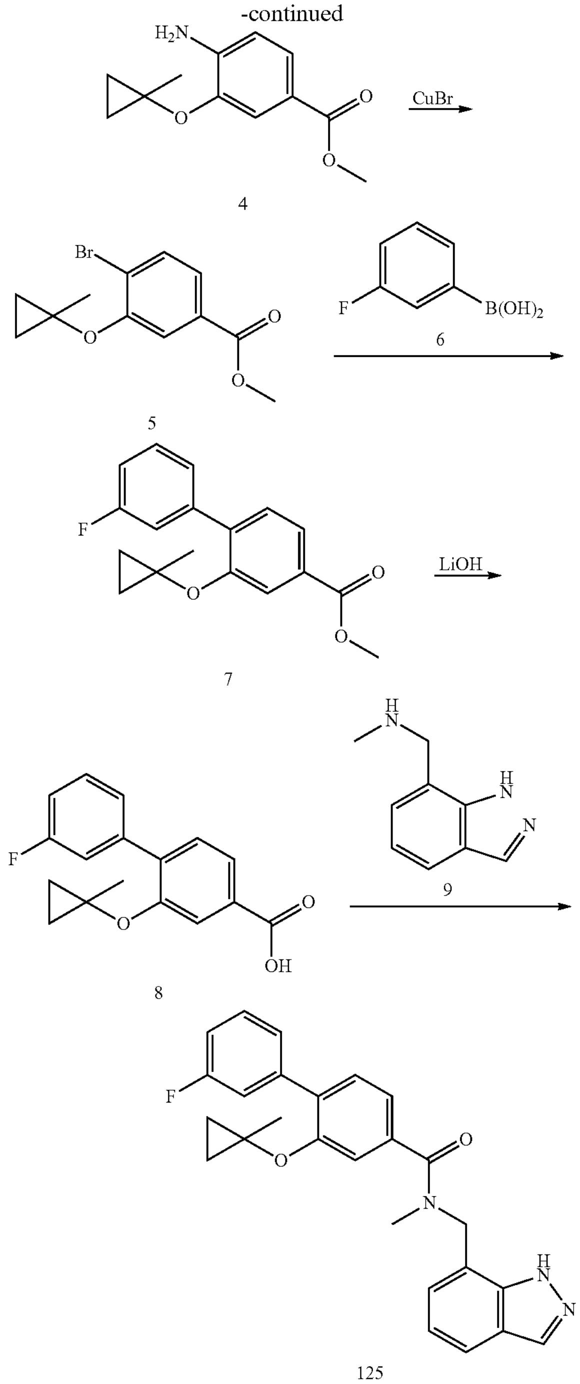

To a solution of compound 1 (800 mg, 4.02 mmol, 1 eq) and compound 2 (579.35 mg, 8.03 mmol, 2 eq) in DMF (10 mL) was added NaH (482.04 mg, 12.05 mmol, 60% purity, 3 eq) at 0° C., the mixture was stirred at 20° C. for 12 h. The mixture was poured into saturated $NH_4Cl$ (50 mL) solution, and extracted with EtOAc (50 mL×3), the combined organic phase was washed with brine (50 mL), dried over anhydrous $Na_2SO_4$, and concentrated to give a crude product. The crude product used for next step without further purification. Compound 3A (2 g, crude) was obtained as red oil. LCMS: m/z=236.1 (M+H+)

To a solution of compound 3A (2 g, 8.43 mmol, 1 eq) in DMF (20 mL) was added $Cs_2CO_3$ (5.49 g, 16.86 mmol, 2 eq) and $CH_3I$ (3.59 g, 25.29 mmol, 1.57 mL, 3 eq), the reaction mixture was stirred at 70° C. for 2 hours under $N_2$. TLC (petroleum:ethyl acetate=10:1, desired product Rf=0.4) showed the starting material was consumed completely. The reaction mixture was partitioned between EtOAc (150 ml) and water (150 ml). The separated organic layer was washed with saturated NaCl solution, dried over $Na_2SO_4$ and evaporated to give a crude product. The crude product was purified by column chromatography on silica gel eluted by petroleum:ethyl acetate=100:0 to 100/10 (desired product Rf=0.4). Compound 3 (362 mg, crude) was obtained as yellow solid. $^1H$ NMR (400 MHz, CHLOROFORM-d) b=8.00-7.95 (m, 1H), 7.73-7.67 (m, 1H), 7.62-7.57 (m, 1H), 3.92-3.89 (m, 3H), 1.58-1.54 (m, 3H), 1.25-1.14 (m, 1H), 1.05-0.99 (m, 2H), 0.79-0.74 (m, 2H).

To a solution of compound 3 (420 mg, 1.67 mmol, 1 eq) in $H_2O$ (10 mL) and MeOH (10 mL) was added Fe (933.58 mg, 16.72 mmol, 10 eq) and $NH_4Cl$ (894.24 mg, 16.72 mmol, 10 eq), the reaction mixture was stirred at 70° C. for 2 hours under $N_2$. The reaction mixture was filtered, the filtrate was concentrated to give a crude product. The product was purified by column chromatography on silica gel eluted by petroleum ether:ethyl acetate=100/0 to 100/10 (desired product Rf=0.4). Compound 4 (256 mg, 1.12 mmol, 66.84% yield, 96.57% purity) was obtained as white solid. LCMS: m/z=222.0 (M+H+)

To a solution of compound 4 (120 mg, 542.37 umol, 1 eq) in MeCN (5 mL) and CuBr (155.61 mg, 1.08 mmol, 33.04 uL, 2 eq) was added isopentyl nitrite (127.07 mg, 1.08 mmol, 146.06 uL, 2 eq) under $N_2$, the reaction mixture was stirred at 70° C. for 12 hours under $N_2$. The reaction mixture was filtered, the filtrate was concentrated to give a crude product. The crude product was purified by prep-TLC (petroleum ether:ethyl acetate=10:1, desired mass Rf=0.8) .Compound 5 (85 mg, 288.39 umol, 53.17% yield, 96.74% purity) was obtained as white solid. LCMS: m/z=284.9 (M+H+)

To a solution of compound 5 (85 mg, 298.11 umol, 1 eq) in dioxane (1 mL) was added compound 6 (50.05 mg, 357.73 umol, 1.2 eq), $K_2CO_3$ (82.40 mg, 596.21 umol, 2 eq) and Pd (dppf) $Cl_2$. $CH_2Cl_2$ (24.34 mg, 29.81 umol, 0.1 eq), the reaction mixture was stirred at 100° C. for 12 hours under $N_2$. The reaction mixture was filtered, the filtrate was concentrated to give a crude product. The crude product was purified by prep-TLC (petroleum ether:ethyl acetate=10:1, desired mass Rf=0.7) Compound 7 (85 mg, 279.07 umol, 93.61% yield, 98.60% purity) was obtained as colorless oil. LCMS: m/z=301.1 (M+H+)

To a solution of compound 7 (85 mg, 283.03 umol, 1 eq) in $H_2O$ (1 mL), THF (1 mL) and MeOH (1 mL) was added $LiOH{\cdot}H_2O$ (59.38 mg, 1.42 mmol, 5 eq), the reaction mixture was stirred at 30° C. for 2 hours under $N_2$. Acidify the reaction mixture by adding 1 mol/L HCl to pH=5, the precipitated brown solid was collected and dried. The crude product was used directly to the next step without purification. Compound 8 (54 mg, 185.26 umol, 65.46% yield, 98.22% purity) was obtained as white solid. LCMS: m/z=287.0 (M+H+)

To a solution of compound 8 (20 mg, 69.86 umol, 1 eq) in DCM (2 mL) was added compound 9 (13.51 mg, 83.83 umol, 1.2 eq), EDCl (20.09 mg, 104.79 umol, 1.5 eq) and DMAP (853.44 ug, 6.99 umol, 0.1 eq), the reaction mixture was stirred at 25° C. for 12 hours under $N_2$. The reaction mixture was filtered, the filtrate was concentrated to give a crude product. The crude product was purified by prep-HPLC (column: Phenomenex luna C18 150*25 mm*10 um; mobile phase: [water (FA)-ACN]; B %: 51%-81%, 9 min).

After prep-HPLC purification, the eluent was concentrated to remove organic solvents. The residual aqueous solution was lyophilized to give white solid. 125 (22.58 mg, 52.57 umol, 75.26% yield, 100% purity) was obtained as white solid. LCMS: m/z=430.1 (M+H+) $^{1}$H NMR (400 MHz, CHLOROFORM-d) δ=12.07-11.90 (m, 1H), 8.15 (s, 1H), 7.83-7.78 (m, 1H), 7.41-7.39 (m, 1H), 7.38-7.35 (m, 1H), 7.35-7.33 (m, 1H), 7.26-7.13 (m, 4H), 7.10-7.03 (m, 2H), 5.01 (s, 2H), 3.06-3.04 (m, 3H), 1.59-1.58 (m, 3H), 1.03-0.96 (m, 2H), 0.78-0.72 (m, 2H).

Compound 138 was prepared in a similar manner to 125 and was obtained as a white solid (6.51 mg, 14.58 umol, 15.57% yield, 100% purity). LCMS: m/z=447.3 (M−H+) $^{1}$H NMR (400 MHz, CHLOROFORM-d) δ=12.36 (m, 1H), 8.36-8.32 (m, 1H), 7.56 (d, J=7.1 Hz, 1H), 7.37-7.33 (m, 2H), 7.13-7.06 (m, 4H), 6.84-6.76 (m, 1H), 5.03 (s, 2H), 4.10 (q, J=6.9 Hz, 2H), 1.43-1.38 (m, 3H), 1.28 (s, 1H).

Compound 139 was prepared in a similar manner to 125 and was obtained as a white solid (4.7 mg, 10.50 umol, 18.39% yield, 100% purity). LCMS: m/z=448.2 (M−H+) $^{1}$H NMR (400 MHz, CHLOROFORM-d) δ=8.31 (s, 1H), 7.74 (d, J=7.6 Hz, 1H), 7.55 (d, J=7.1 Hz, 1H), 7.50 (d, J=7.5 Hz, 1H), 7.36 (d, J=7.1 Hz, 1H), 7.14 (br d, J=6.5 Hz, 2H), 6.84 (s, 1H), 5.03 (s, 2H), 4.43 (d, J=7.0 Hz, 2H), 3.20 (s, 3H), 1.55 (br s, 1H), 1.39 (t, J=7.1 Hz, 3H).

Compound 140 was prepared in a similar manner to 125 and was obtained as a white solid (12.21 mg, 30.11 umol, 26.22% yield, 99% purity). LCMS: 0.552 min, m/z=405.1 (M−H+).

Compound 141 was prepared in a similar manner to 125 and was obtained as a white solid (13 mg, 30.77 umol, 41.28% yield, 97.4% purity). LCMS: m/z=412.2 (M−H+) $^{1}$H NMR (400 MHz, CHLOROFORM-d) δ=11.92 (br s, 1H), 8.98 (d, J=2.1 Hz, 1H), 8.85 (d, J=1.9 Hz, 1H), 8.18 (t, J=2.0 Hz, 1H), 8.15 (s, 1H), 7.81 (d, J=7.9 Hz, 1H), 7.36 (d, J=7.6 Hz, 1H), 7.31 (d, J=6.9 Hz, 1H), 7.18-7.11 (m, 3H), 5.00 (s, 2H), 4.16-4.08 (m, 2H), 3.02 (s, 3H), 1.39 (t, J=7.0 Hz, 3H).

Compound 142 was prepared in a similar manner to 125 and was obtained as a white solid (9 mg, 20.62 umol, 22.47% yield, 100% purity). LCMS: m/z=437.2 (M−H+) $^{1}$H NMR (400 MHz, CHLOROFORM-d) δ=12.25 (br d, J=1.0 Hz, 1H), 8.89-8.88 (m, 1H), 8.77 (d, J=1.9 Hz, 1H), 8.26-8.24 (m, 1H), 8.09 (t, J=2.1 Hz, 1H), 7.50-7.45 (m, 1H), 7.29 (dd, J=2.6, 7.4 Hz, 2H), 7.07-7.01 (m, 2H), 4.95 (s, 2H), 4.03 (q, J=7.0 Hz, 2H), 2.95 (s, 3H), 1.34-1.27 (m, 4H).

Compound 154 was prepared in a similar manner to 125 and was obtained as a white solid (2.7 mg, 5.17 umol, 4.34% yield, 96.5% purity).

Compound 183 was prepared in a similar manner to 125 and was obtained as a white solid (12.9 mg, 32.41 umol, 19.70% yield, 98.6% purity). LCMS: m/z=393.1 (M−H+) $^{1}$H NMR (400 MHz, CHLOROFORM-d) δ=8.47 (d, J=1.6 Hz, 1H), 8.13 (s, 1H), 7.80 (t, J=8.8 Hz, 2H), 7.65 (d, J=1.5 Hz, 1H), 7.29 (s, 1H), 7.18-7.08 (m, 3H), 4.97 (s, 2H), 4.28 (q, J=7.0 Hz, 2H), 2.98 (s, 3H), 1.62 (t, J=6.9 Hz, 3H).

Compound 184 was prepared in a similar manner to 125 and was obtained as a white solid (23.9 mg, 60.46 umol, 50.24% yield, 99.28% purity). LCMS: m/z=393.0 (M−H+) $^{1}$H NMR (400 MHz, CHLOROFORM-d) δ=8.76 (br d, J=1.0 Hz, 1H), 8.47-8.27 (m, 1H), 8.20-8.07 (m, 1H), 7.79 (d, J=8.0 Hz, 1H), 7.72-7.63 (m, 1H), 7.30 (s, 1H), 7.20-7.04 (m, 3H), 5.16-4.80 (m, 2H), 4.37-4.01 (m, 2H), 3.08-2.90 (m, 3H), 1.69-1.39 (m, 3H)

Compound 185 was prepared in a similar manner to 125 and was obtained as a white solid (35 mg, 104.98 umol, 28.52% yield, 100% purity). LCMS: m/z=344.1 (M−H+) $^{1}$H NMR (400 MHz, CHLOROFORM-d) δ=8.14 (s, 1H), 7.81-7.76 (m, 1H), 7.47 (d, J=7.8 Hz, 1H), 7.31-7.28 (m, 1H), 7.17-7.11 (m, 1H), 6.98-6.93 (m, 2H), 4.95 (s, 2H), 4.13 (q, J=7.0 Hz, 2H), 3.34 (s, 1H), 2.94 (s, 3H), 1.47 (t, J=7.0 Hz, 3H).

Compound 196 was prepared in a similar manner to 125 and was obtained as a white solid (2.6 mg, 5.77 umol, 33.00% yield, 98% purity). LCMS: m/z=442.2 (M−H+) $^{1}$H NMR (400 MHz, CHLOROFORM-d) δ=12.66-12.50 (m, 1H) 8.53-8.40 (m, 2H) 7.48 (d, J=1.38 Hz, 1H) 7.43-7.35 (m, 2H) 7.28-7.20 (m, 1H) 7.28-7.19 (m, 1H) 7.14 (dd, J=7.75, 1.50 Hz, 1H) 7.07 (td, J=8.47, 1.81 Hz, 1H) 5.10-5.00 (m, 2H) 3.83-3.74 (m, 1H) 3.13 (s, 3H) 0.87-0.78 (m, 4H).

Compound 197 was prepared in a similar manner to 125 and was obtained as a white solid (2.4 mg, 4.93 umol, 19.01% yield, 92% purity). LCMS: m/z=448.2 (M−H+) $^{1}$H NMR (400 MHz, CHLOROFORM-d) δ=8.44 (d, 2H, J=2.0 Hz), 7.35 (d, 1H, J=7.8 Hz), 7.1-7.1 (m, 4H), 6.80 (tt, 1H, J=2.3, 8.9 Hz), 5.01 (s, 2H), 4.08 (q, 2H, J=6.9 Hz), 3.07 (s, 3H), 1.39 (t, 3H, J=6.9 Hz).

Compound 198 was prepared in a similar manner to 125 and was obtained as a white solid (15.3 mg, 36.84 umol, 66.64% yield, 99.30% purity). LCMS: m/z=413.2 (M−H+) $^{1}$H NMR (400 MHz, CHLOROFORM-d) δ=12.10 (br s, 1H), 9.21-9.14 (m, 1H), 8.98 (d, J=2.1 Hz, 1H), 8.88-8.84 (m, 1H), 8.36 (s, 1H), 8.29 (s, 1H), 8.18 (t, J=2.1 Hz, 1H), 7.37 (d, J=7.8 Hz, 1H), 7.18-7.10 (m, 2H), 5.02-4.92 (m, 2H), 4.19-4.08 (m, 2H), 3.06 (s, 4H), 1.40 (t, J=7.0 Hz, 4H).

Compounds 163 and 259 were prepared in a similar manner to 125 and were separated using an SFC column. Both compounds were obtained as a white solid (9 mg, 20.62 umol, 22.47% yield, 100% purity). $^{1}$H NMR (400 MHz, CHLOROFORM-d) δ=13.19-11.87 (m, 1H), 8.33-8.23 (m, 1H), 7.92-7.85 (m, 1H), 7.81-7.77 (m, 1H), 7.77-7.69 (m, 1H), 7.69-7.63 (m, 1H), 7.60-7.52 (m, 2H), 7.51-7.34 (m, 2H), 6.59-5.53 (m, 1H), 4.69-4.22 (m, 2H), 3.00-2.57 (m, 3H), 1.95-1.70 (m, 3H), 1.40-1.28 (m, 3H).

Scheme 38.

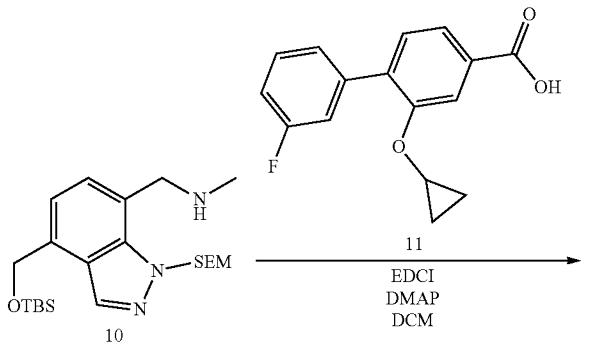

-continued

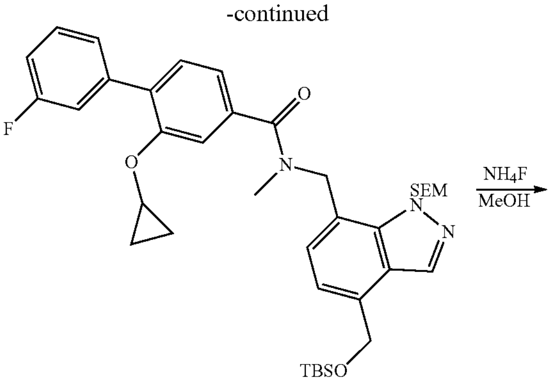

12

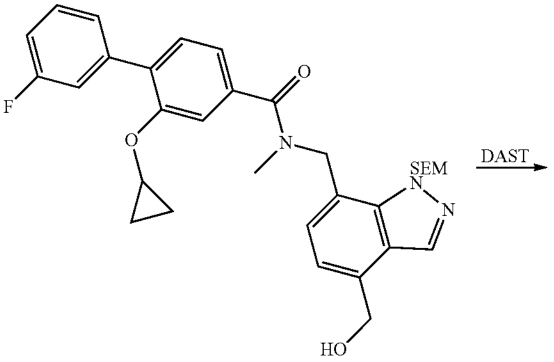

13

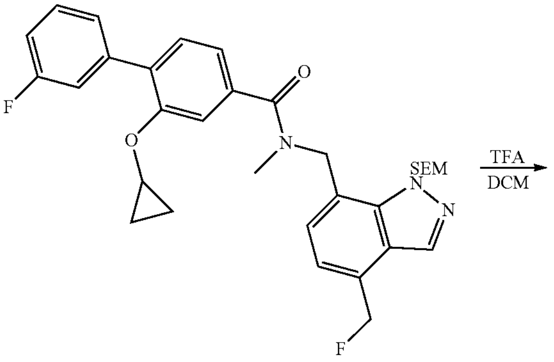

14

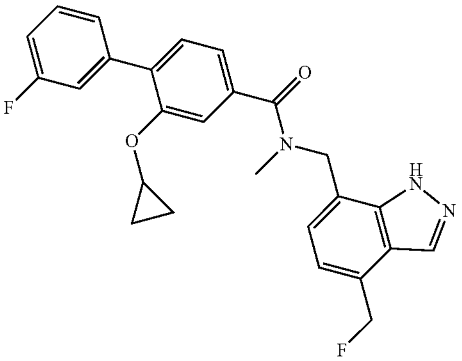

132

The solution of compound 10 (160.04 mg, 367.28 umol, 2 eq) and compound 11 (50 mg, 183.64 umol, 1 eq) in DCM (1 mL) was added in EDCl (52.81 mg, 275.46 umol, 1.5 eq) and DMAP (2.24 mg, 18.36 umol, 0.1 eq). Then stirred at 20° C. for 2 hrs. Evaporate the solution on a water bath under reduced pressure using a rotary evaporator. The residue was purified by prep-TLC ($SiO_2$, PE:EtOAc=10:1, Rf=0.1), filtered and filtrate was concentrated in vacuo to give colourless oil. The compound of 12 (53 mg, 76.81 umol, 41.83% yield) was obtained as yellow oil. LCMS: m/z=572.2 (M+H)+

The solution of compound 12 (53 mg, 76.81 umol, 1 eq) in MeOH (4 mL) was added in $NH_4F$ (28.45 mg, 768.11 umol, 10 eq). Then the mixture was stirred at 60° C. for 2.5 hrs. The mixture was concentrated under reduced pressure to give a residue. The crude product was purified by prep-TLC (PE:EtOAc=2:1, desired product Rf=0.3), the purified solution was concentrated. 3-(cyclopropoxy)-4-(3-fluorophenyl)-N-[[4-(hydroxymethyl)-1-(2-trimethylsilylethoxymethyl) indazol-7-yl]methyl]-N-methyl-benzamide (30 mg, 52.11 umol, 67.84% yield) was obtained as white solid. LCMS: m/z=458.1 (M+H)+

The mixture of compound 13 (30 mg, 52.11 umol, 1 eq) in DCM (1 mL) was added in DAST (12.60 mg, 78.16 umol, 10.33 uL, 1.5 eq). The mixture was stirred at 0° C. for 0.5 hrs under $N_2$. The reaction mixture was cooled in an ice water bath and quenched by addition of saturated $NaHCO_3$. The organic layer was separated, and the aqueous phase was extracted with dichloromethane (20 mL×2). The combined organic solutions were dried over $Na_2SO_4$ and evaporated to give the residue. The crude product was purified by prep-TLC (SiO2, Petroleum ether:EtOAc=1:1). The compound of 14 (20 mg, 34.62 umol, 66.44% yield, N/A purity) was obtained as colourless solid. LCMS: m/z=460.1 (M+H)+1H NMR (400 MHz, CHLOROFORM-d) δ=9.62-9.56 (m, 1H), 8.75-8.51 (m, 3H), 7.27 (s, 2H), 7.21 (d, J=6.0 Hz, 1H), 7.09 (d, J=6.1 Hz, 1H), 6.62 (br d, J=14.4 Hz, 2H), 5.58 (q, J=7.1 Hz, 4H), 5.46-5.30 (m, 2H), 5.22-5.10 (m, 2H), 5.02-4.91 (m, 3H), 4.56-4.42 (m, 4H), 4.30 (s, 1H), 3.71 (s, 2H), 3.59-3.54 (m, 2H), 2.87 (qd, J=8.1, 11.8 Hz, 2H), 2.40-2.23 (m, 3H), 1.56-1.44 (m, 2H)

The mixture of compound 14 (20 mg, 34.62 umol, 1 eq) in DCM (1 mL) was added in TFA (770.00 mg, 6.75 mmol, 0.5 mL, 195.07 eq). The mixture was stirred at 20° C. for 2 hrs. Evaporate the solution on a water bath under reduced pressure using a rotary evaporator.

The residue product was purified by prep HPLC. Column: Welch Xtimate C18 150*25 mm*5 um; mobile phase: [water ($NH_3H_2O$)-ACN]; B %: 55%-85%, 8 min. lyophilized.

The compound 132 (4.29 mg, 9.59 umol, 27.69% yield, 100% purity) was obtained as white solid LCMS: m/z=448.3 (M+H)+1H NMR (400 MHz, CHLOROFORM-d) δ=8.26-8.21 (m, 1H), 7.47-7.32 (m, 4H), 7.25-7.16 (m, 3H), 7.15-7.08 (m, 2H), 7.06-7.00 (m, 1H), 5.83-5.66 (m, 2H), 5.00 (s, 2H), 3.81-3.72 (m, 1H), 3.03 (s, 3H), 0.75 (br s, 4H).

Compound 155 was prepared in a similar manner to 132. LCMS: m/z=493.4 (M−H+) $^1$H NMR (400 MHz, CHLOROFORM-d) δ=8.30-8.19 (m, 2H), 7.71-7.64 (m, 1H), 7.37-7.33 (m, 1H), 7.30-7.27 (m, 1H), 7.19-7.00 (m, 4H), 5.82-5.79 (m, 1H), 5.69 (s, 1H), 5.00-4.97 (m, 2H), 4.11-4.01 (m, 2H), 3.01 (s, 6H), 1.40-1.32 (m, 4H).

Compound 162 was prepared in a similar manner to 132 and isolated as a yellow solid. LCMS: m/z=436.2 (M−H+) $^1$H NMR (400 MHz, CHLOROFORM-d) δ=12.26-11.95 (m, 1H), 8.17-7.47 (m, 1H), 7.38-7.30 (m, 4H), 7.23-7.17 (m, 2H), 7.11-7.01 (m, 3H), 5.94-5.70 (m, 2H), 4.97 (s, 2H), 4.21-3.95 (m, 2H), 3.01 (s, 3H), 1.40-1.34 (m, 3H).

Compound 166 was prepared in a similar manner to 132 and isolated as a white solid (4.82 mg, 10.75 umol, 44.27% yield, 97.160% purity). LCMS: m/z=436.4 (M−H+) $^1$H NMR (400 MHz, CHLOROFORM-d) δ=8.17 (s, 1H), 7.80

(d, J=2.3 Hz, 1H), 7.42-7.28 (m, 5H), 7.17-6.97 (m, 3H), 5.63-5.36 (m, 2H), 4.99 (s, 2H), 4.07 (q, J=7.1 Hz, 2H), 3.29-2.92 (m, 3H), 1.42-1.32 (m, 3H).

Compound 175 was prepared in a similar manner to 132 and isolated as a white solid (4.8 mg, 9.73 umol, 12.75% yield, 96% purity). LCMS: m/z=474.2 (M+H+) $^{1}$H NMR (400 MHz, CHLOROFORM-d) δ=8.26-8.18 (m, 1H), 7.74 (d, J=7.6 Hz, 1H), 7.65-7.59 (m, 2H), 7.54-7.48 (m, 1H), 7.41-7.35 (m, 1H), 7.31 (br d, J=6.9 Hz, 1H), 7.13 (dd, J=2.5, 7.0 Hz, 1H), 5.91-5.58 (m, 2H), 5.01 (s, 2H), 4.48-4.27 (m, 1H), 3.37-3.16 (m, 3H), 0.81-0.70 (m, 4H).

Compound 176 was prepared in a similar manner to 132 and isolated as a gray solid (4.8 mg, 10.14 umol, 23.90% yield, 100% purity). LCMS: m/z=474.2 (M+H+) $^{1}$H NMR (400 MHz, CHLOROFORM-d) δ=8.43-8.38 (m, 1H), 8.25-8.22 (m, 1H), 8.17-8.13 (m, 1H), 8.03-7.97 (m, 1H), 7.84-7.81 (m, 1H), 7.40-7.34 (m, 1H), 7.32-7.28 (m, 1H), 7.13 (dd, J=2.4, 6.9 Hz, 1H), 5.81-5.67 (m, 2H), 5.02-4.98 (m, 2H), 3.90-3.84 (m, 1H), 3.06 (s, 3H), 0.95-0.82 (m, 4H).

Compound 177 was prepared in a similar manner to 132 and isolated as a white solid (10 mg, 22.39 umol, 41.77% yield, 96.144% purity). LCMS: m/z=430.1 (M+H+) $^{1}$H NMR (400 MHz, CHLOROFORM-d) δ=12.51-12.20 (m, 1H), 9.25-9.17 (m, 1H), 8.42 (br s, 1H), 8.36 (s, 1H), 7.93 (s, 1H), 7.66-7.63 (m, 2H), 7.49 (s, 1H), 7.13 (d, J=8.0 Hz, 1H), 4.99 (s, 2H), 3.96-3.88 (m, 1H), 3.07 (s, 3H), 0.93-0.89 (m, 4H).

Compound 206 was prepared in a similar manner to 132 and isolated as a yellow solid (4.14 mg, 9.21 umol, 3.56% yield, 100% purity). $^{1}$H NMR (400 MHz, CHLOROFORM-d) δ=12.38-12.09 (m, 1H), 8.41 (br s, 1H), 8.33-8.20 (m, 1H), 7.75 (br d, J=7.4 Hz, 1H), 7.79-7.71 (m, 1H), 7.60 (br d, J=7.6 Hz, 1H), 7.42-7.36 (m, 1H), 7.31-7.29 (m, 1H), 7.25-7.22 (m, 1H), 7.26-7.22 (m, 1H), 7.08 (br t, J=7.8 Hz, 1H), 5.77 (s, 1H), 5.04-4.95 (m, 2H), 4.39-4.25 (m, 1H), 3.38-3.23 (m, 3H), 0.82-0.69 (m, 4H).

Compound 211 was prepared in a similar manner to 132 and isolated as a yellow solid (7.2 mg, 15.35 umol, 45.64% yield, 99% purity). $^{1}$H NMR (400 MHz, CHLOROFORM-d) δ=12.43-12.00 (m, 1H), 8.44 (d, J=2.4 Hz, 1H), 8.28 (s, 1H), 7.45-7.36 (m, 2H), 7.36-7.29 (m, 2H), 7.17-7.05 (m, 2H), 6.62 (s, 1H), 5.93-5.76 (m, 2H), 5.27-5.20 (m, 1H), 4.99-4.92 (m, 4H), 4.75-4.69 (m, 2H), 3.04 (s, 3H).

Compound 212 was prepared in a similar manner to 132 and isolated as a yellow solid (24 mg, 52.58 umol, 49.76% yield, 100% purity). $^{1}$H NMR (400 MHz, CHLOROFORM-d) δ=8.71-8.67 (m, 1H), 8.57 (s, 1H), 7.84 (s, 1H), 7.77 (t, J=8.2 Hz, 2H), 7.72-7.65 (m, 2H), 7.60-7.54 (m, 1H), 6.26-6.09 (m, 2H), 5.13-5.03 (m, 2H), 4.36-4.31 (m, 1H), 3.40 (s, 3H), 0.83-0.72 (m, 4H).

Compound 219 was prepared in a similar manner to 132 and isolated as a yellow solid (4 mg, 8.76 umol, 10.26% yield, 99.71% purity). LCMS: m/z=456.2 $(M+H)^+$ $^{1}$H NMR (400 MHz, CHLOROFORM-d) δ=8.56 (d, J=2.5 Hz, 1H), 8.44 (br d, J=1.9 Hz, 1H), 7.77 (s, 1H), 7.71-7.68 (m, 1H), 7.66-7.61 (m, 1H), 7.54-7.46 (m, 2H), 7.33 (d, J=7.8 Hz, 1H), 7.14 (dd, J=1.0, 7.8 Hz, 1H), 6.04 (s, 1H), 5.93 (s, 1H), 5.01 (s, 2H), 3.79 (qd, J=3.0, 5.9 Hz, 1H), 3.10 (s, 3H), 0.87-0.82 (m, 2H), 0.77-0.72 (m, 2H).

Compound 220 was prepared in a similar manner to 132 and isolated as a yellow solid (9.1 mg, 20.23 umol, 23.42% yield, 99.7% purity). LCMS: m/z=449.1 $(M+H)^+$ $^{1}$H NMR (400 MHz, CHLOROFORM-d) δ=8.45 (d, J=6.5 Hz, 2H), 7.79-7.75 (m, 1H), 7.72-7.60 (m, 2H), 7.55-7.45 (m, 2H), 7.33 (d, J=7.8 Hz, 1H), 7.16-7.11 (m, 1H), 5.05-5.00 (m, 2H), 3.83-3.75 (m, 1H), 3.10 (s, 3H), 2.66-2.62 (m, 1H), 0.90-0.73 (m, 4H) Compound 221 was prepared in a similar manner to 132 and isolated as a white solid (20.81 mg, 47.79 umol, 31.07% yield, 100% purity). LCMS: m/z=436.1 $(M+H)^+$ $^{1}$H NMR (400 MHz, CHLOROFORM-d) δ=12.20 (br s, 1H), 8.78 (br s, 1H), 8.17 (br d, J=1.8 Hz, 1H), 7.73 (d, J=7.5 Hz, 1H), 7.46-7.34 (m, 4H), 7.08 (br t, J=7.7 Hz, 1H), 5.04 (s, 2H), 4.43 (q, J=7.1 Hz, 2H), 4.20 (s, 3H), 3.25 (s, 3H), 1.39 (t, J=7.1 Hz, 3H).

Compound 222 was prepared in a similar manner to 132 and isolated as a white solid (37.10 mg, 82.67 umol, 39.46% yield, 98.6% purity). LCMS: m/z=443.0 $(M+H)^+$ $^{1}$H NMR (400 MHz, CHLOROFORM-d) δ=11.95 (br s, 1H), 8.76 (s, 1H), 8.16 (s, 1H), 7.92 (s, 1H), 7.81 (br d, J=7.9 Hz, 1H), 7.73 (d, J=7.5 Hz, 1H), 7.67 (d, J=7.6 Hz, 1H), 7.55 (t, J=7.8 Hz, 1H), 7.46 (d, J=7.5 Hz, 1H), 5.04 (s, 2H), 4.44 (q, J=7.0 Hz, 2H), 4.18 (s, 3H), 3.24 (s, 3H), 1.41-1.35 (m, 3H).

Compound 223 was prepared in a similar manner to 132 and isolated as a white solid (11.7 mg, 25.49 umol, 18.63% yield, 99% purity). $^{1}$H NMR (400 MHz, CHLOROFORM-d) δ=11.94 (br s, 1H), 8.74 (s, 1H), 8.14 (s, 1H), 7.83 (s, 1H), 7.77-7.71 (m, 2H), 7.66 (d, J=7.8 Hz, 1H), 7.59-7.52 (m, 2H), 5.06 (s, 2H), 4.37 (tt, J=3.1, 6.1 Hz, 1H), 4.14 (s, 3H), 3.32 (s, 3H), 0.81-0.70 (m, 4H).

Compound 224 was prepared in a similar manner to 132 and isolated as a white solid (3.2 mg, 6.74 umol, 20.39% yield, 100% purity). LCMS: m/z=475.2 (M+H+) $^{1}$H NMR (400 MHz, CHLOROFORM-d) δ=12.26-12.09 (m, 1H), 8.41 (d, J=2.8 Hz, 1H), 8.31-8.24 (m, 1H), 7.78-7.73 (m, 1H), 7.65-7.63 (m, 1H), 7.62-7.58 (m, 1H), 7.53-7.48 (m, 1H), 7.37 (dd, J=1.2, 7.7 Hz, 1H), 5.91-5.75 (m, 2H), 5.01-4.97 (m, 2H), 4.37-4.31 (m, 1H), 3.31-3.26 (m, 3H), 0.83-0.77 (m, 2H), 0.76-0.70 (m, 2H).

Compound 225 was prepared in a similar manner to 132 and isolated as a white solid (3.1 mg, 6.55 umol, 39.53% yield, 100% purity). LCMS: m/z=474.1 (M+H+) $^{1}$H NMR (400 MHz, CHLOROFORM-d) δ=12.31-12.09 (m, 1H), 8.44 (d, J=2.5 Hz, 1H), 8.28 (s, 1H), 7.58 (t, J=1.4 Hz, 1H), 7.48-7.43 (m, 2H), 7.35-7.30 (m, 2H), 7.13 (dd, J=1.4, 7.8 Hz, 1H), 5.92-5.76 (m, 2H), 4.99-4.94 (m, 2H), 3.83-3.76 (m, 1H), 3.08-3.04 (m, 3H), 0.89-0.82 (m, 2H), 0.80-0.72 (m, 2H).

Compound 226 was prepared in a similar manner to 132 and isolated as a yellow solid (4.9 mg, 9.81 umol, 19.78% yield, 95% purity). LCMS: m/z=475.1 (M+H+) $^{1}$H NMR (400 MHz, CHLOROFORM-d) δ=8.49-8.41 (m, 2H), 8.30 (s, 1H), 8.21-8.15 (m, 1H), 8.12-7.99 (m, 1H), 7.88-7.82 (m, 1H), 7.44-7.35 (m, 1H), 5.95-5.75 (m, 2H), 4.99 (s, 2H), 3.89 (dt, J=3.0, 5.9 Hz, 1H), 3.17-3.09 (m, 3H), 0.99-0.92 (m, 2H), 0.89-0.81 (m, 2H).

Compound 227 was prepared in a similar manner to 132 and isolated as a white solid (39.8 mg, 99.18 umol, 86.41% yield, 97.8% purity). LCMS: m/z=393.3 (M+H+) $^{1}$H NMR (400 MHz, CHLOROFORM-d) δ=12.91-11.51 (m, 1H), 9.20-9.12 (m, 1H), 8.39-8.25 (m, 2H), 7.73-7.68 (m, 1H), 7.62-7.58 (m, 1H), 7.40-7.37 (m, 1H), 7.13-7.05 (m, 3H), 4.95 (s, 2H), 4.19 (q, J=7.0 Hz, 2H), 3.05 (s, 3H), 1.55 (t, J=6.9 Hz, 3H).

Compound 228 was prepared in a similar manner to 132 and isolated as a white solid (14.3 mg, 34.25 umol, 46.90% yield, 100% purity). LCMS: m/z=418.2 (M+H+) $^{1}$H NMR (400 MHz, CHLOROFORM-d) δ=12.23-12.43 (m, 1H) 9.14-9.21 (m, 1H) 8.33-8.42 (m, 2H) 7.94 (s, 1H) 7.65-7.71 (m, 2H) 7.08-7.12 (m, 2H) 4.93-5.00 (m, 2H) 4.19-4.26 (m, 2H) 3.02-3.07 (m, 3H) 1.56 (t, J=6.94 Hz, 3H).

Compound 229 was prepared in a similar manner to 132 and isolated as a light yellow solid (7.8 mg, 18.93 umol, 20.25% yield, 98.167% purity). LCMS: m/z=405.2 (M+H+) $^{1}$H NMR (400 MHz, CHLOROFORM-d) δ=12.82-12.21

(m, 1H), 9.35-8.96 (m, 1H), 8.52-8.27 (m, 2H), 7.76-7.63 (m, 1H), 7.54 (br d, J=3.6 Hz, 1H), 7.50-7.44 (m, 1H), 7.41-7.34 (m, 1H), 7.16-7.04 (m, 2H), 5.06-4.85 (m, 2H), 3.90 (br d, J=3.4 Hz, 1H), 3.12-2.98 (m, 3H), 0.97-0.83 (m, 4H).

Compound 230 was prepared in a similar manner to 132 and isolated as a white solid (6.4 mg, 15.78 umol, 60.40% yield, 100% purity). LCMS: m/z=406.1 (M+H+) $^1$H NMR (400 MHz, CHLOROFORM-d) δ=12.45-12.32 (m, 1H), 9.22-9.11 (m, 1H), 8.42-8.27 (m, 2H), 8.03 (d, J=7.8 Hz, 1H), 7.65-7.56 (m, 2H), 7.41 (dd, J=0.9, 5.1 Hz, 1H), 7.12 (dd, J=3.9, 5.0 Hz, 1H), 4.99 (s, 2H), 4.45-4.38 (m, 1H), 3.77-3.70 (m, 1H), 3.38-3.28 (m, 3H), 2.02 (s, 1H), 1.28-1.23 (m, 1H), 0.91-0.86 (m, 2H), 0.86-0.80 (m, 2H).

Compound 231 was prepared in a similar manner to 132 and isolated as a white solid (35 mg, 77.13 umol, 43.25% yield, 94.866% pur). LCMS: m/z=443.2 (M+H+) $^1$H NMR (400 MHz, CHLOROFORM-d) δ=9.20 (br s, 1H), 8.43 (s, 1H), 8.34 (s, 1H), 8.24 (s, 1H), 8.02 (d, J=7.8 Hz, 1H), 7.97 (d, J=0.9 Hz, 1H), 7.72 (s, 1H), 7.63 (d, J=7.9 Hz, 1H), 5.00 (s, 2H), 4.48-4.39 (m, 1H), 3.31 (s, 3H), 0.90-0.83 (m, 4H).

Scheme 39.

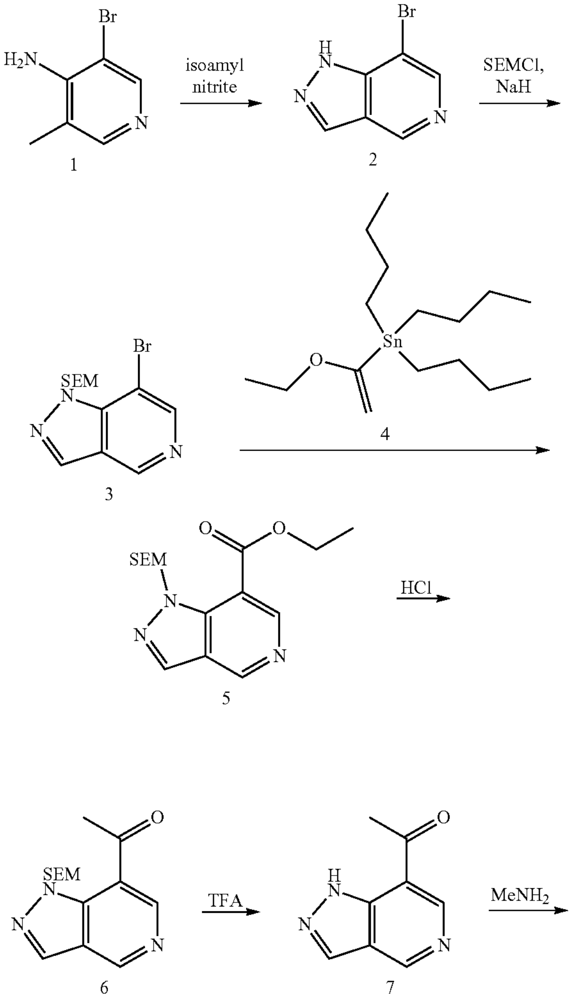

1 2 3 4 5 6 7

-continued

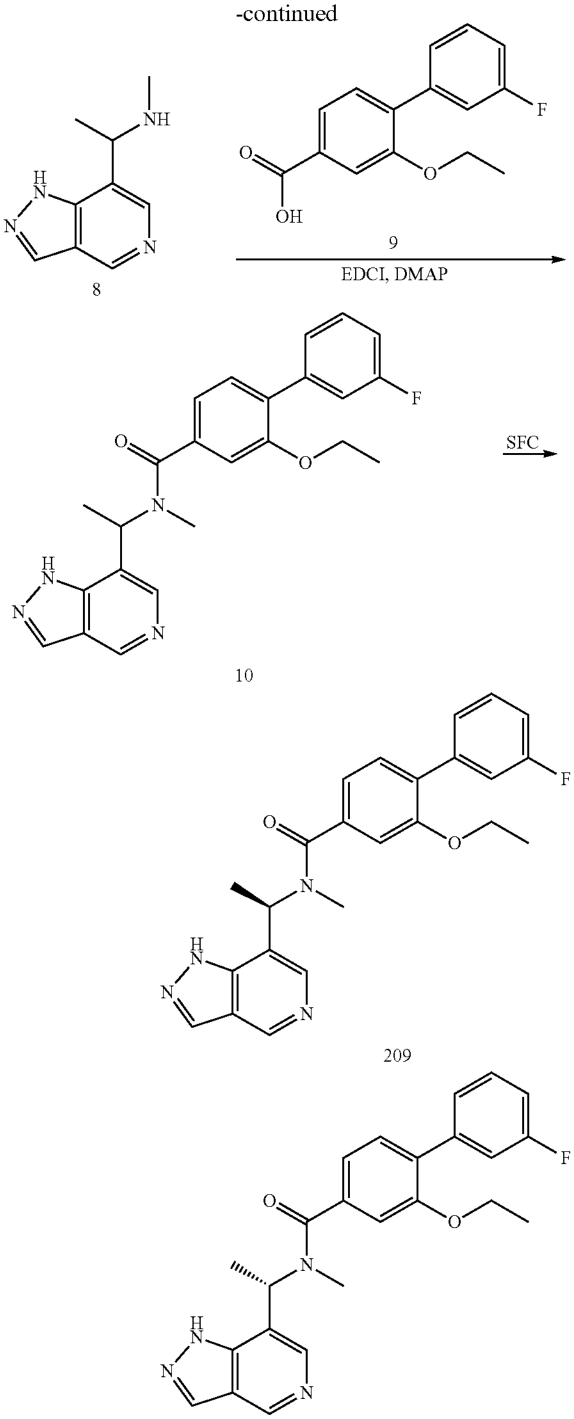

8 9 10 209 210

To a solution of Compound 1 (29.2 g, 156.12 mmol, 1 eq) in $CHCl_3$ (300 mL) was added $Ac_2O$ (79.69 g, 780.59 mmol, 73.11 mL, 5 eq) dropwise at 0° C., the reaction mixture was stirred at 0° C. for 2 hr under $N_2$. Then AcOK (4.60 g, 46.84 mmol, 0.3 eq) and isopentyl nitrite (45.72 g, 390.30 mmol, 52.55 mL, 2.5 eq) was added dropwise at 0° C. under $N_2$, the reaction mixture was stirred at 60° C. for 12 hr. The mixture was concentrated to give a crude product. A lot of solid was formed and the mixture was filtered and the cake was collected, the cake was washed with MTBE (500 mL), and dried to give a crude product, the crude product used for next step without further purification. Compound 2 (25 g, crude) was obtained as brown solid.

To a solution of Compound 2 (15 g, 75.75 mmol, 1 eq) in 2-MeTHF (150 mL) was added NaH (4.54 g, 113.62 mmol, 60% purity, 1.5 eq) at 0° C., the mixture was stirred at 0° C. for 0.5 h, then SEM-Cl (18.94 g, 113.62 mmol, 20.11 mL, 1.5 eq) was added dropwise at 0° C., the mixture was stirred at 20° C. for 2 h. The mixture was poured into saturated $NH_4Cl$ (500 mL) solution, and extracted with EtOAc (500 mL×3), the combined organic phase was washed with brine (500 mL), dried over anhydrous $Na_2SO_4$, and concentrated to give a crude product. The crude product was purified by column chromatography ($SiO_2$, Petroleum ether/Ethyl acetate=10/1 to 1/1, desired product Rf=0.7). Compound 3 (3.5 g, 10.66 mmol, 14.07% yield) was obtained as brown oil.

To a solution of Compound 3 (3.4 g, 10.36 mmol, 1 eq) in dioxane (20 mL) and $H_2O$ (2 mL) was added Compound 4 (4.49 g, 12.43 mmol, 4.19 mL, 1.2 eq), $K_2CO_3$ (4.29 g, 31.07 mmol, 3 eq) and Pd $(PPh_3)_2Cl_2$ (1.09 g, 1.55 mmol, 0.15 eq), the mixture was stirred at 100° C. for 12 h under $N_2$. The mixture was diluted with saturated potassium fluoride solution (100 mL), and stirred at 20° C. for 2 h, then the extracted with EtOAc (100 mL×3), the combined organic phase was washed with brine (100 mL×3), dried over anhydrous $Na_2SO_4$, and concentrated to give a crude product. The crude product was purified by column chromatography ($SiO_2$, Petroleum ether/Ethyl acetate=10/1 to 1/1, desired product Rf=0.4). Compound 5 (2.6 g, 8.14 mmol, 78.58% yield) was obtained as yellow oil.

To a solution of Compound 5 (2.6 g, 8.14 mmol, 1 eq) in MeCOH (30 mL) was added HCl (1 M, 30 mL, 3.69 eq) The reaction mixture was stirred at 20° C. for 1 h. The mixture was poured into water (500 mL), and extracted with EtOAc (500 mL×3), the combined organic phase was washed with brine (500 mL×3), dried over anhydrous $Na_2SO_4$, and concentrated to give a crude product. No purification. Compound 6 (2.12 g, 7.27 mmol, 89.39% yield) was obtained as yellow oil, which was used directly in the next step.

To a solution of Compound 6 (700 mg, 2.40 mmol, 1 eq) in DCM (7 mL) was added TFA (10.78 g, 94.54 mmol, 7 mL, 39.36 eq), the reaction mixture was stirred at 20° C. for 12 hr.

The reaction mixture was filtered, the filtrate was concentrated to give a crude product. The crude product was purified by column chromatography on silica gel eluted with dichloromethane:methanol=1:0 to 10:1 (desired compound Rf=0.5). Compound 7 (370 mg, crude) was obtained as yellow solid.

To a solution of Compound 7 (274 mg, 1.70 mmol, 1 eq) in MeOH (10 mL) was added $MeNH_2$ in THF (2 M, 2.55 mL, 3 eq) and AcOH (10.21 mg, 170.02 umol, 9.72 uL, 0.1 eq), the reaction mixture was stirred at 50° C. for 2 hr. Then $NaBH_4$ (192.96 mg, 5.10 mmol, 3 eq) was added to the reaction mixture slowly at 0° C., the reaction mixture was stirred at 20° C. for 12 hr. The reaction mixture was quenched by saturated $NH_4Cl$ aqueous (20 mL), the resulting mixture was concentrated under vacuum to give a residue. The residue was purified by prep-HPLC (column: Welch Xtimate C18 150*25 mm*5 um; mobile phase: [water ($NH_3H_2O$)-ACN]; B %: 1%-25%, 8 min). After prep-HPLC purification, the eluent was concentrated to remove organic solvents. The residual aqueous solution was lyophilized to give white solid. Compound 8 (128 mg, 646.47 umol, 38.02% yield, 89% purity) was obtained as white solid.

To a solution of Compound 8 (126.39 mg, 645.51 umol, 90% purity, 1.2 eq) in DCM (5 mL) was added Compound 9 (140 mg, 537.92 umol, 1 eq), EDCl (154.68 mg, 806.89 umol, 1.5 eq) and DMAP (6.57 mg, 53.79 umol, 0.1 eq), the reaction mixture was stirred at 20° C. for 12 hr. The reaction mixture was concentrated to give a crude product. The crude product was purified by prep-HPLC (column: Phenomenex luna C18 150*25 mm*10 um; mobile phase: [water (FA)-ACN]; B %: 19%-49%, 9 min). After prep-HPLC purification, the eluent was concentrated to remove organic solvents. The residual aqueous solution was lyophilized to give white solid. Compound 10 (150 mg, 354.87 umol, 65.97% yield, 99% purity) was obtained as white solid.

Compound 10 (80 mg, 191.18 umol, 1 eq) was purified by SFC to give 209 (21.0 mg, 50.18 umol, 26.25% yield, 100% purity) and 210 (23.8 mg, 54.60 umol, 28.56% yield, 96% purity). The product was purified by SFC (column: DAICEL CHIRALCEL OJ (250 mm*30 mm, 10 um); mobile phase: [0.1% $NH_3H_2O$ MEOH]; B %: 15%-15%, 7.7; 162 min). After SFC, the eluent was concentrated to remove organic solvents. The residual aqueous solution was lyophilized to give white solid. 209 (21.0 mg, 50.18 umol, 26.25% yield, and 100% purity) was obtained as white solid. 210 (23.8 mg, 54.60 umol, 28.56% yield, and 96% purity) was obtained as white solid. $^1H$ NMR of 209: $^1H$ NMR (400 MHz, CHLOROFORM-d) δ=12.11 (br s, 1H), 9.26-8.88 (m, 1H), 8.53-8.26 (m, 1H), 8.20 (s, 1H), 7.33-7.21 (m, 4H), 7.01-6.93 (m, 3H), 6.45-6.36 (m, 1H), 4.00 (br dd, J=7.0, 16.9 Hz, 2H), 2.75 (s, 3H), 1.82 (d, J=7.3 Hz, 3H), 1.30 (t, J=7.0 Hz, 3H). $^1H$ NMR of 210: $^1H$ NMR (400 MHz, CHLOROFORM-d) δ=12.20 (br d, J=1.4 Hz, 1H), 9.42-8.89 (m, 1H), 8.67-8.35 (m, 1H), 8.29 (s, 1H), 7.42-7.29 (m, 4H), 7.12-7.04 (m, 3H), 6.51 (br d, J=7.5 Hz, 1H), 4.17-4.01 (m, 2H), 2.84 (s, 3H), 1.91 (d, J=7.1 Hz, 3H), 1.39 (t, J=6.9 Hz, 3H).

Compound 186 was prepared in a similar manner to 209 and 210 and isolated as a white solid (19.2 mg, 55.27 umol, 37.62% yield, 100% purity). LCMS: m/z=348.2 (M+H+) $^1H$ NMR (400 MHz, CHLOROFORM-d) δ=8.11 (s, 1H), 7.79-7.72 (m, 1H), 7.39-7.34 (m, 1H), 7.25 (s, 1H), 7.15-7.09 (m, 1H), 6.97-6.89 (m, 2H), 4.96-4.90 (m, 2H), 4.10 (q, J=7.0 Hz, 2H), 2.93 (s, 3H), 2.11 (s, 3H), 1.46 (t, J=6.9 Hz, 3H).

Compound 389 was prepared in a similar manner to 209 and 210 and isolated as a white solid (4.04 mg, 9.44 umol, 5.88% yield, 99% purity). LCMS: m/z=424.1 (M+H+) $^1H$ NMR (400 MHz, CHLOROFORM-d) δ=8.14 (br s, 1H), 7.78 (br d, J=8.0 Hz, 1H), 7.50-7.40 (m, 4H), 7.35-7.29 (m, 2H), 7.14 (br t, J=7.5 Hz, 1H), 7.09-7.04 (m, 2H), 4.97 (s, 2H), 4.04 (q, J=6.8 Hz, 2H), 3.01 (s, 3H), 2.08 (s, 3H), 1.35 (br t, J=6.9 Hz, 3H) Compounds 258 and 390 were prepared in a similar manner to 209 and 210. 258 (18.5 mg, 45.74 umol, 46.25% yield, and 100% purity) was obtained as white solid. 390 (17.6 mg, 43.52 umol, 44.00% yield, and 100% purity) was obtained as white solid. $^1H$ NMR of 258: (400 MHz, CHLOROFORM-d) δ=12.88-12.58 (m, 1H), 9.00-8.88 (m, 1H), 8.52-8.36 (m, 1H), 8.28 (s, 1H), 8.01-7.73 (m, 1H), 7.57 (s, 1H), 7.46 (br d, J=7.4 Hz, 1H), 7.35-7.24 (m, 3H), 7.22 (br d, J=0.6 Hz, 1H), 7.02-6.88 (m, 1H), 5.89 (br s, 1H), 4.16-4.00 (m, 2H), 1.99-1.93 (m, 3H), 1.32-1.26 (m, 3H) 1H NMR of 390: (400 MHz, CHLOROFORM-d) δ=12.85-12.42 (m, 1H), 8.93 (s, 1H), 8.42 (br s, 1H), 8.24 (s, 1H), 7.76-7.56 (m, 1H), 7.55 (s, 1H), 7.41 (s, 1H), 7.28 (d, J=8.0 Hz, 2H), 7.22 (br d, J=6.6 Hz, 2H), 7.01-6.90 (m, 1H), 5.93-5.84 (m, 1H), 4.09 (br dd, J=4.0, 7.0 Hz, 2H), 1.95 (br d, J=7.1 Hz, 3H), 1.30 (t, J=6.9 Hz, 3H).

Scheme 40

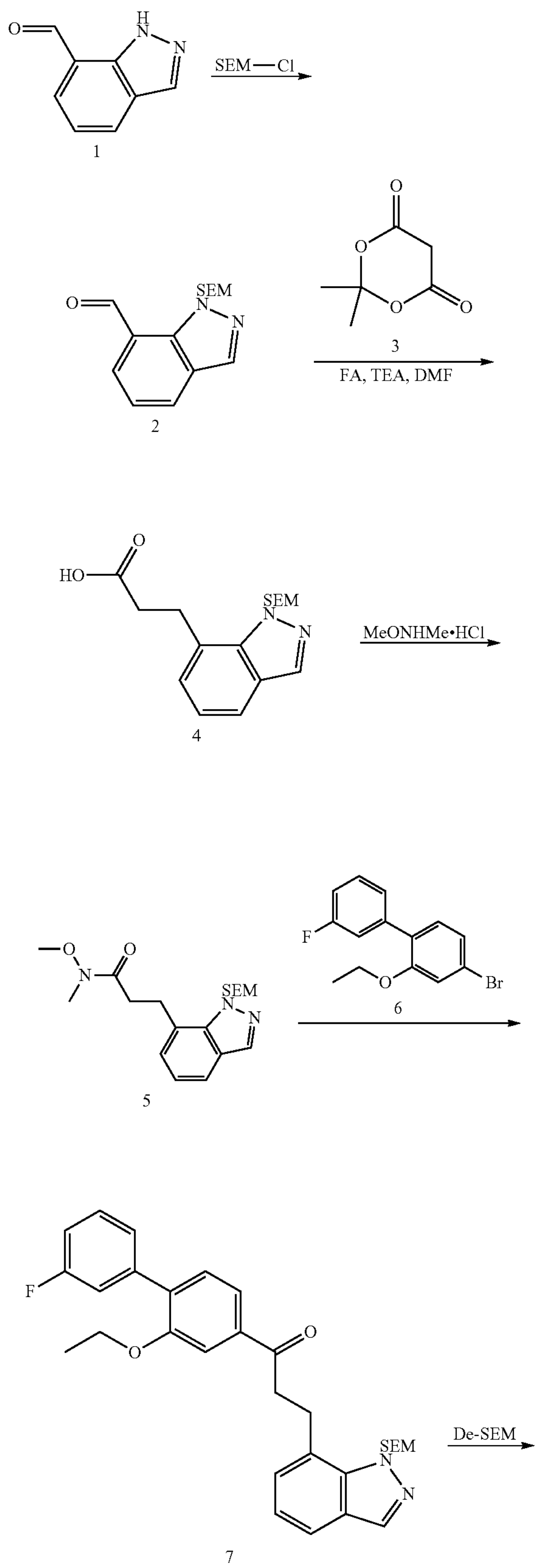

-continued

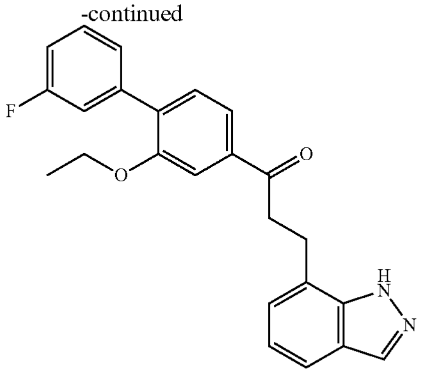

286

To a solution of compound 1 (950 mg, 6.50 mmol, 1 eq) in THF (30 mL) was added NaH (389.98 mg, 9.75 mmol, 60% purity, 1.5 eq) at 0° C., the mixture was stirred at 0° C. for 0.5 h, then SEM-Cl (1.30 g, 7.80 mmol, 1.38 mL, 1.2 eq) was added dropwise, the mixture was stirred at 0° C. for 3 h. TLC (Petroleum ether:Ethyl acetate=5:1) showed the reaction was completed. The mixture was poured into saturated $NH_4Cl$ (100 mL) solution, and extracted with EtOAc (80 mL×2), the combined organic phase was washed with brine (100 mL), dried over anhydrous Na2SO4, and concentrated to give a crude product. The residue was purified by silica gel column chromatography (Petroleum ether:Ethyl acetate=10:1) to give compound 2 (1.37 g, 4.96 mmol, 76.25% yield, N/A purity) as colorless oil. HCOOH (157.10 mg, 3.27 mmol, 3 eq) and $Et_3N$ (132.36 mg, 1.31 mmol, 182.06 uL, 1.2 eq) was combined in a flask and stirred at 20° C. for 15 minutes. Then DMF (1 mL) was added.

To this mixture compound 2 (300 mg, 1.09 mmol, 1 eq) and compound 3 (157.10 mg, 1.09 mmol, 1 eq) was added. The reaction was stirred at 100° C. 16 h. The mixture was poured into $H_2O$ (100 mL). The aqueous phase was extracted with EtOAc (60 mL). The combined organic phase was washed with brine (100 mL×2), dried over $Na_2SO_4$, filtered and concentrated under vacuum. The residue was purified by silica gel column chromatography (Petroleum ether/Ethyl acetate=3:1) to give (177 mg, 552.33 umol, 50.67% yield, N/A purity) was obtained as colourless oil. LCMS: m/z=321.2 $(M+H)^+$ $^1H$ NMR (400 MHz, CHLOROFORM-d) δ=8.13 (s, 1H), 7.58 (d, J=8.4 Hz, 1H), 7.16-7.12 (m, 1H), 7.06 (dd, J=6.7, 8.3 Hz, 1H), 5.80 (s, 2H), 3.67 (dd, J=7.7, 8.9 Hz, 2H), 3.37 (t, J=7.8 Hz, 2H), 2.95-2.87 (m, 2H), 1.02-0.90 (m, 2H), −0.01 (s, 9H).

A solution of compound 4 (157 mg, 489.92 umol, 1 eq), N-methoxymethanamine;hydrochloride (57.35 mg, 587.91 umol, 1.2 eq) and $Et_3N$ (74.36 mg, 734.89 umol, 102.29 uL, 1.5 eq) in DCM (3 mL) was added EDCl (140.88 mg, 734.89 umol, 1.5 eq), DMAP (5.99 mg, 48.99 umol, 0.1 eq) at 20° C. The mixture which resulted was allowed to stir at 20° C. for 12 hrs. The reaction mixture was concentrated under vacuum.

The residue was purified by silica gel column chromatography (Petroleum ether/Ethyl acetate=2/1) to give compound 5 (150 mg, 412.63 umol, 84.22% yield) was obtained as colourless oil. LCMS: m/z=364.1 (M+H)+$^1H$ NMR (400 MHz, CHLOROFORM-d) δ=8.09 (s, 1H), 7.55 (d, J=8.3 Hz, 1H), 7.13 (d, J=6.4 Hz, 1H), 7.03 (dd, J=6.8, 8.4 Hz, 1H), 5.73 (s, 2H), 3.67-3.62 (m, 2H), 3.60 (s, 3H), 3.36 (t, J=7.9 Hz, 2H), 3.19 (s, 3H), 3.11-2.90 (m, 2H), 0.99-0.90 (m, 2H), −0.02 (s, 9H) To a solution of compound 6 (253.31 mg, 858.26 umol, 2 eq) in 2-MeTHF (3 mL) was added n-BuLi (2.5 M, 514.96 uL, 3 eq) at −65° C. under $N_2$ atmosphere, the mixture was stirred at −65° C. for 1.5 hr. Compound 5 (156 mg, 429.13 umol, 1 eq) in 2-MeTHF (0.5 mL) was added to the mixture, the mixture was stirred at −65° C. for another 3 hrs under N2 atmosphere. The mixture was poured into ice-$NH_4Cl$ (sat. 50 mL) and stirred for 1 min. The aqueous phase was extracted with ethyl acetate (40 mL×2). The combined organic phase was washed with brine (60 mL), dried with anhydrous $Na_2SO_4$, filtered and concentrated in vacuum. The residue was purified by prep-HPLC (column: Phenomenex luna C18 150*25 mm*10 um; mobile phase: [water(FA)-ACN]; B %: 70%-100%, 8 min), lyophilizated, to give compound 7 (20 mg, 38.29 umol, 8.92% yield, 99.3% purity) was obtained as white solid. LCMS: m/z=519.2 (M+H)+

To a mixture of compound 7 (20. mg, 38.29 umol, 99.3% purity, 1 eq) in DCM (1 mL) was added TFA (770.00 mg, 6.75 mmol, 0.5 mL, 176.37 eq) at 20° C. The mixture was stirred at 20° C. for 2 hrs. The mixture was concentrated under vacuum. The residue was dessolved with MeCN (1 mL) and based with $Et_3N$ to pH about 8. The residue was purified by prep-HPLC (column: Waters xbridge 150*25 mm 10 um; mobile phase: [water($NH_4HCO_3$)-ACN]; B %: 50%-80%, 11 min), lyophilized to give 286 (12.2 mg, 30.47 umol, 79.57% yield, 97% purity) as off-white solid. LCMS: m/z=389.1 (M+H)+$^1$H NMR (400 MHz, CHLOROFORM-d) δ=8.09-7.94 (m, 1H), 7.56 (d, J=8.0 Hz, 1H), 7.52-7.45 (m, 2H), 7.32-7.28 (m, 1H), 7.27-7.11 (m, 4H), 7.10-6.92 (m, 2H), 4.02 (q, J=6.9 Hz, 2H), 3.44-3.38 (m, 2H), 3.38-3.31 (m, 2H), 1.30 (t, J=6.9 Hz, 3H).

Scheme 41

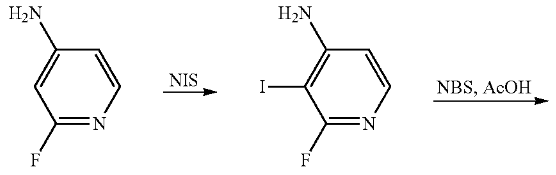

1 2

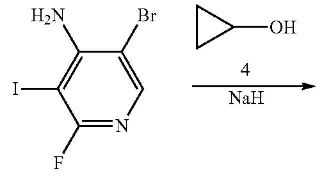

3

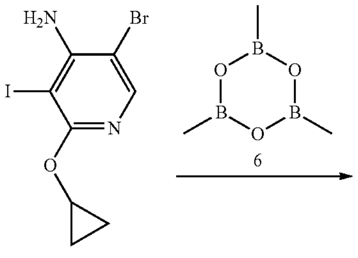

5

-continued

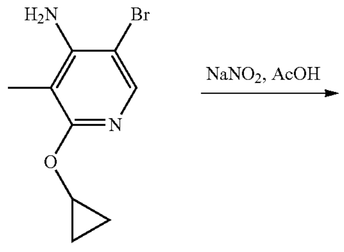

7

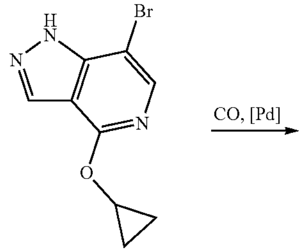

8

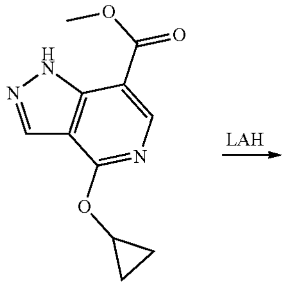

9

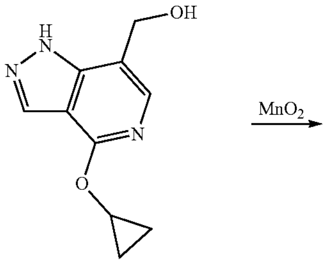

10

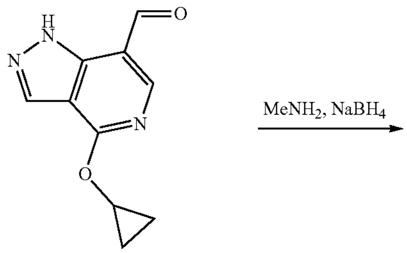

11

-continued

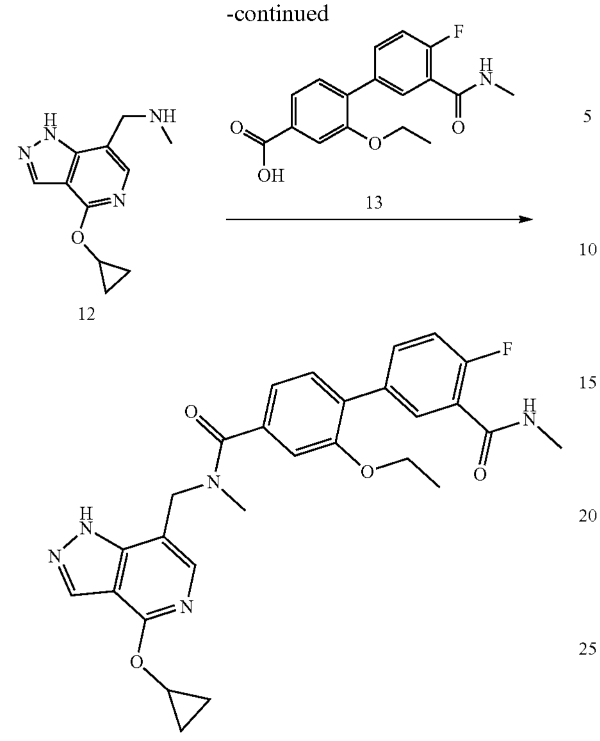

12 13 207

To a solution of Compound 1 (5 g, 44.60 mmol, 1 eq) in DMF (50 mL) was added NIS (10.03 g, 44.60 mmol, 1 eq) at 0° C., the reaction mixture was stirred at 70° C. for 12 hr. The reaction mixture was extracted with EtOAc (150 mL×3), the combined organic phase was washed with brine (150 mL×3), dried over anhydrous $Na_2SO_4$, and concentrated to give a crude product. The crude product was purified by column chromatography on silica gel eluted with petroleum ether:ethyl acetate=1/0 to 0/1 (desired compound Rf=0.9). Compound 2 (9 g, 36.64 mmol, 82.16% yield, 96.9% purity) was obtained as brown solid, LCMS: Rt=0.328 min, m/z=238.9 $(M+H^+)$ To a solution of Compound 2 (9 g, 37.81 mmol, 1 eq) in AcOH (90 mL) was added NBS (6.73 g, 37.81 mmol, 1 eq), the reaction mixture was stirred at 20° C. for 12 hr. The reaction mixture was extracted with EtOAc (100 mL×3), the combined organic phase was washed with brine (100 mL), dried over anhydrous $Na_2SO_4$, and concentrated to give a crude product. The crude product was purified by column chromatography on silica gel eluted with petroleum ether: ethyl acetate=1/0 to 2/1 (desired compound Rf=0.7). Compound 3 (7.8 g, 23.14 mmol, 61.18% yield, 94% purity) was obtained as white solid. LCMS: Rt=0.443 min, m/z=318.7 $(M+H^+)$ To a solution of Compound 4 (3.13 g, 53.96 mmol, 1.5 eq) in 2-MeTHF (120 mL) was added NaH (4.32 g, 107.92 mmol, 60% purity, 3 eq) at 0° C., the mixture was stirred at 0° C. for 0.5 hr. Then Compound 3 (11.4 g, 35.97 mmol, 1 eq) was added at ° C., the reaction mixture was stirred at 20° C. for 12 hr. The mixture was poured into saturated $NH_4Cl$ (500 mL) solution, and extracted with EtOAc (200 mL×3), the combined organic phase was washed with brine (500 mL), dried over anhydrous $Na_2SO_4$, and concentrated to give a crude product. The crude product was purified by column chromatography on silica gel eluted with petroleum ether:ethyl acetate=1:0 to 1:1 (desired compound Rf=0.9). Compound 4 (1.3 g, 2.31 mmol, 6.41% yield, 63% purity) was obtained as brown oil LCMS: Rt=0.520 min, m/z=354.8 $(M+H^+)$ To a solution of Compound 5 (2 g, 2.82 mmol, 50% purity, 1 eq) in dioxane (20 mL) was added $Cs_2CO_3$ (1.84 g, 5.63 mmol, 2 eq), Compound 6 (848.76 mg, 3.38 mmol, 945.16 uL, 50% purity, 1.2 eq) and Pddppf) $Cl_2$—$CH_2Cl_2$ (230.06 mg, 281.71 umol, 0.1 eq), the reaction mixture was stirred at 80° C. for 12 hr. under $N_2$. The reaction mixture was filtered, the filtrate was concentrated to give a crude product. The crude product was purified by column chromatography on silica gel eluted with petroleum ether:ethyl acetate=1:0 to 5:1 (desired compound Rf=0.6). Compound 7 (522 mg, 1.95 mmol, 69.22% yield, 91% purity) was obtained as brown oil LCMS: Rt=0.298 min, m/z=244.9 $(M+H^+)$ To a solution of Compound 7 (500 mg, 1.85 mmol, 90% purity, 1 eq) in AcOH (10 mL) and $H_2O$ (1 mL) was added $NaNO_2$ (255.43 mg, 3.70 mmol, 2 eq), the reaction mixture was stirred at 80° C. for 12 hr. The reaction mixture was extracted with EtOAc (100 mL×3), the combined organic phase was washed with brine (100 mL), dried over anhydrous $Na_2SO_4$, and concentrated to give a crude product. The crude product was purified by column chromatography on silica gel eluted with petroleum ether:ethyl acetate=1:0 to 5:1 (desired compound Rf=0.3). Compound 8 (158 mg, 572.10 umol, 30.91% yield, 92% purity) was obtained as yellow solid. LCMS: Rt=0.410 min, m/z=253.9 $(M+H^+)$ To a solution of Compound 8 (150 mg, 590.36 umol, 1 eq) in MeOH (20 mL) was added DPPF (65.46 mg, 118.07 umol, 0.2 eq), $Pd(OAc)_2$ (26.51 mg, 118.07 umol, 0.2 eq) and TEA (298.69 mg, 2.95 mmol, 410.85 uL, 5 eq), the reaction mixture was stirred at 80° C. for 12 hr under CO (590.36 umol, 1 eq) (50 Psi). TLC (petroleum ether:ethyl acetate=1:1) showed the reaction was completed. After the reaction was completed, the mixture was filtered under $N_2$ and the filtrated was concentrated to give a crude product. The crude product was purified by prep-TLC (petroleum ether:ethyl acetate=1:1, desired compound Rf=0.5). Compound 9 (113 mg, 477.68 umol, 80.91% yield, 98.59% purity) was obtained as white solid. LCMS: Rt=0.403 min, m/z=234.0 $(M+H^+)$ To a solution of Compound 9 (110 mg, 471.65 umol, 1 eq) in 2-MeTHF (5 mL) was added LAH (26.85 mg, 707.48 umol, 1.5 eq) at 0° C., the reaction mixture was stirred at 0° C. for 1 hr. TLC (petroleum ether:ethyl acetate=1:1) showed the starting material was consumed completely. The reaction mixture was quenched by $Na_2SO_4 \cdot 10H_2O$ (1 g), then the mixture was filtered, the filtrate was concentrated under vacuum to give a residue. The residue was used to the next step without purification. Compound 10 (110 mg, crude) was obtained as yellow solid.

To a solution of Compound 10 (90 mg, 438.57 umol, 1 eq) in DCM (5 mL) was added $MnO_2$ (762.56 mg, 8.77 mmol, 20 eq), the reaction mixture was stirred at 30° C. for 12 hr. The reaction mixture was concentrated to give a crude product. The crude product was purified by prep-TLC (petroleum ether:ethyl acetate=1:1, desired compound Rf=0.6). Compound 11 (54 mg, crude) was obtained as white solid. LCMS: m/z=204.0 $(M+H^+)$ To a solution of Compound 11 (54 mg, 265.75 umol, 1 eq) in MeOH (2 mL) was added $MeNH_2$ in THF (2 M, 797.26 uL, 6 eq) and AcOH (1.60 mg, 26.58 umol, 1.52 uL, 0.1 eq), the reaction mixture was stirred at 50° C. for 3 hr. Then $NaBH_4$ (30.16 mg, 797.26 umol, 3 eq) was added slowly at 0° C., the reaction mixture was stirred at 20° C. for 2 hr. The reaction mixture was quenched by saturated $NH_4Cl$ aqueous (10 mL), the resulting mixture was concentrated under vacuum to give a residue. The crude product was used to the next step without purification. Compound 12 (65 mg, crude) was obtained as white solid. LCMS: Rt=0.532 min, m/z=219.2 (M+H$^+$)

To a solution of Compound 12 (65.00 mg, 297.82 umol, 1.5 eq) in DCM (4 mL) was added Compound 13 (63 mg, 198.54 umol, 1 eq), EDCl (38.06 mg, 198.54 umol, 1 eq) and DMAP (2.43 mg, 19.85 umol, 0.1 eq), the reaction mixture was stirred at 20° C. for 12 hr. LCMS (EC2950-181-P1A) showed the reaction was completed and desired mass was detected.

The reaction mixture was concentrated to give a crude product. The crude product was purified by prep-HPLC (column: Phenomenex luna C18 150*25 mm*10 um; mobile phase: [water (FA)-ACN]; B %: 34%-64%, 9 min). After prep-HPLC purification, the eluent was concentrated to remove organic solvents. The residual aqueous solution was lyophilized to give white solid. 207 (10.97 mg, 21.20 umol, 10.68% yield, and 100% purity) was obtained as white solid. LCMS: Rt=0.492 min, m/z=518.2 (M+H$^+$) $^1$H NMR: $^1$H NMR (400 MHz, CHLOROFORM-d) δ=12.04 (br s, 1H), 8.22-8.16 (m, 1H), 8.09-8.05 (m, 1H), 7.84-7.79 (m, 1H), 7.63-7.57 (m, 1H), 7.31-7.26 (m, 1H), 7.11-7.04 (m, 1H), 7.02-6.99 (m, 1H), 6.99-6.97 (m, 1H), 6.76-6.63 (m, 1H), 4.79-4.74 (m, 2H), 4.48-4.39 (m, 1H), 4.02-3.95 (m, 2H), 3.00-2.97 (m, 3H), 2.97-2.93 (m, 3H), 1.31-1.26 (m, 3H), 0.86-0.81 (m, 4H).

Compound 171 was prepared in a similar manner to 207 and isolated as a white solid (13.42 mg, 31.38 umol, 12.48% yield, 99.7% purity). LCMS: m/z=427.2 (M+—H+) $^1$H NMR (400 MHz, CHLOROFORM-d) δ=12.57-11.40 (m, 1H), 8.15 (s, 1H), 7.94 (d, J=1.5 Hz, 1H), 7.78-7.73 (m, 1H), 7.71-7.65 (m, 1H), 7.65-7.58 (m, 1H), 7.54-7.45 (m, 1H), 7.39-7.33 (m, 1H), 7.33-7.28 (m, 1H), 7.22-7.16 (m, 1H), 6.92-6.82 (m, 1H), 6.77-6.68 (m, 1H), 4.95-4.87 (m, 2H), 3.89-3.82 (m, 1H), 0.94-0.85 (m, 2H), 0.78-0.70 (m, 2H)

Scheme 42

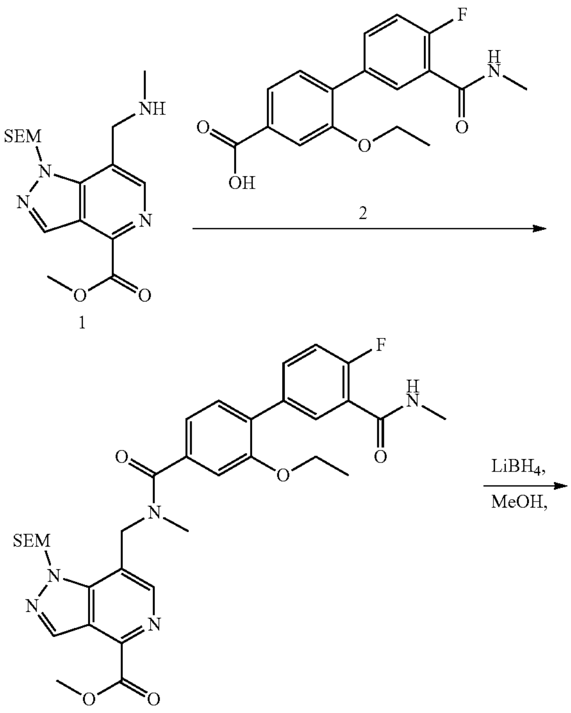

1

2

3

-continued

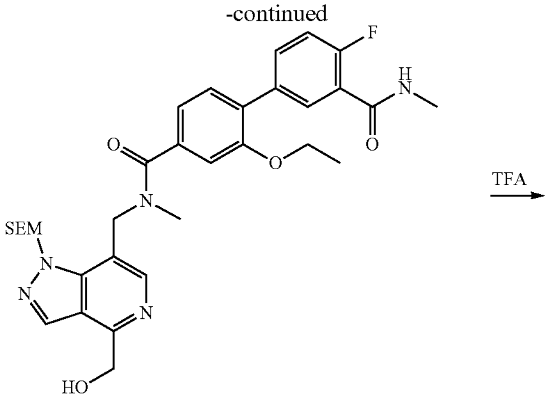

4

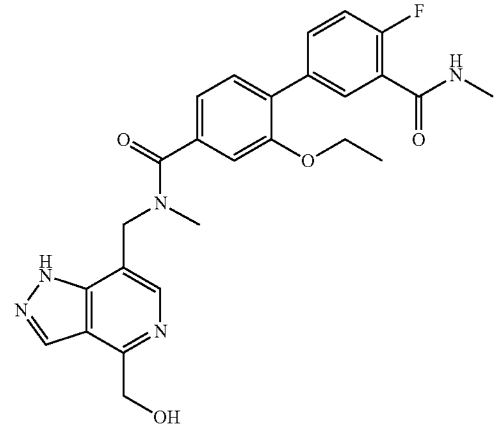

270

To a solution of Compound 1 (100 mg, 285.32 umol, 1 eq) and Compound 2 (90.53 mg, 285.32 umol, 1 eq) in DCM (2 mL) was added EDCl (82.04 mg, 427.98 umol, 1.5 eq) and DMAP (3.49 mg, 28.53 umol, 0.1 eq). The mixture was stirred at 20° C. for 12 hr The reaction mixture was poured into water (10 mL) and extracted by ethyl acetate (10 mL×3), the combined organic phase was dried and concentrated under vacuum to give residue. The residue was purified by prep-TLC (petroleum ether/ethyl acetate=1:2, RF=0.2), the purified solution was concentrated under vacuum to give a residue. Compound 3 (100 mg, 153.90 umol, 53.94% yield) was obtained as a colorless oil. LCMS: m/z=650.5 (M+H)$^+$ To a solution of Compound 3 (100 mg, 153.90 umol, 1 eq) in MeOH (2 mL) was added $LiBH_4$ (2 M, 115.42 uL, 1.5 eq) under 0° C. The mixture was stirred at 0-20° C. for 12 hr. The reaction mixture was quenched by saturated $NH_4Cl$ aqueous (10 mL), the resulting mixture was concentrated under vacuum to give a residue. Compound 4 (70 mg, 112.58 umol, 73.15% yield) was obtained as a yellow oil. LCMS: m/z=622.2 (M+H)$^+$ To a solution of Compound 6 (70 mg, 112.58 umol, 1 eq) in TFA (1 mL). The mixture was stirred at 20° C. for 1 hr. The reaction mixture was poured into water (10 mL) and extracted by ethyl acetate (10 mL×3), the combined organic phase was dried and concentrated under vacuum to give residue. The residue was purified by prep-HPLC (column: Phenomenex luna C18 150*25 mm*10 um; mobile phase: [water (FA)-ACN]; B %: 13%-43%, 15 min), the purified solution was lyophilized to give a white solid. Compound 270 (6.5 mg, 12.70 umol, 11.28% yield, 96% purity) was obtained as a white solid. LCMS: m/z=492.3 $(M+H)^+$1H NMR (400 MHz, CHLOROFORM-d) δ ppm 12.56-12.97 (m, 1H) 8.44-8.52 (m, 1H) 8.33-8.41 (m, 1H) 8.25-8.31 (m, 1H) 7.64-7.71 (m, 1H) 7.36-7.41 (m, 1H) 7.16 (dd, J=11.51, 8.63 Hz, 1H) 7.04-7.11 (m, 2H) 6.73-6.83 (m, 1H) 5.23-5.35 (m, 2H) 4.94-5.06 (m, 2H) 4.07 (q, J=6.84 Hz, 2H) 3.05-3.10 (m, 6H) 1.37 (br t, J=6.88 Hz, 3H).

Scheme 43

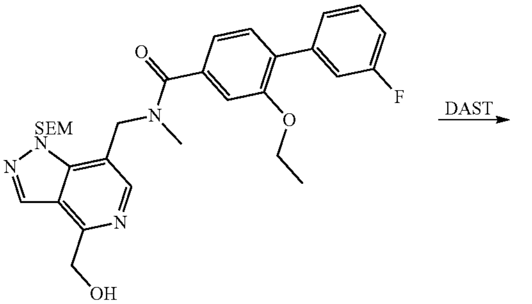

1

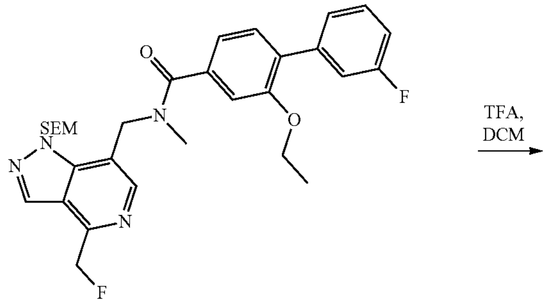

2

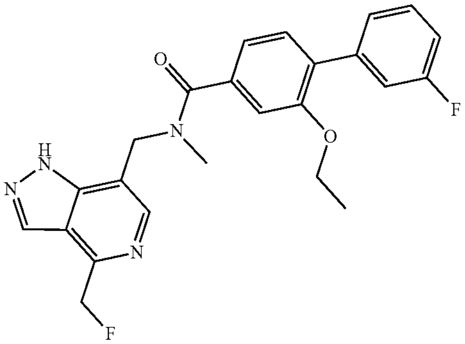

279

To a solution of Compound 1 (100 mg, 177.08 umol, 1 eq) in DCM (2 mL) was added DAST (57.09 mg, 354.16 umol, 46.79 uL, 2 eq) slowly, then the mixture was stirred at 0° C. for 1 hr. The reaction mixture was poured into saturated $NaHCO_3$ aqueous (5 mL) and extracted by ethyl acetate (10 mL×3), the combined organic phase was dried and concentrated under vacuum to give a residue. The residue was purified by prep-TLC (petroleum ether/ethyl acetate=0:1) to give Compound 2 (30 mg, 52.94 umol, 29.89% yield) as a yellow oil. LCMS: m/z=567.2 $(M+H)^+$ A mixture of Compound 2 (30 mg, 52.94 umol, 1 eq) in DCM (0.5 mL) and TFA (1 mL) was stirred at 20° C. for 1 hr. The reaction mixture was concentrated under vacuum to give a residue. The residue was purified by prep-HPLC (column: Phenomenex Luna C18 100*30 mm*5 um; mobile phase: [water(FA)-ACN]; B %: 32%-62%, 8 min), the purified solution was concentrated under vacuum to give Compound 279 (5.1 mg, 11.64 umol, 21.99% yield, 99.6% purity) as a white solid. LCMS: m/z=437.1 $(M+H)^+$ 1H NMR (400 MHz, CHLOROFORM-d) δ=12.40-12.17 (m, 1H), 8.43 (d, J=2.5 Hz, 1H), 8.27 (s, 1H), 7.36 (d, J=7.6 Hz, 2H), 7.33-7.28 (m, 2H), 7.10-7.03 (m, 3H), 5.94-5.75 (m, 2H), 4.96 (s, 2H), 4.07 (q, J=6.9 Hz, 2H), 3.05 (s, 3H), 1.38 (t, J=6.9 Hz, 3H).

Compound 248 was prepared in the same manner as compound 279 and was obtained as a red solid (35.2 mg, 80.47 umol, 53.74% yield, 100% purity). LCMS: m/z=438.3 (M+H)+1H NMR (400 MHz, CHLOROFORM-d) δ=12.90-11.57 (m, 1H), 8.44 (br s, 1H), 8.35-8.17 (m, 1H), 7.75 (br d, J=7.5 Hz, 1H), 7.54-7.46 (m, 1H), 7.42-7.33 (m, 3H), 7.09 (br t, J=8.4 Hz, 1H), 5.96-5.76 (m, 2H), 5.05-4.88 (m, 2H), 4.42 (q, J=7.0 Hz, 2H), 3.29-3.16 (m, 3H), 1.39 (br t, J=7.0 Hz, 3H).

Compound 257 was prepared in the same manner as compound 279 and was obtained as a red solid (16.6 mg, 37.35 umol, 53.66% yield, 100% purity). LCMS: m/z=445.1 (M+H)+1H NMR (400 MHz, CHLOROFORM-d) δ=8.60 (br s, 1H), 8.38 (s, 1H), 7.91 (s, 1H), 7.81 (br d, J=8.0 Hz, 1H), 7.76 (d, J=7.6 Hz, 1H), 7.69 (d, J=7.8 Hz, 1H), 7.60-7.51 (m, 2H), 6.27-6.00 (m, 2H), 5.02 (s, 2H), 4.43 (q, J=7.0 Hz, 2H), 3.27 (s, 3H), 1.39 (t, J=7.1 Hz, 3H).

Scheme 44

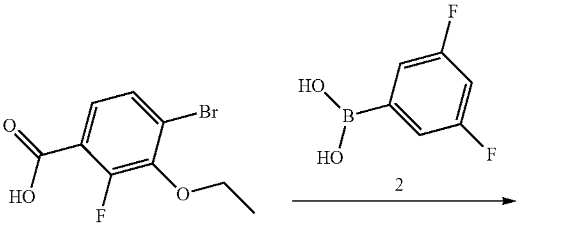

1

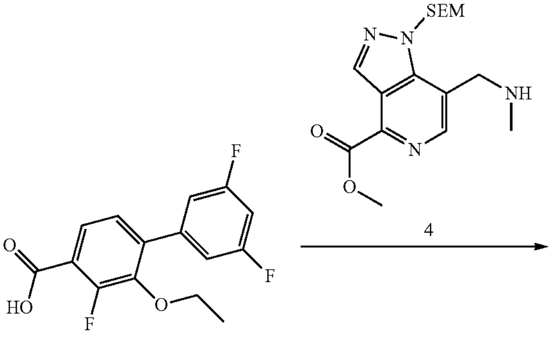

3

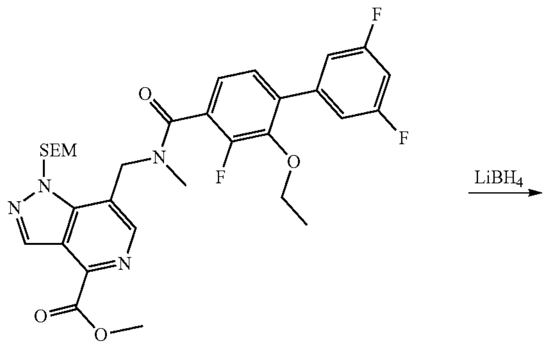

5

-continued

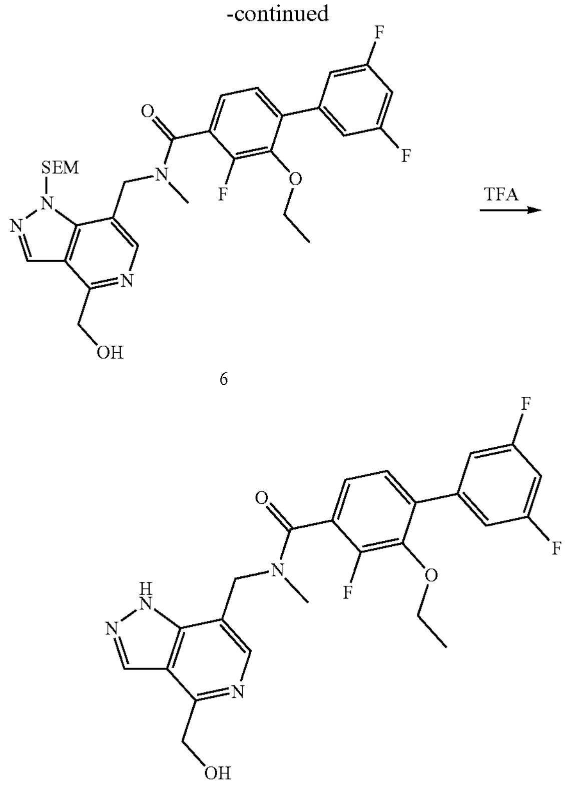

6

236

A mixture in 40 mL bottle of Compound 1 (1.1 g, 4.18 mmol, 1 eq), Compound 2 (990.47 mg, 6.27 mmol, 1.5 eq), $Pd(dppf)Cl_2 \cdot CH_2Cl_2$ (341.48 mg, 418.16 umol, 0.1 eq), $K_2CO_3$ (1.16 g, 8.36 mmol, 2 eq) in dioxane (12 mL), and then the mixture was stirred at 100° C. for 12 hr under $N_2$ atmosphere. After the reaction was completed and cooled, the reaction mixture was filtered by ethyl acetate (50 mL) in 100 mL stand-up bottle, the combined organic phase was dried and concentrated under vacuum to give residue. The residue was purified by RP-HPLC (column: 150 mm*H400 mm Welch Ultimate XB_C18 20-40 µm, 120 A; mobile phase: [water ($H_2O$)-ACN]; B %: 40% 10 min), the purified solution was concentrated under vacuum to give residue. Compound 3 (1 g, 3.38 mmol, 80.73% yield) was obtained as a yellow solid. LCMS: m/z=295.0 $(M-H)^+$ To a 40 mL bottle solution of Compound 4 (200 mg, 570.63 umol, 1 eq), Compound 3 (169.05 mg, 570.63 umol, 1 eq) in DCM (6 mL) was added EDCl (164.09 mg, 855.95 umol, 1.5 eq) and DMAP (6.97 mg, 57.06 umol, 0.1 eq). The mixture was stirred at 20° C. for 12 hr. The reaction mixture was poured into water (15 mL) and extracted by ethyl acetate (15 mL×3), the combined organic phase was dried and concentrated under vacuum to give residue. The residue was purified by column chromatography ($SiO_2$, Petroleum ether/Ethyl acetate=100/1 to 1/3). The purified solution was concentrated under vacuum to give a residue. Compound 5 (230 mg, 365.83 umol, 64.11% yield) was obtained as a green oil. LCMS: m/z=629.3 $(M+H)^+$ To a 100 mL round-bottomed flask solution of Compound 5 (225 mg, 357.87 umol, 1 eq) in THF (5 mL) was added $LiBH_4$ in THF (2 M, 536.81 uL, 3 eq). The mixture was stirred at 20° C. for 2 hr. The reaction mixture was poured into saturated $NH_4Cl$ aqueous (15 mL) and extracted by extracted by ethyl acetate (10 mL×3), the combined organic phase was dried and concentrated under vacuum to give a residue. The residue was purified by column chromatography ($SiO_2$, Petroleum ether/Ethyl acetate=100/1 to 0/1). The purified solution was concentrated under vacuum to give a residue. Compound 6 (65 mg, 108.21 umol, 30.24% yield) was obtained as a green oil. LCMS: m/z=601.3 $(M+H)^+$ To a 100 mL round-bottomed flask solution of Compound 6 (65 mg, 108.21 umol, 1 eq) in TFA (1 mL) was DCM (0.5 mL). The mixture was stirred at 20° C. for 1 hr. The reaction mixture was concentrated under vacuum to give residue. The residue was purified by prep-HPLC (column: Phenomenex luna C18 150*25 mm*10 um; mobile phase: [water (FA)-ACN]; B %: 20%-50%, 10 min), the purified solution was lyophilized to give a white solid. Compound 236 (17.1 mg, 36.35 umol, 33.59% yield, 100% purity) was obtained as a white solid. LCMS: m/z=471.1 $(M+H)^+$1H NMR (400 MHz, CHLOROFORM-d) δ ppm 11.88-12.18 (m, 1H) 8.24-8.32 (m, 2H) 7.14-7.19 (m, 2H) 7.11-7.14 (m, 1H) 7.09 (dd, J=8.25, 2.25 Hz, 2H) 6.81-6.88 (m, 1H) 5.15 (s, 2H) 4.96-5.00 (m, 2H) 3.89-3.97 (m, 2H) 2.99 (s, 3H) 1.21 (t, J=7.07 Hz, 3H).

Compound 240 was prepared in the same manner as compound 236 using (3-cyanophenyl)boronic acid in the first step. Compound 240 (10.1 mg, 21.08 umol, 63.42% yield, 98.4% purity) was obtained as white solid. LCMS: m/z=472.2 (M+H)+1H NMR (400 MHz, CHLOROFORM-d) δ=12.49-12.07 (m, 1H), 8.33 (s, 2H), 7.68-7.63 (m, 2H), 7.61-7.57 (m, 1H), 7.55-7.50 (m, 1H), 7.25 (s, 1H), 6.91 (d, J=9.0 Hz, 1H), 5.19 (s, 2H), 4.97 (s, 2H), 3.76 (td, J=2.9, 5.8 Hz, 1H), 3.10 (s, 3H), 0.85-0.78 (m, 2H), 0.74-0.67 (m, 2H).

Compound 241 was prepared in the same manner as compound 236 and was obtained as yellow solid (26.3 mg, 59.57 umol, 37.84% yield, 100% purity). LCMS: m/z=442.1 (M+H)+1H NMR (400 MHz, CHLOROFORM-d) δ=8.32-8.35 (m, 1H) 8.29 (s, 1H) 7.84-7.87 (m, 1H) 7.75-7.79 (m, 1H) 7.63 (dt, J=7.72, 1.33 Hz, 1H) 7.49-7.55 (m, 1H) 7.33 (d, J=7.75 Hz, 1H) 7.10 (dd, J=7.75, 1.50 Hz, 1H) 7.07-7.08 (m, 1H) 5.16 (s, 2H) 4.96 (s, 2H) 4.08 (q, J=6.92 Hz, 2H) 3.06 (s, 3H) 1.34-1.39 (m, 3H).

Scheme 45

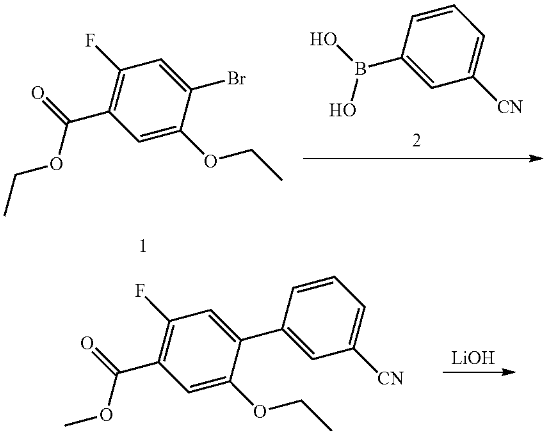

1

3

-continued

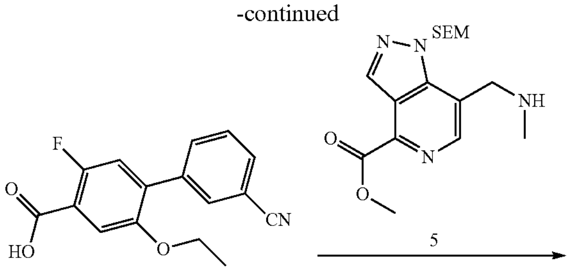

4

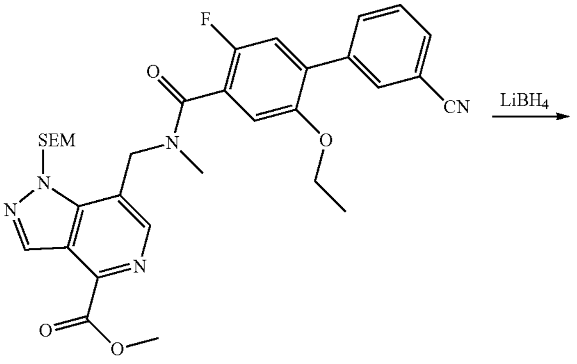

6

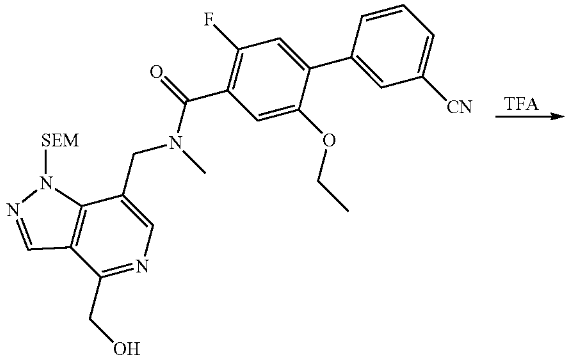

7

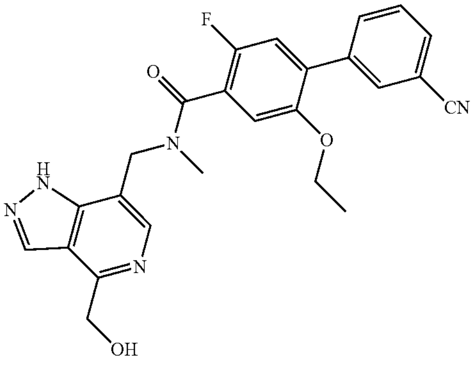

237

A mixture in 40 mL bottle of Compound 1 (500 mg, 1.72 mmol, 1 eq), Compound 2 (504.75 mg, 3.44 mmol, 2 eq), $K_2CO_3$ (474.75 mg, 3.44 mmol, 2 eq), $Pd(dppf)Cl_2 \cdot CH_2Cl_2$ (140.26 mg, 171.75 umol, 0.1 eq) in dioxane (10 mL) at 20° C., and then the mixture was stirred at 100° C. for 12 hr under $N_2$ atmosphere. After the reaction was completed and cooled, the reaction mixture was filtered by ethyl acetate (50 mL) in 100 mL stand-up bottle, the combined organic phase was dried and concentrated under vacuum to give residue. The residue was purified by column chromatography ($SiO_2$, Petroleum ether/Ethyl acetate=100/1 to 10/1). The purified solution was concentrated under vacuum to give a residue.

Compound 3 (425 mg, 1.36 mmol, 78.97% yield) was obtained as a white solid. 1H NMR (400 MHz, CHLOROFORM-d) δ ppm 7.87-7.91 (m, 1H) 7.75-7.81 (m, 1H) 7.63-7.68 (m, 1H) 7.52-7.57 (m, 1H) 7.48-7.51 (m, 1H) 7.09-7.14 (m, 1H) 4.40-4.47 (m, 2H) 4.07-4.12 (m, 2H) 1.40-1.46 (m, 3H) 1.35-1.40 (m, 3H)

To a 100 mL round-bottomed flask solution of Compound 3 (420 mg, 1.34 mmol, 1 eq) in MeOH (6 mL) and $H_2O$ (2 mL) was added $LiOH \cdot H_2O$ (168.75 mg, 4.02 mmol, 3 eq). The mixture was stirred at 20° C. for 3 hr. The solvents was removed by evaporated under reduced pressure, then the mixture was acidified by 1 N HCl to pH 4, The mixture was filtered and the filter cake was washed with 10 mL of MeOH, dried and in vacuum to give a residue. Compound 4 (290 mg, 1.02 mmol, 75.84% yield) was obtained as a white solid which was used in the next step. LCMS: m/z=284.0 $(M-H)^+$ To a 100 mL round-bottomed flask solution of Compound 4 (290 mg, 1.02 mmol, 1 eq), Compound 5 (356.30 mg, 1.02 mmol, 1 eq) in DCM (8 mL) was added EDCl (292.32 mg, 1.52 mmol, 1.5 eq) and DMAP (12.42 mg, 101.66 umol, 0.1 eq). The mixture was stirred at 20° C. for 3 hr. The reaction mixture was poured into water (15 mL) and extracted by ethyl acetate (15 mL×3), the combined organic phase was dried and concentrated under vacuum to give residue. The residue was purified by column chromatography ($SiO_2$, Petroleum ether/Ethyl acetate=10/1 to 0/1). The purified solution was concentrated under vacuum to give a residue. Compound 6 (440 mg, 712.27 umol, 70.07% yield) was obtained as a green oil. LCMS: m/z=618.3 (M+H)+

To a 100 mL round-bottomed flask solution of Compound 6 (440 mg, 712.27 umol, 1 eq) in MeOH (6 mL) was added $LiBH_4$ in THF (2 M, 1.07 mL, 3 eq) at 0° C. The mixture was stirred at 20° C. for 3 hr. The reaction mixture was poured into saturated $NH_4Cl$ aqueous (15 mL) and extracted by extracted by ethyl acetate (10 mL×3), the combined organic phase was dried and concentrated under vacuum to give a residue. Compound 7 (390 mg, 661.32 umol, 92.85% yield) was obtained as a green oil which was used in the next step. LCMS: m/z=590.3 $(M+H)^+$ To a 100 mL round-bottomed flask solution of Compound 7 (90 mg, 152.61 umol, 1 eq) in TFA (1 mL) and DCM (0.5 mL). The mixture was stirred at 20° C. for 2 hr. LCMS (5-95 AB/0.8 min) showed desired mass was detected. The reaction mixture was concentrated under vacuum to give residue. The residue was purified by prep-HPLC (column: Phenomenex luna C18 150*25 mm*10 um; mobile phase: [water (FA)-ACN]; B %: 15%-45%, 10 min), the purified solution was lyophilized to give a white solid. Compound 237 (32.1 mg, 69.86 umol, 45.78% yield, 100% purity) was obtained as a white solid. LCMS: m/z=460.2 $(M+H)^+$1H NMR (400 MHz, CHLOROFORM-d) δ ppm 12.10-12.29 (m, 1H) 8.32 (br d, J=9.38 Hz, 2H) 7.84-7.86 (m, 1H) 7.73-7.77 (m, 1H) 7.64-7.68 (m, 1H) 7.51-7.57 (m, 1H) 7.06-7.10 (m, 1H) 6.94-6.98 (m, 1H) 5.16-5.21 (m, 2H) 4.98 (br s, 2H) 4.00-4.06 (m, 2H) 3.00-3.04 (m, 3H) 1.33-1.37 (m, 3H).

Compound 239 was prepared in the same manner as compound 237 using (3,5-difluorophenyl)boronic acid in the first step. Compound 239 (24.5 mg, 54.15 umol, 52.59% yield, 100% purity) was obtained as off-white solid. LCMS: m/z=453.1 $(M+H^+)$ $^1H$ NMR: (400 MHz, CHLOROFORM-d) δ=8.69-8.29 (m, 2H), 7.35 (br d, J=7.1 Hz, 1H), 7.08 (br d, J=7.1 Hz, 4H), 6.89-6.73 (m, 1H), 5.31 (br s, 2H), 5.00 (br s, 2H), 4.08 (br d, J=6.5 Hz, 2H), 3.09 (br s, 3H), 1.39 (br t, J=5.9 Hz, 3H).

Compound 243 was prepared in the same manner as compound 237 and was obtained as a white solid (15.7 mg, 33.30 umol, 66.79% yield, 100% purity). LCMS: m/z=472.2 ($M+H^+$) $^1H$ NMR: (400 MHz, CHLOROFORM-d) δ=12.58-12.07 (m, 1H), 8.43-8.38 (m, 1H), 8.38-8.32 (m, 1H), 7.81-7.76 (m, 1H), 7.75-7.66 (m, 2H), 7.59-7.52 (m, 1H), 7.21-7.15 (m, 2H), 5.24 (s, 2H), 5.05-4.97 (m, 2H), 3.91 (qt, J=2.9, 6.0 Hz, 1H), 3.03 (d, J=1.5 Hz, 3H), 0.52-0.43 (m, 4H).

Compound 244 was prepared in the same manner as compound 237 and was obtained as a light red solid (10.5 mg, 23.01 umol, 14.93% yield, 99.4% purity). LCMS: m/z=454.2 ($M+H^+$) $^1H$ NMR: (400 MHz, CHLOROFORM-d) δ=12.42-12.09 (m, 1H), 8.30-8.25 (m, 2H), 7.79-7.76 (m, 1H), 7.71-7.67 (m, 1H), 7.65-7.61 (m, 1H), 7.54-7.48 (m, 1H), 7.48-7.45 (m, 1H), 7.33-7.30 (m, 1H), 7.16-7.11 (m, 1H), 5.16-5.13 (m, 2H), 4.99-4.95 (m, 2H), 3.82-3.75 (m, 1H), 3.10-3.05 (m, 3H), 0.87-0.81 (m, 2H), 0.78-0.71 (m, 2H).

Compound 245 was prepared in the same manner as compound 237 and was obtained as a white solid (40.7 mg, 91.16 umol, 65.72% yield, 100% purity). LCMS: m/z=447.3 ($M+H^+$) $^1H$ NMR: (400 MHz, CHLOROFORM-d) δ=8.52-8.47 (m, 1H), 8.43-8.36 (m, 1H), 7.47-7.43 (m, 1H), 7.40-7.32 (m, 2H), 7.26-7.16 (m, 2H), 7.15-7.09 (m, 1H), 7.07-7.00 (m, 1H), 5.34-5.23 (m, 2H), 5.01 (s, 2H), 3.81-3.74 (m, 1H), 3.11 (s, 3H), 2.03-2.00 (m, 1H), 0.85-0.79 (m, 2H), 0.79-0.73 (m, 2H).

Compound 247 was prepared in the same manner as compound 237 and was obtained as a white solid (8 mg, 17.50 umol, 34% yield, 99% purity). LCMS: m/z=453.1 ($M+H^+$) $^1H$ NMR: (400 MHz, CHLOROFORM-d) δ=8.55 (s, 1H), 8.42 (s, 1H), 7.38 (dd, J=6.0, 8.0 Hz, 1H), 7.30 (s, 2H), 7.13-7.05 (m, 2H), 6.93 (d, J=5.6 Hz, 1H), 5.33 (s, 2H), 5.02 (br s, 2H), 4.02 (q, J=7.0 Hz, 2H), 3.06 (d, J=1.4 Hz, 3H), 1.36 (t, J=7.0 Hz, 3H).

Scheme 46

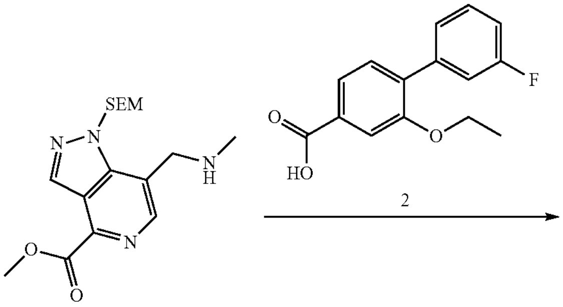

1

-continued

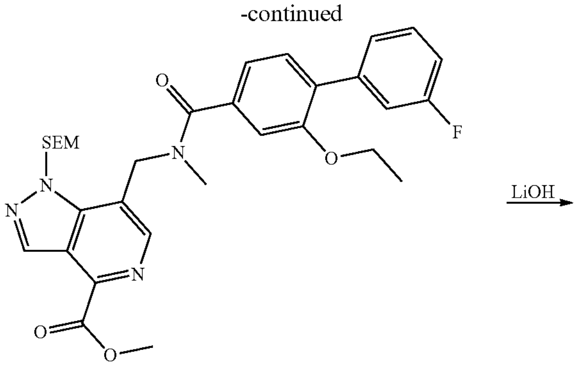

3

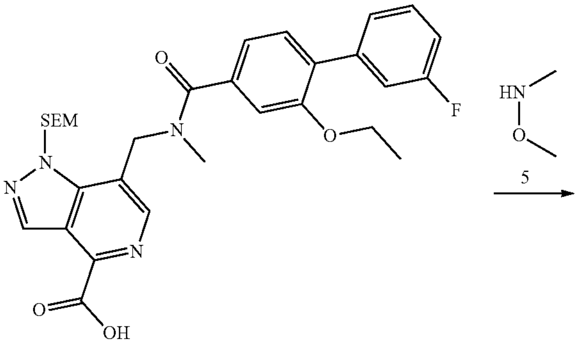

4

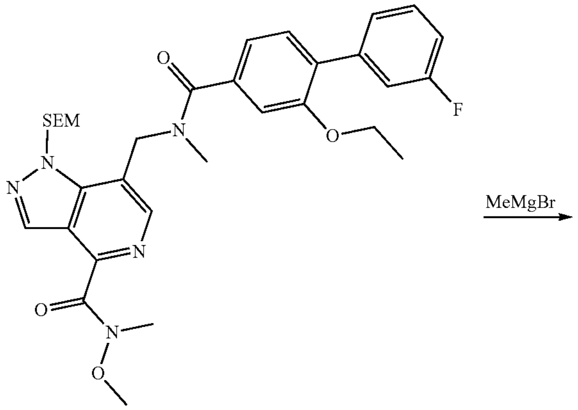

6

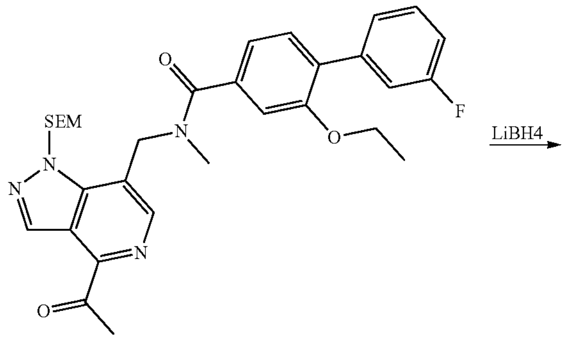

7

-continued

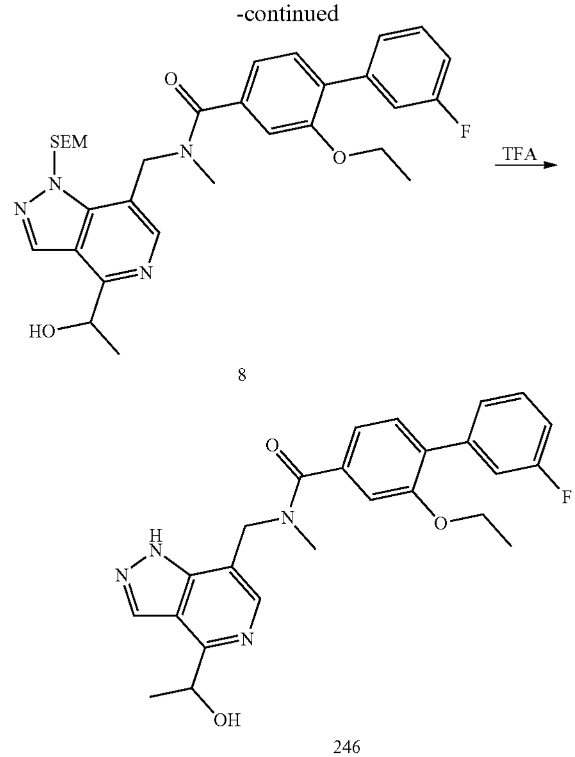

8

246

To a solution of Compound 1 (202.00 mg, 576.35 umol, 1.5 eq) and Compound 2 (100 mg, 384.23 umol, 1 eq) in DCM (5 mL) was added EDCl (110.49 mg, 576.35 umol, 1.5 eq) and DMAP (4.69 mg, 38.42 umol, 0.1 eq), the reaction mixture was stirred at 20° C. for 12 hr. The reaction mixture was concentrated to give a crude product. The crude product was purified by prep-TLC (petroleum ether:ethyl acetate=0: 1, desired compound Rf=0.6). Compound 3 (200 mg, 337.42 umol, 87.82% yield) was obtained as yellow solid. LCMS: m/z=593.2 (M+H+)

To a solution of methyl Compound 3 (200 mg, 337.42 umol, 1 eq) in H2O (2 mL), MeOH (2 mL) and THF (2 mL) was added LiOH·$H_2O$ (70.80 mg, 1.69 mmol, 5 eq), the reaction mixture was stirred at 20° C. for 12 hr. After the reaction was completed, the mixture was extracted with EtOAc (25 mL×3), the combined organic phase was washed with brine (50 ml), dried over anhydrous $Na_2SO_4$, and concentrated to give a crude product. The crude product was used to the next step without purification. Compound 4 (160 mg, 276.48 umol, 81.94% yield) was obtained as brown solid. LCMS: m/z=579.2 (M+H+)

To a solution of Compound 4 (160 mg, 276.48 umol, 1 eq) in DMF (5 mL) was added Compound 5 (40.45 mg, 414.72 umol, 1.5 eq), DIPEA (71.47 mg, 552.96 umol, 96.32 uL, 2 eq) and HATU (157.69 mg, 414.72 umol, 1.5 eq), the mixture was stirred at 20° C. for 12 hr. After the reaction was completed, the mixture was extracted with EtOAc (25 mL×3), the combined organic phase was washed with brine (50 ml), dried over anhydrous $Na_2SO_4$, and concentrated to give a crude product. The crude product was purified by prep-TLC (petroleum ether:ethyl acetate=0:1, desired compound Rf=0.6. Compound 6 (200 mg, crude) was obtained as brown oil. LCMS: m/z=622.2 (M+H+)

To a solution of Compound 6 (200 mg, 321.66 umol, 1 eq) in 2-MeTHF (4 mL) was added MeMgBr in THF (3 M, 214.44 uL, 2 eq) slowly at 0° C. under $N_2$, the reaction mixture was stirred at 20° C. for 12 hr under N2. The mixture was poured into saturated $NH_4Cl$ (25 mL) solution, and extracted with EtOAc (25 mL×3), the combined organic phase was washed with brine (25 mL), dried over anhydrous $Na_2SO_4$, and concentrated to give a crude product The crude product was purified by rep-TLC (petroleum ether:ethyl acetate=0:1, desired compound Rf=0.8). Compound 7 (146 mg, 253.15 umol, 78.70% yield) was obtained as brown oil. LCMS: m/z=577.2 (M+H+)

To a solution of Compound 7 (140 mg, 242.75 umol, 1 eq) in MeOH (5 mL) was added LiBH4 in THF (2 M, 364.12 uL, 3 eq) slowly at 0° C., the reaction mixture was stirred at 20° C. for 12 hr. The reaction mixture was poured into saturated $NH_4Cl$ (10 mL) and extracted by ethyl acetate (10 mL×3), the combined organic phase was dried and concentrated under vacuum to give a crude product. The crude product was purified by prep-TLC (dichloromethane:methanol=10: 1, desired compound Rf=0.6). Compound 8 (110 mg, 190.07 umol, 78.30% yield) was obtained as off-white oil. LCMS: m/z=579.2 (M+H+)

To a solution of Compound 8 (110 mg, 190.07 umol, 1 eq) in DCM (2 mL) was added TFA (1.54 g, 13.51 mmol, 1 mL, 71.06 eq), the reaction mixture was stirred at 20° C. for 1 hr. The reaction mixture was concentrated to give a crude product. The crude product was purified by prep-HPLC (column: Phenomenex luna C18 150*25 mm*10 um; mobile phase: [water (FA)-ACN]; B %: 18%-48%, 9 min). After prep-HPLC purification, the eluent was concentrated to remove organic solvents. The residual aqueous solution was lyophilized to give white solid. Compound 246 (51.2 mg, 114.16 umol, 60.06% yield, and 100% purity) was obtained as white solid. LCMS: m/z=449.1 (M+H+) $^1H$ NMR: (400 MHz, CHLOROFORM-d) δ=13.01-12.49 (m, 1H), 8.47 (s, 1H), 8.35 (s, 1H), 7.45-7.36 (m, 2H), 7.35-7.29 (m, 2H), 7.15-7.03 (m, 3H), 5.55-5.42 (m, 1H), 4.99 (br d, J=3.8 Hz, 2H), 4.09 (q, J=7.0 Hz, 2H), 3.11 (s, 3H), 1.78 (d, J=6.8 Hz, 3H), 1.40 (t, J=6.9 Hz, 3H).

Scheme 47

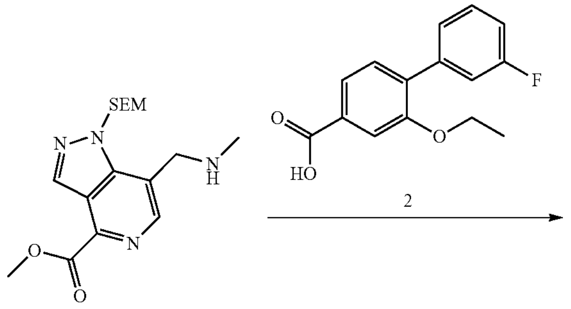

1

2

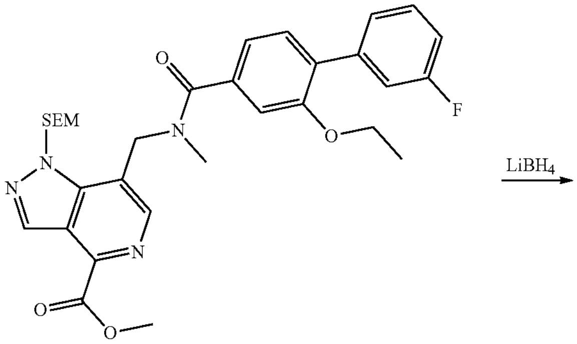

3

-continued

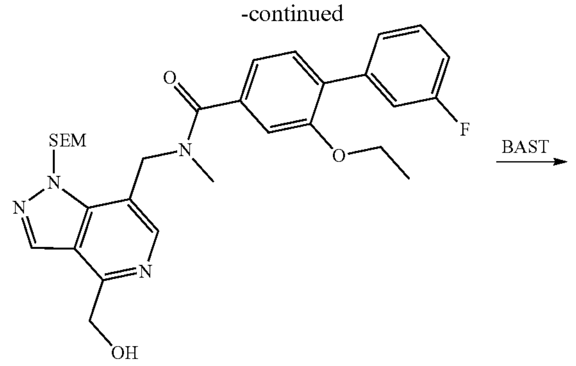

4

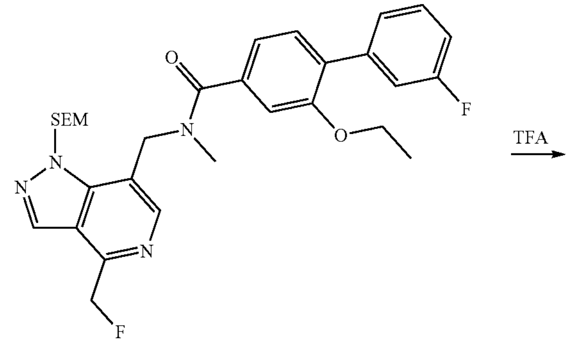

5

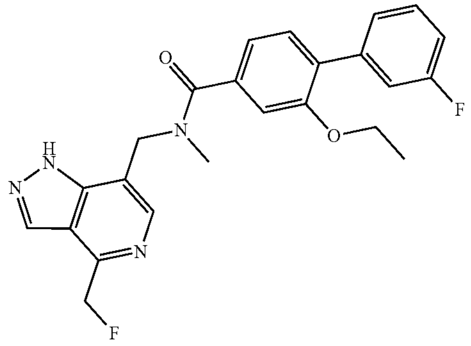

279

To a solution of Compound 2 (371.28 mg, 1.43 mmol, 1 eq) in DCM (10 mL) was added Compound 1 (500 mg, 1.43 mmol, 1 eq), EDCl (410.22 mg, 2.14 mmol, 1.5 eq), DMAP (17.43 mg, 142.66 umol, 0.1 eq), then the mixture was stirred at 20° C. for 1 hr. The reaction mixture was concentrated under vacuum to give a residue. The residue was purified by column chromatography ($SiO_2$, Petroleum ether/Ethyl acetate=1/1 to 0/1), the purified solution was concentrated under vacuum to give Compound 3 (600 mg, 1.01 mmol, 70.96% yield) as a yellow oil. LCMS: m/z=593.9 $(M+H)^+$1H NMR (400 MHz, CHLOROFORM-d) δ=8.78 (s, 1H), 8.64-8.55 (m, 1H), 7.37 (br s, 4H), 7.23-7.05 (m, 3H), 6.09-5.74 (m, 2H), 5.57-5.29 (m, 2H), 4.25-4.15 (m, 5H), 3.74-3.48 (m, 2H), 3.30-3.13 (m, 3H), 1.51-1.36 (m, 3H), 1.08-0.78 (m, 2H), 0.10--0.09 (m, 9H) The mixture of Compound 3 (400 mg, 674.84 umol, 1 eq) in MeOH (10 mL) was added $LiBH_4$ in THF (2 M, 674.84 uL, 2 eq), then the reaction was stirred at 20° C. for 1 hr.

The mixture was added $LiBH_4$ in THF (2 M, 674.84 uL, 2 eq), then the mixture was stirred at 20° C. for 1 hr. The reaction mixture was poured into saturated $NH_4Cl$ (50 mL) and extracted by ethyl acetate (50 mL×3), the combined organic phase was dried and concentrated under vacuum to give a residue. The residue was purified by column chromatography ($SiO_2$, Petroleum ether/Ethyl acetate=1/4), the purified solution was concentrated under vacuum to give Compound 4 (250 mg, 442.70 umol, 65.60% yield) as a yellow oil. LCMS: m/z=565.5 $(M+H)^+$ To a solution of Compound 4 (230 mg, 407.28 umol, 1 eq) in DCM (3 mL) was added BAST (180.21 mg, 814.56 umol, 178.43 uL, 2 eq), the mixture was stirred at 0-20° C. for 1 hr. The reaction mixture was poured into saturated $NaHCO_3$ aqueous (10 mL) and extracted by ethyl acetate (10 mL×3), the combined organic phase was dried and concentrated under vacuum to give a residue. The residue was purified by prep-TLC ($SiO_2$, Petroleum ether/Ethyl acetate=0/1), the purified solution was concentrated under vacuum to give Compound 5 (70 mg, 123.52 umol, 30.33% yield) as a yellow oil. LCMS: m/z=567.2 $(M+H)^+$ To a solution of Compound 5 (70 mg, 123.52 umol, 1 eq) in TFA (1 mL) was stirred at 20° C. for 1 hr. The reaction mixture was basified by saturated $NaHCO_3$ aqueous (10 mL), then the reaction mixture was diluted with $H_2O$ (10 mL) and extracted with EA (10 mL×3). The combined organic layers were washed with brine, dried over $Na_2SO_4$, filtered and concentrated under reduced pressure to give a residue. The residue was purified by prep-HPLC (column: Phenomenex luna C18 150*25 mm*10 um; mobile phase: [water(FA)-ACN]; B %: 38%-68%, 9 min), the purified solution was lyophilized to give Compound 279 (17 mg, 37.63 umol, 30.46% yield, 96.6% purity) as an orange solid. LCMS: m/z=437.1 $(M+H)^+$1H NMR (400 MHz, CHLOROFORM-d) δ=12.47-12.07 (m, 1H), 8.46-8.41 (m, 1H), 8.31-8.23 (m, 1H), 7.41-7.34 (m, 2H), 7.31 (br d, J=7.5 Hz, 2H), 7.12-7.01 (m, 3H), 5.95-5.73 (m, 2H), 5.01-4.89 (m, 2H), 4.11-4.04 (m, 2H), 3.05 (s, 3H), 1.38 (t, J=6.9 Hz, 3H).

Scheme 48

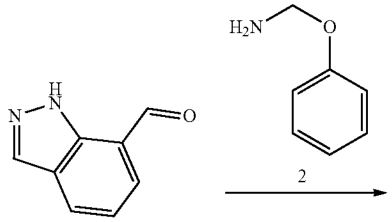

1

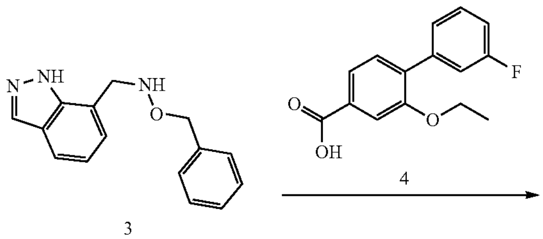

3

-continued

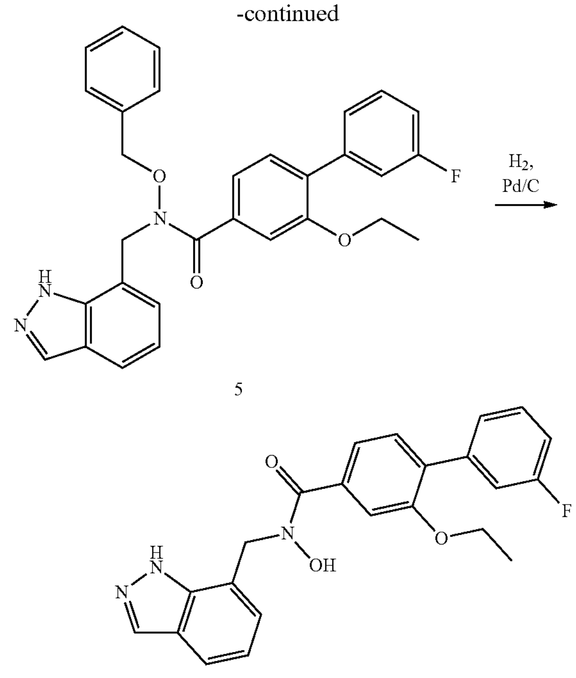

5

388

To the solution of compound 1 (500 mg, 3.42 mmol, 1 eq) and 2 (505.60 mg, 4.11 mmol, 1.2 eq) in MeOH (10 mL) was added in AcOH (20.55 mg, 342.12 umol, 19.57 uL, 0.1 eq). The mixture was stirred at 20° C. for 2 h. The mixture was added in borane; 2-methylpyridine (1.10 g, 10.26 mmol, 3 eq) at 0° C. and stirred for 5 min. The mixture was added in HCl (3 M, 11.40 mL, 10 eq) at 0° C. The mixture was stirred at 20° C. for 12 h. After cooling to 0° C., the mixture was added $Na_2CO_3$ (1 g), the solution was filtered, the mixture was extracted by ethyl acetate(500 mL×3), the combined organic phase was dried and concentrated under vacuum to give a residue. The residue was purified by column chromatography ($SiO_2$, Petroleum ether/Ethyl acetate=10/1 to 5/1. The compound of 3 (200 mg, 789.58 umol, 23.08% yield) was obtained as yellow solid. LCMS: m/z=254.1 ($M+H^+$)

To a solution of 3 (180 mg, 710.62 umol, 1 eq) and 4 (221.94 mg, 852.75 umol, 1.2 eq) in DCM (5 mL) was added EDCl (204.34 mg, 1.07 mmol, 1.5 eq) and DMAP (8.68 mg, 71.06 umol, 0.1 eq) in stand-up flask at 20° C. The mixture was stirred at 20° C. for 12 h. Evaporate the solution on a water bath under reduced pressure using a rotary evaporator. Then the crude product was purified by prep-HPLC. Column: Waters xbridge 150*25 mm 10 um; mobile phase: [water($NH_4HCO_3$)-ACN]; B %: 55%-85%, 8 min. LCMS: m/z=496.3 ($M+H^+$)

To a solution of 35 mL hydrogenated bottle of 5 (130 mg, 262.34 umol, 1 eq) in MeOH (5 mL) was added Pd/C (130 mg, 262.34 umol, 10% purity, 1 eq) at 20° C. The mixture was stirred at 30° C. for 1 h under H2 (528.82 ug, 262.34 umol, 1 eq) (15 PSI). After the reaction was completed, the mixture was filtered under N2 atmosphere, the filtrated was concentrated. The crude product was purified by prep-HPLC. column: Welch Xtimate C18 150*25 mm*5 um; mobile phase: [water($NH_3H_2O$)-ACN]; B %: 35%-65%, 8 min. lyophilized. The compound 388 (9.71 mg, 23.70 umol, 9.03% yield, 98.945% purity) was obtained as white solid. LCMS: m/z=406.3 ($M+H^+$). $^1H$ NMR: (400 MHz, DMSO-$d_6$) δ=12.95 (br s, 1H), 10.96-9.47 (m, 1H), 8.13 (s, 1H), 7.72 (d, J=8.1 Hz, 1H), 7.51-7.31 (m, 7H), 7.21-7.12 (m, 2H), 5.17 (s, 2H), 4.05 (br d, J=6.5 Hz, 2H), 1.26 (br t, J=6.8 Hz, 3H).

Scheme 49

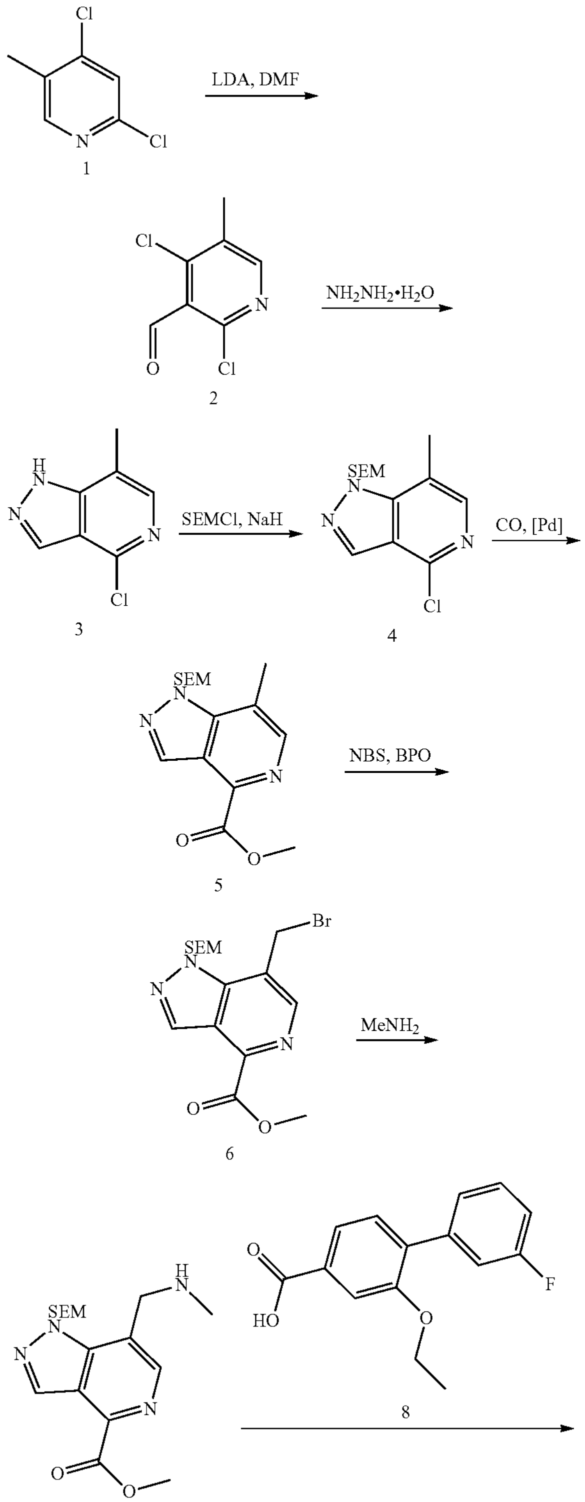

1

2

3

4

5

6

8

7

-continued

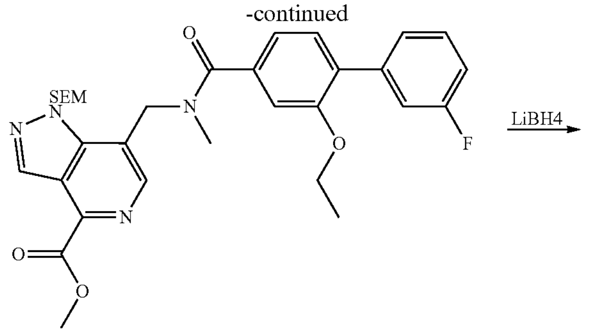

9

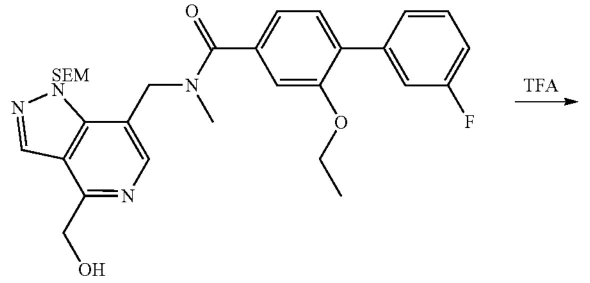

10

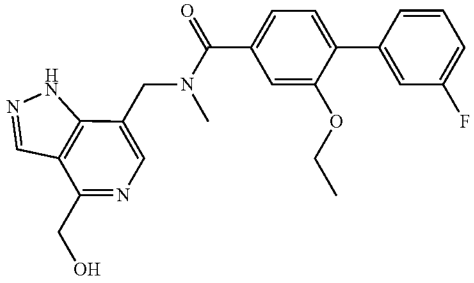

280

To a solution of Compound 1 (25 g, 154.31 mmol, 1 eq) in 2-MeTHF (200 mL) was added LDA (2 M, 115.73 mL, 1.5 eq) under −70° C., then the mixture was stirred at −70° C. for 1 h. DMF (22.56 g, 308.61 mmol, 23.74 mL, 2 eq) was added into the reaction mixture, the resulting mixture was stirred at −70° C. for 2 h under $N_2$ atmosphere. The reaction mixture was quenched by $NH_4Cl$ (500 mL) and extracted by ethyl acetate (500 mL×3), the combined organic phase was dried and concentrated under vacuum to give Compound 2 (58 g, 305.22 mmol, 98.90% yield) as a brown oil which was used directly in the next step.

To a solution of Compound 2 (58 g, 305.22 mmol, 1 eq) in DME (600 mL) was added $N_2H_4{\cdot}H_2O$ (61.12 g, 1.22 mol, 59.34 mL, 100% purity, 4 eq), then the mixture was stirred at 80° C. for 2 hr. The reaction mixture was poured into water (1 L) and extracted by ethyl acetate (1 L×3), the combined organic phase was dried and concentrated under vacuum to give a residue. The crude product was purified by silica gel column chromatography eluted with PE:EtOAc=5:1-1:1 to give Compound 3 (40 g, 238.67 mmol, 78.20% yield) as a yellow solid. LCMS: m/z=168.0 $(M+H)^+$ To a solution of Compound 3 (40 g, 238.67 mmol, 1 eq) in 2-MeTHF (400 mL) was added NaH (14.32 g, 358.01 mmol, 60% purity, 1.5 eq) slowly under 0° C., then the mixture was stirred at 0° C. for 1 h, SEM-Cl (59.69 g, 358.01 mmol, 63.36 mL, 1.5 eq) was added into the reaction mixture slowly, the resulting mixture was stirred at 20° C. for 2 h. LCMS (5-95AB/0.8 min) showed desired mass was detected. The reaction mixture was poured into saturated aqueous $NH_4Cl$ (1 L) and extracted by ethyl acetate (1 L×3), the combined organic phase was dried and concentrated under vacuum to give a residue. The residue was purified by silica on column chromatography eluted by petroleum ether/ethyl acetate=5:1, the purified solution was concentrated under vacuum to give Compound 4 (10 g, 33.57 mmol, 14.07% yield) as a yellow oil. LCMS: m/z=298.1 $(M+H)^+$ A solution of Compound 4 (5 g, 16.79 mmol, 1 eq), TEA (3.40 g, 33.57 mmol, 4.67 mL, 2 eq) and Pd(dppf) $Cl_2{\cdot}CH_2Cl_2$ (685.43 mg, 839.33 umol, 0.05 eq) in MeOH (50 mL) was stirred at 80° C. for 12 hr under CO(50 psi) atmosphere. The reaction was filtered and concentrated under vacuum to give a residue. The residue was purified by silica on column chromatography eluted by petroleum ether/ethyl acetate=5:1 to give a green solid. Compound 5 (4.4 g, 13.69 mmol, 81.54% yield) was obtained as a green solid. LCMS: m/z=322.2 $(M+H)^+$ A mixture of Compound 5 (4.2 g, 13.07 mmol, 1 eq), NBS (3.49 g, 19.60 mmol, 1.5 eq) and BPO (316.49 mg, 1.31 mmol, 0.1 eq) in trifluoromethylbenzene (50 mL) was stirred at 80° C. for 12 hr. The reaction mixture was poured into water (20 mL) and extracted by ethyl acetate (20 mL×3), the combined organic phase was dried and concentrated under vacuum to give a residue. The residue was purified by silica on column chromatography eluted by petroleum ether/ethyl acetate=5:1, the purified solution was concentrated to give Compound 6 (1 g, 2.50 mmol, 19.13% yield) a brown oil. LCMS: m/z=401.9 $(M+H)^+$ To a solution of methanamine (2 M, 3.75 mL, 3 eq) in 2-MeTHF (10 mL) was added Compound 6 (1 g, 2.50 mmol, 1 eq) slowly, then the mixture was stirred at 20° C. for 1 hr. The reaction mixture was filtered and the filtrate was concentrated under vacuum to give Compound 7 (1 g, crude) as a brown oil. LCMS: m/z=351.1 (M+H)+

To a solution of Compound 7 (300 mg, 855.95 umol, 1 eq) and Compound 8 (222.77 mg, 855.95 umol, 1 eq) in DCM (4 mL) was added EDCI (246.13 mg, 1.28 mmol, 1.5 eq) and DMAP (10.46 mg, 85.60 umol, 0.1 eq). The mixture was stirred at 20° C. for 12 hr. The reaction mixture was poured into water (20 mL) and extracted by ethyl acetate (20 mL×3), the combined organic phase was dried and concentrated under vacuum to give residue.

The residue was purified by column chromatography ($SiO_2$, Petroleum ether/Ethyl acetate=100/1 to 1/1). The purified solution was concentrated under vacuum to give Compound 9 (308 mg, 519.63 umol, 60.71% yield) as a yellow oil. LCMS: m/z=593.5 $(M+H)^+$ To a solution of Compound 9 (250 mg, 421.78 umol, 1 eq) in MecOH (10 mL) was added $LiBH_4$ (2 M, 316.33 uL, 1.5 eq) under 0° C., the resulting mixture was stirred at 20° C. for 1 h. The reaction mixture was quenched by saturated $NH_4Cl$ aqueous (10 mL), the resulting mixture was concentrated under vacuum to give Compound 10 (130 mg, 230.20 umol, 54.58% yield) as a yellow oil which was used directly in the next step. LCMS: m/z=593.4 $(M+H)^+$ A mixture of Compound 10 (30 mg, 53.12 umol, 1 eq) in TFA (1 mL) was stirred at 20° C. for 1 hr. The reaction mixture was concentrated under vacuum to give a residue. The residue was purified by prep-HPLC (column: Phenomenex luna C18 150*25 mm*10 um; mobile phase: [water (FA)-ACN]; B %: 16%-46%, 9 min), the purified solution was concentrated under vacuum to give Compound 280 (6.9 mg, 15.41 umol, 29.00% yield, 97% purity) as a white solid. LCMS: m/z=435.1 (M+H)*1H NMR (400 MHz, CHLOROFORM-d) δ=12.77-12.17 (m, 1H), 8.44-8.19 (m, 2H), 7.36 (d, J=7.8 Hz, 2H), 7.31 (br d, J=7.8 Hz, 2H), 7.11-7.01

(m, 3H), 5.20 (s, 2H), 4.96 (s, 2H), 4.07 (q, J=6.9 Hz, 2H), 3.07 (s, 3H), 1.37 (t, J=6.9 Hz, 3H).

Example 2: THP-1 Cell-Based NLRP3 Activation Assay

THP-1 cells are cultured in complete media (CM) until they reach logarithmic growth and achieve a viability >90%. CM is composed of RPMI-1640 (+Glutamax)/10% fetal bovine serum/55 μM β-mercaptoethanol/pen/strep. Cells are spun down and resuspended to 1,000,000 cells/mL in CM containing either 20 nM or 500 nM PMA. 150,000 cells (150 μL) are then added to each well of a 96-well TC plate and incubated for either 24 hr or 3 hr, respectively, in a standard cell culture incubator (37° C.; 5% $CO_2$). After this incubation, the plate is tilted and media carefully removed. 200 μL of CM containing 100 ng/mL LPS is then added to the wells and the cells incubated an additional 3 hrs. The media is again removed and replaced with Opti-Mem medium containing pre-determined dilutions of test compounds in replicate wells. After a 30 min pre-incubation with test compound, 10 μM nigericin (final concentration) in Opti-Mem medium with the corresponding concentration of compound is added to the wells for an additional 1 hr. Positive control wells contain 10 μM nigericin in Opti-Mem in the absence of test compound, while negative control wells contain Opti-Mem only. Supernatants are then transferred to a fresh 96-well plate for storage and assayed for IL-1β (human; DuoSet; R&D) and for TNFα (human; DuoSet; R&D) levels and relative pyroptosis using a CytoTox 96 Kit (do not freeze prior to testing; Promega). Once supernatants are removed, the relative viability of adherent cells in the 96-well TO plate are determined using a CellTiter-Glo® luminescent cell viability assay (Promega).

Table 1 below provides $IC_{50}$ data for the compounds disclosed herein where "+" is indicative of an $IC_{50}$ value of <50 uM, "++" is indicative of an $IC_{50}$ value of <10 uM, and "+++" is indicative of an $IC_{50}$ value of <1 uM.

| Compound No. | $IC_{50}$ |
|---|---|
| 001 | + |
| 002 | ++ |
| 003 | ++ |
| 004 | ++ |
| 005 | ++ |
| 006 | + |
| 007 | ++ |
| 008 | + |
| 009 | ++ |
| 010 | ++ |
| 011 | ++ |
| 012 | ++ |
| 013 | ++ |
| 014 | ++ |
| 015 | + |
| 016 | + |
| 017 | + |
| 018 | + |
| 019 | + |
| 020 | ++ |
| 021 | ++ |
| 022 | ++ |
| 028 | + |
| 029 | +++ |
| 030 | ++ |
| 031 | ++ |
| 032 | + |
| 033 | +++ |
| 034 | ++ |
| 035 | ++ |

-continued

| Compound No. | $IC_{50}$ |
|---|---|
| 036 | +++ |
| 037 | + |
| 038 | +++ |
| 039 | + |
| 040 | + |
| 041 | + |
| 042 | + |
| 043 | +++ |
| 044 | +++ |
| 045 | + |
| 046 | +++ |
| 047 | +++ |
| 048 | ++ |
| 049 | +++ |
| 050 | ++ |
| 051 | + |
| 052 | ++ |
| 053 | ++ |
| 054 | + |
| 055 | + |
| 056 | + |
| 057 | + |
| 058 | ++ |
| 059 | ++ |
| 060 | + |
| 061 | ++ |
| 062 | ++ |
| 063 | +++ |
| 064 | +++ |
| 065 | + |
| 066 | + |
| 067 | + |
| 068 | + |
| 069 | + |
| 070 | + |
| 071 | ++ |
| 072 | +++ |
| 073 | + |
| 074 | + |
| 075 | +++ |
| 076 | +++ |
| 077 | + |
| 078 | + |
| 079 | + |
| 080 | +++ |
| 081 | + |
| 082 | +++ |
| 083 | ++ |
| 084 | + |
| 085 | +++ |
| 086 | + |
| 087 | + |
| 088 | + |
| 089 | + |
| 090 | + |
| 091 | + |
| 092 | + |
| 093 | + |
| 094 | + |
| 095 | + |
| 096 | + |
| 097 | + |
| 099 | + |
| 100 | + |
| 101 | ++ |
| 102 | + |
| 103 | + |
| 104 | + |
| 105 | + |
| 106 | + |
| 107 | + |
| 108 | + |
| 109 | + |
| 110 | + |
| 111 | + |
| 112 | + |
| 113 | + |

-continued

| Compound No. | $IC_{50}$ |
|---|---|
| 114 | ++ |
| 115 | + |
| 116 | ++ |
| 117 | +++ |
| 118 | ++ |
| 119 | ++ |
| 120 | ++ |
| 121 | + |
| 122 | + |
| 123 | + |
| 124 | ++ |
| 125 | + |
| 126 | ++ |
| 127 | ++ |
| 128 | +++ |
| 129 | + |
| 130 | ++ |
| 131 | ++ |
| 132 | +++ |
| 133 | +++ |
| 134 | +++ |
| 135 | + |
| 136 | ++ |
| 137 | ++ |
| 138 | +++ |
| 139 | + |
| 140 | + |
| 141 | + |
| 142 | + |
| 143 | + |
| 144 | +++ |
| 145 | ++ |
| 146 | + |
| 147 | +++ |
| 148 | + |
| 149 | + |
| 150 | + |
| 151 | +++ |
| 152 | + |
| 153 | + |
| 154 | +++ |
| 155 | +++ |
| 156 | + |
| 157 | + |
| 158 | + |
| 151 | +++ |
| 152 | + |
| 153 | + |
| 154 | +++ |
| 155 | +++ |
| 156 | + |
| 157 | + |
| 158 | + |
| 159 | + |
| 160 | + |
| 161 | + |
| 162 | + |
| 163 | + |
| 164 | +++ |
| 165 | + |
| 166 | +++ |
| 167 | ++ |
| 168 | + |
| 169 | ++ |
| 170 | + |
| 171 | ++ |
| 172 | + |
| 173 | + |
| 174 | + |
| 175 | + |
| 176 | ++ |
| 177 | ++ |
| 178 | ++ |
| 179 | ++ |
| 180 | ++ |
| 181 | + |
| 182 | + |

-continued

| Compound No. | $IC_{50}$ |
|---|---|
| 183 | + |
| 184 | + |
| 185 | + |
| 186 | + |
| 187 | ++ |
| 188 | ++ |
| 189 | ++ |
| 190 | ++ |
| 191 | ++ |
| 192 | + |
| 193 | + |
| 194 | ++ |
| 195 | ++ |
| 196 | ++ |
| 197 | ++ |
| 198 | + |
| 199 | + |
| 200 | + |
| 201 | + |
| 202 | ++ |
| 203 | + |
| 204 | + |
| 205 | ++ |
| 206 | ++ |
| 207 | + |
| 208 | + |
| 209 | +++ |
| 210 | +++ |
| 211 | +++ |
| 212 | ++ |
| 213 | + |
| 214 | + |
| 215 | ++ |
| 216 | + |
| 217 | ++ |
| 218 | + |
| 219 | ++ |
| 220 | + |
| 221 | ++ |
| 222 | + |
| 223 | + |
| 224 | ++ |
| 225 | +++ |
| 226 | +++ |
| 227 | +++ |
| 228 | ++ |
| 229 | ++ |
| 230 | + |
| 231 | ++ |
| 232 | ++ |
| 233 | +++ |
| 234 | +++ |
| 235 | ++ |
| 236 | ++ |
| 237 | ++ |
| 238 | ++ |
| 239 | +++ |
| 240 | +++ |
| 241 | +++ |
| 242 | +++ |
| 243 | +++ |
| 244 | +++ |
| 245 | +++ |
| 246 | +++ |
| 247 | +++ |
| 248 | +++ |
| 249 | +++ |
| 250 | ++ |
| 251 | ++ |
| 252 | +++ |
| 253 | ++ |
| 254 | ++ |
| 255 | ++ |
| 256 | +++ |
| 257 | +++ |
| 258 | ++ |
| 259 | + |

-continued

| Compound No. | $IC_{50}$ |
|---|---|
| 260 | ++ |
| 261 | + |
| 262 | ++ |
| 263 | + |
| 264 | +++ |
| 265 | +++ |
| 266 | +++ |
| 267 | +++ |
| 268 | +++ |
| 269 | +++ |
| 270 | + |
| 271 | + |
| 272 | ++ |
| 273 | +++ |
| 274 | + |
| 275 | ++ |
| 276 | +++ |
| 277 | +++ |
| 278 | +++ |
| 279 | +++ |
| 280 | +++ |
| 281 | +++ |
| 282 | +++ |
| 283 | +++ |
| 284 | +++ |
| 285 | +++ |
| 286 | + |
| 287 | +++ |
| 288 | + |
| 289 | +++ |
| 290 | + |
| 291 | +++ |
| 292 | + |
| 293 | ++ |
| 294 | +++ |
| 295 | ++ |
| 296 | + |
| 297 | +++ |
| 298 | +++ |
| 299 | +++ |
| 300 | + |
| 301 | +++ |
| 302 | +++ |
| 303 | + |
| 304 | + |
| 305 | +++ |
| 306 | +++ |
| 307 | + |
| 308 | +++ |
| 309 | ++ |
| 310 | + |
| 311 | + |
| 312 | +++ |
| 313 | +++ |
| 314 | +++ |
| 315 | + |
| 316 | + |
| 317 | +++ |
| 318 | ++ |
| 319 | ++ |
| 320 | +++ |
| 321 | +++ |
| 322 | +++ |
| 323 | + |
| 324 | ++ |
| 325 | ++ |
| 326 | +++ |
| 327 | +++ |
| 328 | +++ |
| 329 | +++ |
| 330 | +++ |
| 331 | +++ |
| 332 | + |
| 333 | +++ |
| 334 | +++ |
| 335 | + |
| 336 | + |

-continued

| Compound No. | $IC_{50}$ |
|---|---|
| 337 | + |
| 338 | ++ |
| 339 | +++ |
| 340 | +++ |
| 341 | + |
| 342 | ++ |
| 343 | + |
| 344 | + |
| 345 | + |
| 346 | + |
| 347 | + |
| 348 | + |
| 349 | + |
| 350 | + |
| 351 | +++ |
| 352 | +++ |
| 353 | + |
| 354 | +++ |
| 355 | +++ |
| 356 | +++ |
| 357 | +++ |
| 358 | + |
| 359 | + |
| 360 | +++ |
| 361 | +++ |
| 362 | +++ |
| 363 | ++ |
| 364 | + |
| 365 | + |
| 366 | ++ |
| 367 | + |
| 368 | + |
| 369 | + |
| 370 | + |
| 371 | + |
| 372 | + |
| 373 | + |
| 374 | + |
| 375 | + |
| 376 | + |
| 377 | + |
| 378 | +++ |
| 379 | +++ |
| 380 | + |
| 381 | + |
| 382 | + |
| 383 | + |
| 384 | + |
| 385 | +++ |
| 386 | +++ |
| 387 | +++ |
| 388 | +++ |
| 389 | + |

The disclosed subject matter is not to be limited in scope by the specific embodiments and examples described herein. Indeed, various modifications of the disclosure in addition to those described will become apparent to those skilled in the art from the foregoing description and accompanying FIGURES. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A method of treating inflammation in a subject in need thereof comprising administering to the subject a therapeutically effective amount of a compound of Formula VII:

(VII)

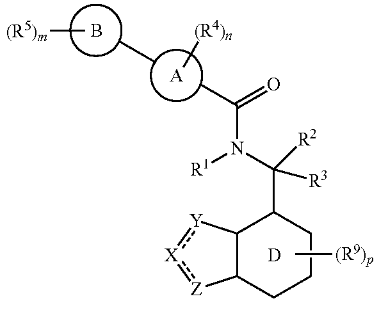

or a pharmaceutically acceptable salt thereof, wherein

X, Y, and Z, together with the ring to which they are attached, form

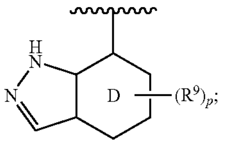

Ring A is selected from the group consisting of $C_{6-10}$ aryl, 5-10 membered heteroaryl, $C_{3-10}$ cycloalkyl, and 4-10 membered heterocycloalkyl;

Ring B is selected from the group consisting of phenyl, 5-6 membered heteroaryl, $C_{3-6}$ cycloalkyl, and 3-6 membered heterocycloalkyl;

alternatively, Ring B is absent and m is 0;

Ring D is pyridinyl;

$R^1$ is selected from the group consisting of H, $C_{1-6}$ alkyl, and $C_{3-6}$ cycloalkyl, wherein alkyl and cycloalkyl are each optionally substituted with $R^6$;

$R^2$ and $R^3$ are each independently selected from the group consisting of H, $C_{1-6}$ alkyl, $C_{3-6}$ cycloalkyl, and 3-6 membered heterocycloalkyl;

each $R^4$ is independently selected from the group consisting of $C_{1-6}$ alkyl, halo, —OH, —$OR^6$, $C_{3-7}$ cycloalkyl, 3-7 membered heterocycloalkyl, and —$COR^6$;

each $R^5$ is independently selected from the group consisting of $C_{1-6}$ alkyl, $C_{1-6}$ haloalkyl, halo, —CN, —$COR^6$, and —$SO_2R^6$;

each $R^6$ is independently selected from the group consisting of $C_{1-6}$ alkyl, $C_{3-6}$ cycloalkyl, 3-6 membered heterocycloalkyl, —$NH_2$, —NH($C_{1-6}$ alkyl), and —N($C_{1-6}$ alkyl)$_2$;

each $R^9$ is independently selected from the group consisting of $C_{1-6}$ alkyl, $C_{1-6}$ haloalkyl, $C_{1-6}$ alkyl-OH, —$OC_{1-6}$ alkyl, $C_{1-6}$ alkyl-O—$C_{1-6}$ alkyl, O($C_{3-6}$ cycloalkyl), halo, —CN, —OH, —$NH_2$, —NH($C_{1-6}$ alkyl), and —N($C_{1-6}$ alkyl)$_2$;

m is 0, 1, 2, or 3;

n is 0, 1, 2, or 3; and p is 0, 1, 2, or 3.

2. The method of claim 1, wherein the compound of Formula VII is a compound of Formula VI:

(VI)

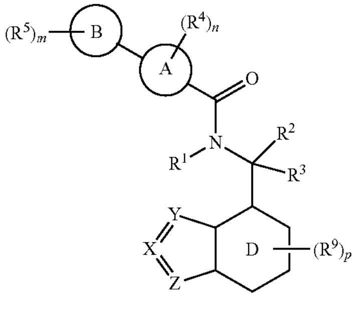

or a pharmaceutically acceptable salt thereof;

wherein

X, Y, and Z, together with the ring to which they are attached, form

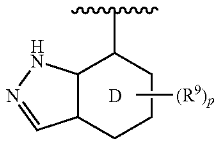

Ring A is selected from the group consisting of $C_{6-10}$ aryl, 5-6 membered heteroaryl, $C_{3-10}$ cycloalkyl, and 4-10 membered heterocycloalkyl;

Ring B is selected from the group consisting of phenyl, 5-6 membered heteroaryl, $C_{3-6}$ cycloalkyl, and 3-6 membered heterocycloalkyl;

alternatively, Ring B is absent and m is 0;

Ring D is pyridinyl;

$R^1$ is selected from the group consisting of H, $C_{1-6}$ alkyl, and $C_{3-6}$ cycloalkyl, wherein alkyl and cycloalkyl are each optionally substituted with $R^6$;

$R^2$ and $R^3$ are each independently selected from the group consisting of H, $C_{1-6}$ alkyl, $C_{3-6}$ cycloalkyl, and 3-6 membered heterocycloalkyl;

each $R^4$ is independently selected from the group consisting of $C_{1-6}$ alkyl, halo, —OH, —$OR^6$, $C_{3-7}$ cycloalkyl, 3-7 membered heterocycloalkyl, and —$COR^6$;

each $R^5$ is independently selected from the group consisting of $C_{1-6}$ alkyl, $C_{1-6}$ haloalkyl, halo, —CN, —$COR^6$, and —$SO_2R^6$;

each $R^6$ is independently selected from the group consisting of $C_{1-6}$ alkyl, $C_{3-6}$ cycloalkyl, —$NH_2$, —NH($C_{1-6}$ alkyl), and —N($C_{1-6}$ alkyl)$_2$;

each $R^9$ is independently selected from the group consisting of $C_{1-6}$ alkyl, —$OC_{1-6}$ alkyl, halo, —CN, —OH, —$NH_2$, —NH($C_{1-6}$ alkyl), and —N($C_{1-6}$ alkyl)$_2$;

m is 0, 1, or 2;

n is 0, 1, or 2; and p is 0, 1, or 2.

3. The method of claim 1, wherein

Ring A is phenyl or 5-6 membered heteroaryl;

Ring B is phenyl or 5-6 membered heteroaryl;

Ring D is pyridinyl;

$R^1$ is H or $C_{1-3}$ alkyl;

$R^2$ and $R^3$ are each independently selected from the group consisting of H and $C_{1-3}$ alkyl;

each $R^4$ is independently selected from the group consisting of halo, —OH, —$OR^6$, $C_{3-7}$ cycloalkyl, 3-7 membered heterocycloalkyl, and —$COR^6$;

each $R^5$ is independently selected from the group consisting of $C_{1-3}$ alkyl, $C_{1-3}$ haloalkyl, halo, —$COR^6$, and —$SO_2R^6$;

each $R^6$ is independently selected from the group consisting of $C_{1-6}$ alkyl, $C_{3-6}$ cycloalkyl, 3-6 membered heterocycloalkyl, —$NH_2$, —$NH(C_{1-3}$ alkyl), and —$N(C_{1-3}$ alkyl$)_2$;

each $R^9$ is independently selected from the group consisting of $C_{1-3}$ haloalkyl, $C_{1-3}$ alkyl-OH, —$OC_{1-3}$ alkyl, halo, and —CN;

m is 0, 1, or 2;

n is 0, 1, or 2; and p is 0 or 1.

4. The method of claim 3, wherein the compound of Formula VI is a compound of Formula VIa, IVb, or VIc:

(VIa)

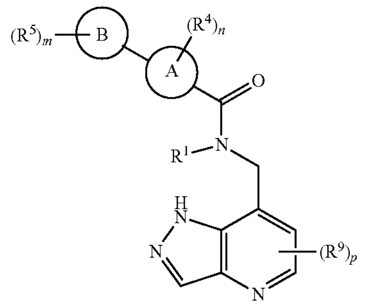

(VIb)

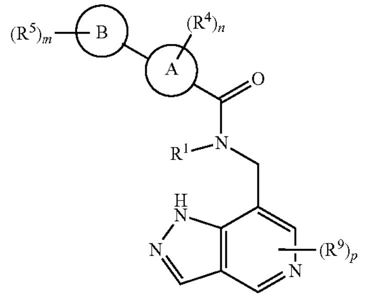

or (VIc)

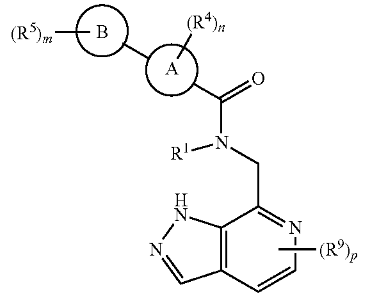

or a pharmaceutically acceptable salt thereof.

5. The method of claim 1, wherein Ring A is selected from the group consisting of phenyl, pyridinyl, pyrimidinyl, and pyrazinyl.

6. The method of claim 1, wherein Ring B is selected from phenyl and 5-6 membered heteroaryl.

7. The method of claim 1, wherein $R^1$ is $C_{1-6}$ alkyl or $C_{3-6}$ cycloalkyl optionally substituted with $C_{1-6}$ alkyl.

8. The method of claim 1 wherein $R^2$ and $R^3$ are each independently selected from the group consisting of H and $C_{1-3}$ alkyl.

9. The method of claim 1, wherein $R^4$ is —$OC_{1-6}$ alkyl.

10. The method of claim 1, wherein $R^5$ is selected from the group consisting of $C_{1-6}$ alkyl, $C_{1-6}$ haloalkyl, halo, —CN, —$CONH_2$, —$CONH(C_{1-6}$ alkyl), and —$SO_2NH_2$.

11. The method of claim 1, wherein each $R^9$ is independently selected from the group consisting of $C_{1-6}$ alkyl, $C_{1-6}$ haloalkyl, $C_{1-6}$ alkyl-OH, —$OC_{1-6}$ alkyl, $C_{1-6}$ alkyl-O—$C_{1-6}$ alkyl, —$O(C_{3-6}$ cycloalkyl), halo, and —CN.

12. The method of claim 1, wherein the compound of Formula VII is selected from the group consisting of

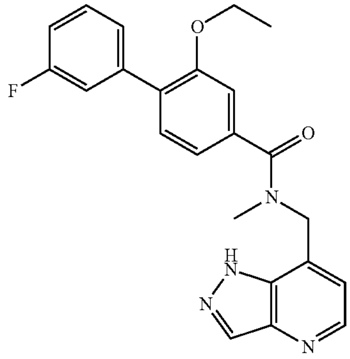

,

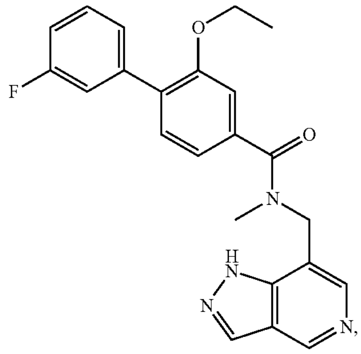

,

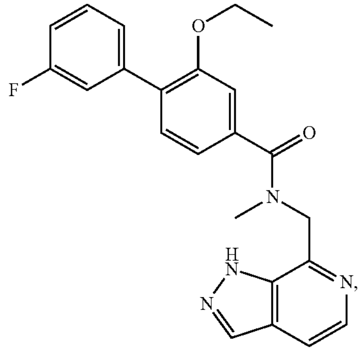

,

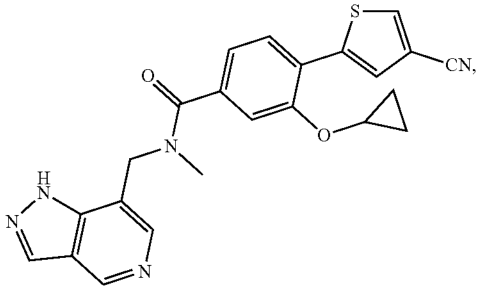

,

-continued
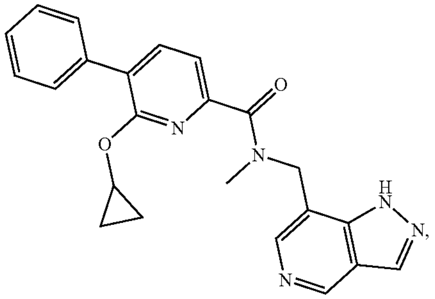
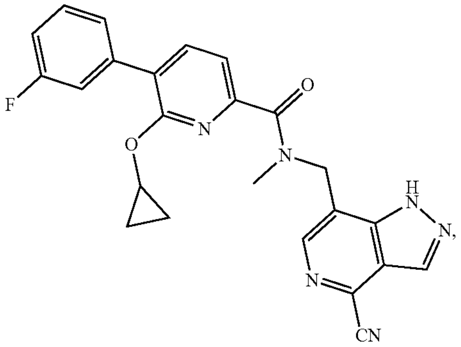
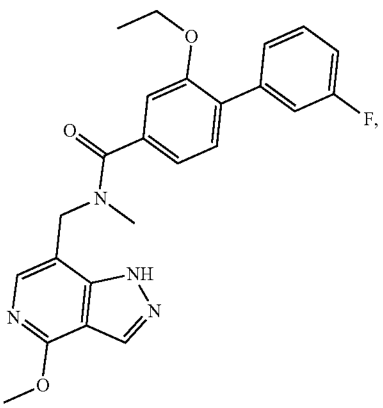
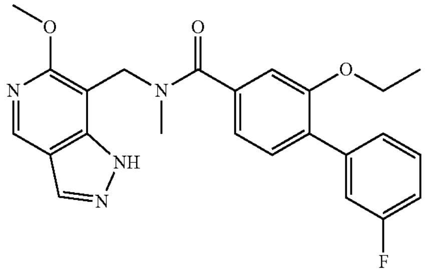
,
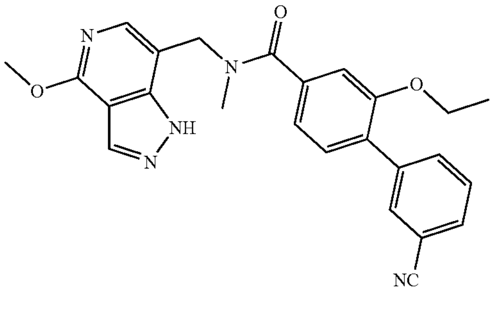
,
-continued
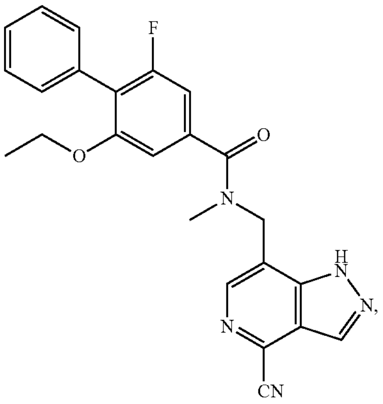
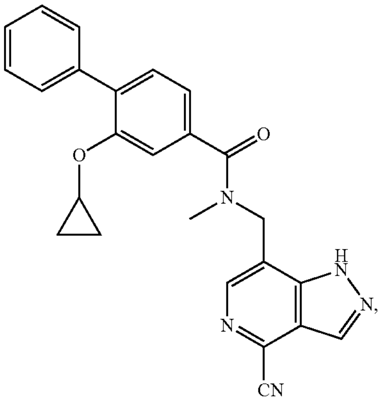
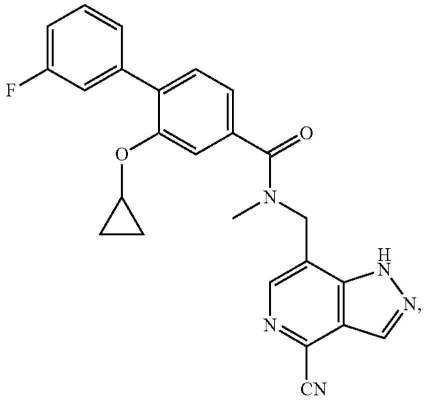
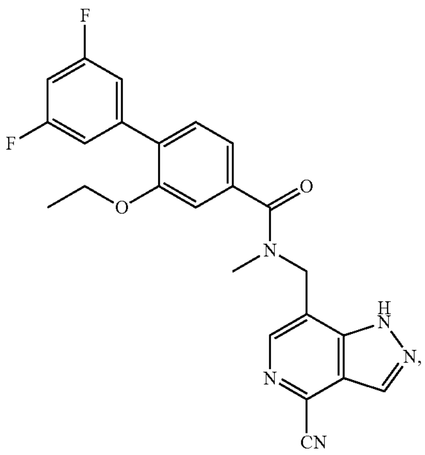

-continued
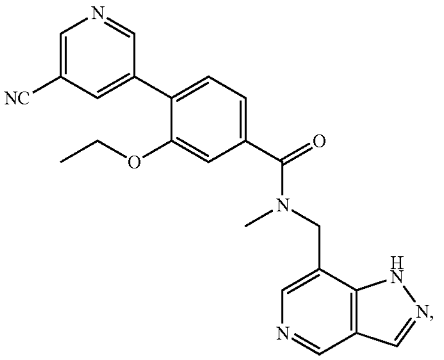
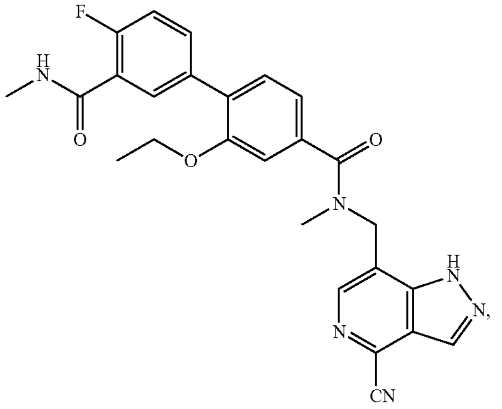
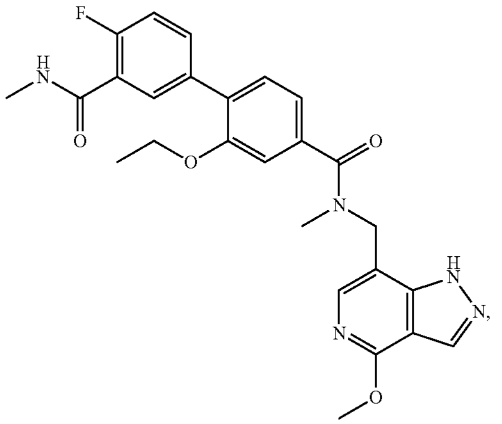
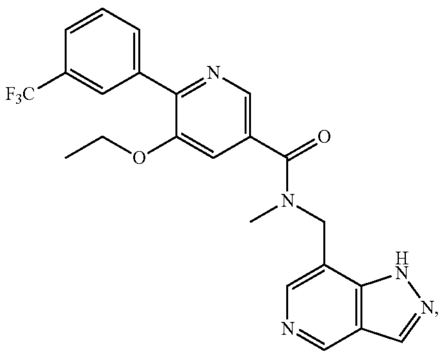
-continued
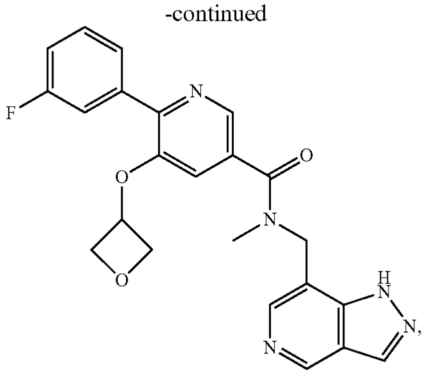
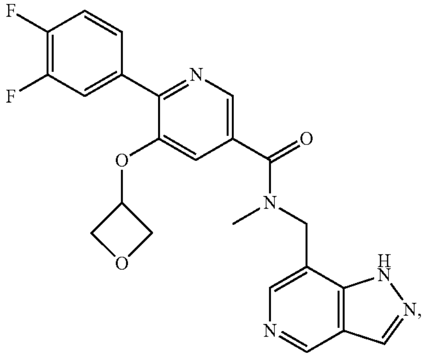
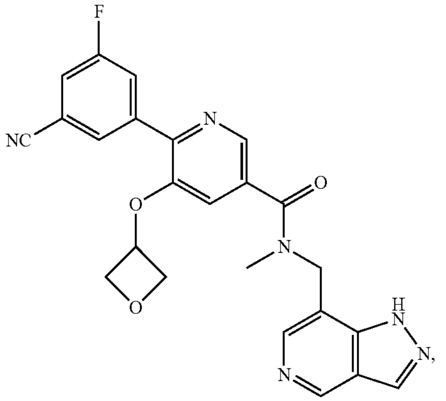
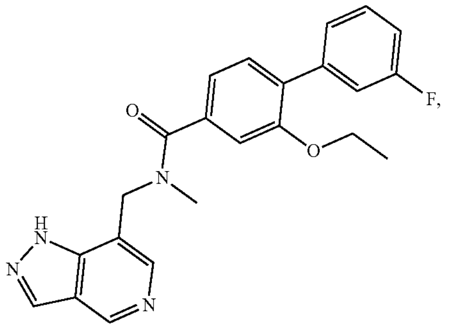

-continued
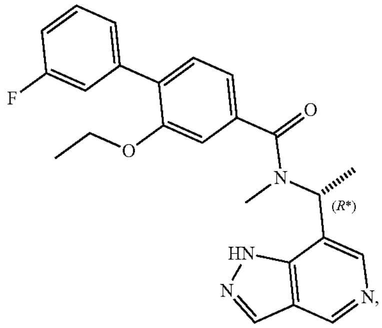
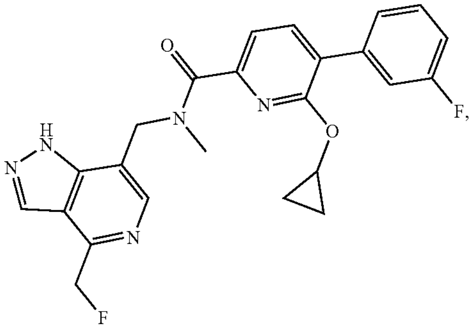
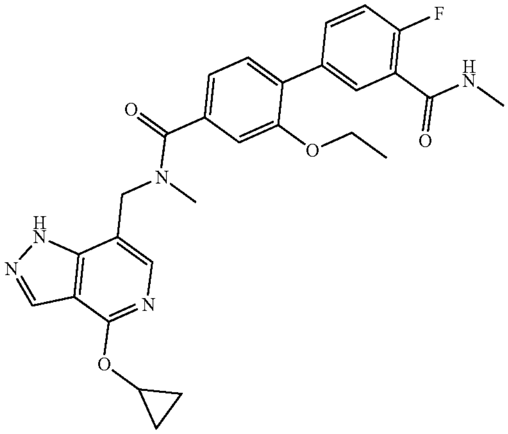
,
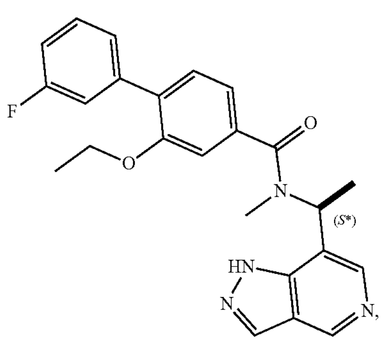
-continued
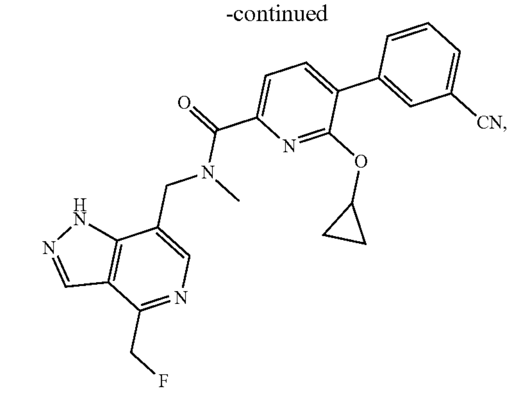
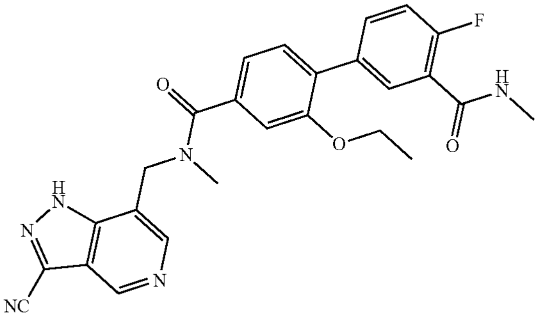
,
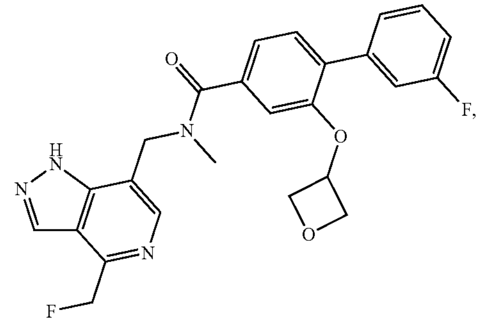
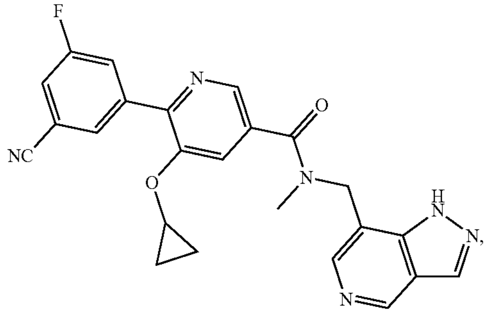
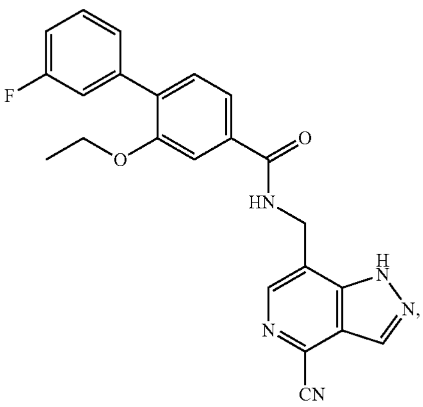

-continued
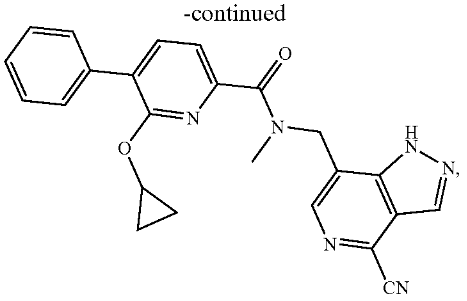
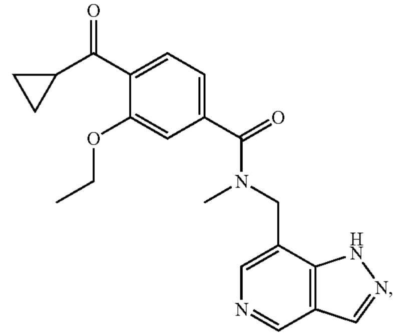
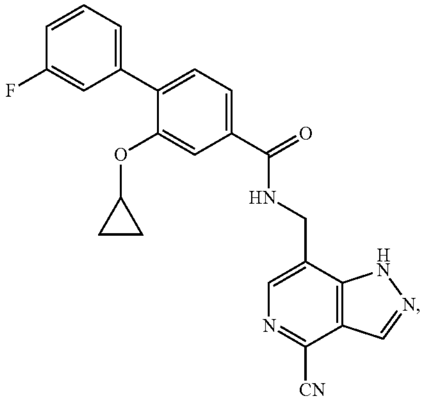
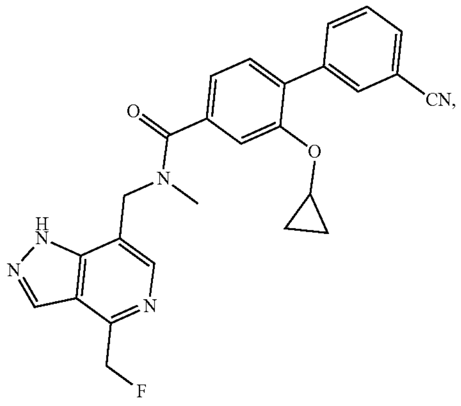
-continued
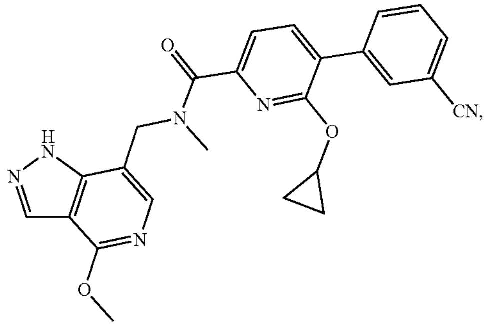
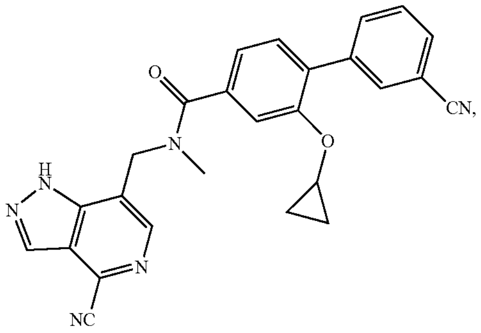
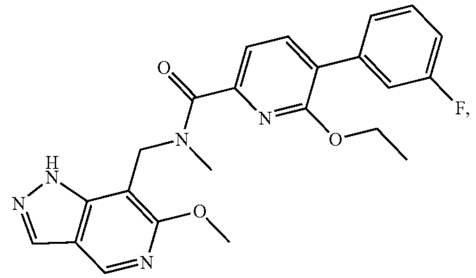
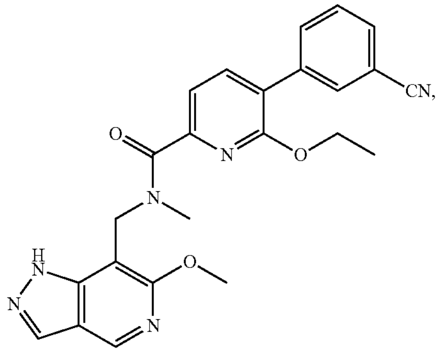
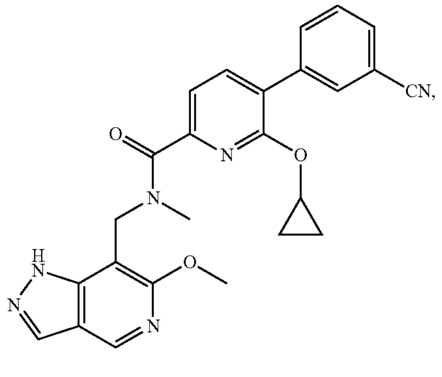

-continued
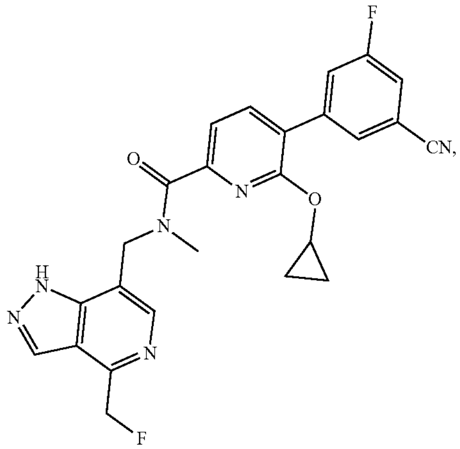
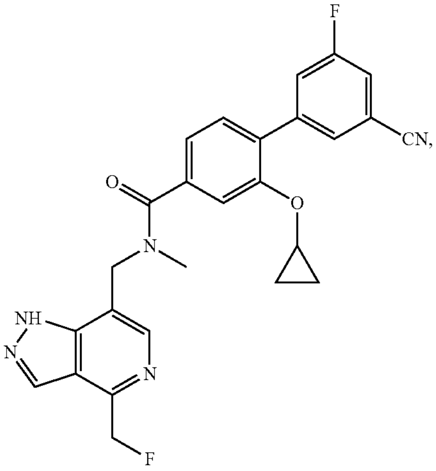
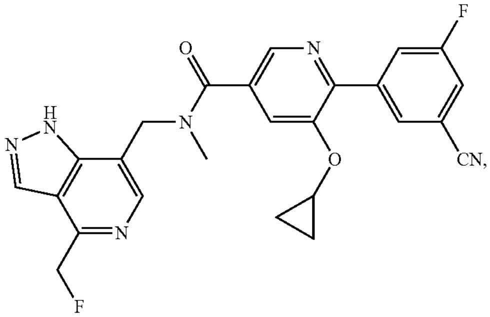
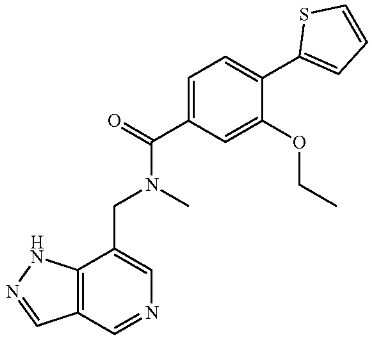
,
-continued
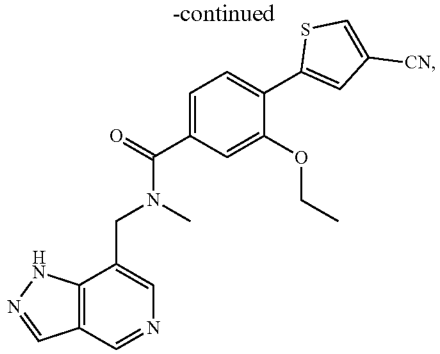
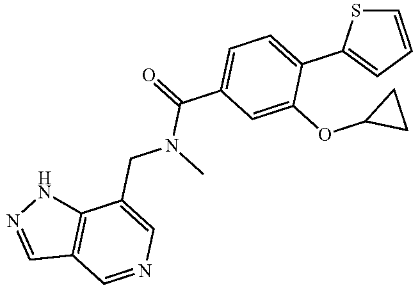
,
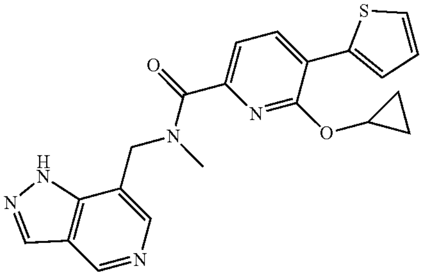
,
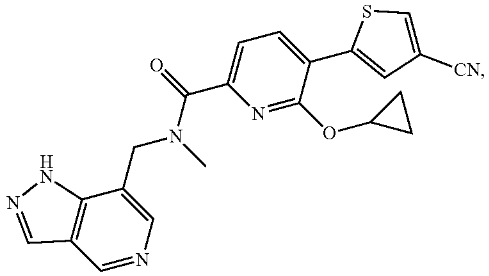
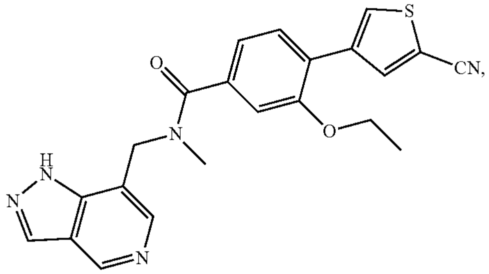
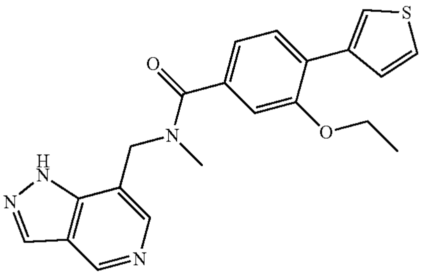
, -continued
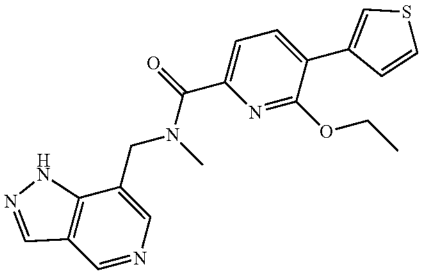
,
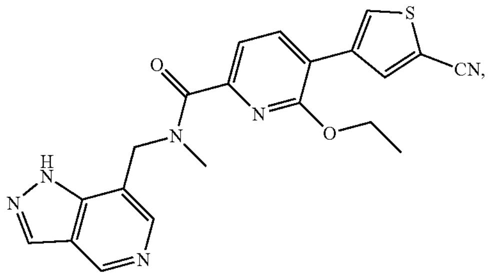
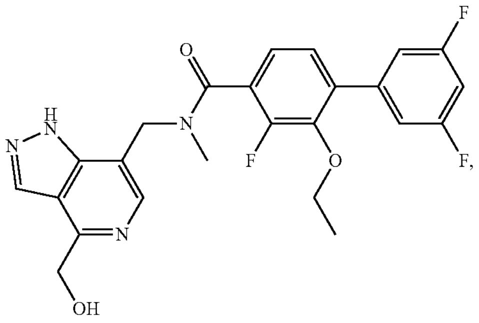
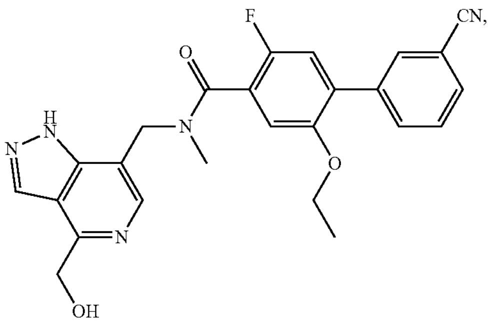
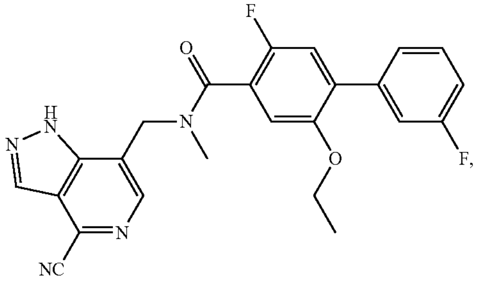
-continued
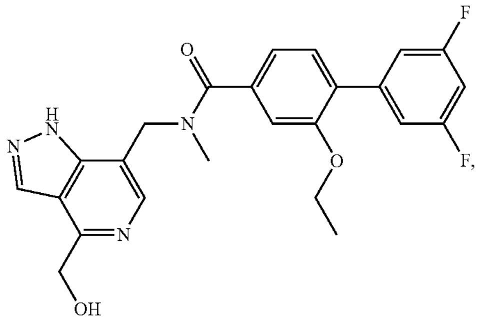
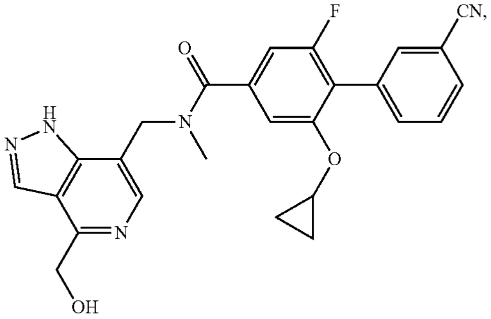
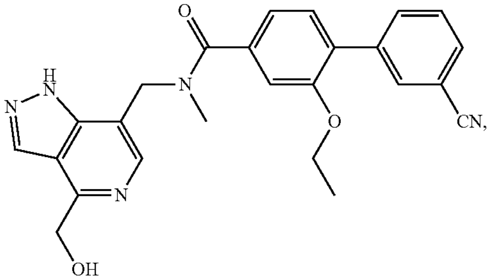
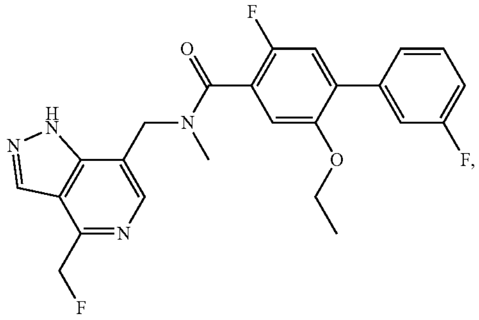
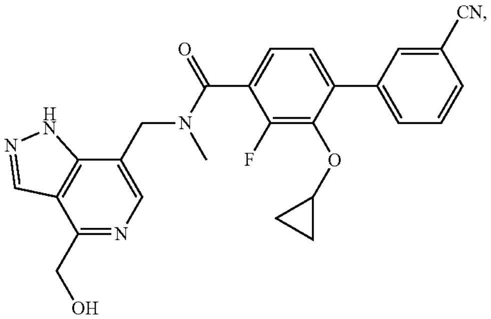

-continued
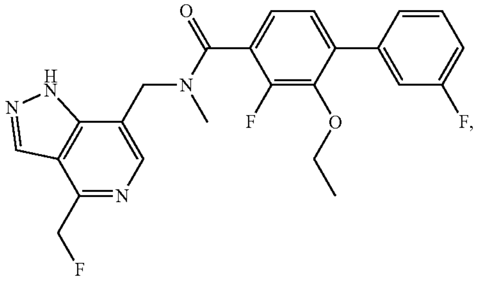
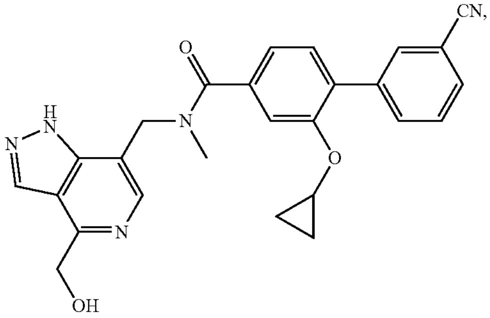
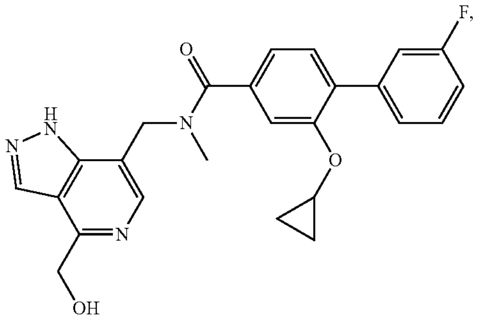
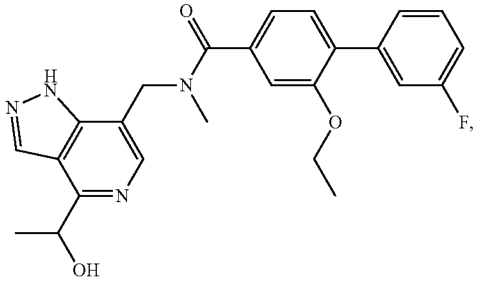
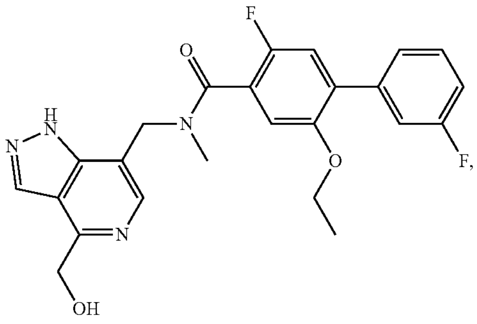
-continued
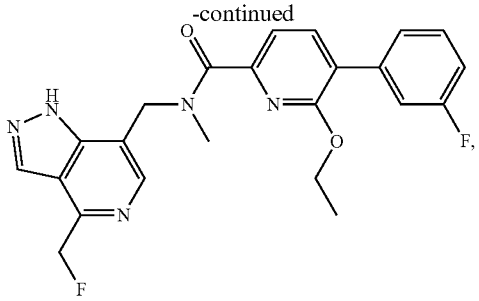
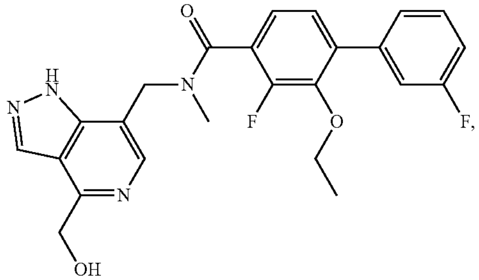
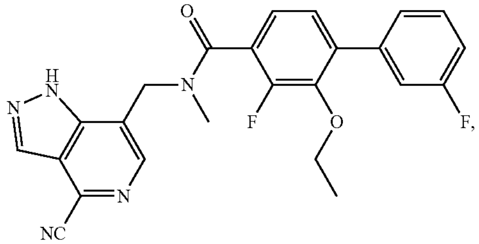
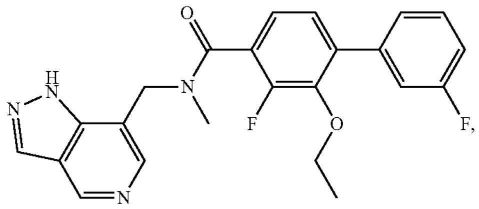
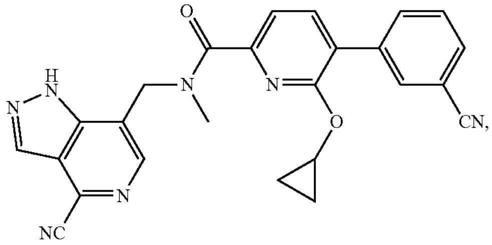
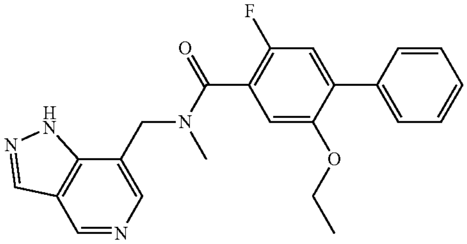
, -continued
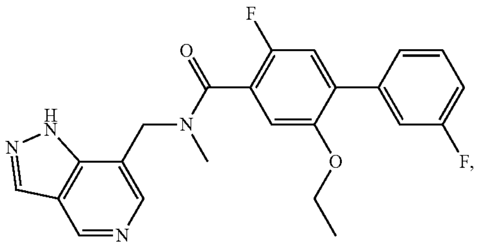
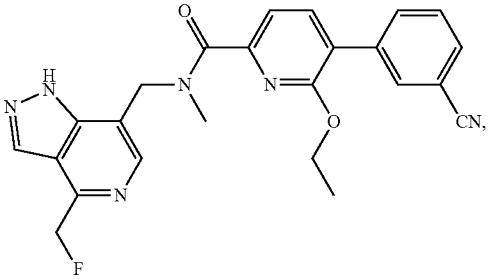
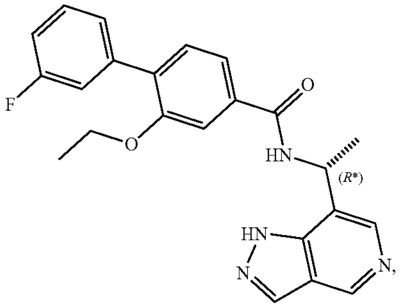
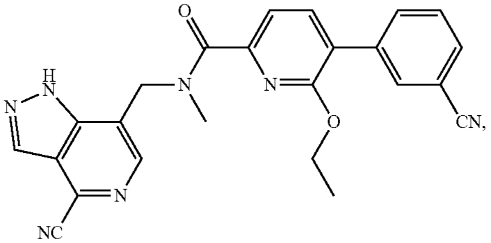
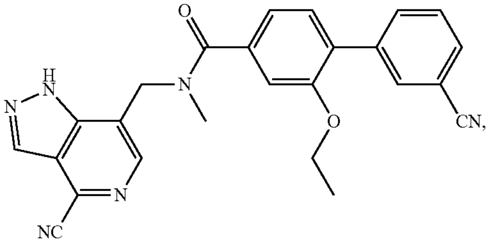
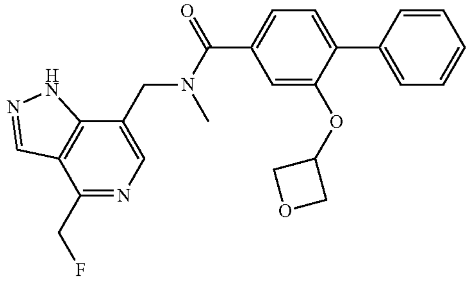
,
-continued
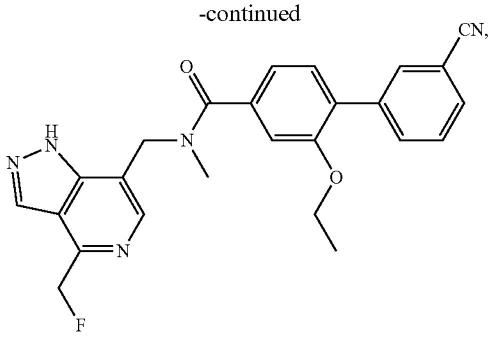
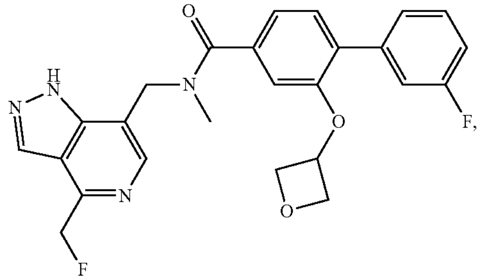
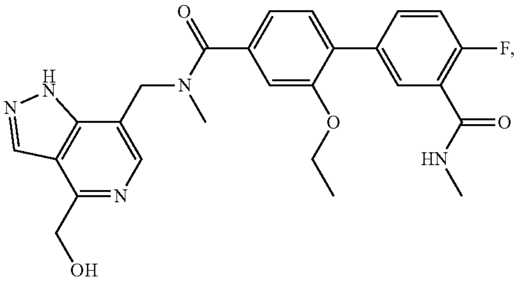
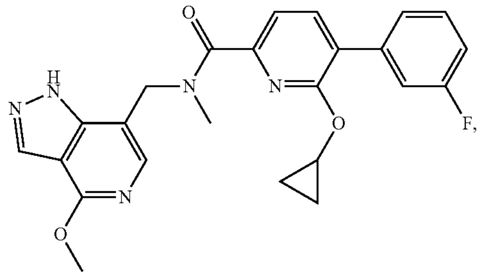
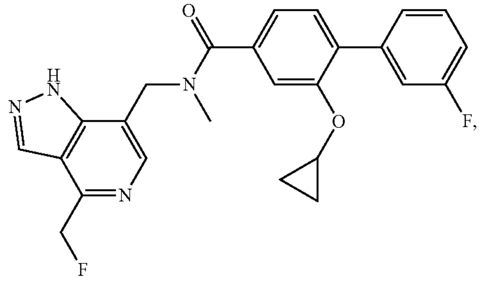
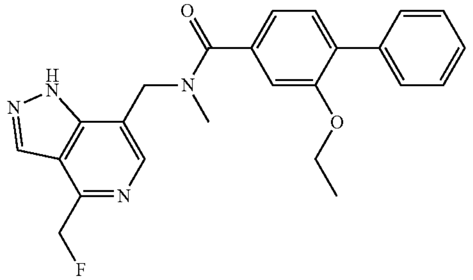
, -continued
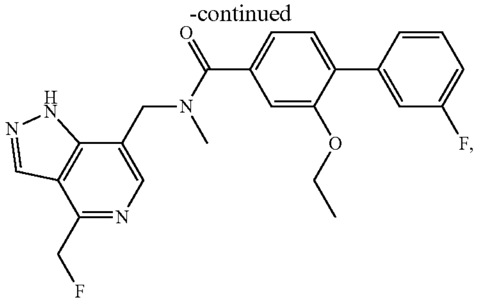
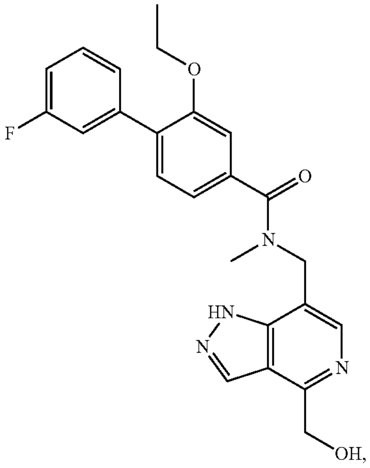
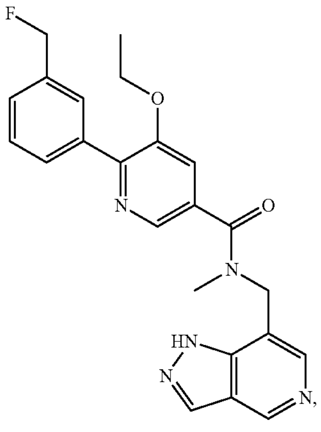
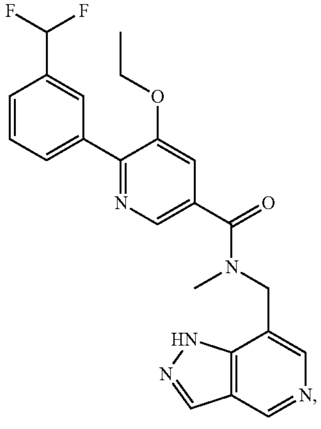
-continued
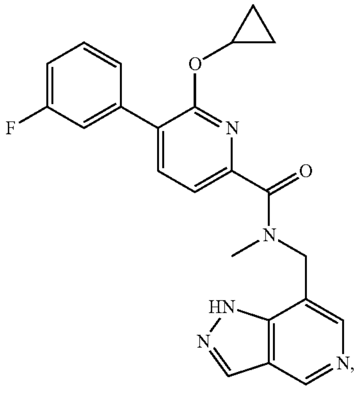
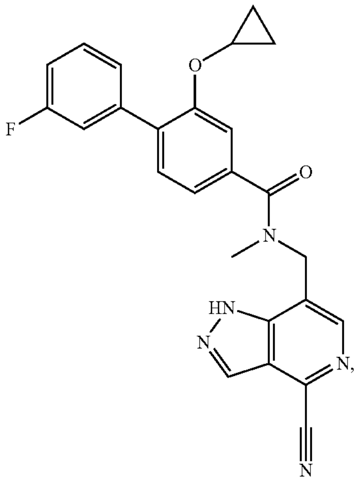
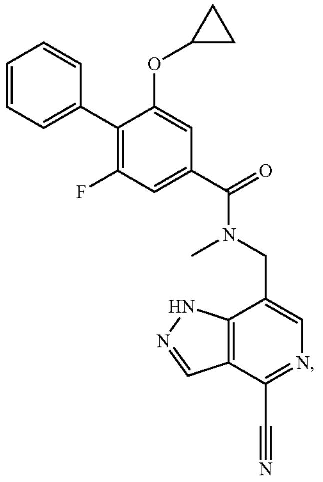

-continued
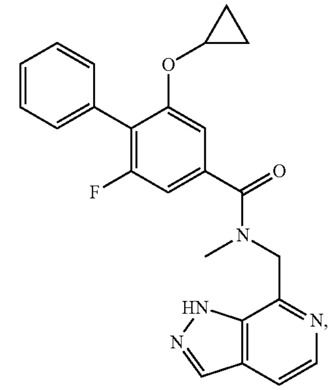
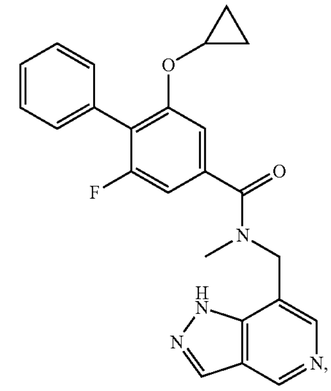
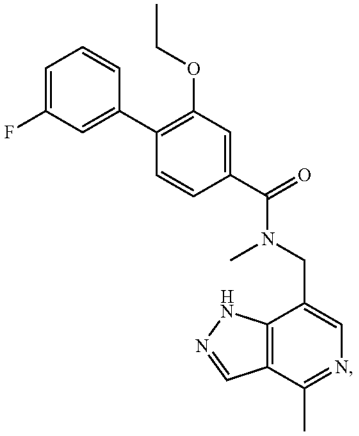
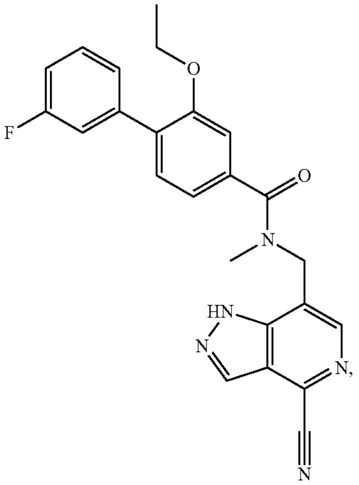
-continued
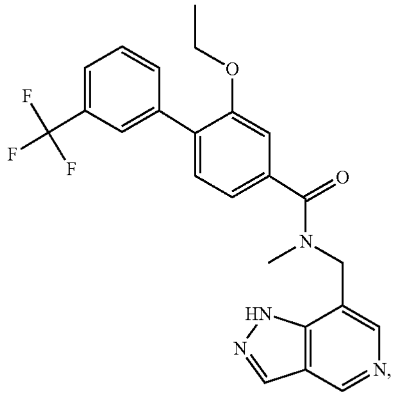
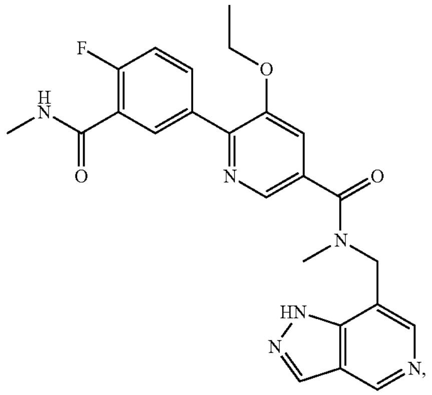
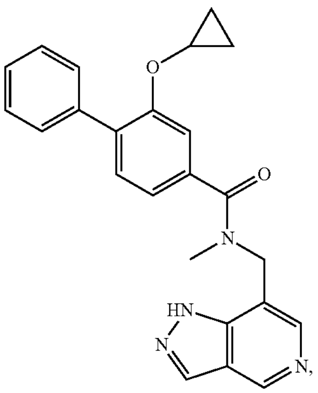
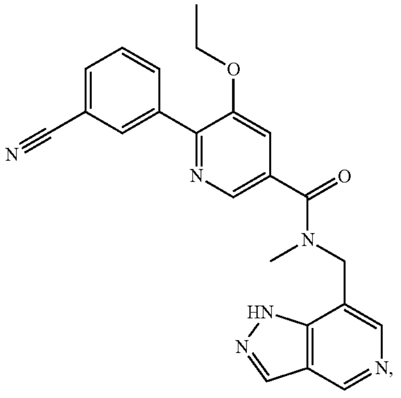

-continued
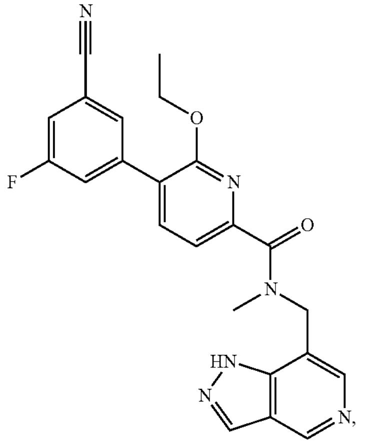
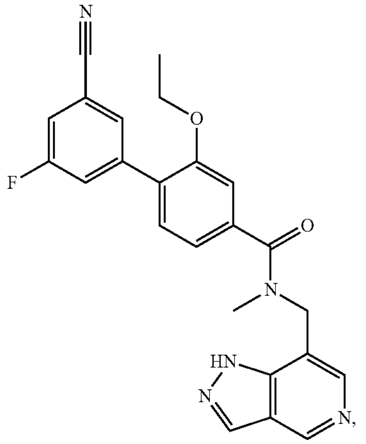
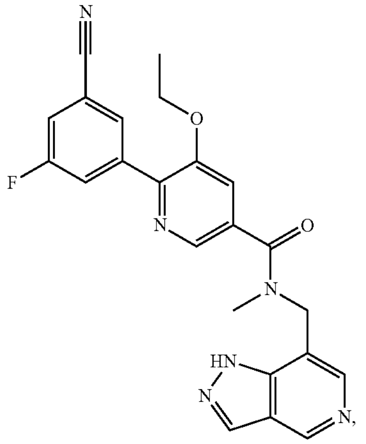
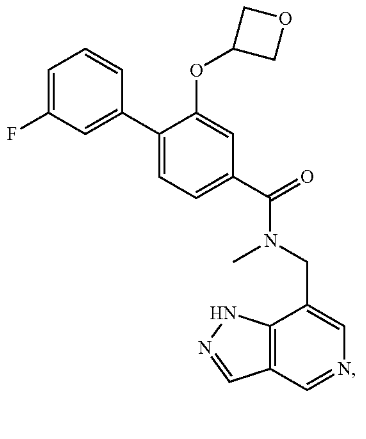
-continued
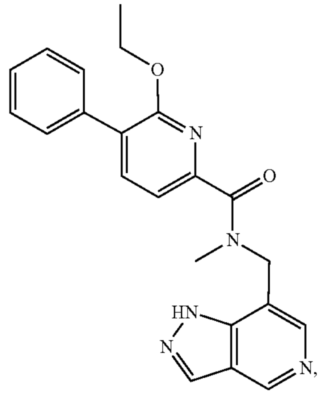
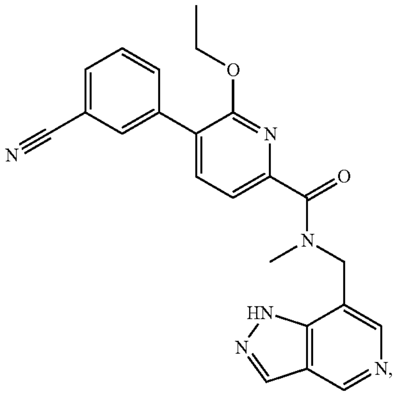
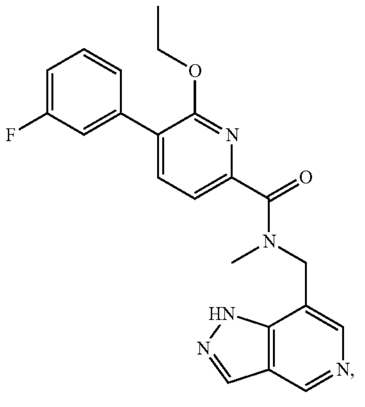
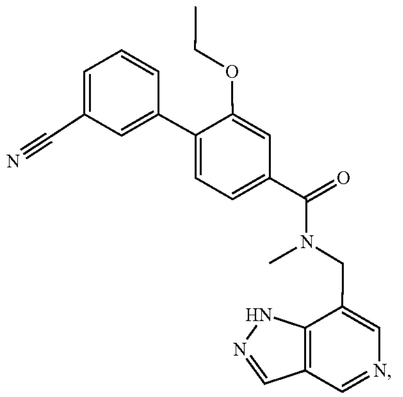

-continued
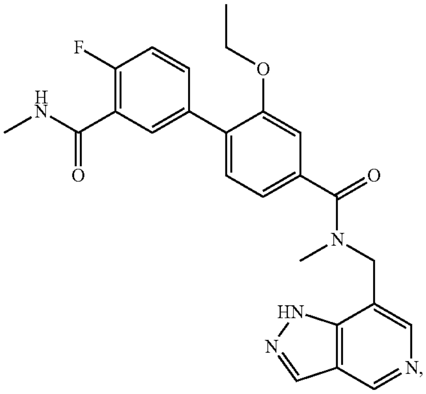,
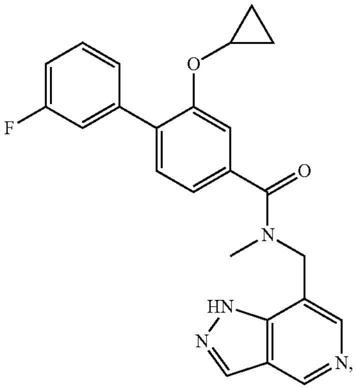,
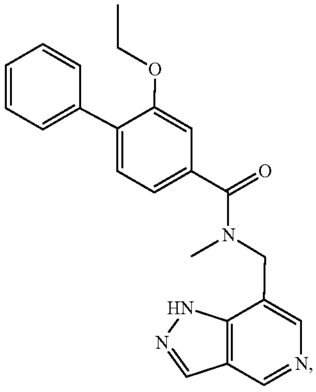,
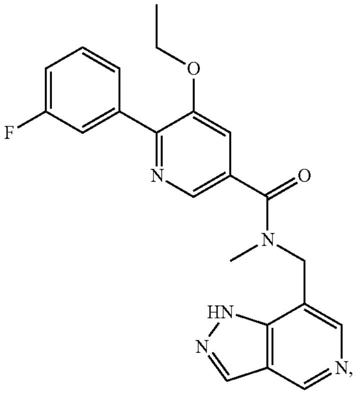,
-continued
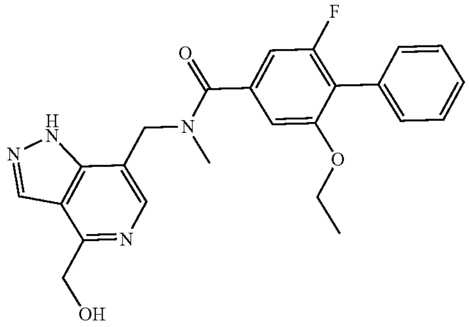,
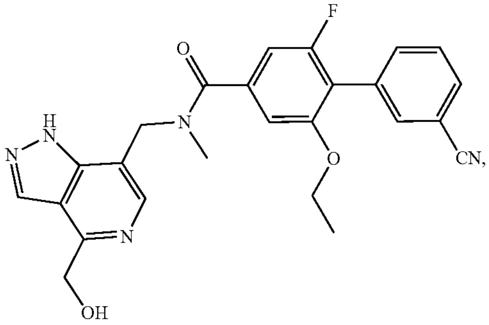,
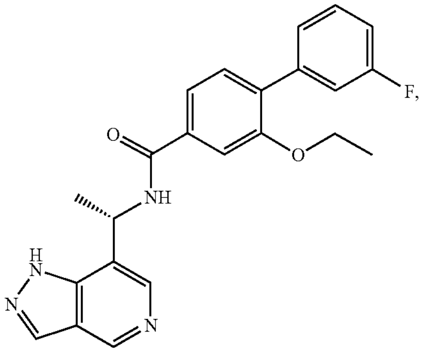,
or a pharmaceutically acceptable salt thereof.
13. The method of claim 1, wherein the compound of Formula VII is selected from the group consisting of:
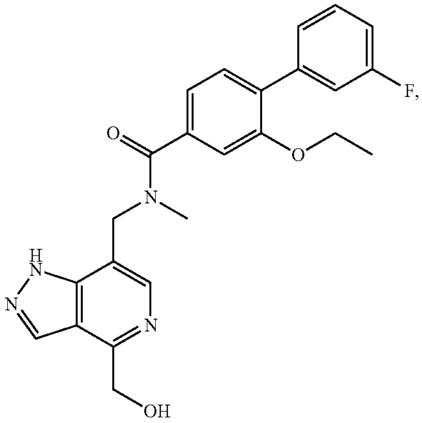, -continued
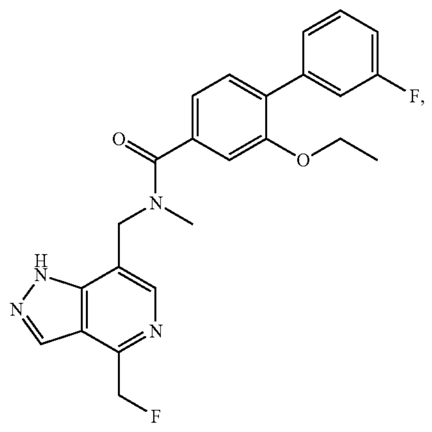
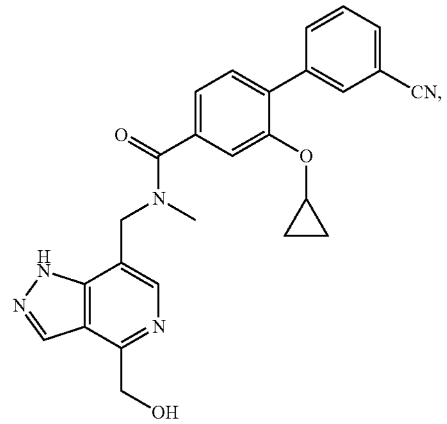
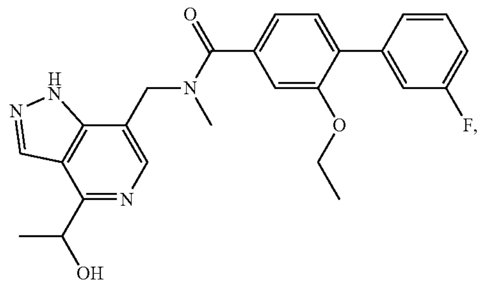
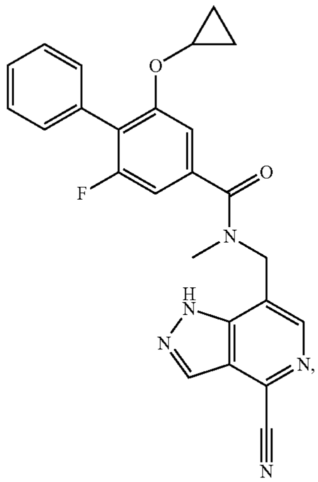
-continued
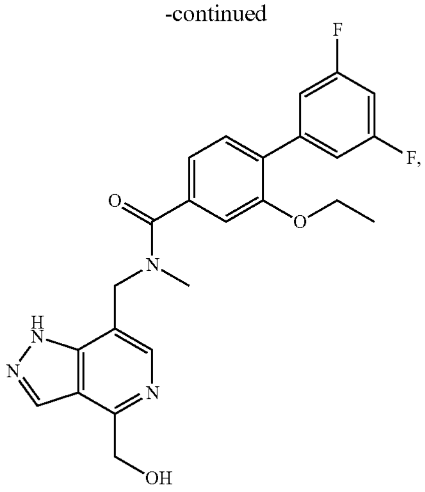
or a pharmaceutically acceptable salt thereof.
14. The method of claim 1, wherein the compound of Formula VII is
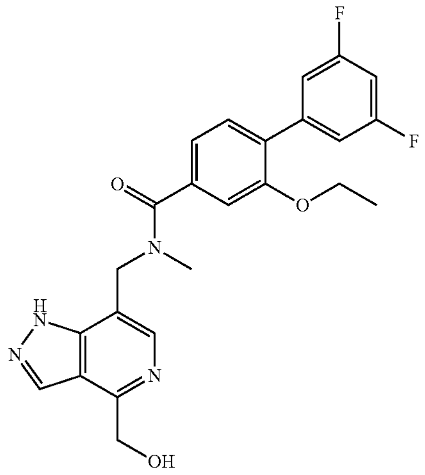 [SMILES: CCOc1cc(C(=O)N(C)Cc2cnc(CO)c3cn[nH]c23)ccc1-c1cc(F)cc(F)c1]
or a pharmaceutically acceptable salt thereof.
15. The method of claim 1, wherein the compound of Formula VII is
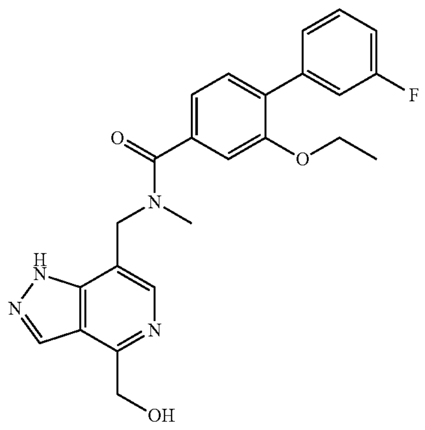 [SMILES: CCOc1cc(C(=O)N(C)Cc2cnc(CO)c3cn[nH]c23)ccc1-c1cccc(F)c1]
or a pharmaceutically acceptable salt thereof.
* * * * *